(12) United States Patent
Motamedi et al.

(10) Patent No.: US 12,396,996 B2
(45) Date of Patent: Aug. 26, 2025

(54) COMPOUNDS, PHARMACEUTICAL COMPOSITIONS, AND METHODS OF THEIR USE IN REVERSING CANCER CHEMORESISTANCE

(71) Applicants: The General Hospital Corporation, Boston, MA (US); Massachusetts Institute of Technology, Cambridge, MA (US); Beth Israel Deaconess Medical Center, Inc., Boston, MA (US)

(72) Inventors: Mo Motamedi, Boston, MA (US); Junichi Hanai, Boston, MA (US); Vikas Sukhatme, Boston, MA (US); Mohammad Movassaghi, Cambridge, MA (US)

(73) Assignees: The General Hospital Corporation, Boston, MA (US); Massachusetts Institute of Technology, Cambridge, MA (US); Beth Israel Deaconess Medical Center, Inc., Boston, MA (US)

(*) Notice: Subject to any disclaimer, the term of this patent is extended or adjusted under 35 U.S.C. 154(b) by 603 days.

(21) Appl. No.: 17/632,543

(22) PCT Filed: Aug. 6, 2020

(86) PCT No.: PCT/US2020/045289
§ 371 (c)(1),
(2) Date: Feb. 3, 2022

(87) PCT Pub. No.: WO2021/026395
PCT Pub. Date: Feb. 11, 2021

(65) Prior Publication Data
US 2022/0280528 A1 Sep. 8, 2022

Related U.S. Application Data

(60) Provisional application No. 62/883,308, filed on Aug. 6, 2019.

(51) Int. Cl.
*A61K 31/548* (2006.01)
*A61P 35/00* (2006.01)

(52) U.S. Cl.
CPC ............ *A61K 31/548* (2013.01); *A61P 35/00* (2018.01)

(58) Field of Classification Search
CPC .. A61K 2300/00; A61K 31/548; A61K 45/06; A61P 31/00; A61P 35/00; C07D 487/14; C07D 513/22; C07D 519/00
See application file for complete search history.

(56) References Cited

U.S. PATENT DOCUMENTS

| | | |
|---|---|---|
| 2009/0264421 A1 | 10/2009 | Bible et al. |
| 2015/0104429 A1 | 4/2015 | Gribble et al. |
| 2016/0303135 A1 | 10/2016 | Keilhack et al. |

FOREIGN PATENT DOCUMENTS

| | | |
|---|---|---|
| WO | WO-2012/161799 A1 | 11/2012 |
| WO | WO-2017/190009 A1 | 11/2017 |
| WO | WO-2018/234367 A1 | 12/2018 |

OTHER PUBLICATIONS

International Search Report and Written Opinion for International Patent Application No. PCT/US2020/045289, mailed Dec. 22, 2020 (20 pages).

(Continued)

*Primary Examiner* — Savitha M Rao
(74) *Attorney, Agent, or Firm* — Clark & Elbing LLP

(57) ABSTRACT

Described herein are compounds, pharmaceutical compositions, and methods for use in reversing cancer chemoresistance.

14 Claims, 85 Drawing Sheets

(56) References Cited

OTHER PUBLICATIONS

Devin et al., "Inhibition of SUV39H Methyltransferase As a Potent Therapeutic Target in Multiple Myeloma," Blood. 126(23):1771 Abstract 651 (Dec. 2015) (2 pages).

Hansen et al., "H3K9 dimethylation safeguards cancer cells against activation of the interferon pathway," Sci Adv. 8(11):eabf8627 (Mar. 2022) (17 pages).

Shen et al., "FBXO44 promotes DNA replication-coupled repetitive element silencing in cancer cells," Cell. 184(2):352-369.e23 (Jan. 2021) (Epub Dec. 2020) (41 pages).

Control (no treatment)

Chaetocin (nM)

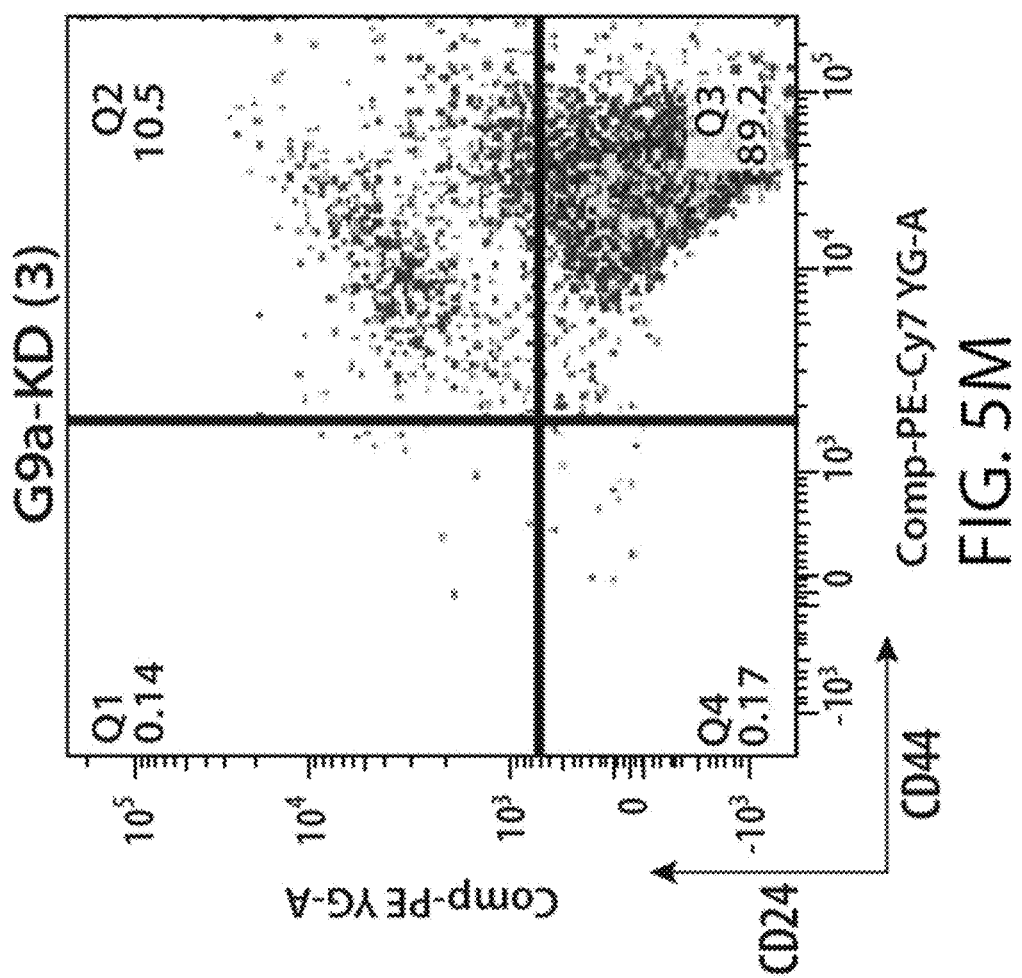

COMPOUNDS, PHARMACEUTICAL COMPOSITIONS, AND METHODS OF THEIR USE IN REVERSING CANCER CHEMORESISTANCE

FIELD OF THE INVENTION

The invention relates to compounds, pharmaceutical compositions, and methods of using the same.

BACKGROUND

Cancer remains one of the deadliest threats to human health. In 2012, there were 14 million new cases of cancer worldwide and 8.2 million cancer-related deaths. The number of new cancer cases is expected to rise to 22 million by 2030, and worldwide cancer deaths are projected to increase by 60%. Cancers often become multi-drug resistant, thereby further complicating cancer treatment.

There is a need for new therapeutics for the treatment of cancer. In particular, there is a need for new therapeutic approaches addressing drug resistant cancers.

SUMMARY OF THE INVENTION

In one aspect, the invention provides a method of killing a chemoresistant cancer cell by (i) contacting the chemoresistant cancer cell with an effective amount of a compound selected from the group consisting of chaetocin, a chaetocin analogue, a Suv39H1/Suv39H2 inhibitor, and pharmaceutically acceptable salts thereof, and (ii) contacting the cell with an anti-cancer agent or a pharmaceutically acceptable salt thereof.

In another aspect, the invention provides a method of treating a chemoresistant cancer in a subject by (i) administering to the subject in need thereof a therapeutically effective amount of a compound selected from the group consisting of chaetocin, a chaetocin analogue, a Suv39H1/Suv39H2 inhibitor, and pharmaceutically acceptable salts thereof, and, (ii) administering to the subject a therapeutically effective amount of an anti-cancer agent or a pharmaceutically acceptable salt thereof.

In preferred embodiments of any of the aspects described herein, the chemoresistant cancer includes a chemoresistant cancer cell. In preferred embodiments of any of the aspects described herein, the chemoresistant cancer cell is a chemoresistant mesenchymal cancer cell or a chemoresistant cancer cell expressing Suv39H1/Suv39H2.

In one aspect, the invention provides a method of killing a chemoresistant cancer cell by contacting the chemoresistant cancer cell with an effective amount of a compound selected from the group consisting of chaetocin, a chaetocin analogue, a Suv39H1/Suv39H2 inhibitor, and pharmaceutically acceptable salts thereof. The method may further include, after a period of at least 1 hour (e.g., at least 5 hours, at least 6 hours, at least 10 hours, at least 12 hours, at least 15 hours, at least 18 hours, at least 1 day, at least 2 days, at least 3 days, at least 4 days, at least 5 days, at least 6 days, at least 1 week, or at least 2 weeks; e.g., within 1 month, within 3 weeks, within 2 weeks, or within 1 week; e.g., 1 hour to 1 month, 5 hours to 1 month, 6 hours to 1 month, 10 hours to 1 month, 12 hours to 1 month, 15 hours to 1 month, 18 hours to 1 month, 1 day to 1 month, 2 days to 1 month, 3 days to 1 month, 4 days to 1 month, 5 days to 1 month, 6 days to 1 month, 1 week to 1 month, 2 weeks to 1 month, 3 weeks to 1 month, 1 hour to 3 weeks, 5 hours to 3 weeks, 6 hours to 3 weeks, 10 hours to 3 weeks, 12 hours to 3 weeks, 15 hours to 3 weeks, 18 hours to 3 weeks, 1 day to 3 weeks, 2 days to 3 weeks, 3 days to 3 weeks, 4 days to 3 weeks, 5 days to 3 weeks, 6 days to 3 weeks, 1 week to 3 weeks, 2 weeks to 3 weeks, 1 hour to 2 weeks, 5 hours to 2 weeks, 6 hours to 2 weeks, 10 hours to 2 weeks, 12 hours to 2 weeks, 15 hours to 2 weeks, 18 hours to 2 weeks, 1 day to 2 weeks, 2 days to 2 weeks, 3 days to 2 weeks, 4 days to 2 weeks, 5 days to 2 weeks, 6 days to 2 weeks, 1 week to 2 weeks, 1 hour to 1 week, 5 hours to 1 week, 6 hours to 1 week, 10 hours to 1 week, 12 hours to 1 week, 15 hours to 1 week, 18 hours to 1 week, 1 day to 1 week, 2 days to 1 week, 3 days to 1 week, 4 days to 1 week, 5 days to 1 week, 6 days to 1 week, 1 hour to 6 days, 5 hours to 6 days, 6 hours to 6 days, 10 hours to 6 days, 12 hours to 6 days, 15 hours to 6 days, 18 hours to 6 days, 1 day to 6 days, 2 days to 6 days, 3 days to 6 days, 4 days to 6 days, 5 days to 6 days, 1 hour to 5 days, 5 hours to 5 days, 6 hours to 5 days, 10 hours to 5 days, 12 hours to 5 days, 15 hours to 5 days, 18 hours to 5 days, 1 day to 5 days, 2 days to 5 days, 3 days to 5 days, 4 days to 5 days, 1 hour to 4 days, 5 hours to 4 days, 6 hours to 4 days, 10 hours to 4 days, 12 hours to 4 days, 15 hours to 4 days, 18 hours to 4 days, 1 day to 4 days, 2 days to 4 days, 3 days to 4 days, 1 hour to 3 days, 5 hours to 3 days, 6 hours to 3 days, 10 hours to 3 days, 12 hours to 3 days, 15 hours to 3 days, 18 hours to 3 days, 1 day to 3 days, or 2 days to 3 days), contacting the cell with an anti-cancer agent or a pharmaceutically acceptable salt thereof. In some embodiments, the step of containing the cell with an anti-cancer agent kills the chemoresistant cancer cell. In certain embodiments, the anti-cancer agent is an anti-cancer agent, to which the cell was resistant. Alternatively, the step of contacting with an anti-cancer agent may take place concomitantly with the step of contacting with chaetocin, a chaetocin analogue, a Suv39H1/Suv39H2 inhibitor, or a pharmaceutically acceptable salt thereof.

In another aspect, the invention provides a method of treating a chemoresistant cancer in a subject by administering to the subject in need thereof a therapeutically effective amount of a compound selected from the group consisting of chaetocin, a chaetocin analogue, a Suv39H1/Suv39H2 inhibitor, and pharmaceutically acceptable salts thereof. The method may further include, after a period of at least 1 hour (e.g., at least 5 hours, at least 6 hours, at least 10 hours, at least 12 hours, at least 15 hours, at least 18 hours, at least 1 day, at least 2 days, at least 3 days, at least 4 days, at least 5 days, at least 6 days, at least 1 week, or at least 2 weeks; e.g., within 1 month, within 3 weeks, within 2 weeks, or within 1 week; e.g., 1 hour to 1 month, 5 hours to 1 month, 6 hours to 1 month, 10 hours to 1 month, 12 hours to 1 month, 15 hours to 1 month, 18 hours to 1 month, 1 day to 1 month, 2 days to 1 month, 3 days to 1 month, 4 days to 1 month, 5 days to 1 month, 6 days to 1 month, 1 week to 1 month, 2 weeks to 1 month, 3 weeks to 1 month, 1 hour to 3 weeks, 5 hours to 3 weeks, 6 hours to 3 weeks, 10 hours to 3 weeks, 12 hours to 3 weeks, 15 hours to 3 weeks, 18 hours to 3 weeks, 1 day to 3 weeks, 2 days to 3 weeks, 3 days to 3 weeks, 4 days to 3 weeks, 5 days to 3 weeks, 6 days to 3 weeks, 1 week to 3 weeks, 2 weeks to 3 weeks, 1 hour to 2 weeks, 5 hours to 2 weeks, 6 hours to 2 weeks, 10 hours to 2 weeks, 12 hours to 2 weeks, 15 hours to 2 weeks, 18 hours to 2 weeks, 1 day to 2 weeks, 2 days to 2 weeks, 3 days to 2 weeks, 4 days to 2 weeks, 5 days to 2 weeks, 6 days to 2 weeks, 1 week to 2 weeks, 1 hour to 1 week, 5 hours to 1 week, 6 hours to 1 week, 10 hours to 1 week, 12 hours to 1 week, 15 hours to 1 week, 18 hours to 1 week, 1 day to 1 week, 2 days to 1 week, 3 days to 1 week, 4 days to 1 week, 5 days to 1 week, 6 days to 1 week, 1 hour to 6 days, 5 hours to 6 days, 6 hours to 6 days, 10 hours to 6 days, 12 hours to 6 days, 15 hours to 6 days, 18 hours to 6 days, 1 day to 6 days, 2 days to 6 days, 3 days to 6 days, 4 days to 6 days, 5 days to 6 days, 1 hour to 5 days, 5 hours to 5 days, 6 hours to 5 days, 10 hours to 5 days, 12 hours to 5 days, 15 hours to 5 days, 18 hours to 5 days, 1 day to 5 days, 2 days to 5 days, 3 days to 5 days, 4 days to 5 days, 1 hour to 4 days, 5 hours to 4 days, 6 hours to 4 days, 10 hours to 4 days, 12 hours to 4 days, 15 hours to 4 days, 18 hours to 4 days, 1 day to 4 days, 2 days to 4 days, 3 days to 4 days, 1 hour to 3 days, 5 hours to 3 days, 6 hours to 3 days, 10 hours to 3 days, 12 hours to 3 days, 15 hours to 3 days, 18 hours to 3 days, 1 day to 3 days, or 2 days to 3 days), administering to the subject a therapeutically effective amount of an anti-cancer agent or a pharmaceutically acceptable salt thereof. In some embodiments, the step of administering an anti-cancer agent treats the chemoresistant cancer in the subject. In certain embodiments, the anti-cancer agent is an anti-cancer agent, to which the cell was resistant. Alternatively, the step of administering an anti-cancer agent may take place concomitantly with the step of administering chaetocin, a chaetocin analogue, a Suv39H1/Suv39H2 inhibitor, or a pharmaceutically acceptable salt thereof.

In some embodiments, the period is 5 hours to 2 weeks. In certain embodiments, the period is 5 hours to 1 week. In particular embodiments, the period is 5 hours to 6 days. In further embodiments, the period is 5 hours to 2 days. In yet further embodiments, the period is 5 to 15 hours. In still further embodiments, the period is 2 days to 2 weeks. In other embodiments, the period is 2 days to 1 week. In yet other embodiments, the period is 2 to 6 days. In still other embodiments, the compound is chaetocin or a pharmaceutically acceptable salt thereof. In some embodiments, the compound if a chaetocin analogue or a pharmaceutically acceptable salt thereof.

In yet another aspect, the invention provides a method of reversing chemoresistance of a chemoresistant cancer cell by contacting the chemoresistant cancer cell with an effective amount of a compound selected from the group consisting of a chaetocin analogue, a Suv39H1/Suv39H2 inhibitor, and pharmaceutically acceptable salts thereof.

In some embodiments, the chaetocin analogue is a compound of formula (I):

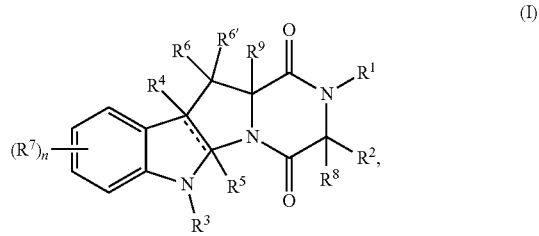

(I)

or a pharmaceutically acceptable salt thereof,
wherein
⫶ is a single or double bond, as valency requires;
each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur;

or two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur;

$R^1$ is R, —C(O)R, —C(O)N(R)$_2$, —S(O)R, —S(O)$_2$R, —S(O)$_2$OR, —C(R)$_2$OR, or —S(O)$_2$N(R)$_2$; and $R^2$ is R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$;

or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen or sulfur;

each q is independently 0, 1, 2, 3, or 4;

$R^3$ is an electron-withdrawing group;

$R^4$ is absent when ⫶ is a double bond, or $R^4$ is R or halogen;

$R^5$ is absent when ⫶ is a double bond, or $R^5$ is hydrogen or an optionally substituted $C_{1-6}$ aliphatic group;

n is 0, 1, 2, 3, or 4;

each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or $R^6$ and $R^{6'}$ are taken together to form =O, =C(R)$_2$, or =NR;

each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$;

or two $R^7$ are taken together with their intervening atoms to form an optionally substituted 4-7 membered ring having 0-2 heteroatoms independently selected from nitrogen, oxygen, or sulfur;

and $R^8$ is —(S)$_m$—$R^x$ wherein m is 1-3 and $R^x$ is R, —SR, —C(O)R, —C(O)OR, —C(O)N(R)$_2$, —C(S)R, —S(O)R, —S(O)$_2$R, or —S(O)$_2$N(R)$_2$; and $R^9$ is —(S)$_p$—$R^y$, wherein p is 1-3 such that m+p is 2-4, and $R^y$ is R, —SR, —C(O)R, —C(O)OR, —C(O)N(R)$_2$, —C(S)R, —S(O)R, —S(O)$_2$R, or —S(O)$_2$N(R)$_2$;

or $R^8$ and $R^9$ are taken together to form —S—, —(S)$_m$—[C(R)$_2$]$_q$(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—, wherein p is 1-3 such that m+p is 2-4.

In certain embodiments, $R^3$ is —SO$_2$R or —COCF$_3$. In particular embodiments, $R^3$ is —SO$_2$Ph. In further embodiments, $R^8$ and $R^9$ are taken together to form —S—, —(S)$_m$—(CH$_2$)—(S)$_p$—, —(S)$_m$—(S)$_p$—, —(S)$_m$—C(O)—(S)$_p$—, or —(S)$_m$—C(S)—(S)$_p$—. In yet further embodiments, each of $R^5$, $R^6$ and $R^{6'}$ is independently hydrogen. In still further embodiments, Ra and $R^9$ are taken together to form —S—S—.

In other embodiments, the chaetocin analogue is a compound of formula (II):

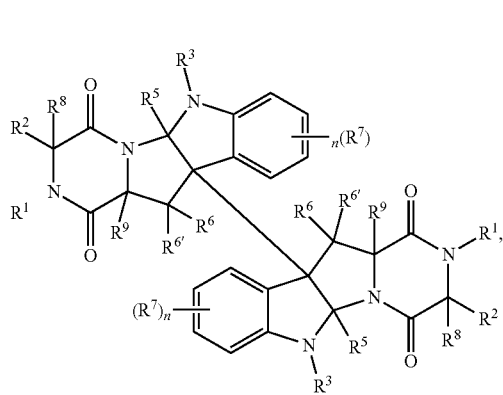

(II)

or a pharmaceutically acceptable salt thereof,
wherein
each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$;
each R is independently hydrogen or a group selected from C$_{1-20}$ aliphatic, C$_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur;
or
two R groups are optionally taken together with their intervening atoms to form a 3-14 membered, saturated, partially unsaturated, or aryl ring having, in addition to the intervening atoms, 0-4 heteroatoms independently selected from nitrogen, oxygen, or sulfur;
each $R_2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$;

each q is independently 0, 1, 2, 3, or 4;
each $R^3$ is hydrogen or an electron-withdrawing group;
each $R^5$ is independently hydrogen or a C$_{1-6}$ aliphatic group;
each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or
$R^6$ and $R^{6'}$ are taken together to form =O, =C(R)$_2$ or =NR;
each n is independently 0, 1, 2, 3, or 4;
each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$;
each $R^8$ is independently —(S)$_p$—$R^x$ wherein m is 1, 2, or 3, and $R^x$ is R, —SR, —C(O)R, —C(O)OR, —C(O)N(R)$_2$, —C(S)R, —S(O)R, —S(O)$_2$R, or —S(O)$_2$N(R)$_2$; and
each $R^9$ is independently —(S)$_p$—$R^y$ wherein p is 1, 2, or 3, such that the sum of m and p is 2, 3, or 4, and $R^y$ is R, —SR, —C(O)R, —C(O)OR, —C(O)N(R)$_2$, —C(S)R, —S(O)R, —S(O)$_2$R, or —S(O)$_2$N(R)$_2$; or
$R^8$ and $R^9$ are taken together to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—.

In yet other embodiments, $R^3$ is —SO$_2$R or —COCF$_3$. In still other embodiments, $R^3$ is —SO$_2$Ph. In some embodiments, $R^8$ and $R^9$ are taken together to form —S—, —(S)$_m$—(CH$_2$)—(S)$_p$—, —(S)$_m$ (S)$_p$—, —(S)$_m$—C(O)—(S)$_p$—, or —(S)$_m$—C(S)—(S)$_p$—. In certain embodiments, each of $R^5$, $R^6$, and $R^{6'}$ is independently hydrogen. In particular embodiments, $R^8$ and $R^9$ are taken together to form —S—S—.

In further embodiments, the chaetocin analogue is a compound of formula (III):

(III)

or a pharmaceutically acceptable salt thereof,
wherein
M is a cell-specific ligand unit;
each L is independently a linker unit;
each D independently has the structure of formula (IIIA) or (IIIB):

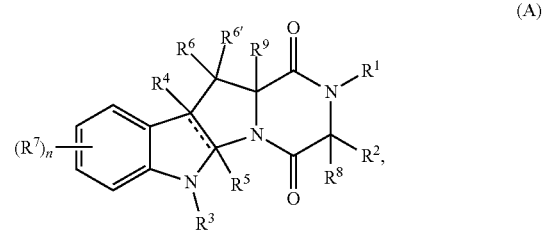

(A)

-continued (B)

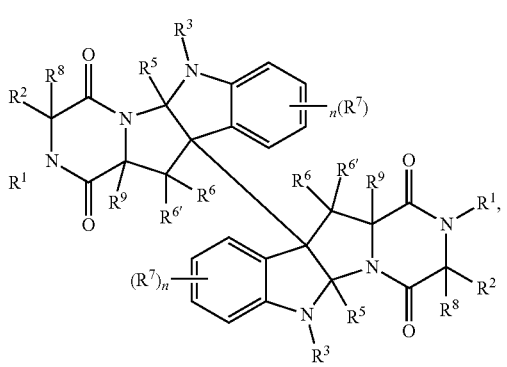

wherein
each |¦ is a single or double bond, as valency requires;
each R$^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$;
each R is independently hydrogen or an optionally substituted group selected from C$_{1\text{-}20}$ aliphatic, C$_{1\text{-}20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, and sulfur, a 3-7 membered saturated or partially unsaturated heterocyclic ring having 1-3 heteroatoms independently selected from nitrogen, oxygen, and sulfur, a 7-14 membered bicyclic or polycyclic saturated or partially unsaturated heterocyclic ring having 1-5 heteroatoms independently selected from nitrogen, oxygen, and sulfur, and an 8-14 membered bicyclic or polycyclic heteroaryl ring having 1-5 heteroatoms independently selected from nitrogen, oxygen, and sulfur; or
two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur;
each R$^2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$; or
R$^1$ and R$^2$ are taken together with their intervening atoms to form an optionally substituted 4-7 membered heterocyclic ring having, in addition to the nitrogen atom to which R$^1$ is attached, 0-2 heteroatoms independently selected from oxygen, nitrogen, and sulfur;
each q is independently 0, 1, 2, 3, or 4;
each R$^3$ is independently R or an electron-withdrawing group;
each R$^4$ is independently absent, when |¦ is a double bond, or is independently R or halogen;
each R$^5$ is independently absent, when |¦ is a double bond, or is independently hydrogen or an optionally substituted C$_{1\text{-}6}$ aliphatic group;
each of R$^6$ and R$^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or
R$^6$ and R$^{6'}$ are taken together to form =O, =C(R)$_2$, or =NR;
each n is independently 0, 1, 2, 3, or 4;
each R$^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$; or
two R$^7$ are taken together with their intervening atoms to form an optionally substituted 4-7 membered ring having 0-2 heteroatoms independently selected from nitrogen, oxygen, and sulfur;
each R$^8$ is independently —(S)$_m$—R$^x$ wherein m is 1, 2, or 3, and R$^x$ is R, —SR, —C(O)R, —C(O)OR, —C(O)N(R)$_2$, —C(S)R, —S(O)R, —S(O)$_2$R, or —S(O)$_2$N(R)$_2$;
each R$^9$ is independently —(S)$_p$—R$^y$ wherein p is 1, 2, or 3, such that the sum of m and p is 2, 3, or 4, and R$^y$ is R, —SR, —C(O)R, —C(O)OR, —C(O)N(R)$_2$, —C(S)R, —S(O)R, —S(O)$_2$R, or —S(O)$_2$N(R)$_2$; or
R$^8$ and R$^9$ are taken together to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—;
s is 1, 2, 3, 4, 5, 6, 7, 8, 9, or 10; and
t is 1, 2, 3, 4, 5, 6, 7, 8, 9, or 10;
provided that one of R$^1$, R$^2$, R$^3$, R$^4$, R$^5$, R$^6$, R$^{6'}$, R$^7$, R$^8$, and R$^9$ is substituted with a bond to L.

In further embodiments, the chaetocin analogue is a compound of formula (IIIA):

(IIIA)

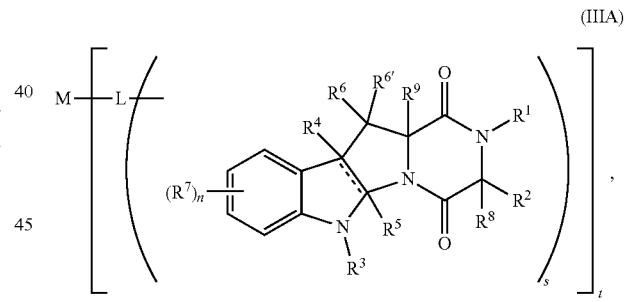

or a pharmaceutically acceptable salt thereof.

In yet further embodiments, the chaetocin analogue is a compound of formula (IIIB):

(IIIB)

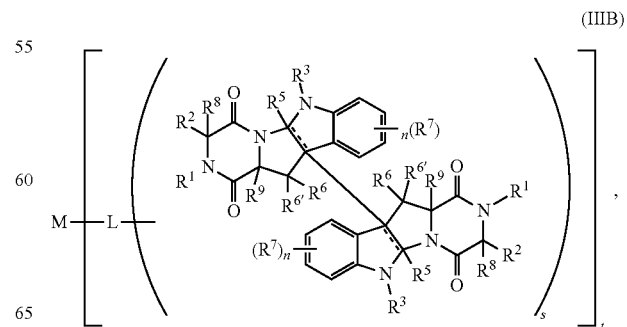

or a pharmaceutically acceptable salt thereof.

In still further embodiments, is 1. In other embodiments, L is self-immolative. In yet other embodiments, M is an antibody. In still other embodiments, $R^3$ is R. In some embodiments, $R^3$ is an electron-withdrawing group. In certain embodiments, $R^3$ is —S(O)$_2$R, —S(O)$_2$—[C(R)$_2$]$_q$—R, —S(O)$_2$—[C(R)$_2$]$_q$—B(OR)$_2$, —S(O)$_2$—[C(R)$_2$]$_q$—Si(R)$_3$, —S(O)$_2$OR, —S(O)$_2$N(R)$_2$, —S(O)R, —C(O)R, —C(O)OR, —C(O)N(R)$_2$, —C(O)N(R)—OR, —P(O)(R)$_2$, —P(O)(OR)$_2$, or —P(O)[N(R)$_2$]$_2$. In particular embodiments, $R^3$ is —SO$_2$R. In further embodiments, each $R^4$ is independently an optionally substituted group selected from phenyl, an 8-14 membered bicyclic or tricyclic aryl ring, a 5-6 membered monocyclic heteroaryl ring having 1-4 heteroatoms independently selected from nitrogen, oxygen, and sulfur, and an 8-14 membered bicyclic or tricyclic heteroaryl ring having 1-5 heteroatoms independently selected from nitrogen, oxygen, and sulfur.

In yet further embodiments, $R^8$ is —(S)$_m$—$R^x$, wherein m is 1, 2, or 3, and $R^x$ is —SR, —C(O)R, —C(O)OR, —C(O)N(R)$_2$, —C(S)R, —S(O)R, —S(O)$_2$R, or —S(O)$_2$N(R)$_2$; and $R^9$ is —(S)$_p$—$R^y$ wherein p is 1, 2, or 3, such that the sum of m and p is 2, 3, or 4, and $R^y$ is —SR, —C(O)R, —C(O)OR, —C(O)N(R)$_2$, —C(S)R, —S(O)R, —S(O)$_2$R, or —S(O)$_2$N(R)$_2$; or $R^8$ and $R^9$ are taken together to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—.

In still further embodiments, $R^8$ and $R^9$ are taken together to form —S—, —(S)$_m$—C(R)$_2$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—.

In other embodiments, $R^8$ is —(S)$_m$—$R^x$ wherein m is 1 and $R^x$ is —SR or —C(O)R; and $R^9$ is —(S)$_p$—$R^y$ wherein p is 1 and $R^y$ is —SR or —C(O)R. In yet other embodiments, $R^8$ and $R^9$ are taken together to form —(S)$_m$—(S)$_p$—, —S—C(O)—S—, or —S—C(S)—S—.

In still other embodiments, each ⫶ is independently a single bond;

each $R^4$ is independently R or halogen; and each $R^5$ is independently hydrogen or an optionally substituted $C_{1-6}$ aliphatic group.

In some embodiments, the chaetocin analogue is a compound selected from the group consisting of:

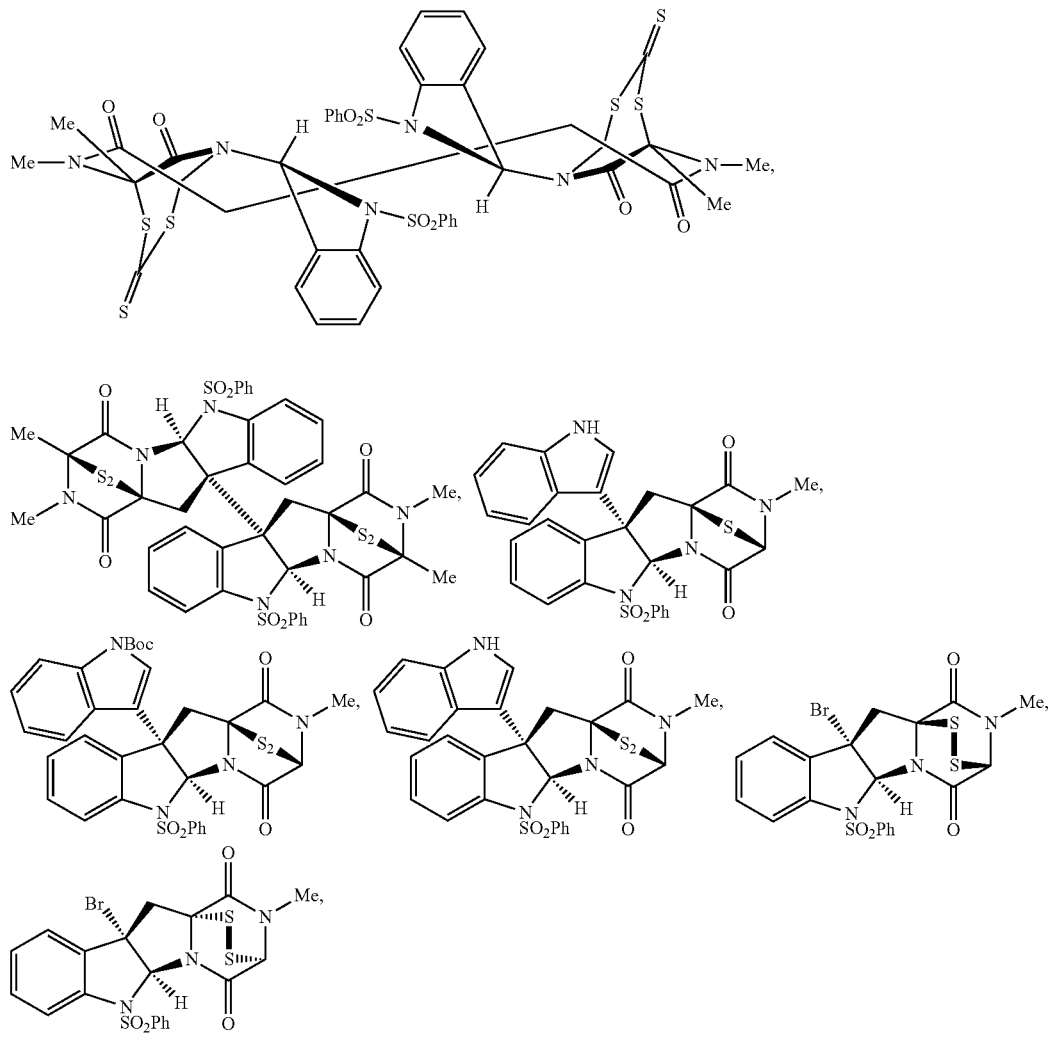

and pharmaceutically acceptable salt thereof.

In particular embodiments, the chemoresistant cancer has an epithelial-to-mesenchymal transition (EMT) pathway implicated. In certain embodiments, the chemoresistant cancer comprises a mesenchymal cancer cell. In further embodiments, the chemoresistant cancer is a chemoresistant glioblastoma, breast cancer, lung cancer, or blood cancer. In yet further embodiments, the chemoresistant cancer is a chemoresistant breast cancer, kidney cancer, or lung cancer.

In some embodiments, the invention is as described in the following enumerated items:

1. A method of killing a chemoresistant cancer cell, the method including (i) contacting the chemoresistant cancer cell with an effective amount of a compound selected from the group consisting of chaetocin, a chaetocin analogue, a Suv39H1/Suv39H2 inhibitor, and pharmaceutically acceptable salts thereof, and (ii) contacting the cell with an anti-cancer agent or a pharmaceutically acceptable salt thereof;
where the chemoresistant cancer cell is a chemoresistant mesenchymal cancer cell or a chemoresistant cancer cell expressing Suv39H1/Suv39H2; and
where step (ii) kills the chemoresistant cancer cell.

2. The method of item 1, where the chemoresistant cancer cell is a chemoresistant mesenchymal cancer cell.

3. The method of item 1 or 2, where the chemoresistant cancer cell is a chemoresistant cancer cell expressing Suv39H1/Suv39H2.

4. A method of treating a chemoresistant cancer in a subject, the method including (i) administering to the subject in need thereof a therapeutically effective amount of a compound selected from the group consisting of chaetocin, a chaetocin analogue, a Suv39H1/Suv39H2 inhibitor, and pharmaceutically acceptable salts thereof, and, (ii) administering to the subject a therapeutically effective amount of an anti-cancer agent or a pharmaceutically acceptable salt thereof;
where the chemoresistant cancer includes a chemoresistant mesenchymal cancer cell or a chemoresistant cancer cell expressing Suv39H1/Suv39H2; and
where step (ii) treats the chemoresistant cancer in the subject.

5. The method of item 4, where the chemoresistant cancer includes a chemoresistant mesenchymal cancer cell.

6. The method of item 4 or 5, where the chemoresistant cancer includes a chemoresistant cancer cell expressing Suv39H1/Suv39H2.

7. A method of killing a chemoresistant cancer cell, the method including (i) contacting the chemoresistant cancer cell with an effective amount of a compound selected from the group consisting of chaetocin, a chaetocin analogue, a Suv39H1/Suv39H2 inhibitor, and pharmaceutically acceptable salts thereof, and, (ii) after a period of at least 5 hours, contacting the cell with an anti-cancer agent or a pharmaceutically acceptable salt thereof;
where step (ii) kills the chemoresistant cancer cell.

8. The method of item 7, where the period is 5 hours to 2 weeks.

9. The method of item 8, where the period is 5 hours to 1 week.

10. The method of item 9, where the period is 5 hours to 6 days.

11. The method of item 10, where the period is 5 hours to 2 days.

12. The method of item 11, where the period is 5 to 15 hours.

13. The method of item 7, where the period is at least 15 hours.

14. A method of treating a chemoresistant cancer in a subject, the method including (i) administering to the subject in need thereof a therapeutically effective amount of a compound selected from the group consisting of chaetocin, a chaetocin analogue, a Suv39H1/Suv39H2 inhibitor, and pharmaceutically acceptable salts thereof, and, (ii) after a period of at least 2 days, administering to the subject a therapeutically effective amount of an anti-cancer agent or a pharmaceutically acceptable salt thereof;
where step (ii) treats the chemoresistant cancer in the subject.

15. The method of item 14, where the period is 2 days to 2 weeks.

16. The method of item 15, where the period is 2 days to 1 week.

17. The method of item 16, where the period is 2 to 6 days.

18. The method of any one of items 1 to 17, where the compound is chaetocin or a pharmaceutically acceptable salt thereof.

19. The method of any one of items 1 to 17, where the compound is a chaetocin analogue or a pharmaceutically acceptable salt thereof.

20. A method of reversing chemoresistance of a chemoresistant cancer cell, the method including contacting the chemoresistant cancer cell with an effective amount of a compound selected from the group consisting of chaetocin, a chaetocin analogue, a Suv39H1/Suv39H2 inhibitor, and pharmaceutically acceptable salts thereof.

21. The method of item 19 or 20, where the chaetocin analogue is a compound of formula (I):

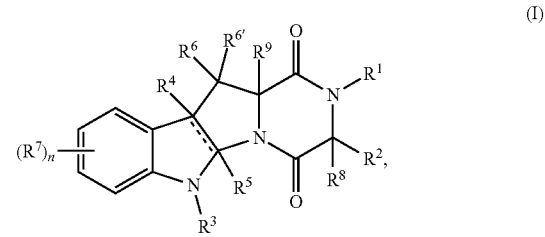

or a pharmaceutically acceptable salt thereof,
where
⋮ is a single or double bond, as valency requires;
each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur;
or
two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur;

R¹ is R, —C(O)R, —C(O)N(R)₂, —S(O)R, —S(O)₂R, —S(O)₂OR, —C(R)₂OR, or —S(O)₂N(R)₂; and R² is R, —[C(R)₂]$_q$—OR, —[C(R)₂]$_q$—N(R)₂, —[C(R)₂]$_q$—SR, —[C(R)₂]$_q$—OSi(R)₃, —[C(R)₂]$_q$—OC(O)R, —[C(R)₂]$_q$—OC(O)OR, —[C(R)₂]$_q$—OC(O)N(R)₂, —[C(R)₂]$_q$—OC(O)N(R)—SO₂R or —[C(R)₂]$_q$—OP(OR)₂;

or

R¹ and R² are taken together with their intervening atoms to form an optionally substituted 4-7 membered heterocyclic ring having, in addition to the nitrogen atom to which R¹ is attached, 0-2 heteroatoms independently selected from oxygen, nitrogen or sulfur;

each q is independently 0, 1, 2, 3, or 4;

R³ is an electron-withdrawing group;

R⁴ is absent when ⫴ is a double bond, or R⁴ is R or halogen;

R⁵ is absent when ⫴ is a double bond, or R⁵ is hydrogen or an optionally substituted $C_{1-6}$ aliphatic group;

n is 0, 1, 2, 3, or 4;

each of R⁶ and R⁶' is independently R, halogen, —CN, —NO₂, —OR, —SR, —N(R)₂, —S(O)₂R, —S(O)₂N(R)₂, —S(O)R, —C(O)R, —C(O)OR, —C(O)N(R)₂, —C(O)N(R)—OR, —N(R)C(O)OR, —N(R)C(O)N(R)₂, —N(R)S(O)₂R, or —OSi(R)₃; or R⁶ and R⁶' are taken together to form =O, =C(R)₂, or =NR;

each R⁷ is independently R, halogen, —CN, —NO₂, —OR, —OSi(R)₃, —SR, —N(R)₂, —S(O)₂R, —S(O)₂OR, —S(O)₂N(R)₂, —S(O)R, —C(O)R, —C(O)OR, —C(O)N(R)₂, —C(O)N(R)—OR, —N(R)C(O)OR, —N(R)C(O)N(R)₂, —N(R)S(O)₂R, —P(R)₂, —P(OR)₂, —P(O)(R)₂, —P(O)(OR)₂, —P(O)[N(R)₂]2, —B(R)₂, —B(OR)₂, or —Si(R)₃;

or two R⁷ are taken together with their intervening atoms to form an optionally substituted 4-7 membered ring having 0-2 heteroatoms independently selected from nitrogen, oxygen, or sulfur;

and

R⁸ is —(S)$_m$—R$^x$ where m is 1-3 and R$^x$ is R, —SR, —C(O)R, —C(O)OR, —C(O)N(R)₂, —C(S)R, —S(O)R, —S(O)₂R, or —S(O)₂N(R)₂; and R⁹ is —(S)$_p$—R$^y$, where p is 1-3 such that m+p is 2-4, and R$^y$ is R, —SR, —C(O)R, —C(O)OR, —C(O)N(R)₂, —C(S)R, —S(O)R, —S(O)₂R, or —S(O)₂N(R)₂;

or

R⁸ and R⁹ are taken together to form —S—, —(S)$_m$—[C(R)₂]$_q$(S)$_p$—, —(S)$_m$—(S)$_p$—, —(S)$_m$—C(O)(S)$_p$—, —(S)$_m$—C(S)—(S)$_p$—, —(S)$_m$—S(O)(S)$_p$—, or —(S)$_m$—S(O)₂—(S)$_p$—, where p is 1-3 such that m+p is 2-4.

22. The method of item 21, where R³ is —SO₂R or —COCF₃.

23. The method of item 22, where R³ is —SO₂Ph.

24. The method of any one of items 21 to 23, where R⁸ and R⁹ are taken together to form —S—, —(S)$_m$—(CH₂)—(S)$_p$—, —(S)$_m$—(S)$_p$—, —(S)$_m$—C(O)—(S)$_p$—, or —(S)$_m$—C(S)—(S)$_p$—.

25. The method of any one of items 21 to 24, where each of R⁵, R⁶ and R⁶' is independently hydrogen.

26. The method of any one of items 21 to 25, where R⁸ and R⁹ are taken together to form —S—S—.

27. The method of item 19 or 20, where the chaetocin analogue is a compound of formula

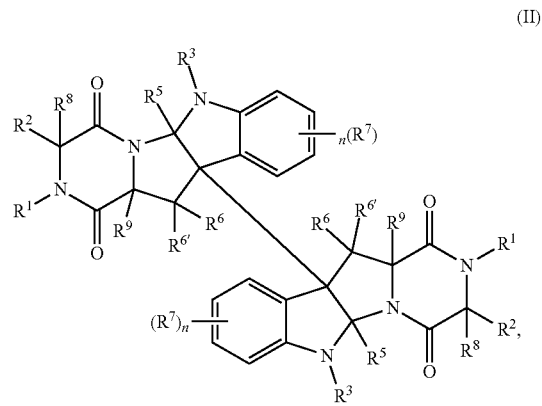

(II)

or a pharmaceutically acceptable salt thereof, where each R¹ is independently R, —C(O)R, —C(O)N(R)₂, —S(O)R, —S(O)₂R, —S(O)₂OR, —C(R)₂OR, or —S(O)₂N(R)₂;

each R is independently hydrogen or a group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur;

or two R groups are optionally taken together with their intervening atoms to form a 3-14 membered, saturated, partially unsaturated, or aryl ring having, in addition to the intervening atoms, 0-4 heteroatoms independently selected from nitrogen, oxygen, or sulfur;

each R₂ is independently R, —[C(R)₂]$_q$—OR, —[C(R)₂]$_q$—N(R)₂, —[C(R)₂]$_q$—SR, —[C(R)₂]$_q$—OSi(R)₃, —[C(R)₂]$_q$—OC(O)R, —[C(R)₂]$_q$—OC(O)OR, —[C(R)₂]$_q$—OC(O)N(R)₂, —[C(R)₂]$_q$—OC(O)N(R)—SO₂R or —[C(R)₂]$_q$—OP(OR)₂;

each q is independently 0, 1, 2, 3, or 4;

each R³ is hydrogen or an electron-withdrawing group;

each R⁵ is independently hydrogen or a $C_{1-6}$ aliphatic group;

each of R⁶ and R⁶' is independently R, halogen, —CN, —NO₂, —OR, —SR, —N(R)₂, —S(O)₂R, —S(O)₂N(R)₂, —S(O)R, —C(O)R, —C(O)OR, —C(O)N(R)₂, —C(O)N(R)—OR, —N(R)C(O)OR, —N(R)C(O)N(R)₂, —N(R)S(O)₂R, or —OSi(R)₃; or R⁶ and R⁶' are taken together to form =O, =C(R)₂ or =NR;

each n is independently 0, 1, 2, 3, or 4;

each R⁷ is independently R, halogen, —CN, —NO₂, —OR, —OSi(R)₃, —SR, —N(R)₂, —S(O)₂R, —S(O)₂OR, —S(O)₂N(R)₂, —S(O)R, —C(O)R, —C(O)OR, —C(O)N(R)₂, —C(O)N(R)—OR, —N(R)C(O)OR, —N(R)C(O)N(R)₂, —N(R)S(O)₂R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$;

each R$^8$ is independently —(S)$_p$—R$^x$ where m is 1, 2, or 3, and R$^x$ is R, —SR, —C(O)R, —C(O)OR, —C(O)N(R)$_2$, —C(S)R, —S(O)R, —S(O)$_2$R, or —S(O)$_2$N(R)$_2$; and each R$^9$ is independently —(S)$_p$—R$^y$ where p is 1, 2, or 3, such that the sum of m and p is 2, 3, or 4, and R is R, —SR, —C(O)R, —C(O)OR, —C(O)N(R)$_2$, —C(S)R, —S(O)R, —S(O)$_2$R, or —S(O)$_2$N(R)$_2$; or R$^8$ and R$^9$ are taken together to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—.

28. The method of item 27, where R$^3$ is —SO$_2$R or —COCF$_3$.

29. The method of item 28, where R$^3$ is —SO$_2$Ph.

30. The method of any one of items 27 to 29, where R$^8$ and R$^9$ are taken together to form —S—, —(S)$_m$—(CH$_2$)—(S)$_p$—, —(S)$_m$—(S)$_p$—, —(S)$_m$—C(O)—(S)$_p$—, or —(S)$_m$—C(S)—(S)$_p$—.

31. The method of any one of items 27 to 30, where each of R$^5$, R$^6$, and R$^{6'}$ is independently hydrogen.

32. The method of any one of items 27 to 31, where R$^8$ and R$^9$ are taken together to form —S—S—.

33. The method of item 19 or 20, where the chaetocin analogue is a compound of formula (III):

or a pharmaceutically acceptable salt thereof,
where
M is a cell-specific ligand unit;
each L is independently a linker unit;
each D independently has the structure of formula (IIIA) or (IIIB):

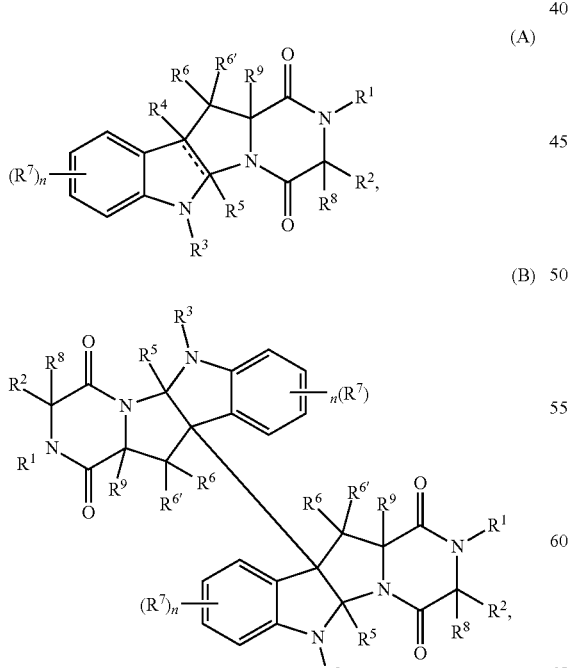

where each ⫶ is a single or double bond, as valency requires;

each R$^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$;

each R is independently hydrogen or an optionally substituted group selected from C$_{1-20}$ aliphatic, C$_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, and sulfur, a 3-7 membered saturated or partially unsaturated heterocyclic ring having 1-3 heteroatoms independently selected from nitrogen, oxygen, and sulfur, a 7-14 membered bicyclic or polycyclic saturated or partially unsaturated heterocyclic ring having 1-5 heteroatoms independently selected from nitrogen, oxygen, and sulfur, and an 8-14 membered bicyclic or polycyclic heteroaryl ring having 1-5 heteroatoms independently selected from nitrogen, oxygen, and sulfur; or two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur;

each R$^2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$; or R$^1$ and R$^2$ are taken together with their intervening atoms to form an optionally substituted 4-7 membered heterocyclic ring having, in addition to the nitrogen atom to which R$^1$ is attached, 0-2 heteroatoms independently selected from oxygen, nitrogen, and sulfur;

each q is independently 0, 1, 2, 3, or 4;

each R$^3$ is independently R or an electron-withdrawing group;

each R$^4$ is independently absent, when ⫶ is a double bond, or is independently R or halogen;

each R$^5$ is independently absent, when ⫶ is a double bond, or is independently hydrogen or an optionally substituted C$_{1-6}$ aliphatic group;

each of R$^6$ and R$^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or R$^6$ and R$^{6'}$ are taken together to form =O, =C(R)$_2$, or =NR;

each n is independently 0, 1, 2, 3, or 4;

each R$^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$; or two $R^7$ are taken together with their intervening atoms to form an optionally substituted 4-7 membered ring having 0-2 heteroatoms independently selected from nitrogen, oxygen, and sulfur;

each $R^8$ is independently $-(S)_m-R^x$ where m is 1, 2, or 3, and $R^x$ is R, —SR, —C(O)R, —C(O)OR, —C(O)N$(R)_2$, —C(S)R, —S(O)R, —S(O)$_2$R, or —S(O)$_2$N$(R)_2$;

each $R^9$ is independently $-(S)_p-R^y$ where p is 1, 2, or 3, such that the sum of m and p is 2, 3, or 4, and R is R, —SR, —C(O)R, —C(O)OR, —C(O)N$(R)_2$, —C(S)R, —S(O)R, —S(O)$_2$R, or —S(O)$_2$N$(R)_2$; or $R^8$ and $R^9$ are taken together to form —S—, $-(S)_m-[C(R)_2]_q-(S)_p-$, $-(S)_m-(S)_p-$, $-(S)_m-C(O)-(S)_p-$, $-(S)_m-C(S)-(S)_p-$, $-(S)_m-S(O)-(S)_p-$, or $-(S)_m-S(O)_2-(S)_p-$;

s is 1, 2, 3, 4, 5, 6, 7, 8, 9, or 10; and t is 1, 2, 3, 4, 5, 6, 7, 8, 9, or 10;

provided that one of $R^1$, $R^2$, $R^3$, $R^4$, $R^5$, $R^6$, $R^{6'}$, $R^7$, $R^8$, and $R^9$ is substituted with a bond to L.

34. The method of item 33, where the chaetocin analogue is a compound of formula (IIIA):

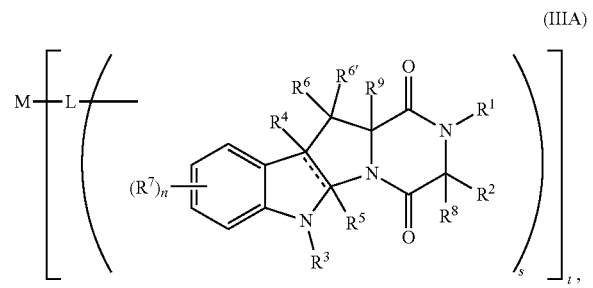

(IIIA)

or a pharmaceutically acceptable salt thereof.

35. The method of item 33, where the chaetocin analogue is a compound of formula (IIIB):

36. The method of any one of items 33 to 35, where s is 1.

37. The method of any one of items 33 to 36, where L is self-immolative.

38. The method of any one of items 33 to 37, where M is an antibody.

39. The method of any one of items 33 to 38, where $R^3$ is R.

40. The method of any one of items 33 to 38, where $R^3$ is an electron-withdrawing group.

41. The method of any one of items 33 to 38, where $R^3$ is —S(O)$_2$R, —S(O)$_2$—[C(R)$_2$]$_q$—R, —S(O)$_2$—[C(R)$_2$]$_q$—B(OR)$_2$, —S(O)$_2$—[C(R)$_2$]$_q$—Si(R)$_3$, —S(O)$_2$OR, —S(O)$_2$N$(R)_2$, —S(O)R, —C(O)R, —C(O)OR, —C(O)N$(R)_2$, —C(O)N(R)—OR, —P(O)$(R)_2$, —P(O)(OR)$_2$, or —P(O)[N$(R)_2$]$_2$.

42. The method of any one of items 33 to 38, where $R^3$ is —SO$_2$R.

43. The method of any one of items 33 to 42, where each $R^4$ is independently an optionally substituted group selected from phenyl, an 8-14 membered bicyclic or tricyclic aryl ring, a 5-6 membered monocyclic heteroaryl ring having 1-4 heteroatoms independently selected from nitrogen, oxygen, and sulfur, and an 8-14 membered bicyclic or tricyclic heteroaryl ring having 1-5 heteroatoms independently selected from nitrogen, oxygen, and sulfur.

44. The method of any one of items 33 to 43, where $R^8$ is $-(S)_m-R^x$, where m is 1, 2, or 3, and $R^x$ is —SR, —C(O)R, —C(O)OR, —C(O)N$(R)_2$, —C(S)R, —S(O)R, —S(O)$_2$R, or —S(O)$_2$N$(R)_2$; and $R^9$ is $-(S)_p-R$ where p is 1, 2, or 3, such that the sum of m and p is 2, 3, or 4, and $R^y$ is —SR, —C(O)R, —C(O)OR, —C(O)N$(R)_2$, —C(S)R, —S(O)R, —S(O)$_2$R, or —S(O)$_2$N$(R)_2$; or $R^8$ and $R^9$ are taken together to form —S—, $-(S)_m-[C(R)_2]_q-(S)_p-$, $-(S)_m-(S)_p-$, $-(S)_m-C(O)-(S)_p-$, $-(S)_m-C(S)-(S)_p-$, $-(S)_m-S(O)-(S)_p-$, or $-(S)_m-S(O)_2-(S)_p-$.

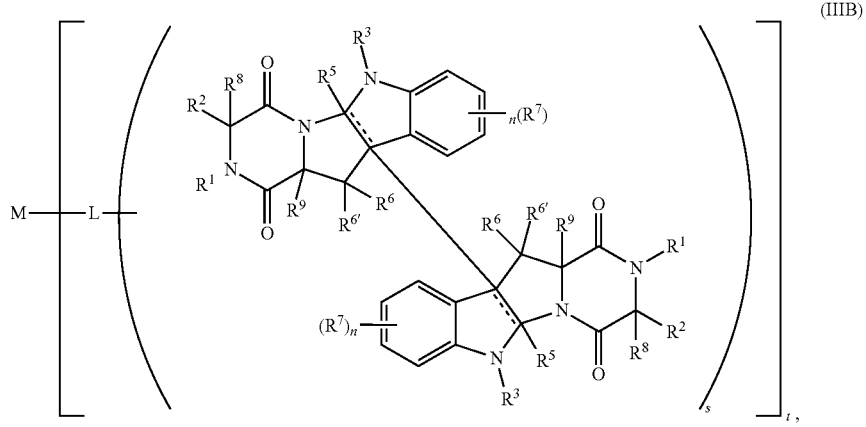

(IIIB)

or a pharmaceutically acceptable salt thereof.

45. The method of any one of items 33 to 43, where $R^8$ and $R^9$ are taken together to form —S—, —$(S)_m$—$C(R)_2$—$(S)_p$—, —$(S)_m$—$(S)_p$—, —$(S)_m$—C(O)—$(S)_p$—, —$(S)_m$—C(S)—$(S)_p$—, —$(S)_m$—S(O)—$(S)_p$—, or —$(S)_m$—$S(O)_2$—$(S)_p$—.

46. The method of any one of items 33 to 43, where:
$R^8$ is —$(S)_m$—$R^x$ where m is 1 and $R^x$ is —SR or —C(O)R; and
$R^9$ is —$(S)_p$—$R^y$ where p is 1 and $R^y$ is —SR or —C(O)R.

47. The method of any one of items 33 to 43, where $R^8$ and $R^9$ are taken together to form —$(S)_m$—$(S)_p$—, —S—C(O)—S—, or —S—C(S)—S—.

48. The method of any one of items 33 to 47, where:
each ┆ is independently a single bond;
each $R^4$ is independently R or halogen; and
each $R^5$ is independently hydrogen or an optionally substituted $C_{1-5}$ aliphatic group.

49. The method of item 19 or 20, where the chaetocin analogue is a compound selected from the group consisting of:

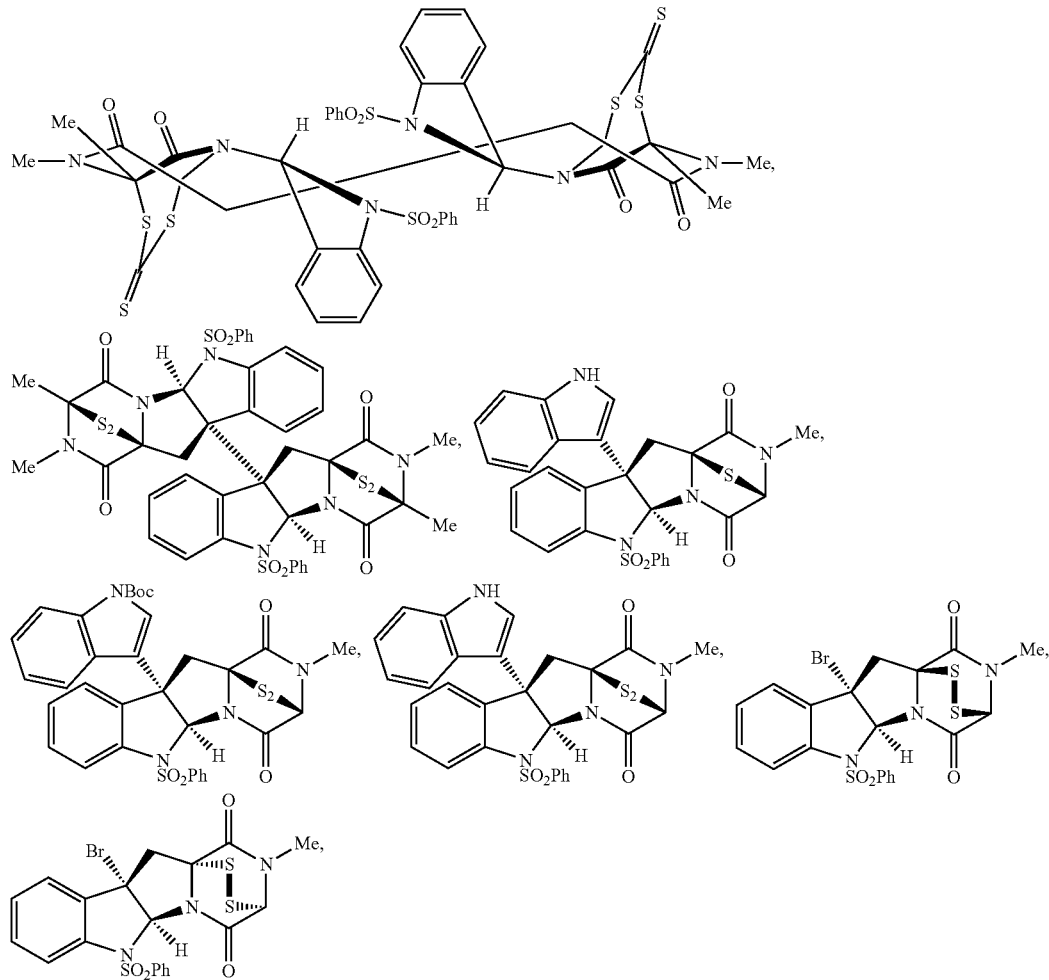

and pharmaceutically acceptable salt thereof.

50. The method of any one of items 1 to 49, where the chemoresistant cancer has an epithelial-to-mesenchymal transition (EMT) pathway implicated.

51. The method of any one of items 1 to 50, where the chemoresistant cancer includes a mesenchymal cancer cell.

52. The method of any one of items 1 to 51, where the chemoresistant cancer is a chemoresistant glioblastoma, breast cancer, lung cancer, or blood cancer.

53. The method of item 52, where the chemoresistant cancer is a chemoresistant breast cancer, kidney cancer, or lung cancer.

Definitions

By "administration event" is meant an instance in which a chemoresistant cancer cell or a subject having a chemoresistant cancer is administered an effective amount of a therapeutically active compound. For example, an administration event may be an administration event for chaetocin, a chaetocin analogue, a Suv39H1/Suv39H2 inhibitor, or a pharmaceutically acceptable salt thereof. An administration event for chaetocin, a chaetocin analogue, a Suv39H1/Suv39H2 inhibitor, or a pharmaceutically acceptable salt thereof is prior to the administration event for an anti-cancer agent or a pharmaceutically acceptable salt thereof. Administration of chaetocin, a chaetocin analogue, a Suv39H1/Suv39H2 inhibitor, or a pharmaceutically acceptable salt may occur once prior to one or more (e.g., 1, 2, 3, 4, 5, or more) instances of administration of an anti-cancer agent. Alternatively, administration of chaetocin, a chaetocin analogue, a Suv39H1/Suv39H2 inhibitor, or a pharmaceutically acceptable salt thereof may occur prior to each of one or more (e.g., 1, 2, 3, 4, 5, or more) instances of administration of an anti-cancer agent. The administration of an anti-cancer agent to a chemoresistant cancer cell may follow the administration of chaetocin, a chaetocin analogue, a Suv39H1/Suv39H2 inhibitor, or a pharmaceutically acceptable salt thereof after a period of, for example, 5 hours to 2 weeks, 5 hours to 1 week, 5 hours to 6 days, 5 hours to 2 days, or 5 hours to 15 hours. The administration of an anti-cancer agent to a subject having a chemoresistant cancer may follow the administration of chaetocin, a chaetocin analogue, a Suv39H1/Suv39H2 inhibitor, or a pharmaceutically acceptable salt thereof after a period of, for example, 2 days to 2 weeks, 2 days to 1 week, or 2 days to 6 days.

By "aliphatic" or "aliphatic group" is meant a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or polycyclic hydrocarbon that is completely saturated or that contains one or more units of unsaturation, but which is not aromatic (also referred to herein as "carbocycle," "cycloaliphatic" or "cycloalkyl"), that has, unless otherwise specified, a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

By "alkenyl" is meant an alkyl group, as defined herein, having one or more double bonds.

By "alkyl" is meant an acyclic straight or branched chain saturated hydrocarbon group, which, when unsubstituted, has from 1 to 12 carbons, unless otherwise specified. In certain preferred embodiments, unsubstituted alkyl has from 1 to 6 carbons. Alkyl groups are exemplified by methyl; ethyl; n- and iso-propyl; n-, sec-, iso- and tert-butyl; neopentyl, and the like.

By "alkynyl" is meant an alkyl group, as defined herein, having one or more triple bonds.

By "aryl," as used alone or as part of a larger moiety as in "aralkyl," "aralkoxy," or "aryloxyalkyl," are meant monocyclic, bicyclic or polycyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

By "chaetocin" is meant a compound of the following structure:

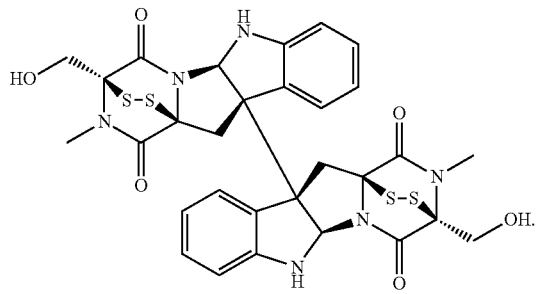 [SMILES: CN1C(=O)[C@@]23C[C@]4([C@]56C[C@@]78SS[C@](CO)(C(=O)N7[C@H]5Nc5ccccc56)N(C)C8=O)c5ccccc5N[C@@H]4N2C(=O)[C@@]1(CO)SS3]

By "chaetocin analogue" is meant a compound of formula (I), (II), or (III). The compound of formula (I) is of the following structure:

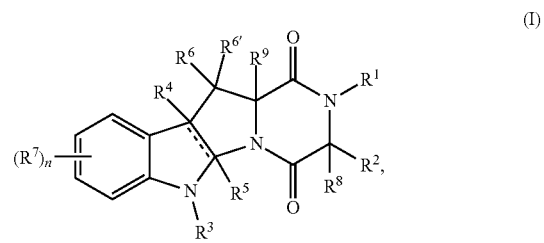

where
⫶ is a single or double bond, as valency requires;
each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur;
or
two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur;
$R^1$ is R, —C(O)R, —C(O)N(R)$_2$, —S(O)R, —S(O)$_2$R, —S(O)$_2$OR, —C(R)$_2$OR, or —S(O)$_2$N(R)$_2$; and $R^2$ is R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$;
or
$R^1$ and $R^2$ are taken together with their intervening atoms to form an optionally substituted 4-7 membered heterocyclic ring having, in addition to the nitrogen atom to which R$^1$ is attached, 0-2 heteroatoms independently selected from oxygen, nitrogen or sulfur;

each q is independently 0, 1, 2, 3, or 4;

R$^3$ is an electron-withdrawing group;

R$^4$ is absent when $|\vdots|$ is a double bond, or R$^4$ is R or halogen;

R$^5$ is absent when $|\vdots|$ is a double bond, or R$^5$ is hydrogen or an optionally substituted C$_{1-6}$ aliphatic group;

n is 0, 1, 2, 3, or 4;

each of R$^6$ and R$^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or R$^6$ and R$^{6'}$ are taken together to form =O, =C(R)$_2$, or =NR;

each R$^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]2, —B(R)$_2$, —B(OR)$_2$, or —Si(R)$_3$;

or two R$^7$ are taken together with their intervening atoms to form an optionally substituted 4-7 membered ring having 0-2 heteroatoms independently selected from nitrogen, oxygen, or sulfur;

and

R$^8$ is —(S)$_m$—R$^x$ wherein m is 1-3 and R$^x$ is R, —SR, —C(O)R, —C(O)OR, —C(O)N(R)$_2$, —C(S)R, —S(O)R, —S(O)$_2$R, or —S(O)$_2$N(R)$_2$; and R$^9$ is —(S)$_p$—R$^y$, wherein p is 1-3 such that m+p is 2-4, and R$^y$ is R, —SR, —C(O)R, —C(O)OR, —C(O)N(R)$_2$, —C(S)R, —S(O)R, —S(O)$_2$R, or —S(O)$_2$N(R)$_2$;

or

R$^8$ and R$^9$ are taken together to form —S—, —(S)$_m$—[C(R)$_2$]$_q$(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—, wherein p is 1-3 such that m+p is 2-4.

The compound of formula (I) may be referred to as a monomeric analogue of chaetocin.

The compound of formula (II) is of the following structure:

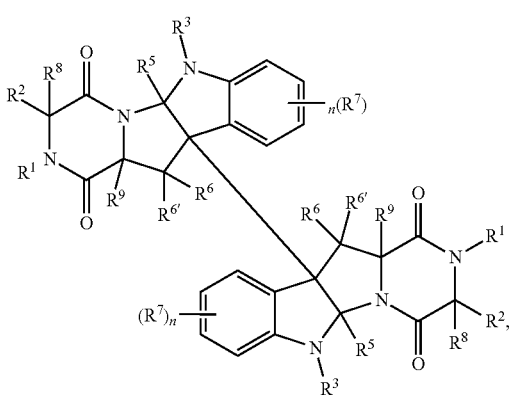

(II)

where each R$^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$;

each R is independently hydrogen or a group selected from C$_{1-20}$ aliphatic, C$_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur;

or two R groups are optionally taken together with their intervening atoms to form a 3-14 membered, saturated, partially unsaturated, or aryl ring having, in addition to the intervening atoms, 0-4 heteroatoms independently selected from nitrogen, oxygen, or sulfur;

each R$_2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$;

each q is independently 0, 1, 2, 3, or 4;

each R$^3$ is hydrogen or an electron-withdrawing group;

each R$^5$ is independently hydrogen or a C$_{1-6}$ aliphatic group;

each of R$^6$ and R$^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or R$^6$ and R$^{6'}$ are taken together to form =O, =C(R)$_2$ or =NR;

each n is independently 0, 1, 2, 3, or 4;

each R$^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$;

each R$^8$ is independently —(S)$_p$—R$^x$ wherein m is 1, 2, or 3, and R$^x$ is R, —SR, —C(O)R, —C(O)OR, —C(O)N(R)$_2$, —C(S)R, —S(O)R, —S(O)$_2$R, or —S(O)$_2$N(R)$_2$; and each R$^9$ is independently —(S)$_p$—R$^y$ wherein p is 1, 2, or 3, such that the sum of m and p is 2, 3, or 4, and R$^y$ is R, —SR, —C(O)R, —C(O)OR, —C(O)N(R)$_2$, —C(S)R, —S(O)R, —S(O)$_2$R, or —S(O)$_2$N(R)$_2$; or R$^8$ and R$^9$ are taken together to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—.

The compound of formula (II) may be referred to as a dimeric analogue of chaetocin.

The compound of formula (III) is of the following structure:

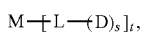

(III)

where
M is a cell-specific ligand unit;
each L is independently a linker unit;
each D independently has the structure of formula (IIIA) or (IIIB):

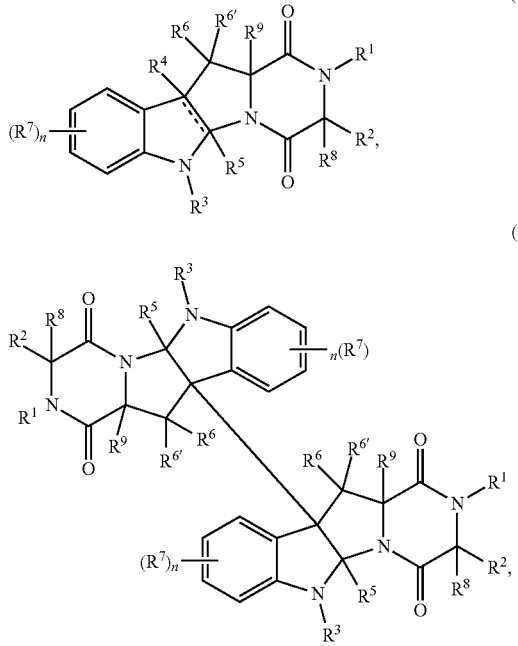

where
each $|\!|$ is a single or double bond, as valency requires;
each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$;
each R is independently hydrogen or an optionally substituted group selected from C$_{1-20}$ aliphatic, C$_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, and sulfur, a 3-7 membered saturated or partially unsaturated heterocyclic ring having 1-3 heteroatoms independently selected from nitrogen, oxygen, and sulfur, a 7-14 membered bicyclic or polycyclic saturated or partially unsaturated heterocyclic ring having 1-5 heteroatoms independently selected from nitrogen, oxygen, and sulfur, and an 8-14 membered bicyclic or polycyclic heteroaryl ring having 1-5 heteroatoms independently selected from nitrogen, oxygen, and sulfur; or
two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, and sulfur;
each $R^2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$; or
$R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen, and sulfur;
each q is independently 0, 1, 2, 3, or 4;
each $R^3$ is independently R or an electron-withdrawing group;
each $R^4$ is independently absent, when $|\!|$ is a double bond, or is independently R or halogen;
each $R^5$ is independently absent, when $|\!|$ is a double bond, or is independently hydrogen or an optionally substituted C$_{1-6}$ aliphatic group;
each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or
$R^6$ and $R^{6'}$ are taken together to form =O, =C(R)$_2$, or =NR;
each n is independently 0, 1, 2, 3, or 4;
each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$; or
two $R^7$ are taken together with their intervening atoms to form an optionally substituted 4-7 membered ring having 0-2 heteroatoms independently selected from nitrogen, oxygen, and sulfur;
each $R^8$ is independently —(S)$_m$—R$^x$ wherein m is 1, 2, or 3, and R$^x$ is R, —SR, —C(O)R, —C(O)OR, —C(O)N(R)$_2$, —C(S)R, —S(O)R, —S(O)$_2$R, or —S(O)$_2$N(R)$_2$;
each $R^9$ is independently —(S)$_p$—R$^y$ wherein p is 1, 2, or 3, such that the sum of m and p is 2, 3, or 4, and R$^y$ is R, —SR, —C(O)R, —C(O)OR, —C(O)N(R)$_2$, —C(S)R, —S(O)R, —S(O)$_2$R, or —S(O)$_2$N(R)$_2$; or
$R^8$ and $R^9$ are taken together to form —S—, —(S)$_m$—[C(R)$_2$]$_q$—(S)$_p$—, —(S)$_m$—(S)$_p$—, —(S)$_m$—C(O)—(S)$_p$—, —(S)$_p$—, —(S)$_m$—C(S)—(S)$_p$—, —(S)$_m$—S(O)—(S)$_p$—, or —(S)$_m$—S(O)$_2$—(S)$_p$—;
s is 1, 2, 3, 4, 5, 6, 7, 8, 9, or 10; and
t is 1, 2, 3, 4, 5, 6, 7, 8, 9, or 10;
provided that one of $R^1$, $R^2$, $R^3$, $R^4$, $R^5$, $R^6$, $R^{6'}$, $R^7$, $R^8$, and $R^9$ is substituted with a bond to L.

By "chemoresistant" is meant a cancer cell, a cancer, or a cancerous tumor that fails to respond to treatment by conventional anti-cancer agents. Chemoresistance may be characterized by recurrence or continuation of cancer growth following a treatment regimen with anti-cancer agents. Chemoresistant cancer cells, cancers, or cancerous tumors may be chemoresistant as a result of, for example, an alteration in cellular transcriptional programs that control cell metabolism, resistance to stress, epithelial-to-mesenchymal transition, cell cycle regulation, among others.

By "$C_{x-y}$" is meant that the group, the name of which immediately follows the expression, when unsubstituted, contains a total of from x to y carbon atoms. If the group is a composite group (e.g., aryl alkyl), $C_{x-y}$ indicates that the portion, the name of which immediately follows the expression, when unsubstituted, contains a total of from x to y carbon atoms.

By "cycloaliphatic" is meant saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic C3-C6 hydrocarbon, or a C8-C10 bicyclic hydrocarbon that is completely saturated or that contains one or more units of unsaturation, but which is not aromatic, that has a single point of attachment to the rest of the molecule, or a C9-C16 tricyclic hydrocarbon that is completely saturated or that contains one or more units of unsaturation, but which is not aromatic, that has a single point of attachment to the rest of the molecule.

"Electron-withdrawing group" is given its ordinary meaning in the art and refers to an atom or group that draws electron density from a neighboring atom or group, usually by resonance and/or inductive effects. In some embodiments, an electron-withdrawing group withdraws electron density from an aromatic ring system by resonance and/or inductive effects. In some embodiments, an electron-withdrawing group withdraws electron density from an aromatic ring system by resonance and inductive effects. In some embodiments, an electron-withdrawing group lowers the electron density of an aromatic ring system such as phenyl. Exemplary electron-withdrawing groups are extensively described in the art, including but not limited to halogen, carbonyl moieties (e.g., aldehyde and ketone groups), —COOH and its derivatives (e.g., ester and amide moieties), protonated amines, quaternary ammonium groups, —CN, —NO2, —S(O)— moieties, —P(O)— moieties and —S(O)2-moieties. In some embodiments, an electron-withdrawing group comprises one or more —C(O)—, —C(=N—)—, —C(S)—, —S(O)—, —S(O)2- or —P(O)— groups, and is connected to the rest of a molecule via one or more —C(O)—, —C(=N—)—, —C(S)—, —S(O)—, —S(O)2- or —P(O)— groups. In some embodiments, an electron-withdrawing group is halogen. In some embodiments, an electron-withdrawing group is —F. In some embodiments, an electron-withdrawing group is —Cl. In some embodiments, an electron-withdrawing group is —Br. In some embodiments, an electron-withdrawing group is —I. In some embodiments, hydrogen is used as reference and regarded as having no effect.

By a "cell expressing Suv39H1/Suv39H2" is meant a chemoresistant cancer cell having the Suv39H1 and/or Suv39H2 expression levels greater than the Suv39H1 and/or Suv39H2 expression levels in the corresponding chemotherapy-sensitive cell.

By "halo" is meant a halogen selected from bromine, chlorine, iodine, and fluorine.

By "heteroalkyl" is meant an alkyl group, in which at least one carbon atom, optionally with one or more attached hydrogen atoms, is replaced with a heteroatom (e.g., oxygen, nitrogen, sulfur, phosphorus, selenium, boron and the like). Examples of heteroalkyl groups include, but are not limited to, alkoxy, poly(ethylene glycol)-, alkyl-substituted amino, tetrahydrofuranyl, piperidinyl, morpholinyl, etc. In some embodiments, a heteroatom may be oxidized (e.g., —S(O)—, —S(O)2-, —N(O)—, —P(O)— and the like).

By "heteroaryl" and "heteroar-" used alone or as part of a larger moiety, e.g., "heteroaralkyl," or "heteroaralkoxy," are meant groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

By "heterocycle," "heterocyclyl," "heterocyclic radical," and "heterocyclic ring" are meant stable 5- to 7-membered monocyclic or 7-10-membered bicyclic heterocyclic moieties that are either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

By "hydroxyl" and "hydroxy," as used interchangeably herein, is meant —OH.

By "killing a chemoresistant cancer cell" is meant the process of causing a cell death (e.g., apoptotic or necrotic death) of a chemoresistant cancer cell. For example, the cell death may be caused by contacting a chemoresistant cancer cell with a compound or a combination of compounds that result in the cell death after the treatment. The cell death may occur after the cell is contacted with the compound or a combination of compounds disclosed herein, or after the cell is first contacted with chaetocin, a chaetocin analogue, or a Suv39H1/Suv39H2 inhibitor and further contacted within at least 5 hours (e.g., 5 hours to 2 weeks, 5 hours to 1 week, 5 hours to 6 days, 5 hours to 2 days, or 5 hours to 15 hours) with an anti-cancer agent to which the cell had been resistant. A non-limiting example of killing a chemoresistant cancer cell includes first contacting a chemoresistant cancer cell with chaetocin, a chaetocin analogue, a Suv39H1/Suv39H2 inhibitor, or a pharmaceutically acceptable salt thereof and either immediately after, or after a period of 5 hours to 2 weeks, contacting the cell with an anti-cancer agent or a pharmaceutically acceptable salt thereof, thereby killing the cell.

By "oxo" is meant represents a divalent oxygen atom (e.g., the structure of oxo may be shown as =O).

By "partially unsaturated" is meant a ring moiety that includes at least one double or triple bond. The term "partially unsaturated" is intended to encompass rings having multiple sites of unsaturation, but is not intended to include aryl or heteroaryl moieties, as herein defined.

By "pharmaceutically acceptable salt" is meant a salt which is, within the scope of sound medical judgment, suitable for use in contact with the tissues of humans and animals without undue toxicity, irritation, allergic response and the like and is commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

By "pharmaceutical composition" is meant a composition containing a compound described herein, formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

By "protecting group" is meant a group intended to protect a hydroxy, an amino, or a carbonyl from participating in one or more undesirable reactions during chemical synthesis. By "O-protecting group" is meant represents a group intended to protect a hydroxy or carbonyl group from participating in one or more undesirable reactions during chemical synthesis. By "N-protecting group" is meant represents a group intended to protect a nitrogen containing (e.g., an amino or hydrazine) group from participating in one or more undesirable reactions during chemical synthesis. Commonly used O- and N-protecting groups are disclosed in Greene, "Protective Groups in Organic Synthesis," $3^{rd}$ Edition (John Wiley & Sons, New York, 1999), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkyl ethers (e.g., trityl; methylthiomethyl; methoxymethyl; benzyloxymethyl; siloxymethyl; 2,2,2-trichloroethoxymethyl; tetrahydropyranyl; tetrahydrofuranyl; ethoxyethyl; 1-[2-(trimethylsilyl) ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2, 2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

By "reversing chemoresistance" is meant treating a cancer cell that fails to respond to treatment by conventional anti-cancer agents with a compound that sensitizes the cancer cell to be killed by anti-cancer agents. A non-limiting example of reversing chemoresistance includes contacting a chemoresistant cancer cell with an effective amount of chaetocin, a chaetocin analog, a Suv39H1/Suv39H2 inhibitor, or a pharmaceutically acceptable salt thereof. Such treatment may then sensitize the chemoresistant cancer cell to killing with an anti-cancer agent.

By "subject" is meant a human or non-human animal (e.g., a mammal) that is suffering from a disease, disorder, or condition or is at risk of a disease, disorder, or condition, as determined by a qualified professional (e.g., a doctor or a nurse practitioner) with or without known in the art laboratory test(s) of sample(s) from the subject.

By "Suv39H1" is meant a human suppressor of variegation 3-9 homolog 1 gene, transcript, or protein.

By "Suv39H2" is meant a human suppressor of variegation 3-9 homolog 2 gene, transcript, or protein.

By "Suv39H1/Suv39H2 inhibitor" is meant a compound capable of inhibiting one or both of Suv39H1 and Suv39H2. Preferably, IC50 of Suv39H1/Suv39H2 inhibitor is 1 μM or less, as measured in vitro. An Suv39H1/Suv39H2 inhibitor may be, e.g., an siRNA, antisense oligonucleotide, an antibody, or a small molecule. Preferably, an Suv39H1/Suv39H2 inhibitor is a small molecule (e.g., a small molecule satisfying Lipinski's rule of five, e.g., a small molecule having 5 hydrogen bond donors or fewer, 10 hydrogen bond acceptors or fewer, a molecular mass of 500 g/mol or less, and an octanol-water partition coefficient log P of 5 or less). More preferably, an Suv39H1/Suv39H2 inhibitor is chaetocin or a chaetocin analogue.

As described herein, compounds described herein may contain "optionally substituted" moieties. In general, the term "substituted," whether preceded by the term "optionally" or not, means that one or more hydrogen atoms of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$(CH_2)_{0-4}SR°$; —$(CH_2)_{0-4}S(O)R°$; —$O(CH_2)_{0-4}R°$, —O—$(CH_2)_{0-4}C(O)OR°$; —$(CH_2)_{0-4}CH(OR°)_2$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)RO$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR$; —SC(S)SR°; —$(CH_2)_{0-4}SC(O)R°$; —$(CH_2)_{0-4}C(O)NR°_2$; —C(S)NR°_2; —C(S)SR°; —SC(S)SR°; —$(CH_2)_{0-4}OC(O)NR°_2$; —C(O)N(OR°)R°; —C(O)C(O)R°; —C(O)$CH_2$C(O)R°; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —S(O)_2NR°_2; —$(CH_2)_{0-4}S(O)R°$; —N(R°)S(O)_2NR°_2; —N(R°)S(O)_2R°; —N(OR°)R°; —C(NH)NR°_2; —P(O)_2R°; —P(O)R°_2; —P(O)(OR°)R°; —P(O)(OR°)_2; —OP(O)R°_2; —OP(O)(OR°)R°; —OP(O)(OR°)_2; —PR°_2; —P(OR°)R°; —P(OR°)_2; —OPR°_2; —OP(OR°)R°; —OP(OR°)_2; —SiR°_3; —OSiR°_3; —SeR°; —$(CH_2)_{0-4}SeSeR°$; —B(R°)_2, —B(OR°)_2, —($C_{1-4}$ straight or branched alkylene)O—N(R°)_2; or —($C_{1-4}$ straight or branched alkylene)C(O)O—N(R°)_2; wherein each R° may be substituted as defined below and is independently hydrogen, $C_{1-6}$ aliphatic, —$CH_2Ph$, —$O(CH_2)_{0-1}Ph$, —$CH_2$-(5-5 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-6 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R•$, -(haloR•), —$(CH_2)_{0-2}OH$, —$(CH_2)_{0-2}OR•$, —$(CH_2)_{0-2}CH(OR•)_2$; —O(haloR•), —CN, —$N_3$, —$(CH_2)_{0-2}C(O)R•$, —$(CH_2)_{0-2}C(O)OH$, —$(CH_2)_{0-2}C(O)OR•$, —$(CH_2)_{0-2}SR•$, —$(CH_2)_{0-2}SH$, —$(CH_2)_{0-2}NH_2$, —$(CH_2)_{0-2}NHR•$, —$(CH_2)_{0-2}NR•_2$, —$NO_2$, —SiR•_3, —OSiR•_3, —C(O)SR•, —($C_{1-4}$ straight or branched alkylene)C(O)OR•, or —SSR• wherein each R• is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a suitable carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH2, —NHR•, —NR†$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

By "treatment" and "treating," is meant the medical management of a subject with the intent to improve, ameliorate, stabilize, prevent or cure a disease, disorder, or condition. This term includes active treatment (treatment directed to improve the disease, disorder, or condition); causal treatment (treatment directed to the cause of the associated disease, disorder, or condition); palliative treatment (treatment designed for the relief of symptoms of the disease, disorder, or condition); preventative treatment (treatment directed to minimizing or partially or completely inhibiting the development of the associated disease, disorder, or condition); and supportive treatment (treatment employed to supplement another therapy).

By "unsaturated" is meant that a moiety has one or more units of unsaturation

BRIEF DESCRIPTION OF THE DRAWINGS

FIG. 1A shows the intensity of cleaved caspase 3 proteins, an indicator of apoptosis, in two cultured breast cancer cell lines (MDA-MB-231 and MDA-MB-468) upon treatment with increasing concentrations (0 nM (control), 100 nM, and 200 nM) of chaeotocin. The MDA-MB-231 cell line displays mesenchymal properties, is rich in tumor initiating cells (TICs) and resistant to conventional chemotherapies used to treat breast cancer, while the MDA-MB-468 cell line displays epithelial properties, is largely devoid of TICs and sensitive to conventional chemotherapies used to treat breast cancer. FIG. 1B shows the same experiment with an increased dosing regimen for chaetocin (0 nM (control), 400 nM, and 800 nM). At higher doses of chaetocin (0 nM, 400 nM, and 800 nM), MDA-MB-468 cells show increased sensitivity to chaetocin as compared to MDA-MB-231 cells (FIG. 1B). The data presented in FIGS. 1A and 1B indicate that at lower doses especially chaetocin specifically induces apoptosis of mesenchymal, TIC-rich, chemotherapy-resistant breast cancer cell lines compared to the epithelial, non-TIC-rich and chemotherapy-responsive cell-line.

FIG. 1C shows a bar plot quantifying the percent (%) inhibition of proliferation of a number of normal and cancer cell lines in culture. Mesenchymal, TIC-rich, chemotherapy-resistant cell lines used in this experiment are the clear cell renal carcinoma cell line 786-0 and the human mammary epithelial (HMLE) cell line in which the zinc finger protein SNAI1 (SNAIL) is overexpressed, E-SNAIL. The isogenic epithelial, TIC-depleted, chemotherapy sensitive cell lines used as controls are the clear cell renal carcinoma cell line WT7 (modified 786-0 cells) and the human mammary epithelial (HMLE) cell with SNAI1 overexpression. Non-cancerous human renal epithelial cells (HK-2), non-cancerous mouse renal epithelial cells (NP-1 normal mammary epithelial cells (BEAS-2B) provide additional controls. The results of FIG. 1C indicate that chaetocin treatment specifically inhibits the growth of mesenchymal, TIC-rich, chemotherapy-resistant breast and renal cancer cell lines compared to epithelial, TIC-depleted, chemotherapy-sensitive cell lines.

FIGS. 1D-1E are a series of scatter plots showing the results of a Gene Set Enrichment Analysis (GSEA) screen of 800 cancer cell lines for sensitivity to chaetocin applied at 9 different concentrations (0.005 µM, 0.01 µM, 0.02 µM, 0.04 µM, 0.08 µM, 0.16 µM, 0.32 µM, 0.64 µM, and 1.28 µM) in culture. Cell viability was measured several days after chaetocin treatment. FIG. 1D is a scatter plot showing the chaetocin sensitivity of all tested cells lines: mesenchymal gene expression signature (SNAIL-induced early-repressed gene set) (Y-axis) is plotted against area under the curve (AUC) calculated by measuring percent cell death caused by increasing doses of chaetocin (X-axis). Mesenchymal gene expression signature (SNAIL-induced early-repressed gene set) used in the Y-axis was based on the the Javaid et al 2013 paper. These data demonstrate a positive correlation between mesenchymal transcriptional signature and sensitivity to chaetocin. FIG. 1E shows the same analysis as in FIG. 1D depicting cancer cell lines from different tissues separately. The findings of FIGS. 1D-1E indicate that cells with mesenchymal transcriptional signature are sensitive to chaetocin.

FIGS. 1F-1I show the results of a 3-D tumor spheroid assay formed by the chemotherapy-resistant breast cancer cell line, HMLE-SNAIL. FIG. 1F shows a schematic of 3-D tumor spheroid assay well system used for growing tumor spheroids. Tumor spheroids are a model of real in vivo tumors, as they form a 3-D cell mass in which the hypoxic and often nutrient depleted microenvironment at the center of the tumor is enriched with mesenchymal, chemotherapy-resistant TIC cells. FIG. 1G shows HMLE-SNAIL spheroids under control conditions (no treatment); FIG. 1H show HMLE-SNAIL spheroids treated with a variety of experimental chemotherapeutic agents (Y-27632, LY-450139, and IWP-L6 (Wnt)) which are thought to specifically target TICs; and FIG. 1I show HMLE-SNAIL cell spheroids treated with chaetocin. By staining spheroids with Sytox, which stains dead cells green, and DAPI, which stains the nuclei of all cells (living or dead), total fraction of dead cells is calculated. Also, the location of dead cells within the sphere is visualized with Sytox (green) staining. The results of FIGS. 1F-1I indicate that chaetocin a selective and potent killer of inner cells of the spheroids, enriched with mesenchymal, chemotherapy-resistant TIC cells, compared to other compounds tested. FIGS. 1J-1K show the results of a tumorsphere assay performed with TICs grown on serum-free, non-adherent culture conditions. FIG. 1J shows TIC tumorspheres grown at three chaetocin concentrations (0 nM, 30 nM, and 80 nM) of chaetocin. FIG. 1K shows the quantification of tumorspheres per well across multiple after 14 days of culture with varying concentrations of chaetocin. The results of FIGS. 1J-1K indicate that chaetocin is effective in eliminating TICs in a dose dependent-manner.

FIGS. 2A-2E show the survival plots of clear cell renal cell adenocarcinoma patients having high or low expression of SNAI1 (FIG. 2A), SNAI2 (FIG. 2B), TWIST1 (FIG. 2C), Zeb1 (FIG. 2D), and Zeb2 (FIG. 2E) FIGS. 2K-2O show the survival plots of brain lower grade glioma patients having high or low expression of SNAI1 (FIG. 2K), SNAI2 (FIG. 2L), TWIST1 (FIG. 2M), Zeb1 (FIG. 2N), and Zeb2 (FIG. 2O). The results of FIGS. 2A-2O indicate that increased expression of EMT TFs predicts poor patient survival in several cancers.

FIG. 3A shows fluorescence activated cell sorting (FACS) heat maps of mesenchymal, TIC-rich HMLE-SNAIL cells under control conditions (no treatment). The y- and the x-axes represent fluorescence intensity of CD24 and CD44 cell surface markers, respectively. In this cell line, high CD44 and low CD24 expression indicate TIC cell populations. Cells that express CD24 are considered non-TICs. FIG. 3A demonstrates that HMLE-SNAIL cells are enriched for TICs.

Epigenetic changes are those which the phenotypic change induced upon transient exposure to a signal (e.g. chaetocin) persists stably even in the absence of the inducing signal. FIG. 3D demonstrates that HMLE-TWIST cells are enriched for TICs.

FIG. 3N demonstrates that HMLE-TWIST cells are enriched for TICs.

FIG. 3X show a bar plot demonstrating E cadherin (E-cad) expression at multiple time points under two chaetocin concentrations. The results of FIG. 3X indicate that chaetocin treatment results in an epigenetic change that converts mesenchymal HMLE-TWIST cells into an epithelial phenotype as determined by increase in E-cad protein levels. Together, the data presented in FIGS. 3A-3X indicate that a short pulse of chaetocin is sufficient to bring about a stable epigenetic change converting mesenchymal, TIC cells into an epithelial, non-TIC phenotype.

FIG. 4A shows a schematic of the experiment in which mesenchymal, TIC-rich HMLE-TWIST cells were treated for 5 hours (FIG. 4B) or 15 hours (FIG. 4C) with different concentrations of chaetocin (20 nM, 50 nM, 100 nM), then washed and incubated in chaetocin-free media for two days. Doxorubicin was added after two days and cell death was assayed with cleaved caspase-3 intensity. Comparing the cell death caused by chaetocin or doxorubicin alone versus chaetocin first and doxorubicin second treatments, the results of FIGS. 4A-4C indicate that a short treatment with chaetocin reverses chemotherapy resistance of mesenchymal, TIC-rich HMLE-TWIST cells to doxorubicin.

FIGS. 4D-4E show a set of bar plots and schematics of experiments in which chaetocin (80 nM) was administered for 15 hours either alone, two days before (FIG. 4E) or after a 2 day treatment with a chemotherapeutic drug (FIG. 4D; 300 nM cisplatin or 10 nM Doxorubicin) to 786-0 clear cell renal carcinoma cells, A549 lung cancer cells, and HMLE-TWIST (E-Twist) breast cancer cells. Cell death was assayed with cleaved caspase 3 fluorescent intensity. These experiments were designed to test the prediction of an epigenetic model for chaetocin-mediated reversal of chemotherapy resistance, namely that chaetocin must be added transiently for a short duration (15 hours) 2 days prior to chemotherapy to sensitize the cells to treatment. If the order was reversed (FIG. 4D), there should be no effect. The results of FIGS. 4A-4E indicate that chaetocin primes cancer cells for apoptotic death by chemotherapy through epigenetic reversal of chemotherapy resistance.

Because chaetocin has been shown as a specific inhibitor of constitutive heterochromatin proteins SUV39H1 and SUV39H2, we asked whether a transient knockdown of different constitutive heterochromatin proteins also causes an epigenetic reversal of mesenchymal phenotype.

FIG. 5A shows a schematic delineating the experimental strategy for using dicer-generated siRNA technology (dsiRNAs) for transient knock-down of constitutive heterochromatin proteins in HMLE-TWIST cells followed by FACS analysis three days later to track the levels of CD44/CD24 cell surface markers.

FIG. 5B), after knock-down of suppressor of variegation 3-9 homolog 1 (Suv39H1; SUV39H1-KD (E-Twist)) using three different dsiRNAs resulting in different levels of Suv39H1 knockdown ((1; FIG. 5C), (2; FIG. 5D), (3; FIG. 5E)). The results of FIGS. 5B-5E show that single knock-down of the constitutive heterochromatin protein Suv39H1 converts mesenchymal, TIC cells to a non-TIC phenotype, similar to the effect of chaetocin. This effect is more obvious, the greater the Suv39H1 knockdown.

FIGS. 5G-5J show a similar experiment as described in FIGS. 5B-5E, targeting the constitutive heterochromatin protein suppressor of variegation 3-9 homolog 2 (Suv39H2) using three different dsiRNAs resulting in different levels of protein knockdown (1; FIG. 5G), (2; FIG. 5H), (3; FIG. I). The bar plot in FIG. 5J shows the results of qRT-PCR analysis measuring Suv39H2 RNA levels in HMLE-TWIST cells for the three different dsiRNAs described above. Similar to the effects of Suv39H1 knock-down and chaetocin treatment, single knock-down of Suv39H2 converts mesenchymal, TIC cells to a non-TIC phenotype. This effect is more obvious, the greater the Suv39H2 knockdown.

FIGS. 5K-5N show a similar experiment as described in FIGS. 5B-5L, targeting a histone H3 lysine 9 methyltransferase, G9a. Unlike single knock-down of Suv39H1 and Suv39H2, G9a knock-down has little impact on converting mesenchymal, TICs to a non-TIC phenotype using three different dsiRNAs (1; FIG. 5K), (2; FIG. 5L), (3; FIG. M). The bar plot in FIG. 5N shows the results of qRT-PCR analysis measuring G9a RNA levels in HMLE-TWIST cells for the three different dsiRNAs described above. FIG. 5O shows a bar plot summarizing the results of single, double, triple, and quadruple knockdown of heterochromatin proteins in HMLE-TWIST cells. Suv39H1 (H1) and Suv39H2 (H2) single knockdowns have the largest effect in converting mesenchymal, TICs to a non-TIC phenotype.

FIG. 6A shows the fraction of HMLE or HMLE-TWIST cancer cells surviving following treatment with chaetocin or its dimeric or monomeric derivatives. FIGS. 6B-6C show the fraction of HMLE-TWIST (FIG. 6B) and HMLE (FIG. 6C) breast cancer cells surviving following treatment with chaetocin or its dimeric or monomeric derivatives. FIGS. 6D-6E show the fraction of HMLE and HMLE-TWIST cells surviving following treatment with chaetocin and its dimeric derivative (FIG. 6D) or with chaetocin alone (FIG. 6E). FIGS. 6F-6H show the fraction of E or ET cells surviving following treatment with chaetocin or its monomeric derivative (FIG. 6F), treatment with the dimeric chaetocin derivative (FIG. 6G), and treatment with the monomeric chaetocin derivative (FIG. 6H). These findings indicate that the dimeric derivative of chaetocin is more effective at killing mesenchymal cancer cells compared to chaetocin or the monomeric control compound.

DETAILED DESCRIPTION

Figure 1A:
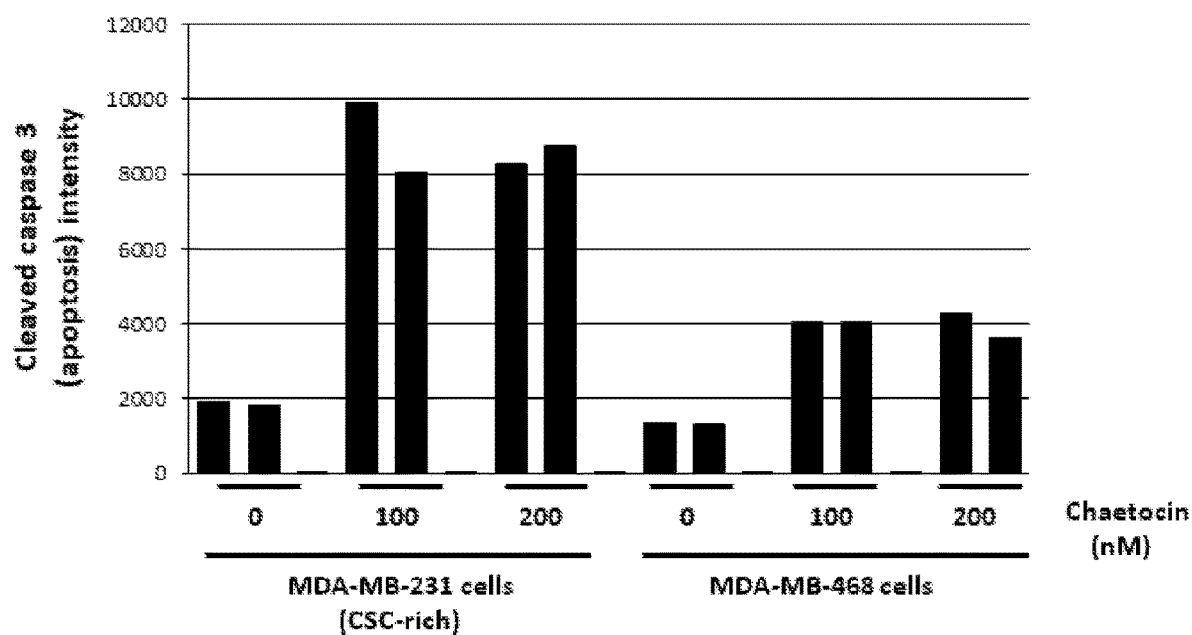
FIGS. 1A-1K are a series of figures showing sensitivity of tumor initiating cell (TICs)-rich, chemoresistant breast cancer and clear cell renal cell carcinoma cell lines to chaetocin compared to non-cancerous epithelial or isogenic cancerous epithelial, TIC-deplete, chemosensitive breast cancer and clear cell renal cell carcinoma cell lines.

Generally, the invention provides methods for treating cancer, e.g., by addressing the problem of cancer chemoresistance. In particular, the invention provides methods of treatment of cancer (e.g., chemoresistant cancer or mesenchymal cancer (e.g., a chemoresistant mesenchymal cancer)) in a subject (e.g., a mammalian subject, such as a human) in need thereof by administering chaetocin, a chaetocin analogue, a Suv39H1/Suv39H2 inhibitor, or a pharmaceutically acceptable salt thereof prior to the administration of an anti-cancer agent (e.g., a chemotherapeutic agent). In some embodiments, the methods of the invention may be used in the treatment of a mesenchymal cancer. In some embodiments, the methods of the invention may be used in the treatment of a chemoresistant cancer. The invention also provides methods of killing cancer cells (e.g., chemoresistant cancer cells or mesenchymal cancer cells (e.g., chemoresistant mesenchymal cancer cells)). The invention also provides methods of reversing chemoresistance and killing of chemoresistant cancer cells.

Without wishing to be bound by theory, it is believed that the compounds disclosed herein elicit an epigenetic change converting mesenchymal, chemotherapy-resistant cancer cells to an epithelial, chemotherapy-sensitive phenotype. It is believed that this reversal is responsible, at least in part, for the restoration of chemotherapy sensitivity in cancer cells. A cancer may become mesenchymal in response to chemotherapy or other stresses, or as the cancer progresses and metastasizes converting some cancer cells into a mesenchymal state. Preferably, the cancers (e.g., chemoresistant cancers) treated using methods disclosed herein include a mesenchymal cancer cell (e.g., a chemoresistant, mesenchymal cancer cell). Also, preferably, the chemoresistant cancer cells are chemoresistant mesenchymal cancer cells.

Pharmaceutical Compositions

The compounds used in the methods described herein are preferably formulated into pharmaceutical compositions for administration to human subjects in a biologically compatible form suitable for administration in vivo. Pharmaceutical compositions typically include a compound as described herein and a pharmaceutically acceptable excipient.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the composition in the required amount in an appropriate solvent with one or a combination of ingredients enumerated above, as required, followed by filtered sterilization. Generally, dispersions are prepared by incorporating the composition into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compositions can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable carriers. These can be prepared according to methods known to those skilled in the art.

Pharmaceutical compositions can be included in a container, pack, or dispenser together with instructions for administration. Methods of formulating pharmaceutical agents are known in the art. The compositions described herein can be administered locally, e.g., to the site of a cancer in a subject. Examples of local administration include epicutaneous, inhalational (e.g. byway of a nebulizer), intra-articular, intrathecal, intravaginal, intravitreal, intrauterine, intra-lesional administration, lymph node administration, intratumoral administration and administration to a mucous membrane of the subject, wherein the administration is intended to have a local and not a systemic effect. As an example, for the treatment of a cancer described herein, the compositions described herein may be administered locally (e.g., intratumorally) in a compound-impregnated substrate such as a wafer, microcassette, or resorbable sponge placed in direct contact with the affected tissue. Alternatively, the composition is infused into the brain or cerebrospinal fluid using standard methods. A composition for use in the methods described herein can be administered at the site of a tumor, e.g., intratumorally. In certain embodiments, the agent is administered to a mucous membrane of the subject.

Preparation of Compounds

Compounds disclosed herein may be prepared using methods and techniques known in the art. Non-limiting examples of the search strategies may be found, e.g., in: (a) P. W. Trown, Biochem. Biophys. Res. Commun., 1968, 33, 402; (b) T. Hino and T. Sato, Tetrahedron Lett., 1971, 12, 3127; (c) H. Poisel and U. Schmidt, Chem. Ber., 1971, 104, 1714; (d) H. Poisel and U. Schmidt, Chem. Ber., 1972, 105, 625; (e) E. Ohler, F. Tataruch and U. Schmidt, Chem. Ber., 1973, 106, 396; (f) H. C. J. Ottenheijm, J. D. M. Herscheid, G. P. C. Kerkhoff and T. F. Spande, J. Org. Chem., 1976, 41, 3433; (g) D. L. Coffen, D. A. Katonak, N. R. Nelson and F. D. Sancilio, J. Org. Chem., 1977, 42, 948; (h) J. D. M. Herscheid, R. J. F. Nivard, M. W. Tijhuis, H. P. H. Scholten and H. C. J. Ottenheijm, J. Org. Chem., 1980, 45, 1885; (i) R. M. Williams, R. W. Armstrong, L. K. Maruyama, J.-S. Dung and O. P. Anderson, J. Am. Chem. Soc., 1985,107, 3246; (j) C. J. Moody, A. M. Z. Slawin and D. Willows, Org. Biomol. Chem., 2003, 1, 2716; (k) A. E. Aliev, S. T. Hilton, W. B. Motherwell and D. L. Selwood, Tetrahedron Lett., 2006, 47, 2387; (l) L. E. Overman and T. Sato, Org. Lett., 2007, 9, 5267; (m) N. W. Polaske, R. Dubey, G. S. Nichol and B. Olenyuk, Tetrahedron: Asym., 2009, 20, 2742; (n) B. M. Ruff, S. Zhong, M. Nieger and S. Brase, Org. Biomol. Chem., 2012, 10, 935; (o) K. C. Nicolaou, D. Giguere, S. Totokotsopoulos and Y.-P. Sun, Angew. Chem. Int. Ed., 2012, 51, 728; for selected epidithiodiketopiperazine total syntheses, see: (a) Y. Kishi, T. Fukuyama and S. Nakatsuka, J. Am. Chem. Soc., 1973, 95, 6492; (b) Y. Kishi, S. Nakatsuka, T. Fukuyama and M. Havel, J. Am. Chem. Soc., 1973, 95, 6493; (c) T. Fukuyama and Y. Kishi, J. Am. Chem. Soc., 1976, 98, 6723; (d) R. M. Williams and W. H. Rastetter, J. Org. Chem., 1980, 45, 2625; (e) G. F. Miknis and R. M. Williams, J. Am. Chem. Soc., 1993, 115, 536; (f) E. Iwasa, Y. Hamashima, S. Fujishiro, E. Higuchi, A. Ito, M. Yoshida and M. Sodeoka, J. Am. Chem. Soc., 2010, 132, 4078; (g) J. E. DeLorbe, S. Y. Jabri, S. M. Mennen, L. E. Overman and F.-L. Zhang, J. Am. Chem. Soc., 2011, 133, 6549; (h) K. C. Nicolaou, S. Totokotsopoulos, D. Giguere, Y.-P. Sun and D. Sarlah, J. Am. Chem. Soc., 2011, 133, 8150; (i) J. A. Codelli, A. L. A. Puchlopek and S. E. Reisman, J. Am. Chem. Soc., 2012, 134, 1930; for other synthetic strategies relevant to epipolythiodiketopiperazines, see: (a) J. Kim, J. A. Ashenhurst and M. Movassaghi, Science, 2009, 324, 238; (b) J. Kim and M. Movassaghi, J. Am. Chem. Soc., 2010, 132, 14376).

Regimens

Timing of Administration

In the methods disclosed herein, a chemoresistant cancer cell may be killed by contacting the chemoresistant cancer cell with an effective amount of chaetocin, a chaetocin, analogue, a Suv39H1/Suv39H2 inhibitor, or a pharmaceutically acceptable salt thereof, and after a period of at least 5 hours (e.g., at least 5, 6, 7, 8, 9, 10, 11, 12, 13, 14, 15, 16, 17, 18, 19, 20, 21, 22, 23, 24 hours or more), contacting the cell with an anti-cancer agent or a pharmaceutically acceptable salt thereof, thereby killing the chemoresistant cancer cell.

The invention further provides methods of treating a chemoresistant cancer in a subject in need thereof (e.g., a mammalian subject, such as a human) by administering to the subject a therapeutically effective amount of chaetocin, a chaetocin analogue, a Suv39H1/Suv39H2 inhibitor, or a pharmaceutically acceptable salt thereof, and after a period of at least 5 hours (e.g., at least 5, 6, 7, 8, 9, 10, 11, 12, 13, 14, 15, 16, 17, 18, 19, 20, 21, 22, 23, 24 hours or more), administering to the subject a therapeutically effective amount of an anti-cancer agent or a pharmaceutically acceptable salt thereof, thereby treating the chemoresistant cancer in the subject.

In some embodiments, the period is 5 hours to 2 weeks (e.g., for the methods of killing a chemoresistant cancer cell). For example, the period may be 5 hours to 2 weeks, 6 hours to 2 weeks, 9 hours to 2 weeks, 12 hours to 2 weeks, 18 hours to 2 weeks, 24 hours to 2 weeks, 2 days to 2 weeks, 3 days to 2 weeks, 4 days to 2 weeks, 5 days to 2 weeks, 6 days to 2 weeks, 7 days to 2 weeks, 8 days to 2 weeks, 9 days to 2 weeks, 10 days to 2 weeks, 11 days to 2 weeks, 12 days to 2 weeks, or 13 days to 2 weeks.

In some embodiments, the period is 2 days to 2 weeks (e.g., for the methods of treating a chemoresistant cancer). For example, the period may be 2 days to 2 weeks, 3 days to 2 weeks, 4 days to 2 weeks, 5 days to 2 weeks, 6 days to 2 weeks, 7 days to 2 weeks, 8 days to 2 weeks, 9 days to 2 weeks, 10 days to 2 weeks, 11 days to 2 weeks, or 13 days to 2 weeks.

The treatment regimen described herein can treat chemoresistant cancer by increasing cancer cell death in a subject (e.g., a mammalian subject, such as a human) or in a cancer cell culture (e.g., a culture generated from a patient tumor sample, a cancer cell line, or a repository of patient samples). Treatment can increase cancer cell death by at least 1%, 2%, 5%, 10%, 15%, 20%, 25%, 30%, 35%, 40%, 50%, 60%, 70%, 80%, 90%, 95% or more compared to before treatment to a subject or cancer cell culture. Treatment can increase cancer cell death in a subject or cancer cell culture between 5-20%, between 5-50%, between 10-50%, between 20-80%, between 20-70%. The treatment can also act to inhibit cancer cell growth, proliferation, metastasis, migration, or invasion. Cancer cell growth, proliferation, metastasis, migration, or invasion can be decreased in the subject or cancer cell culture at least 1%, 2%, 5%, 10%, 15%, 20%, 25%, 30%, 35%, 40%, 50%, 60%, 70%, 80%, 90%, 95% or more, compared to before the treatment. Cancer cell growth, proliferation, metastasis, migration, or invasion can be decreased in the subject or cancer cell culture between 5-20%, between 5-50%, between 10-50%, between 20-80%, between 20-70%.

The methods described herein may act to alter (e.g., increase or decrease) the expression level and/or activity of an mRNA or protein of a gene associated with the cancer. For example, the compositions disclosed herein may increase/decrease the expression level and/or activity of chromatin-modifying proteins by 10%, 15%, 20%, 25%, 30%, 35%, 40%, 45%, 50%, 55%, 60%, 65%, 70%, 75%, 80%, 85%, 90%, 95%, 99%, or more. In some embodiments, the chromatin regulator protein is Suppressor of Variegation 3-9 Homolog 1. In some embodiments, the chromatin regulator protein is Suppressor of Variegation 3-9 Homolog 2. Expression levels and or activity levels may be measured using standard methods known in the art such as, e.g., western blots, immunohistochemistry, immunoprecipitation, qRT-PCR, in situ hybridization, ELISA assay, among others.

Routes of Administration

Therapeutic agents used in the methods described herein may be administered to a subject in need thereof by standard methods. For example, the composition can be administered by any of a number of different routes including, e.g., systemic administration such as intravenous, intraperitoneal, intradermal, subcutaneous, percutaneous injection, oral, intranasal, transdermal (topical), or transmucosal. The composition can be administered orally or administered by injection, e.g., intramuscularly, intravenously, intraperitoneally, intrathecally, intracerebroventricularly, intraparenchymally, or intratumorally. In some embodiments, the composition is administered intratumorally. The most suitable route for administration in any given case will depend on the particular agent administered, the patient, the particular disease or condition being treated, pharmaceutical formulation methods, administration methods (e.g., administration time and administration route), the patient's age, body weight, sex, severity of the diseases being treated, the patient's diet, and the patient's excretion rate. The agent can be encapsulated or injected, e.g., in a viscous form, for delivery to a chosen site, e.g., a tumor site. The agent can be provided in a matrix capable of delivering the agent to the chosen site. Matrices can provide slow release of the agent and provide proper presentation and appropriate environment for cellular infiltration. Matrices can be formed of materials presently in use for other implanted medical applications. The choice of matrix material is based on any one or more of: biocompatibility, biodegradability, mechanical properties, and cosmetic appearance and interface properties. One example is a collagen matrix.

The compositions described herein can be incorporated into pharmaceutical compositions suitable for administration to a subject, e.g., a human. Such compositions typically include the agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

Anti-Cancer Agents i. Chemotherapeutic Agents

Chemotherapeutic agents suitable for use with the methods described herein include alkylating agents, antimetabolites, folic acid analogs, pyrimidine analogs, purine analogs and related inhibitors, vinca alkaloids, epipodophyllotoxins, L-asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analogue. Non-limiting examples of chemotherapeutic agents include alkylating agents (e.g., cisplatin, carboplatin, oxalipiatin, mechlorethamine, cyclophosphamide, chlorambucil, dacarbazine, lomustine, carmustine, procarbazine, chlorambucil, or ifosfamide), antimetabolites (e.g., fluorouracil (5-FU), gemcitabine, methotrexate, cytosine arabinoside, fludarabine, and floxuridine), antimitotics (e.g., a taxane (e.g., paclitaxel or decetaxel) or a vinca alkaloid (e.g., vincristine, vinblastine, vinorelbine, or vindesine)), anthracyclines (e.g., doxorubicin, daunorubicin, valrubicin, idarubicin, epirubicin, or an actinomycin (e.g., actinomycin D)), cytotoxic antibiotics (e.g., mitomycin, plicamycin, or bleomycin), topoisomerase inhibitors (e.g., a camptothecin (e.g., irinotecan or topotecan) or an epipodophyllotoxin derivative (e.g., amsacrine, etoposide, or teniposide), and pharmaceutically acceptable salts thereof.

One of skill in the art would recognize that other chemotherapeutic agents may also be used with the methods of the invention.

ii. Checkpoint Inhibitors

One type of agent that can be also administered in combination with the methods described herein is a checkpoint inhibitor. One having skill in the art would be able to select a known checkpoint inhibitor suitable for treatment of a particular chemoresistant cancer in conjunction with the methods described herein.

iii. Non-Drug Modalities

Another type of therapeutic modality that can be administered in conjunction with the methods disclosed herein is a therapeutic modality that is a non-drug treatment. For example, the therapeutic modality may be radiation therapy, cryotherapy, alternating electric field therapy, hyperthermia and/or surgical excision of tumor tissue iv. Biologic Anti-Cancer Agents Another type of therapeutic agent that can be administered in conjunction with the methods described herein is an anti-cancer agent that is a biologic, such as a cytokine (e.g., interferon or an interleukin) used in cancer treatment. In other embodiments, the biologic is an anti-angiogenic agent, such as an anti-VEGF agent. In some embodiments, the biologic is an immunoglobulin-based biologic, such as, for example, a monoclonal antibody (e.g., a humanized antibody, a fully human antibody, an Fc fusion protein, or a functional fragment thereof) that agonizes a target to stimulate an anti-cancer response, or antagonizes an antigen important for cancer. Biologic anti-cancer agents are known in the art.

Cancers

In the methods described herein, the cancer may be any solid or liquid cancer and includes benign or malignant tumors, and hyperplasias. In some embodiments, the cancer is breast cancer. In some embodiments, the cancer is kidney cancer. In some embodiments, the cancer is lung cancer. Other cancers suitable for treatment using the methods described herein include gastrointestinal cancer (such as non-metastatic or metastatic colorectal cancer, pancreatic cancer, gastric cancer, esophageal cancer, hepatocellular cancer, cholangiocellular cancer, oral cancer, lip cancer); urogenital cancer (such as hormone sensitive or hormone refractory prostate cancer, renal cell cancer, bladder cancer, penile cancer); gynecological cancer (such as ovarian cancer, cervical cancer, endometrial cancer); lung cancer (such as small-cell lung cancer and non-small-cell lung cancer); head and neck cancer (e.g., head and neck squamous cell cancer); CNS cancer including malignant glioma, astrocytomas, retinoblastomas and brain metastases; malignant mesothelioma; non-metastatic or metastatic breast cancer (e.g., hormone refractory metastatic breast cancer); skin cancer (such as malignant melanoma, basal and squamous cell skin cancers, Merkel Cell Carcinoma, lymphoma of the skin, Kaposi Sarcoma); thyroid cancer; bone and soft tissue sarcoma; and hematologic neoplasias (such as multiple myeloma, acute myelogenous leukemia, chronic myelogenous leukemia, myelodysplastic syndrome, acute lymphoblastic leukemia, Hodgkin's lymphoma). Preferably, a chemoresistant cancer is a chemoresistant glioblastoma, breast cancer, lung cancer, or blood cancer.

Subjects who can be treated with the methods disclosed herein include subjects who have had one or more tumors resected, received chemotherapy or other pharmacological treatment for the cancer, received radiation therapy, and/or received other therapy for the cancer. Subjects who have not previously been treated for cancer can also be treated with the methods disclosed herein.

In some embodiments, the compounds described herein may be administered in an amount and for a time effective to result in one of (or more, e.g., 2 or more, 3 or more, 4 or more of): (a) reduced tumor size, (b) reduced rate of tumor growth, (c) increased tumor cell death (d) reduced tumor progression, (e) reduced number of metastases, (f) reduced rate of metastasis, (g) reduced tumor migration, (h) reduced tumor invasion, (i) reduced tumor volume, (j) decreased tumor recurrence, (k) increased survival of subject, (l) increased progression free survival of subject.

The methods described herein may include a step of selecting a treatment for a patient. The method includes (a) identifying (e.g., diagnosing) a patient who has cancer or is at risk of developing cancer, and treating the condition in the patient. In some embodiments, the method includes administering the selected treatment to the subject. In some embodiments, a patient is identified as having cancer based on imaging (e.g., MRI, CT, or PET scan), biopsy, or blood sample (e.g., detection of blood antigen markers, circulating tumor DNA (e.g., by PCR).

The method may also include a step of assessing the subject for a parameter of cancer progression or remission, e.g., assessing the subject for one or more (e.g., 2 or more, 3 or more, 4 or more) of: primary tumor size (e.g., by imaging), number of metastases (e.g., by imaging or biopsy), cell death in situ (e.g., by biopsy), blood antigen markers (e.g., by ELISA), circulating tumor DNA (e.g., by PCR), or function of the affected organ (e.g., by a test of circulating enzymes for liver, albuminuria for kidney, lung capacity for lung, etc.).

Preferably, the chemoresistant cancer are all cancers which are mesenchymal in nature, or individual cancer cells which are mesenchymal or become mesenchymal in response to chemotherapy or other stresses, or as the cancer progresses and metastasizes generating mesenchymal cancer cells. Any of the above-listed cancers may be a chemoresistant cancer including chemoresistant, mesenchymal cancer cells.

Epithelial-to-Mesenchymal Transition

Without wishing to be bound by theory, cancer cells may acquire chemotherapeutic resistance by undergoing an epithelial-to-mesenchymal transition (EMT) through which cells acquire mesenchymal migratory properties and enhance their radiation and chemotherapy resistance as well as their tumor-initiating potential. This process is often accompanied by acquisition of stem-cell like properties among cancer cells (e.g., cancer stem cells). The key inducers of EMT are a set of transcription factors, including Snail Family Transcriptional Repressor 1 (SNAIL) and Twist Family BHLH Transcription Factor 1 (TWIST), which reprogram epithelial cells into a mesenchymal fate, increasing their resistance to a variety of stresses, including chemotherapy. EMT is critical for cancer resistance and metastasis. It is one of the most important targets for cancer therapy for which few drugs exist. The compounds, pharmaceutical compositions, and methods described herein may be used as an effective treatment in reversing chemoresistance in cancer by reversing EMT in chemoresistant cancers and/or cancer cells. Without wishing to be bound by theory, this process may convert mesenchymal, TIC-rich, chemotherapy-resistant cancer cells into an epithelial, TIC-depleted, chemotherapy-sensitive cancer.

EXAMPLES

The following are various exemplary compositions and methods which describe the invention. It is understood that other embodiments may be practiced given the general description provided above.

Figure 1B:
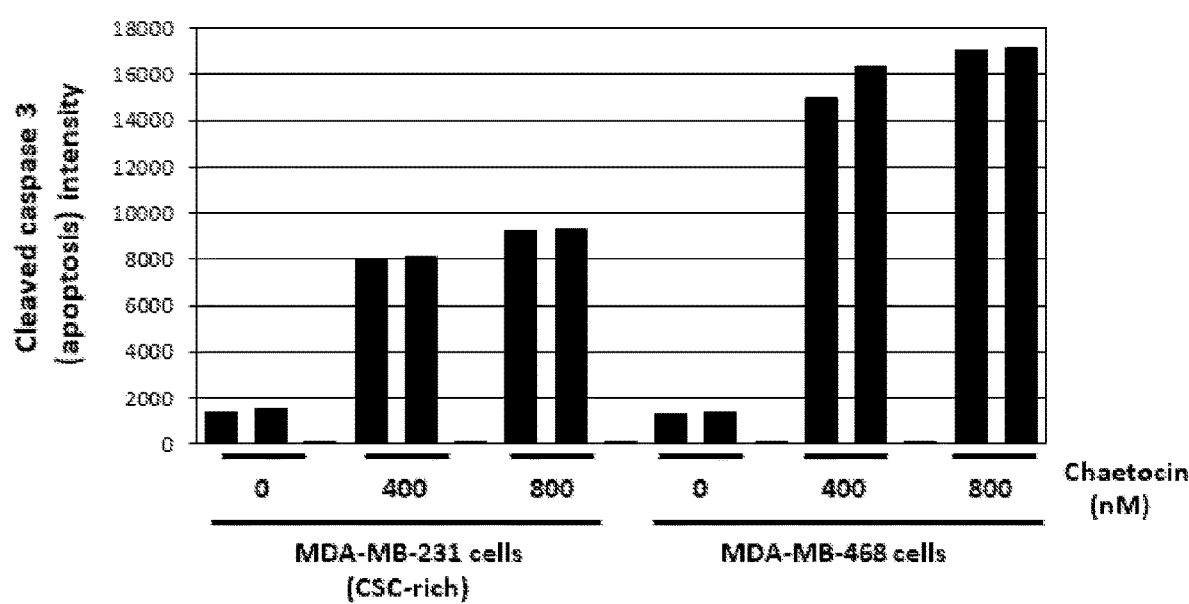

Example 1. Mesenchymal Cancer Stem Cells are Sensitive to a Heterochromatin Inhibitor Previous work in the fission yeast revealed that heterochromatin proteins play an essential role in establishing an adaptive transcriptional program, permitting cells to resist stress in reversible dormancy. To determine whether constitutive heterochromatin proteins are similarly required for the development of chemotherapy in cancer, the efficacy of a heterochromatin inhibitor, which selectively represses the activities of two proteins critical for constitutive heterochromatin formation, namely suppressor of variegation 3-9 homolog 1 (Suv39H1) and suppressor of variegation 3-9 homolog 2 (Suv39H2), was tested in human cells, using 2-D, spheroid and tumorsphere assays. To determine the sensitivity of well-established mesenchymal and epithelial cancer cells to a heterochromatin inhibitor, chaetocin, the degree of apoptotic cell death was measured in two cancer cell lines, MDA-MB-231 and MDA-MB-468. MDA-MB-231 is a well-established breast cancer cell line which is rich for the so called 'cancer stem cells' or (CSC). Another term used for these cells is 'tumor-initiating cells' (TIC), which is generally accepted as a more accurate term for describing these cells. These cells have a high propensity to initiate a tumor compared to their non-TIC cells, such as MDA-MB-468 cells. Under separate culture conditions, both cancer cell lines were exposed to increasing doses of chaetocin (0 nM, 100 nM, and 200 nM) and apoptosis was measured by assaying cleaved caspase 3, a marker of apoptotic cell death. As shown in FIG. 1A, the TIC cell line MDA-MB-231 is more sensitive to chaetocin compared to the non-TIC, MDA-MB-468 cells, especially at lower chaetocin concentrations. This response is the opposite of what has been observed for these cell lines using chemotherapeutic agents, the response being resistance of MDA-MB-231 cells and high sensitivity of MDA-MB-468 cells to chemotherapy. At higher doses of chaetocin (0 nM, 400 nM, and 800 nM), MDA-MB-468 cells show increased sensitivity to chaetocin as compared to MDA-MB-231 cells (FIG. 1B). The results of FIGS. 1A and 1B indicate that the sensitivity of mesenchymal, TIC-rich MDA-MB-231 cells to chaetocin is especially evident at lower doses, suggesting that chaetocin specifically kills TIC/chemotherapy-resistant breast cancer cell lines at lower doses compared to non-TIC cells.

Figure 1C:
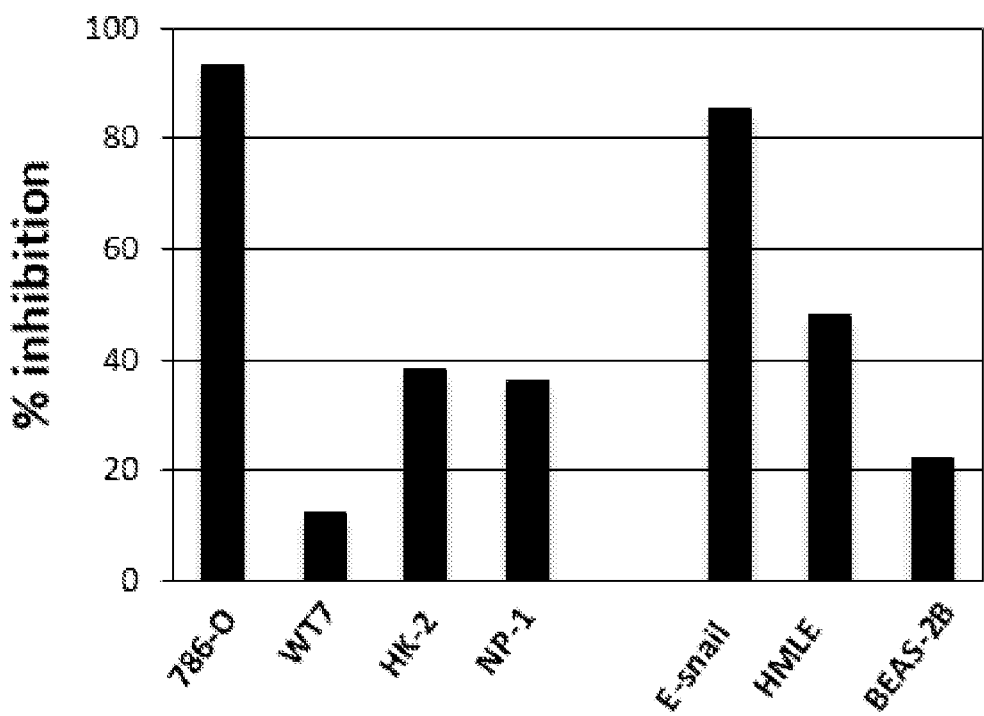

To test if other mesenchymal, TIC-rich, chemotherapy resistant cell lines of different tissue origin (e.g. kidney) are also sensitive to chaetocin treatment, normal and cancerous breast (control) and renal cells were treated in culture with 100 nM chaetocin for 1 day, after which cell growth was assayed using a proliferation assay (FIG. 1C). The tested cells included a 786-0 clear cell renal cell carcinoma (ccRCC) cell line, which is defective in the Von Hippel-Lindau tumor suppressor (VHL), enriched in TIC, and difficult to eliminate by conventional chemotherapy in patients carrying this mutation. WT7 cell line is a modified 786-0 cell line in which VHL is re-introduced artificially, rendering them epithelial, TIC-depleted and susceptible to chemotherapy. Also, a non-cancerous HK-2 human renal epithelial cell line (proximal), a non-cancerous NP-1 mouse epithelial cell line (distal), human mammary epithelial cells (HMLE) overexpressing human telomerase reverse transcriptase (hTERT) and simian virus 40 (SV40) T antigen were used as controls. These epithelial cell lines are especially sensitive to chemotherapeutic agents and are easy to treat. HMLE-Snail (E-Snail) cell line is an HMLE cell line in which SNAIL (Snail) is overexpressed. SNAIL is a transcription factor whose overexpression converts epithelial, TIC-deplete, sensitive cancer cells into mesenchymal, TIC-rich, chemotherapy resistant cell lines through a process called epithelial-to-mesenchymal transition. Also, a normal human mammary epithelial cell line (BEAS-2B) was used as a control in these experiments. Overall, by comparing the aforementioned controls used in this experiment, FIG. 1C shows that chaetocin selectively inhibits the growth of mesenchymal, TIC-rich, chemotherapy resistant breast and kidney cancer cell lines compared to epithelial, TIC-depleted, chemotherapy sensitive cell lines.

Figure 1D:
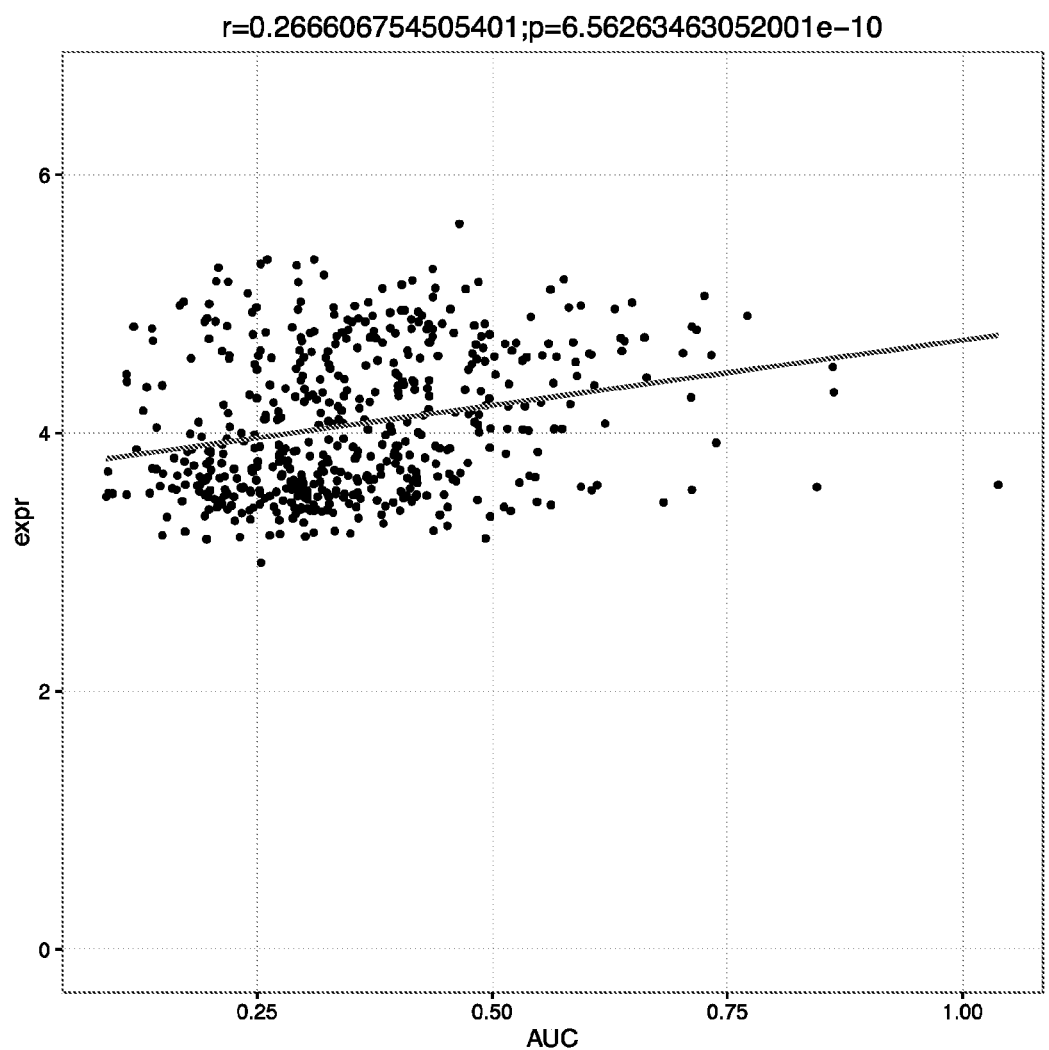
Figure 1E:
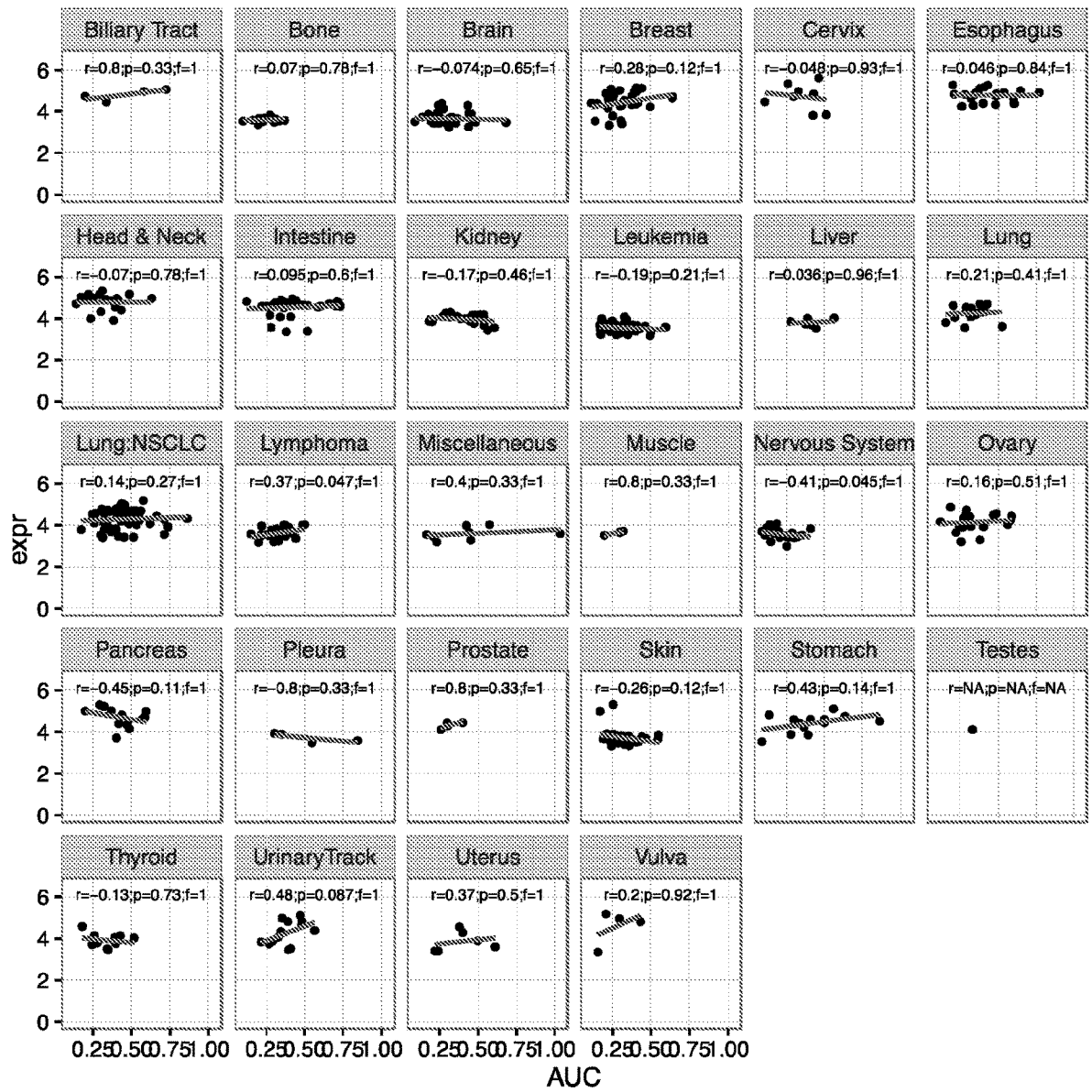
Figure 1F:
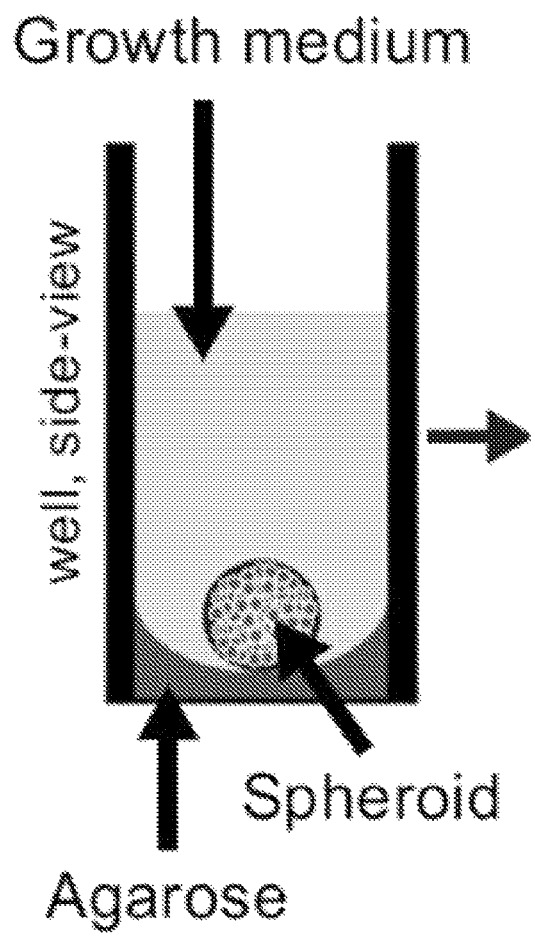

To determine whether sensitivity of cancer cells to chaetocin correlates with mesenchymal cell phenotype, the sensitivity or resistance of 800 cancer cell lines to chaetocin was assayed by the group of Cyril Benes treating each cell line with chaetocin at concentrations of 0.005 μM, 0.01 μM, 0.02 μM, 0.04 μM, 0.08 μM, 0.16 μM, 0.32 μM, 0.64 μM, and 1.28 μM. Cell viability was measured several days following treatment. Because the transcriptomes of the cell lines are available, a gene set enrichment analysis (GSEA) was performed in which cells were ranked based on their mesenchymal gene expression signature (y-axis) versus sensitivity to chaetocin (x-axis) FIGS. 1D-E. Chaetocin sensitivity was determined by calculating the area under the curve (AUC) of percent cells death versus chaetocin dose and calculating the area under the curve (AUC) for each cell line (x-axis). The mesenchymal gene signature used in this analysis was derived from the gene expression profile of an epithelial breast cancer cell line (MCF10) in which SNAIL was overexpressed (Javaid et al 2013). These cells display a mesenchymal phenotype upon SNAIL overexpression. The SNAIL-induced early-repressed gene set was used to calculate mesenchymal gene expression signature in this analysis. GSEA was done to ask whether chaetocin sensitivity correlates with the mesenchymal gene signature (r=coefficient of correlation, p=p-value). The findings of FIGS. 1D-1E indicate that cells with mesenchymal transcriptional signature are sensitive to chaetocin.

Tables 1-2 show the results of elastic net (EN) regression, a penalized linear modelling technique, to identify cooperative interactions among multiple transcripts which correlate with sensitivity (Table 1) or resistance (Table 2) to chaetocin treatment.

TABLE 1

Elastic net regression analysis of chaetocin sensitivity

| Gene | Frequency | Effect |
|---|---|---|
| NREP | 1 | −0.4950443 |
| ZEB2 | 0.99 | −0.2174459 |
| ARHGEF6 | 0.94 | −0.0887254 |
| TMEM131L | 0.92 | −0.0806591 |
| MEX3B | 0.75 | −0.0538461 |
| AFF3 | 0.72 | −0.0395303 |
| FBXL7 | 0.69 | −0.0356776 |
| PLEKHO1 | 0.68 | −0.0337116 |
| FOXN3 | 0.68 | −0.0297147 |
| ZNF549 | 0.64 | −0.0242701 |
| KATNAL1 | 0.64 | −0.0216114 |
| HMGXB4 | 0.48 | −0.0155139 |
| TTBK2 | 0.57 | −0.0145324 |
| TSHZ3 | 0.57 | −0.0144108 |
| TNPO2 | 0.42 | −0.006318 |
| SLC16A2 | 0.18 | −0.0040996 |
| RNF122 | 0.33 | −0.0036895 |
| VAMP4 | 0.33 | −0.0035611 |
| NIN | 0.33 | −0.0030086 |
| MAGEB10 | 0.18 | −0.0020914 |
| GFRA2 | 0.16 | −0.0013702 |
| JARID2 | 0.07 | −0.0009996 |
| SEPT6 | 0.03 | −0.0009556 |
| ADGRA2 | 0.03 | −0.0008249 |
| GPC2 | 0.03 | −0.0008043 |
| ESS2 | 0.07 | −0.0007965 |
| ZNF136 | 0.07 | −0.0007581 |
| IFFO1 | 0.03 | −0.000747 |
| PI4KA | 0.07 | −0.0007168 |
| PBRM1 | 0.03 | −0.0006938 |
| EVL | 0.03 | −0.0006415 |
| LIMD2 | 0.03 | −0.0006163 |
| JAM2 | 0.03 | −0.0005928 |
| RNF150 | 0.03 | −0.0005375 |
| TCF4 | 0.03 | −0.0004947 |
| PTBP2 | 0.03 | −0.0004588 |
| ZNF439 | 0.03 | −0.0004488 |
| RIMS3 | 0.03 | −0.0004462 |
| *TNRC6C* | 0.03 | −0.0004301 |
| MAP3K3 | 0.03 | −0.0004246 |

TABLE 1-continued

Elastic net regression analysis of chaetocin sensitivity

| Gene | Frequency | Effect |
|---|---|---|
| EIF3G_CN | 0.03 | −0.0004179 |
| FAM212A | 0.03 | −0.000386 |
| SAP30 | 0.03 | −0.0003717 |
| AP1M1 | 0.03 | −0.0003477 |
| METTL14 | 0.03 | −0.000329 |
| EBF1 | 0.03 | −0.0003269 |
| SMARCA4 | 0.03 | −0.0003253 |

TABLE 2

Elastic net regression analysis of chaetocin resistance

| Gene Name | Frequency | Effect |
|---|---|---|
| PPARG | 0.03 | 0.00094769 |
| AKR1C2 | 0.03 | 0.00098325 |
| DHCR7 | 0.18 | 0.00156451 |
| PPAP2C | 0.24 | 0.00249999 |
| VWDE | 0.18 | 0.00279531 |
| PNO1 | 0.33 | 0.0039486 |
| SRXN1 | 0.5 | 0.00445076 |
| FERMT1 | 0.61 | 0.00569307 |
| SGK2 | 0.46 | 0.00693698 |
| EPCAM | 0.5 | 0.00711634 |
| SLC35F2 | 0.35 | 0.00758156 |
| CYP2S1 | 0.44 | 0.00913731 |
| ECI1 | 0.46 | 0.00961131 |
| C11orf54 | 0.48 | 0.01157074 |
| LSR | 0.63 | 0.01684451 |
| FTL | 0.49 | 0.01978019 |
| ZDHHC23 | 0.61 | 0.0251087 |
| CMTM4 | 0.67 | 0.0259746 |
| SH3BGRL2 | 0.68 | 0.02649864 |
| MROH9 | 0.54 | 0.02853239 |
| KLF5 | 0.68 | 0.03227002 |
| CYSTM1 | 0.7 | 0.03510757 |
| TXNRD1 | 0.7 | 0.038292 |
| SYNGR2 | 0.74 | 0.04247359 |
| AKT1S1 | 0.75 | 0.05141428 |
| CYP4F11 | 0.85 | 0.05607174 |
| EID3 | 0.83 | 0.08004353 |
| CMTM8 | 0.89 | 0.08562629 |
| NQO1 | 0.96 | 0.08968791 |
| GDE1 | 0.94 | 0.09767863 |
| KRT8 | 0.96 | 0.10380447 |
| ABCC3 | 1 | 0.1175382 |
| MGAT4B | 0.97 | 0.13354118 |
| BAIAP2L1 | 1 | 0.14460199 |
| UGDH | 1 | 0.15593392 |
| HTATIP2 | 0.98 | 0.15980576 |
| LIPH | 1 | 0.17505171 |
| AGPAT9 | 1 | 0.19069813 |
| GCLC | 1 | 0.19122061 |
| SLC7A11 | 0.98 | 0.19141043 |
| F2RL1 | 1 | 0.19283263 |
| SQSTM1 | 1 | 0.21184296 |
| GPX2 | 1 | 0.21406466 |
| TLCD1 | 1 | 0.22138448 |
| FZD5 | 1 | 0.23072741 |
| KRT18 | 1 | 0.23216695 |
| RPE | 1 | 0.36878775 |

TABLE 3

Summary of elastic net regression analysis focusing on chromatin genes which contribute to sensitivity

| Gene Name | Effect |
|---|---|
| *ZEB2* | −0.2174459 |
| *FOXN3* | −0.0297147 |

TABLE 3-continued

Summary of elastic net regression analysis focusing on chromatin genes which contribute to sensitivity

| Gene Name | Effect |
| --- | --- |
| TSHZ3 | −0.0144108 |
| JARID2 | −0.0009996 |
| ZNF136 | −0.0007581 |
| SMARCA4 | −0.0003717 |
| SAP30 | −0.0003253 |
| ZNF85 | −0.0002408 |
| HDAC5 | −0.0001952 |
| BEND5 | −0.0001146 |
| PBRM1 | −0.0006938 |
| NFATC4 | −6.32E−05 |
| SMARCB1 | −3.68E−05 |
| BRD1 | −4.06E−05 |
| TRIM22 | −1.44E−05 |
| SUFU | −8.75E−06 |
| JAZF1 | −3.17E−06 |

In Tables 1-3, Gene: the name of the gene in EN regression model; Frequency: 100 modeling iterations were performed and the frequency at which each transcript is present in the resulting model is reported (e.g. a frequency of 1 indicates that the feature was present in all 100 models); and Effect: Strength of the association between a gene and chaetocin response. Effect <0: Sensitizing feature. Effect >0 resistant-inducing feature. Bolded genes correspond to those encoding proteins involved in chromatin regulation. Italicized letters correspond to chromatin-regulatory genes that have been shown to be involved in EMT.

Gene ontology analysis revealed that chaetocin sensitivity correlated with a set of 16 gene clusters, encompassing genes involved in transcriptional co-repression, chromatin regulation, DNA-binding via zinc finger proteins, mental retardation, chromatin/neurogenesis, and transcription. The same analysis performed with respect to chaetocin resistance revealed 30 gene clusters, encompassing oxidation/reduction processes, NADP binding, reactive oxygen species response, tight junctions, and actin binding, among others. Table 3 is the results of EN analysis focusing only one chromatin regulators. Together these EN regression analyses reveal that expression of several chromatin-regulatory proteins with previously identified roles in EMT correlate with chaetocin sensitivity.

Figure 1G:
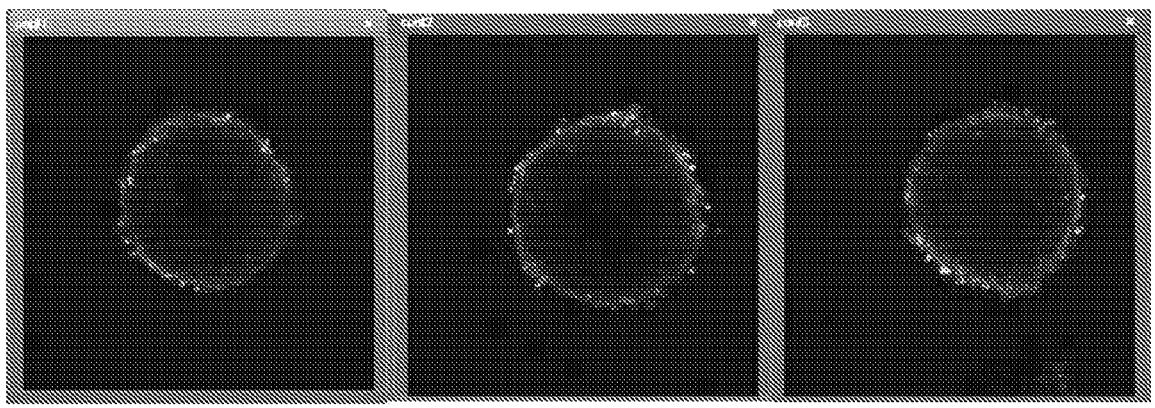
Figure 1H:
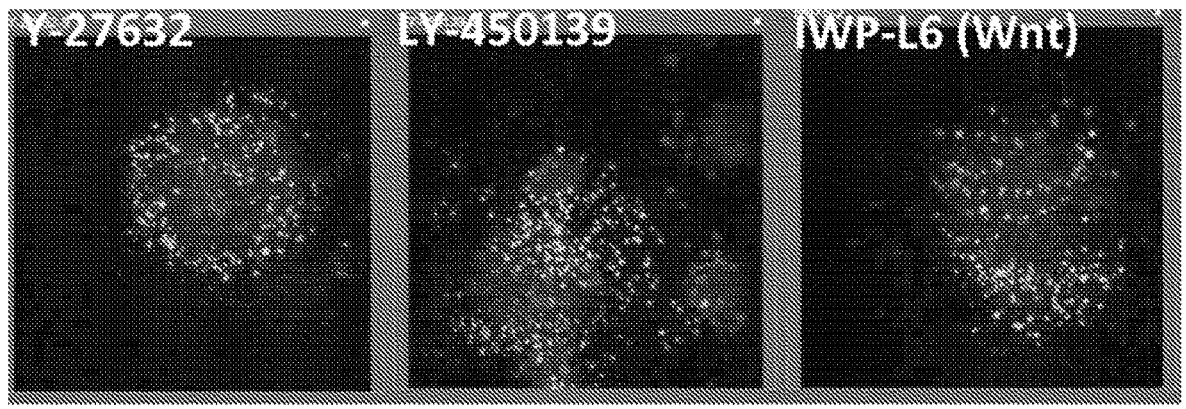
Figure 1I:
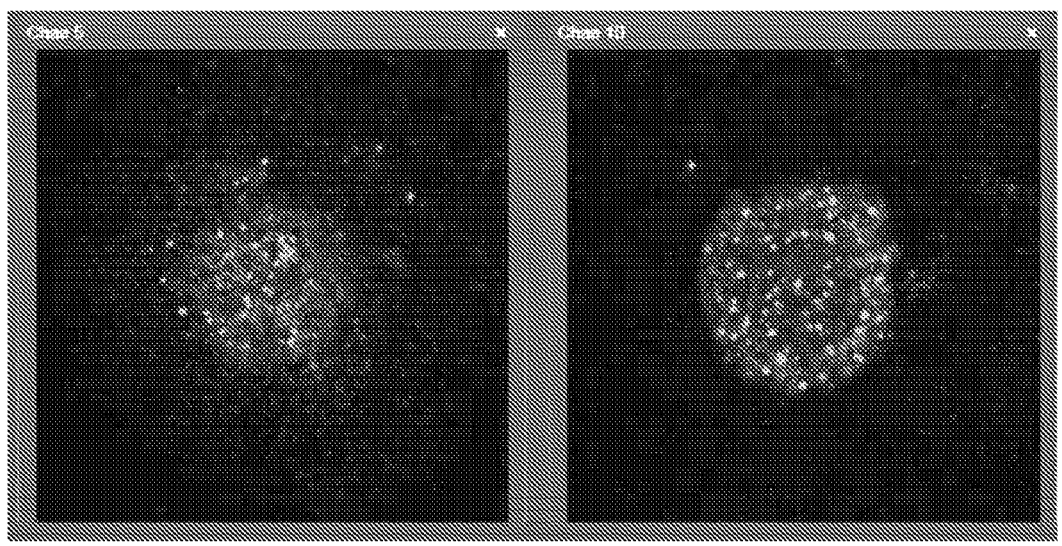

To determine whether chaetocin affects TIC death in a tumor-like environment, 3-D tumor spheroid assays were performed in the presence or absence of chaetocin. Tumor spheroids are a model of a real tumor, as they form a 3-D cell mass similar to tumors in vivo. The local microenvironment of a spheroid recapitulates many of the in vivo properties of tumor. Importantly, the hypoxic and often nutrient depleted microenvironment at the center of the tumor is favorable for converting epithelial, non-TIC, chemotherapy-sensitive cancer cells into mesenchymal, TIC-rich, chemotherapy-resistant cells. In this assay, cells were grown on 2-dimensional plates for two days and then transferred to the spheroid system showed in FIG. 1F and grown for another 3 days. Pharmacological agents were added and cell viability was calculated by staining cells with Sytox, which stains dead cells green, and DAPI, which stains the nuclei of all cells (living or dead). to provide the total cell number. Using this method, the total fraction of dead cells was calculated and compared between different drug conditions. More importantly, the location of dead cells within the sphere is visualized with Sytox (green) staining. FIGS. 1G-1I show fluorescence images of tumor spheroids under control conditions (no treatment; FIG. 1G), under treatment with various experimental chemotherapeutic agents (Y-27632, LY-450139, and IWP-L6 (Wnt); FIG. 1H), and with chaetocin treatment (FIG. 1I). Y-27632 is an experimental chemotherapeutic agent which specifically inhibits ROCK family of kinases. This family of kinases are thought to be important for survival of TIC cells. IWP-L6 is an inhibitor of Wnt pathway—a pathway important for TIC cell survival and formation. LY-450139 is a NOTCH pathway inhibitor. NOTCH is also important for TIC cell viability and survival. These three agents were used as positive controls and to determine the effectiveness of chaetocin in killing TICs compared to other promising chemotherapeutics agents currently under clinical consideration for killing TIC cells. These results of FIGS. 1F-1I show that treatment with Y-27632, LY-450139, and IWP-L6 mostly result in death of cells on the exterior of the spheroid (with little effect on the cells in the interior of spheroids), whereas chaetocin preferentially and effectively kills the inner spheroid cells, revealing its selective and potent cytotoxic activity on mesenchymal, TIC-rich niches which are often found in the interior of solid tumors.

Figure 1J:
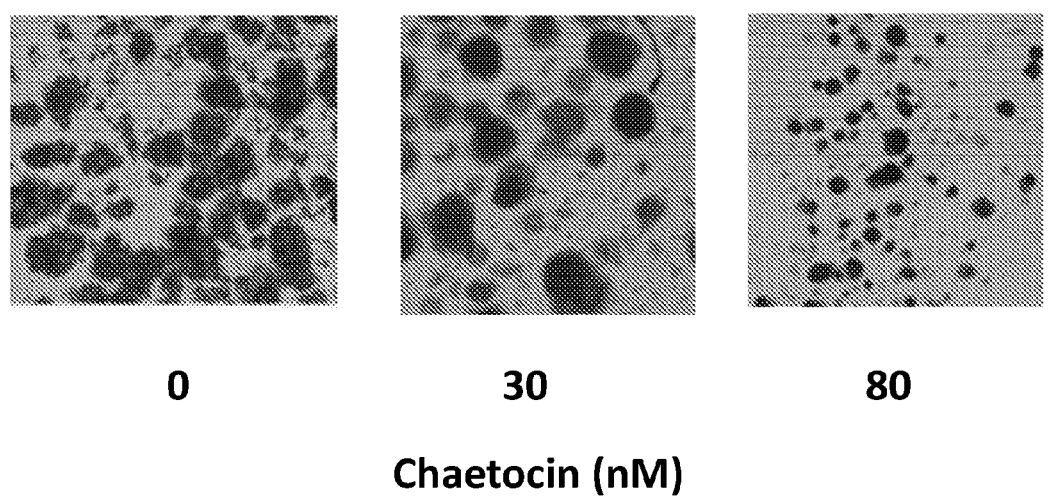
Figure 1K:
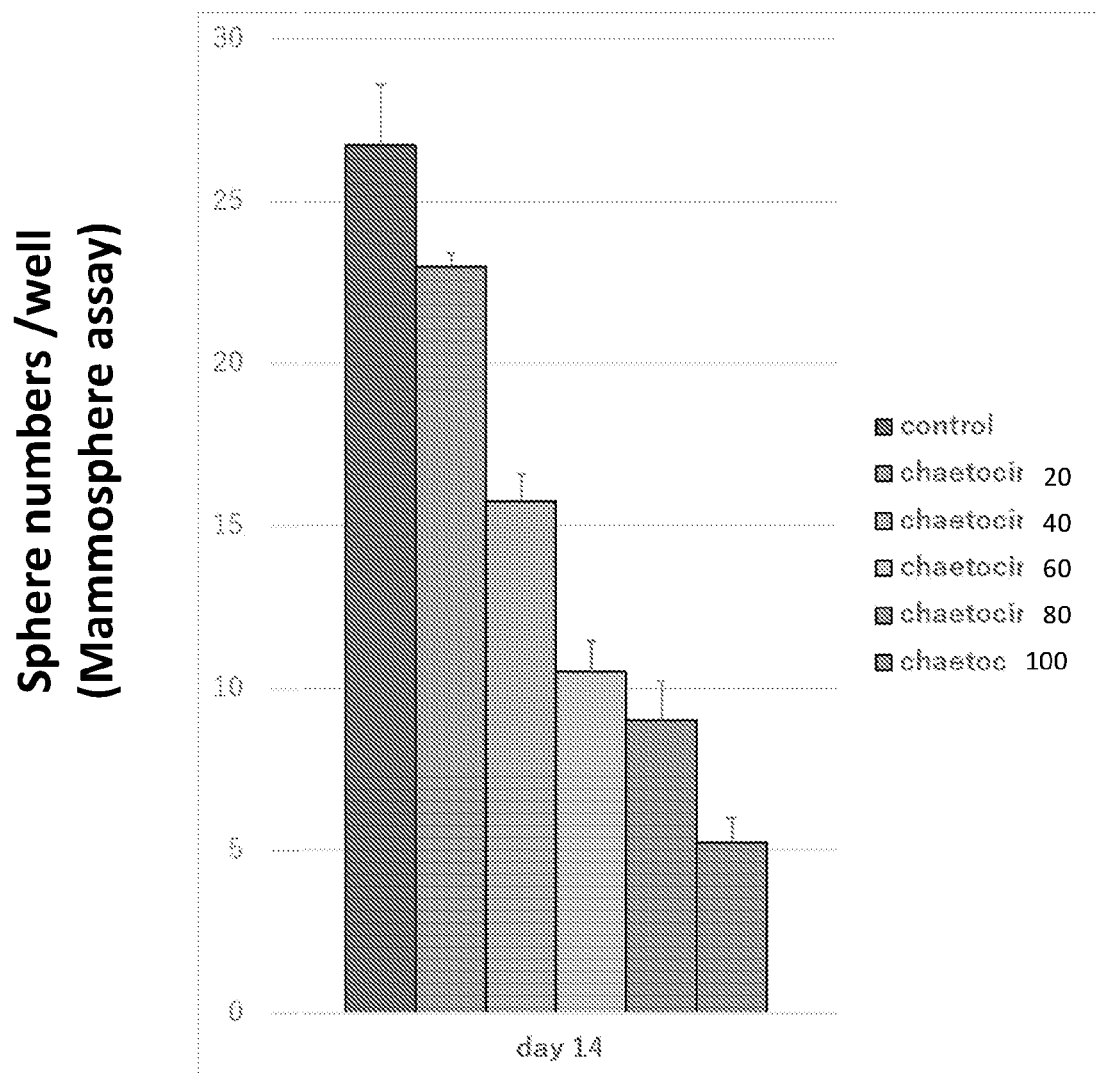

To further determine the effect of chaetocin on eliminating TICs, a tumorsphere assay was performed on cancer cells under increasing concentrations of chaetocin. A tumorsphere is a solid spherical formation developed from the proliferation of one cancer stem/progenitor cell. These tumorspheres are easily distinguishable from single or aggregated cells as the cells appear to become fused together and individual cells cannot be identified. The size of the tumorspheres vary from less than 50 micrometers to 250 micrometers, and number of tumorspheres formed was used to characterize the cancer stem/progenitor cell population within a population of in vitro cultured cancer cells. Cells were enriched for TICs and grown in serum-free, non-adherent conditions in order to enrich the cancer stem/progenitor cell population as only cancer stem/progenitor cells can survive and proliferate in this environment. FIG. 1J shows tumorspheres in culture treated with varying concentrations of chaetocin (0 nM, 30 nM, and 80 nM). FIG. 1K shows the quantification of the number of tumorspheres per well under different chaetocin concentrations. These results indicate that chaetocin can eliminate TICs at low doses.

Figure 2A:
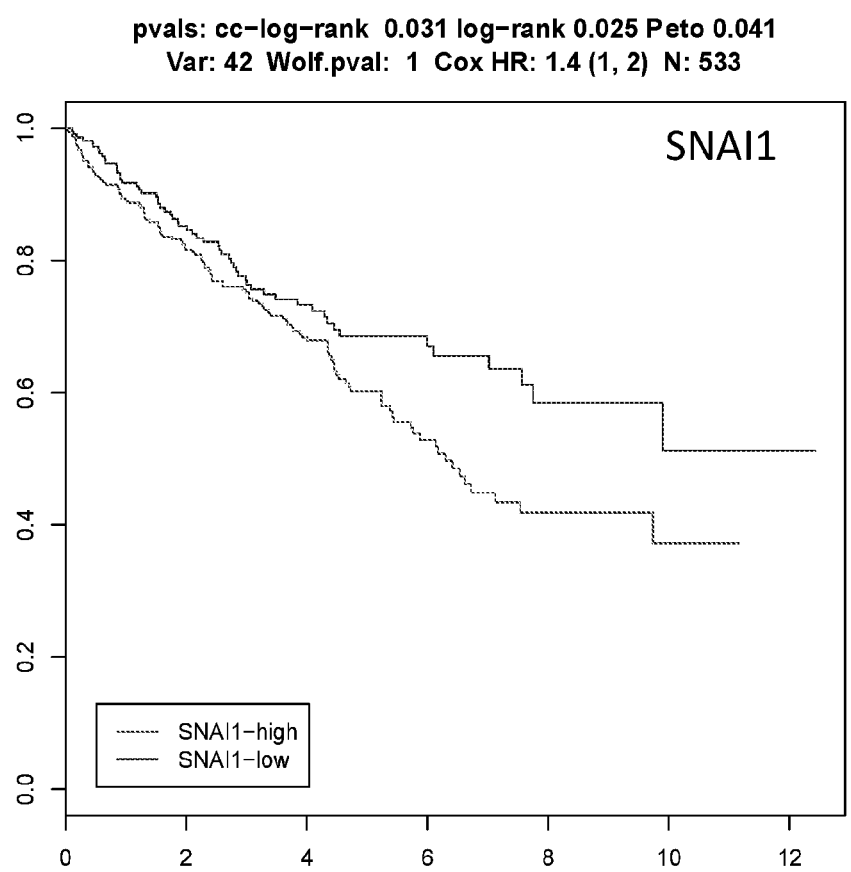
FIGS. 2A-2O are a series of survival plots of cancer patients stratified by high or low expression of epithelial-to-mesenchymal transition (EMT) transcription factors (TFs), SNAI1, SNAI2, TWIST1, ZEB1, and ZEB2. These TFs are critical inducers of EMT which are upregulated in mesenchymal cells.
Figure 2B:
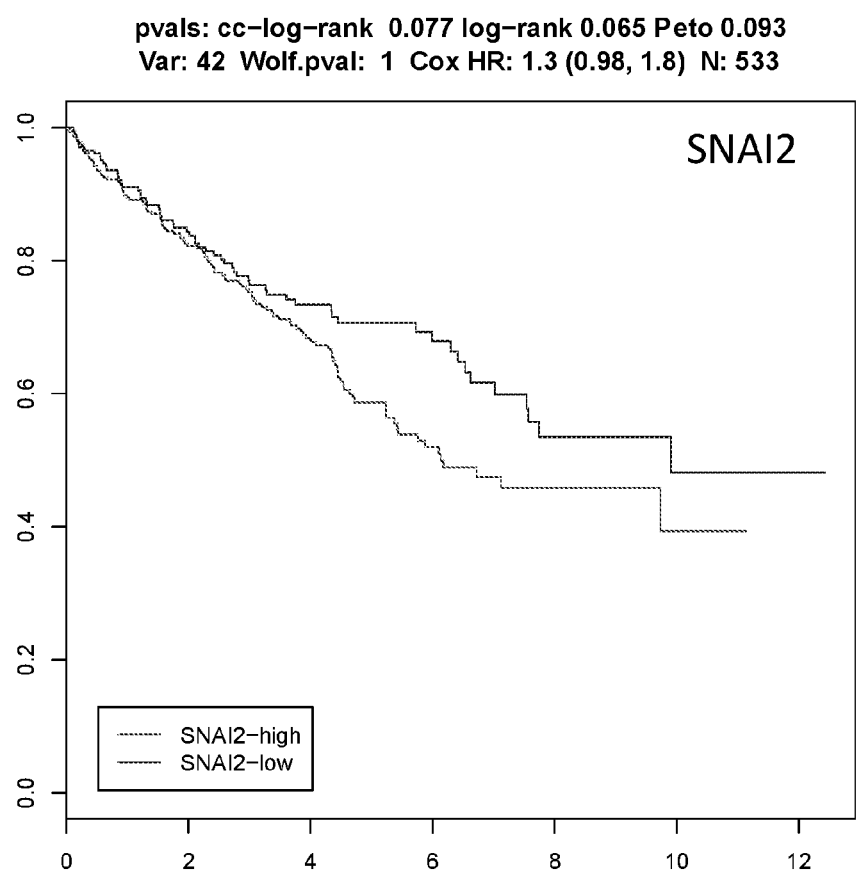
Figure 2C:
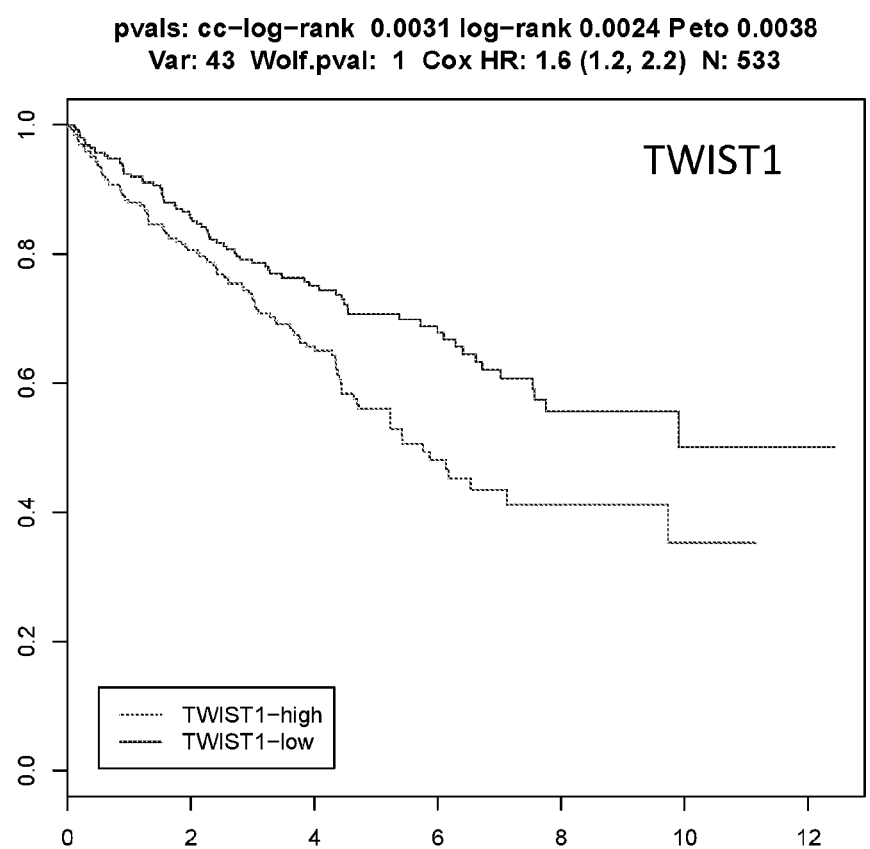
Figure 2D:
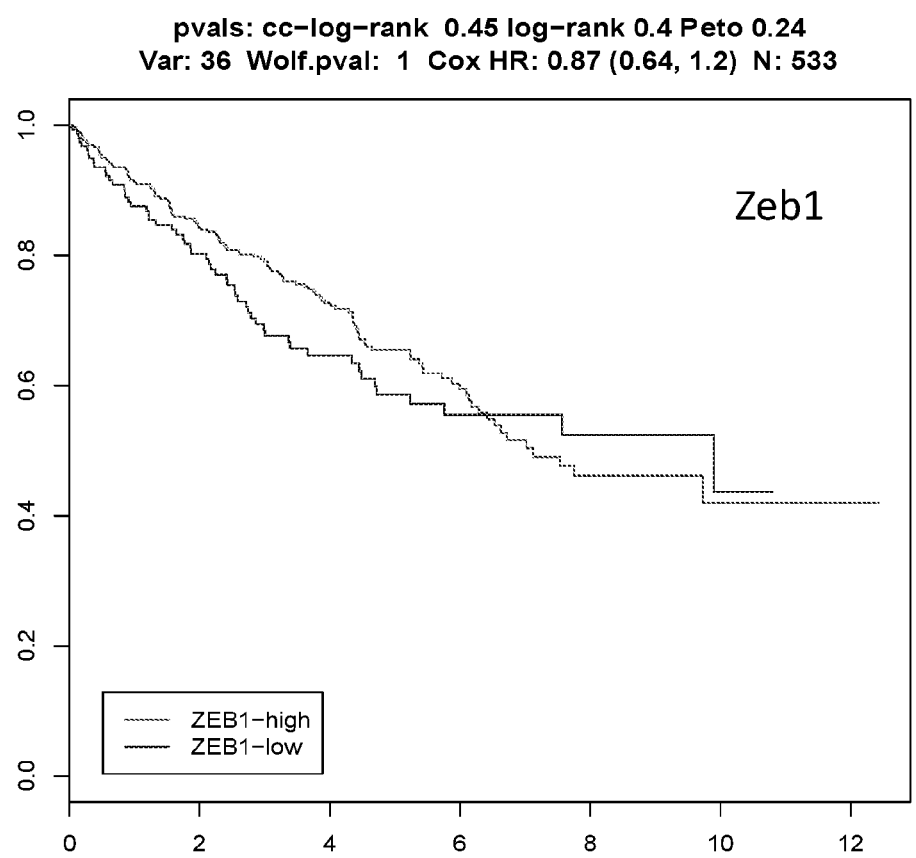

Example 2. Increased Expression of Mesenchymal Markers Predicts Poor Outcomes in Cancer Patients To determine whether increased expression of mesenchymal transcription factors predicts poor patient outcomes in cancer, the survival rates of patients stratified by high or low expression of mesenchymal transcription factors (TF) SNAI1 (snail family transcriptional repressor 1), SNAI2 (snail family transcriptional repressor 2), TWIST1 (twist family BHLH transcription factor 1), ZEB1 (zinc finger E-box binding homeobox 1), and ZEB2 (zinc finger E-box binding homeobox 2) were compared across clear cell renal cell carcinoma cancer (ccRCC) patients (FIGS. 2A-2E), kidney renal papillary cell carcinoma patients (FIGS. 2F-2J), and brain lower grade glioma patients (FIGS. 2K-2O). These TFs are critical inducers of EMT which are upregulated in mesenchymal cells. These results indicate that increased expression of mesenchymal TFs SNAI1 (FIG. 2A, FIG. 2F, FIG. 2K), SNAI2 (FIG. 2B, FIG. 2G, FIG. 2L), TWIST1 (FIG. 2C, FIG. 2H, FIG. 2M), Zeb1 (FIG. 2D, FIG. 2I, FIG.

Figure 2E:
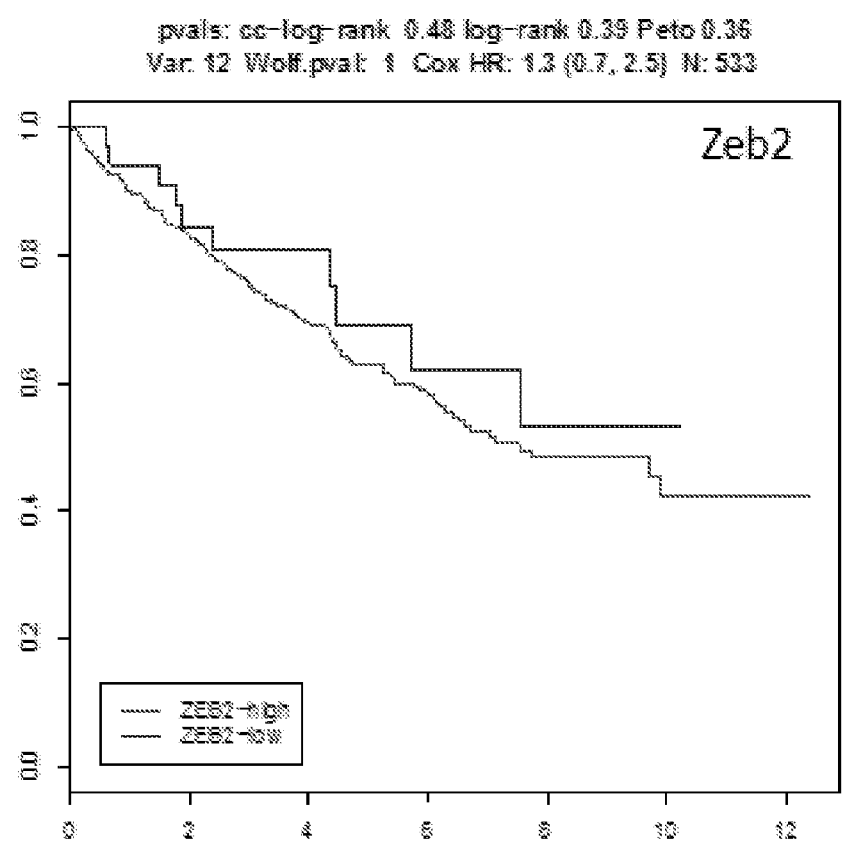
Figure 2F:
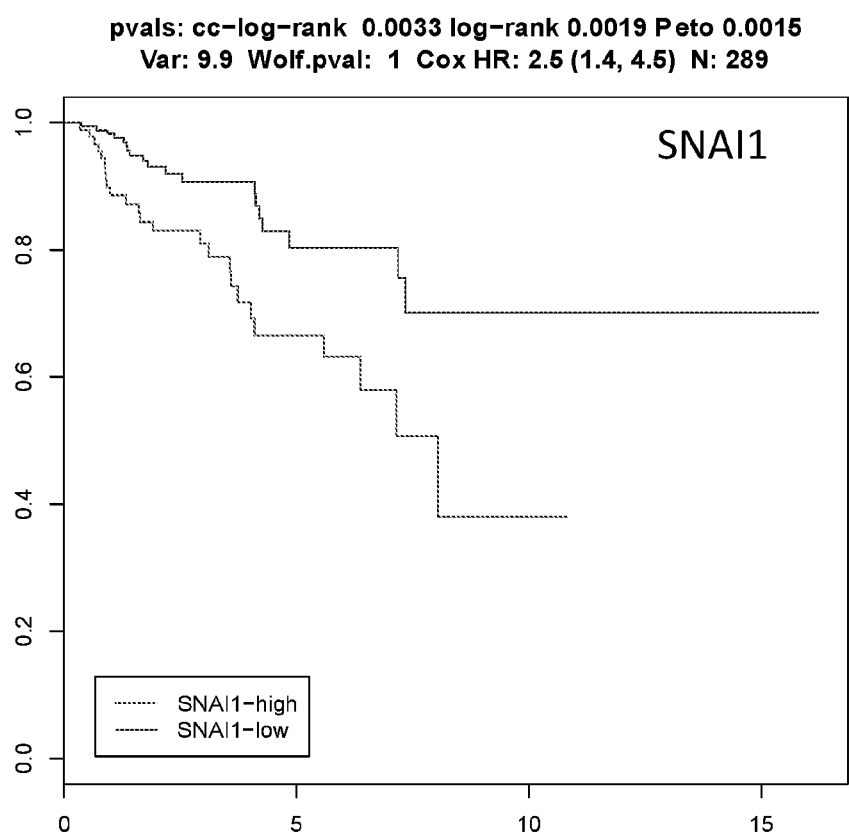
FIGS. 2F-2J show the survival plots of kidney renal papillary cell carcinoma patients having high or low expression of SNAI1 (FIG. 2F), SNAI2 (FIG. 2G), TWIST1 (FIG. 2H), Zeb1 (FIG. 2I), and Zeb2 (FIG. 2J).
Figure 2G:
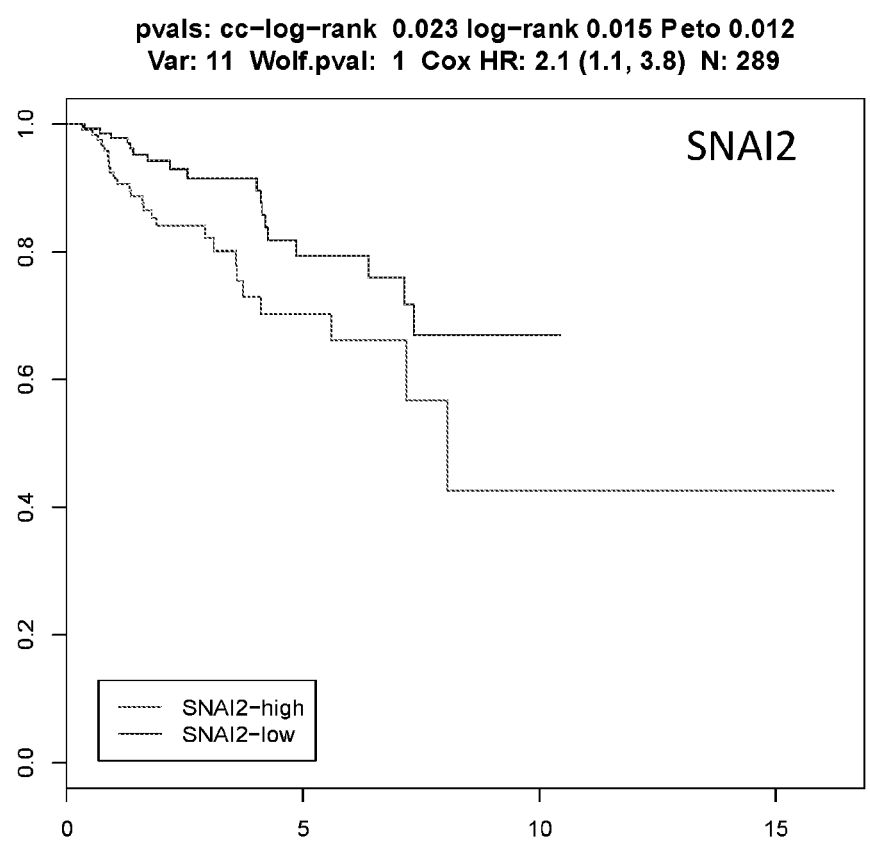
Figure 2H:
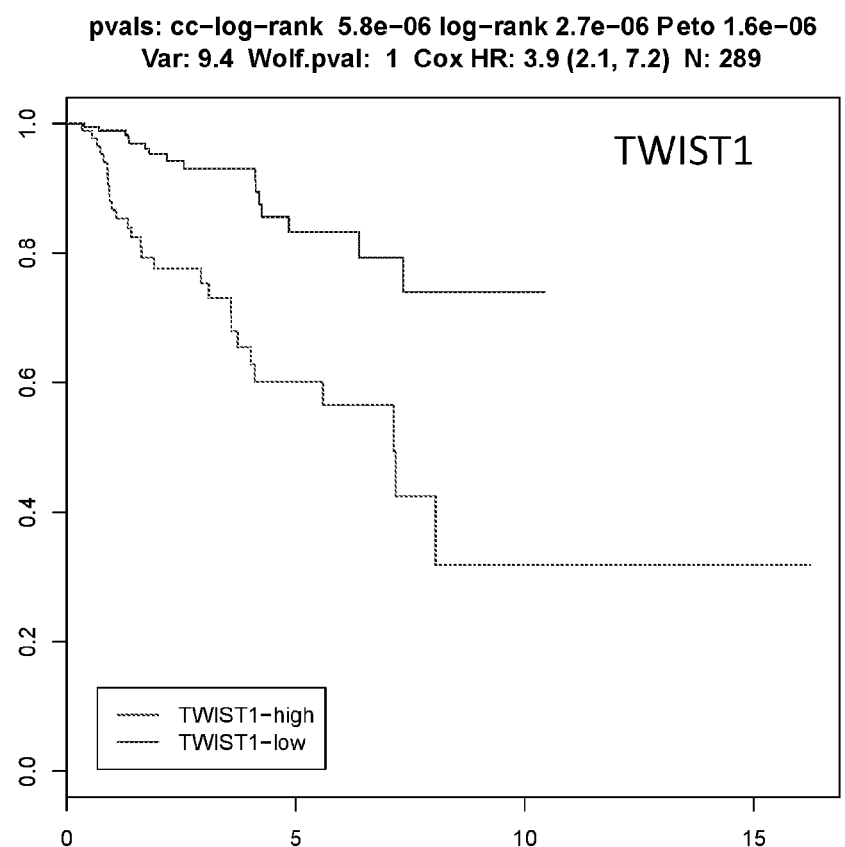
Figure 2I:
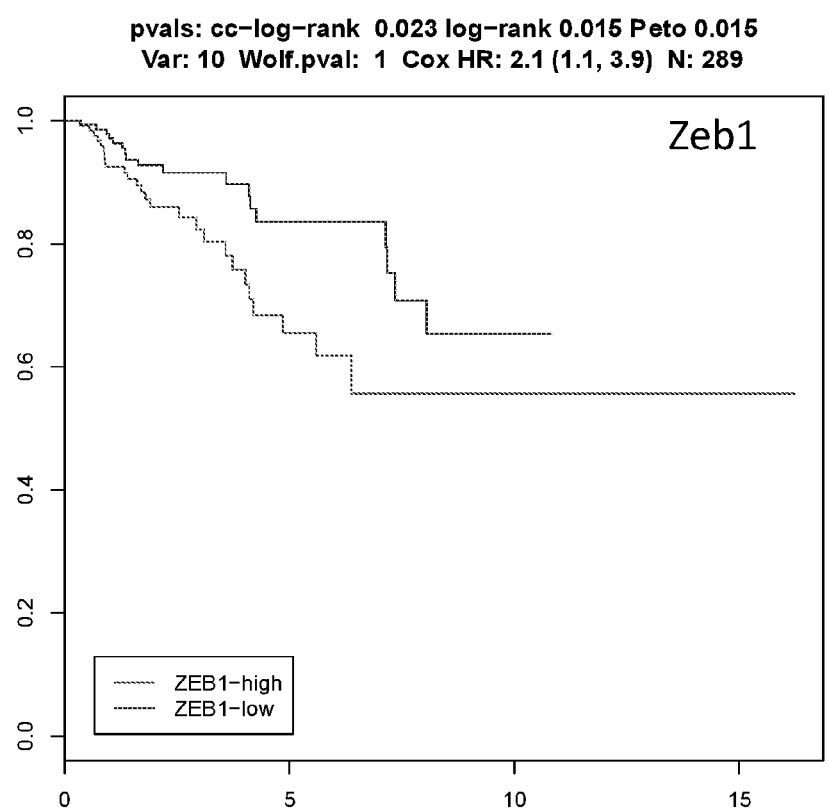
Figure 2J:
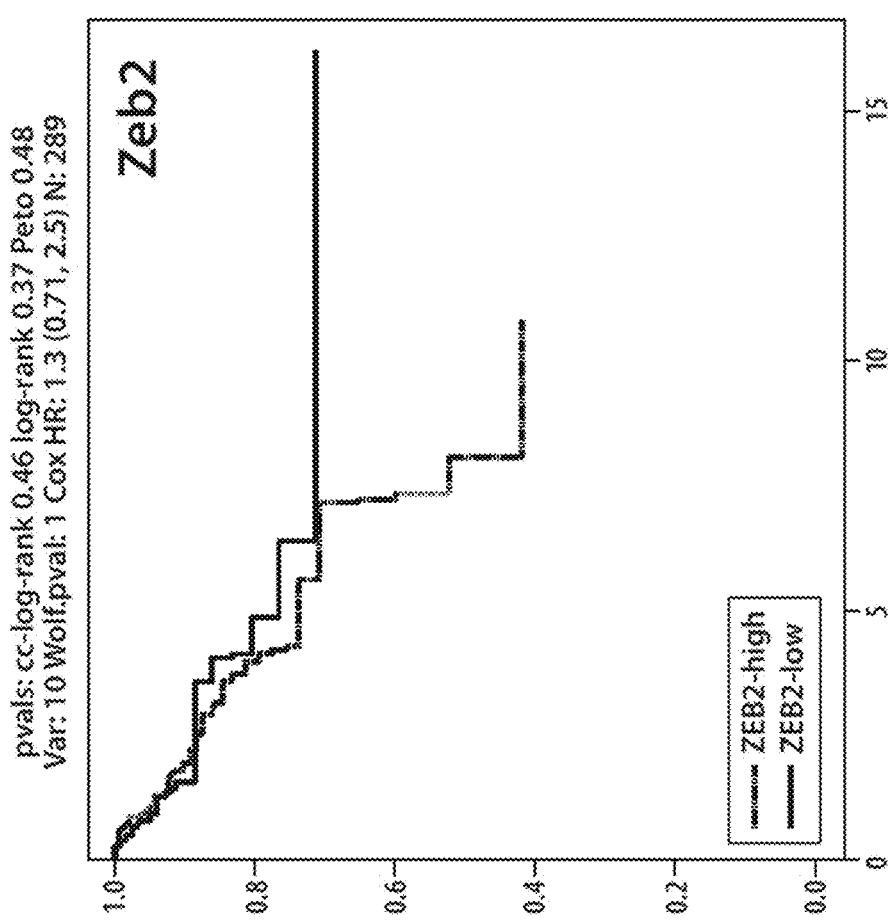
Figure 2K:
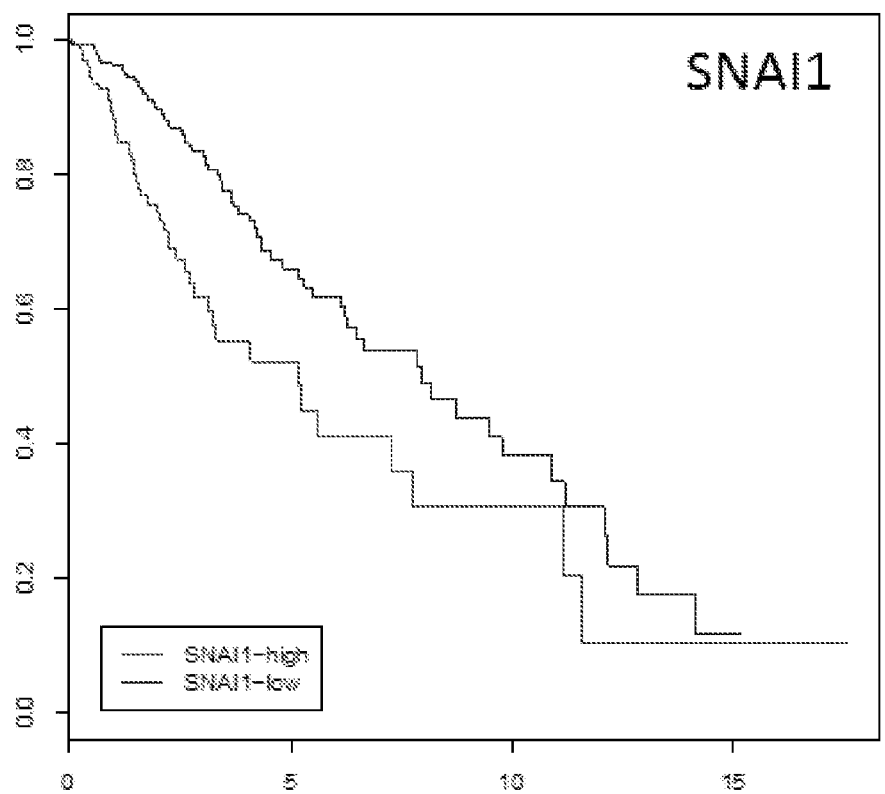
Figure 2L:
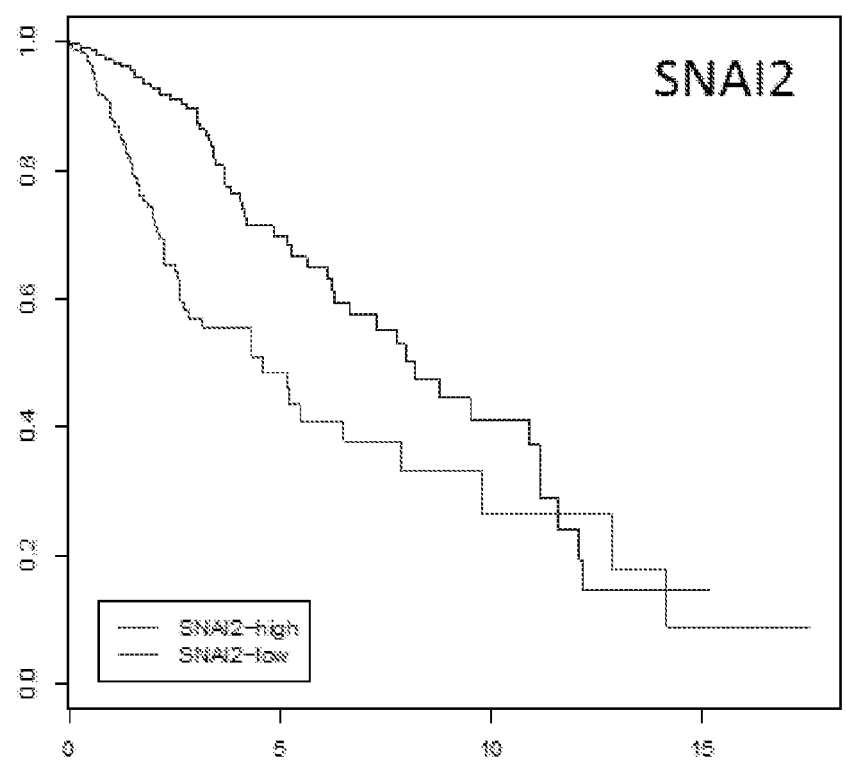
Figure 2M:
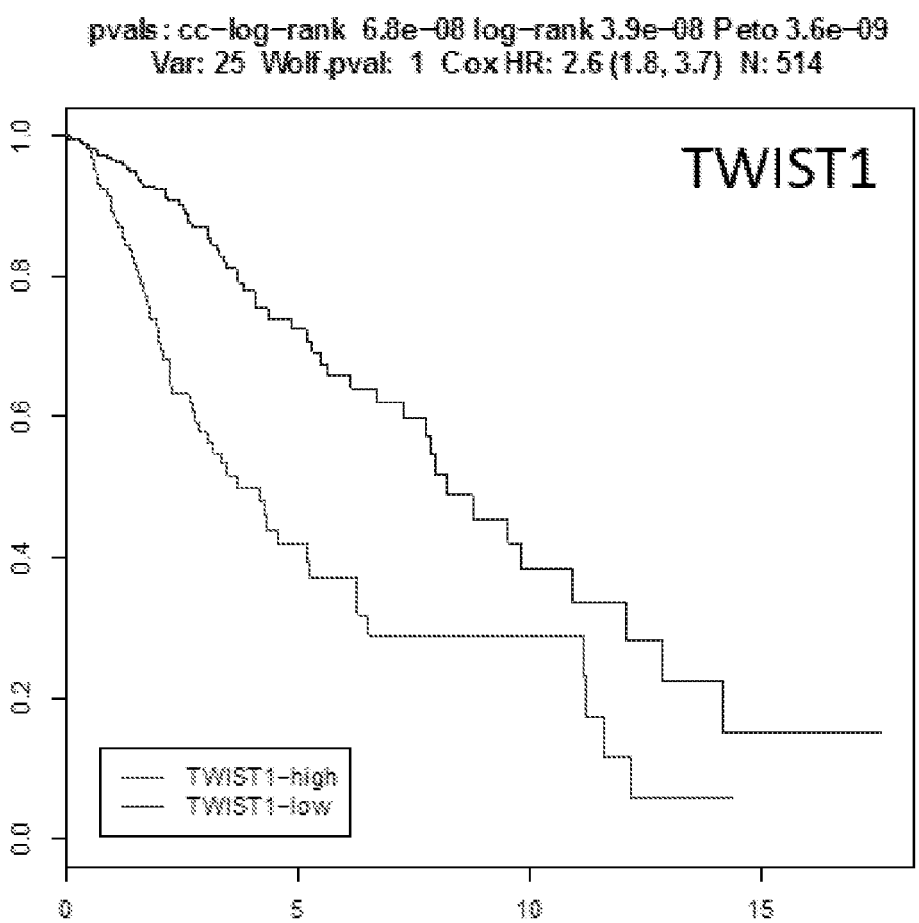
Figure 2N:
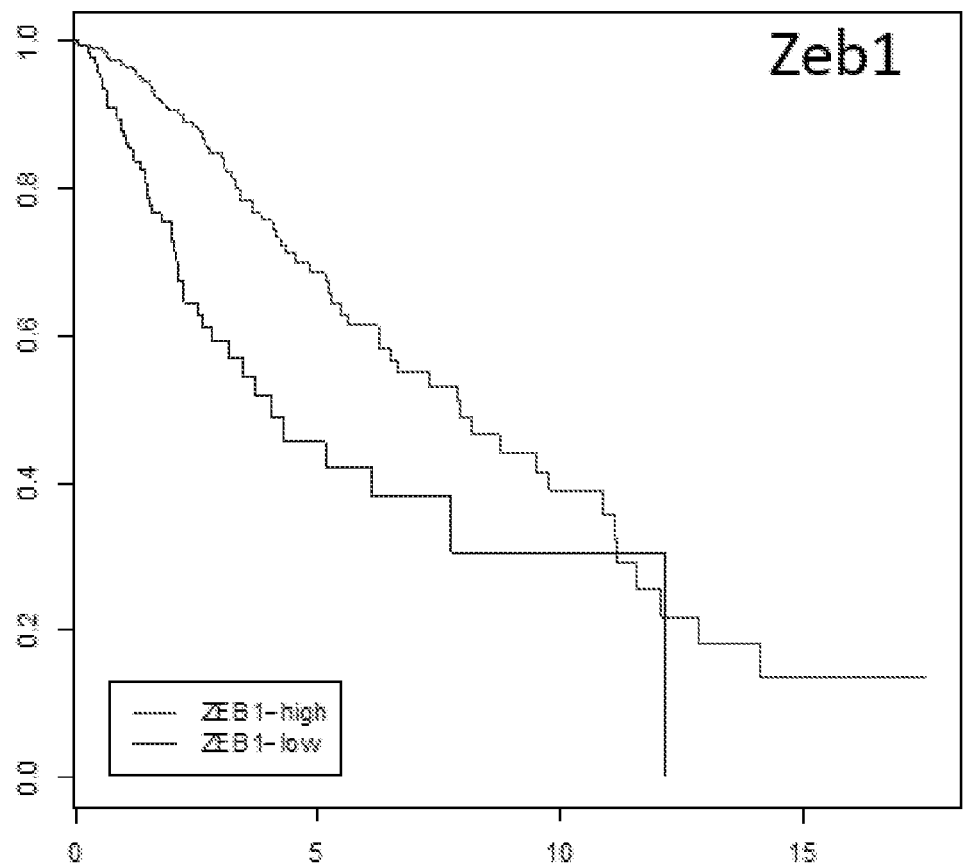
Figure 2O:
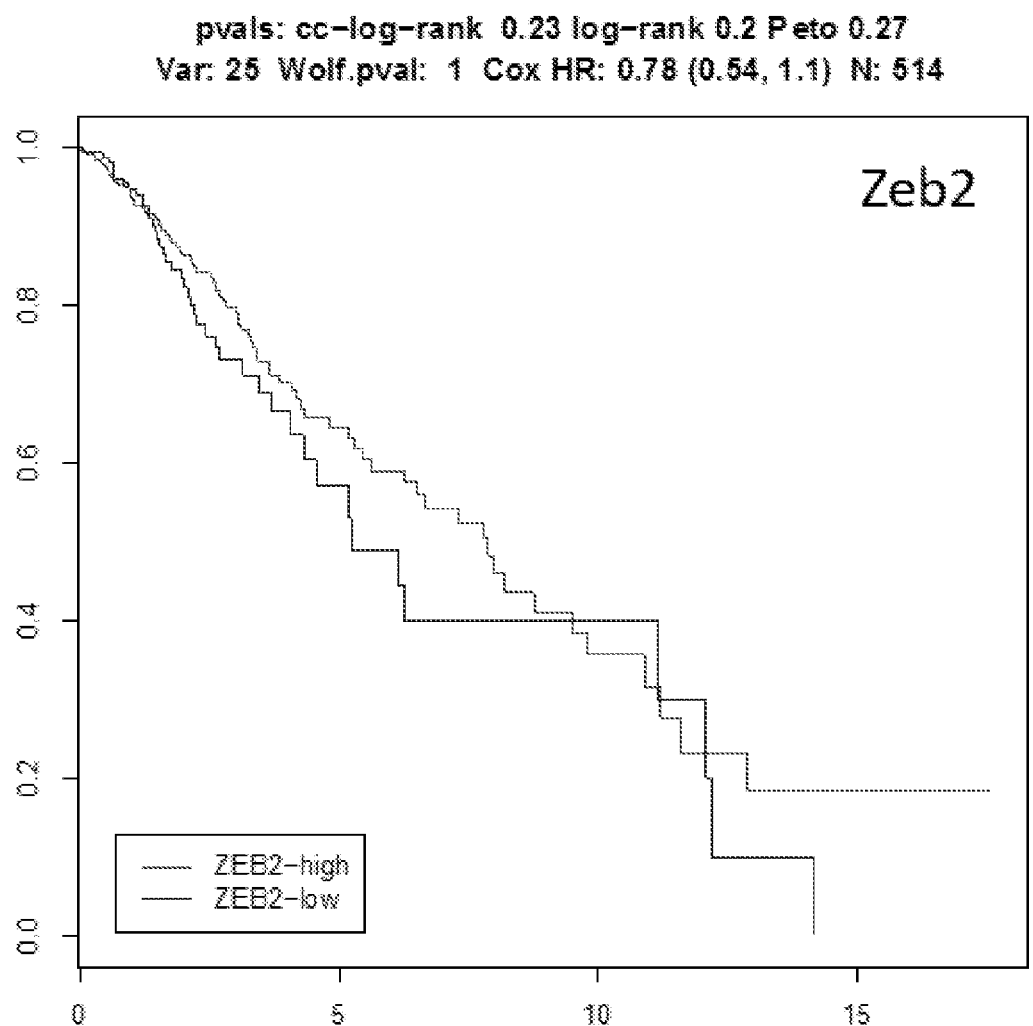

2N), and Zeb2 (FIG. 2E, FIG. 2J, FIG. 2O predicts poor patient survival in several cancers.

Figure 3A:
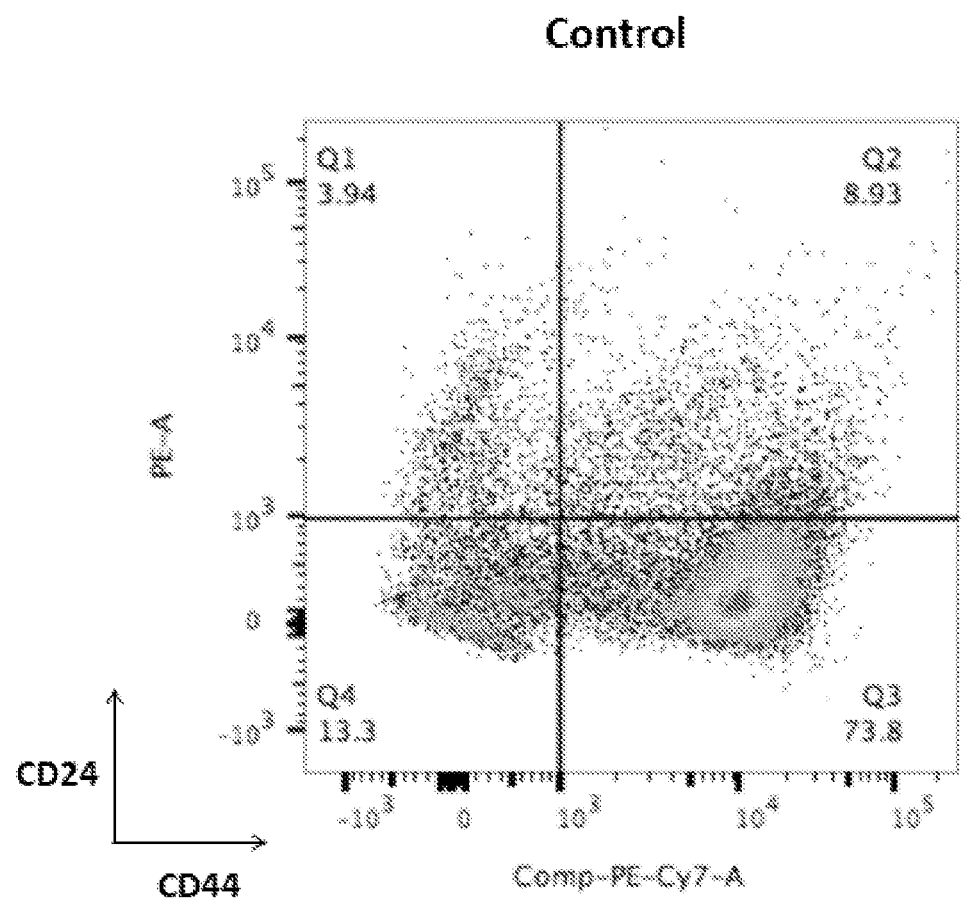
FIGS. 3A-3X are a series of figures demonstrating that treatment with chaetocin results in epigenetic reprogramming of breast cancer TICs into non-TICs.
Figure 3B:
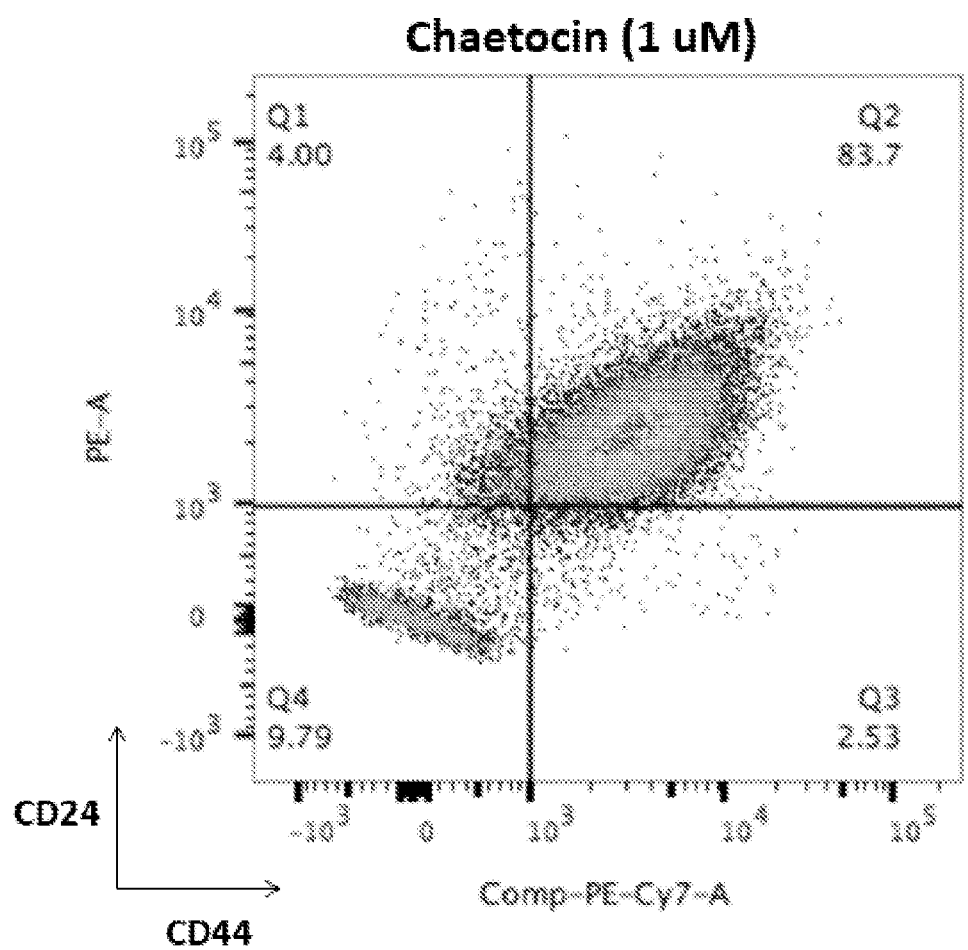
FIG. 3B shows FACS heat maps of HMLE-SNAIL cells treated with 1 µM chaetocin after two days. These data show that chaetocin effectively reprograms TICs into a non-TIC cell fate.

Example 3. Transient Heterochromatin Inhibition Causes an Epigenetic Change, Stably Reversing EMT and Chemotherapy Resistance in Cancer Models Cell surface markers can be used to identify mesenchymal, TIC cells. In breast cancer, the presence of CD44 and absence of CD24 markers are indicators of TICs. Specifically, cells expressing high levels of CD44 and no expression of CD24 are considered TICs, whereas cells expressing CD24 are considered non-TICs. HMLE cells display these cell surface markers upon overexpression of SNAIL or TWIST, which turns on the EMT transcriptional program and promotes a mesenchymal TIC state in cancer cells. To determine whether chaetocin treatment alters the mesenchymal phenotype of TICs, these markers were used to track the fate of HMLE-SNAIL cells following chaetocin treatment (1 µM) using fluorescence-activated cell sorting (FACS) analysis. FIGS. 3A-3B show a heat map plot of FACS results under control conditions (FIG. 3A) and following chaetocin treatment (FIG. 3B). The y-axis corresponds to CD24 fluorescence intensity and the x-axis corresponds to CD44 fluorescence intensity. FIG. 3A demonstrates that HMLE-SNAIL cells are enriched for TICs by the prevalence of CD44+/CD24-cells. FIG. 3B shows FACS heatmap of HMLE-SNAIL cells treated with 1 uM of chaetocin for two days. These results indicate that chaetocin treatment reprograms TICs into a non-TIC phenotype.

Figure 3C:
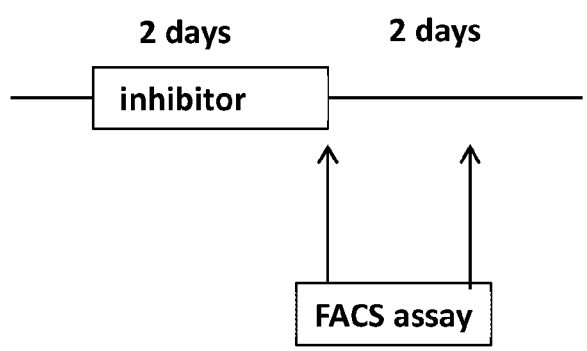
FIG. 3C shows a schematic (top panel) of an experiment to test whether chaetocin causes an epigenetic change in TICs converting them into non-TICs. Cultured mesenchymal, TIC-rich HMLE-TWIST cells were treated with increasing concentrations of chaetocin for 2 days, washed and then incubated in chaetocin-free media for two days. CD44/CD24 FACS analyses were performed either immediately or two days after chaetocin removal. This experimental design will reveal whether a transient exposure to chaetocin is sufficient to cause an epigenetic change, which would persist even after chaetocin removal, reprogramming mesenchymal TICs into non-TICs.
Figure 3D:
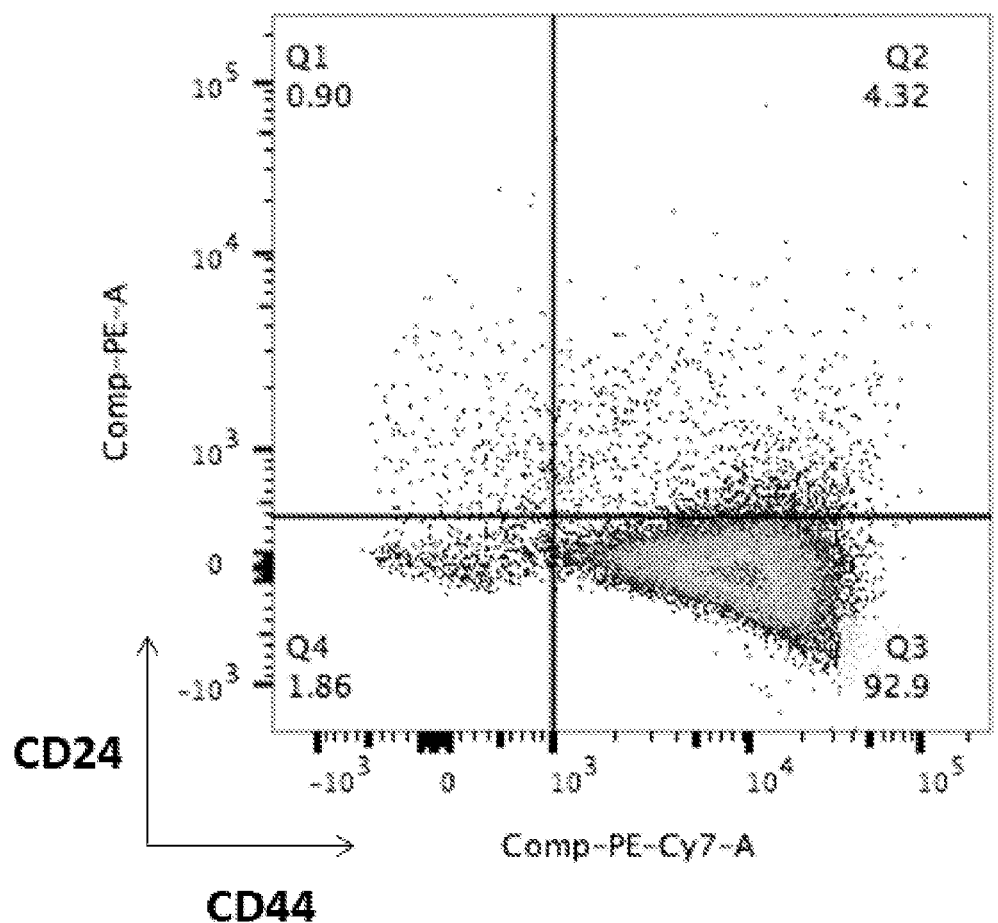
FIG. 3D shows a heat map of CD44/CD24 FACS analysis of HMLE-TWIST cells under control condition (e.g., no chaetocin).
Figure 3E:
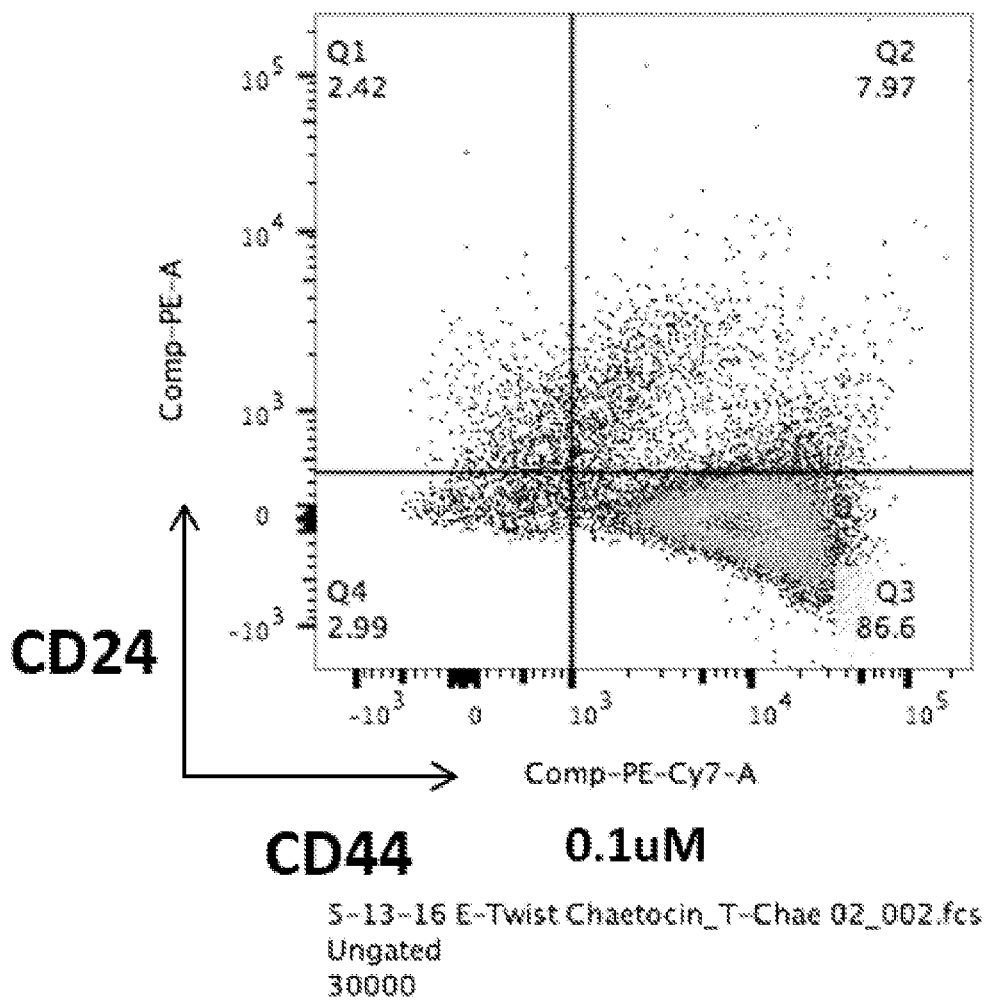
FIGS. 3E-3H show the results of FACS analysis of HMLE-TWIST cells immediately after treatment with four different concentrations of chaetocin (0.1 µM, FIG. 3E; 0.15 µM, FIG. 3F; 0.2 µM, FIG. 3G; and 0.5 µM, FIG. 3H). Compared to FIG. 3D, these graphs show that chaetocin converts TICs into non-TICs in a dose dependent manner.
Figure 3F:
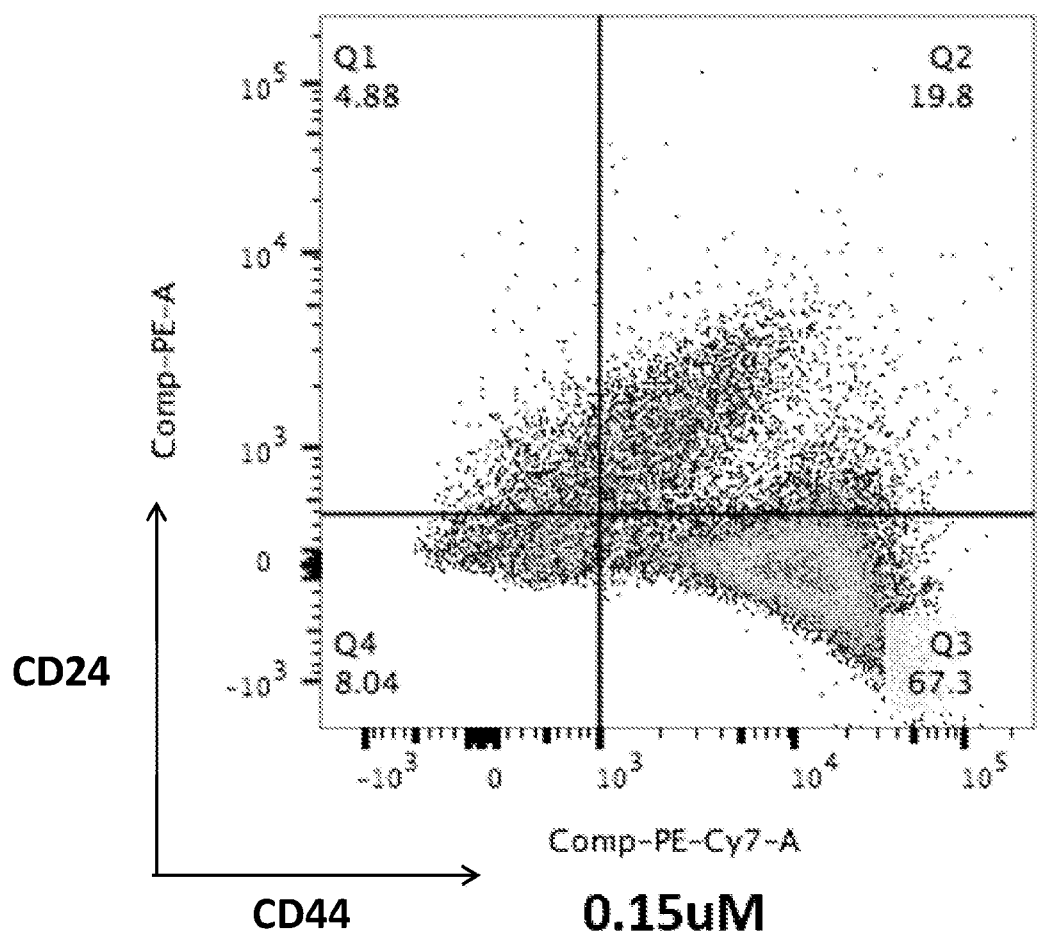
Figure 3G:
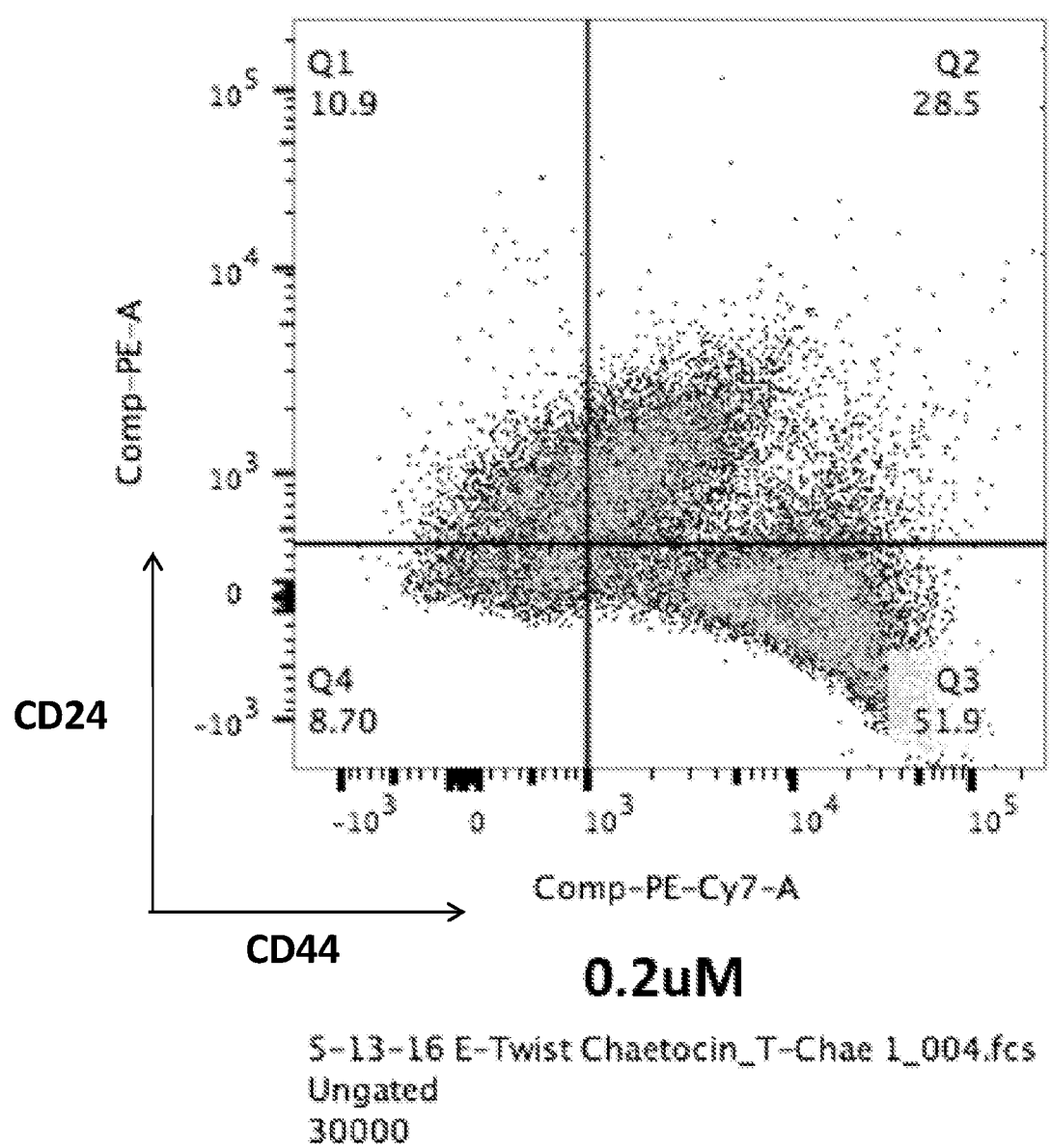
Figure 3H:
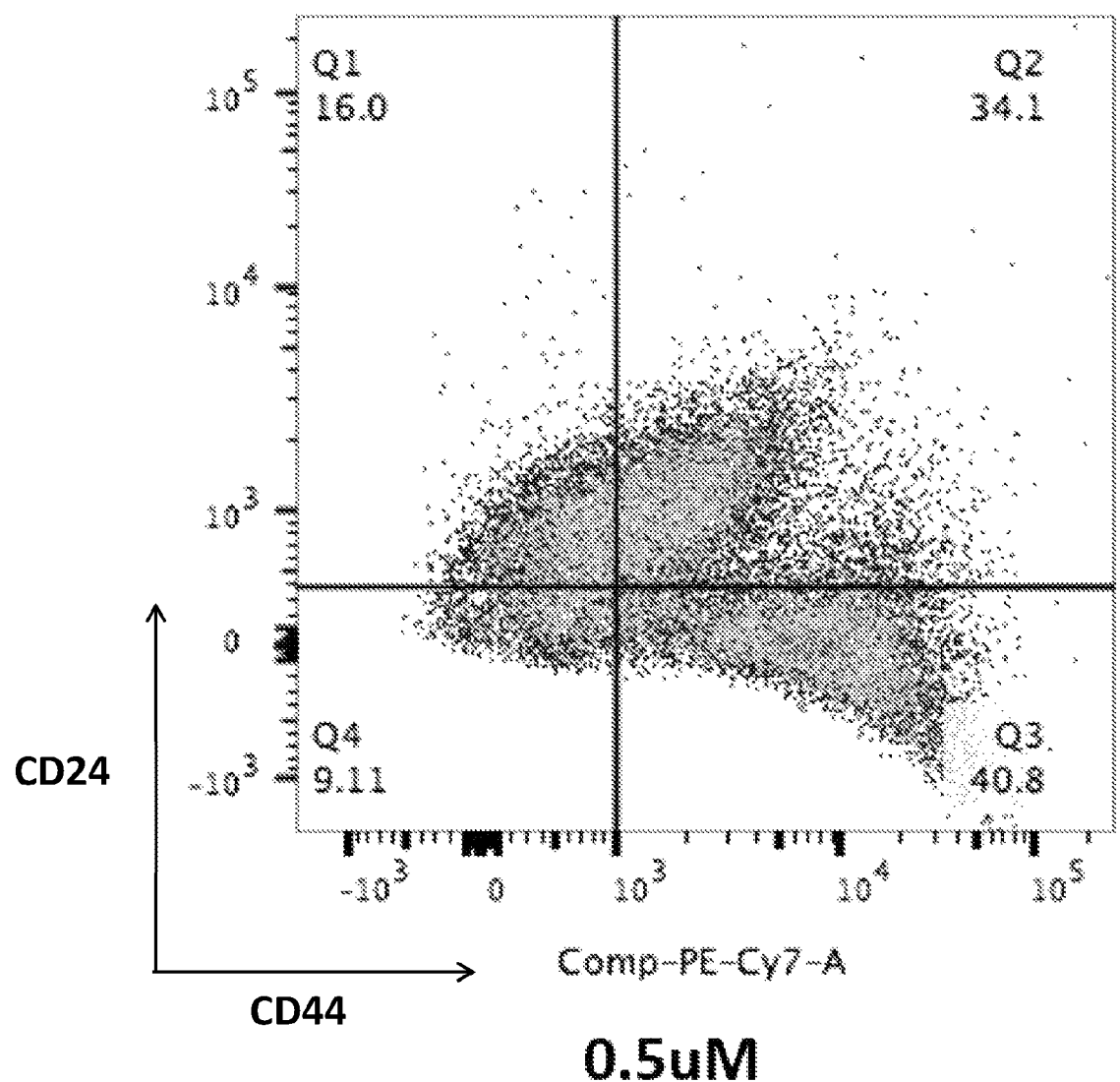
Figure 3I:
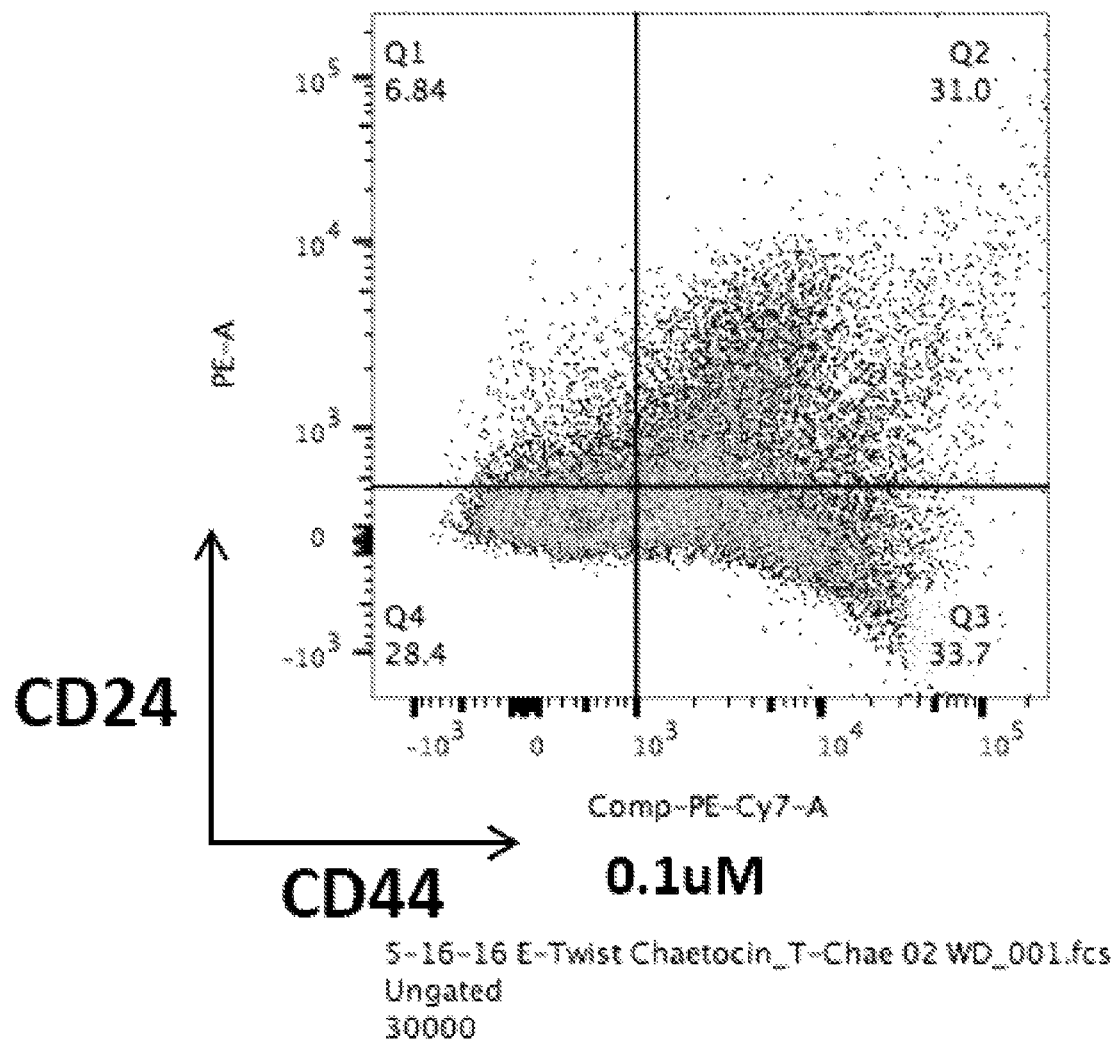
FIGS. 3I-3L show the results of FACS analysis of HMLE-TWIST cells two days after treatment with four different concentrations of chaetocin (0.1 µM, FIG. 3I; 0.15 µM, FIG. 3J; 0.2 µM, FIG. 3K; and 0.5 µM, FIG. 3L). Compared to FIG. 3D-H, these graphs show that the dose-dependent, chaetocin-mediated conversion of TICs into non-TICs persists for up to 2 days after the chaetocin removal. These data demonstrate that chaetocin treatment causes an epigenetic reprogramming of TICs into non-TICs.
Figure 3J:
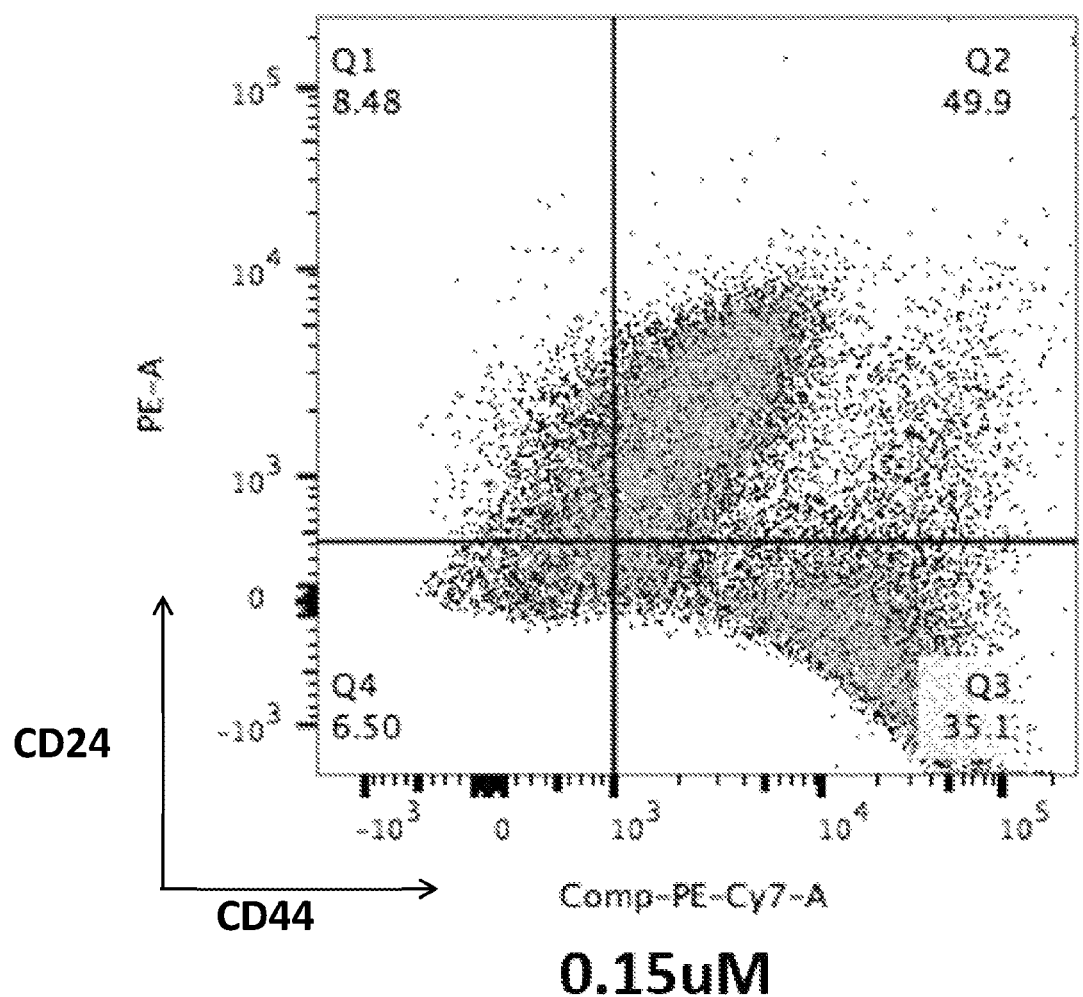
Figure 3K:
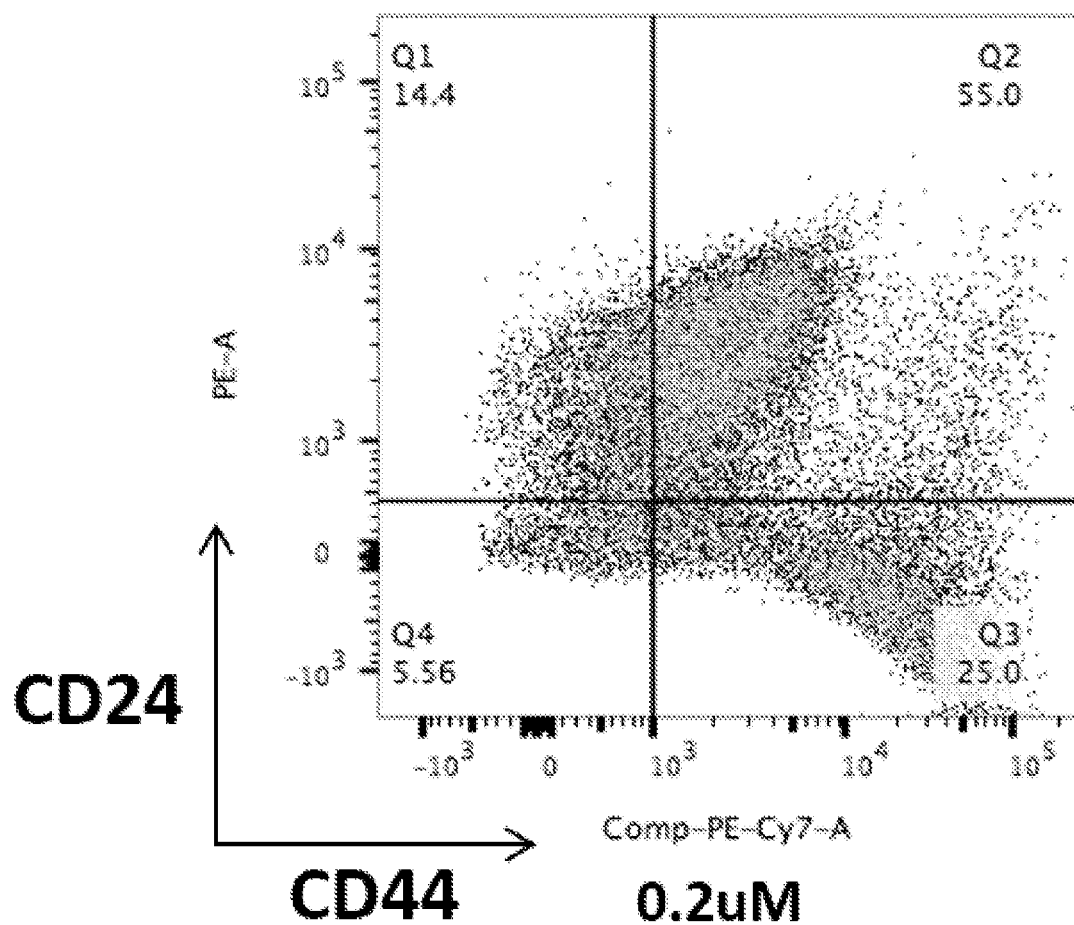
Figure 3L:
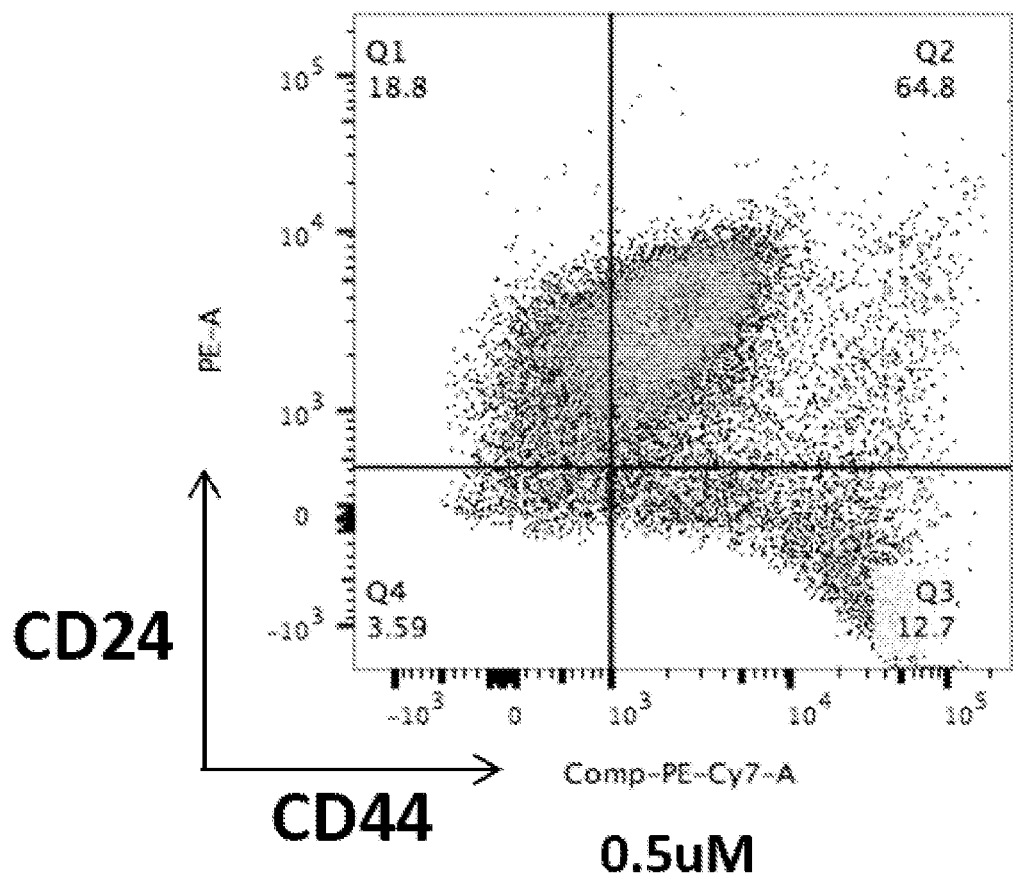
Figure 3M:
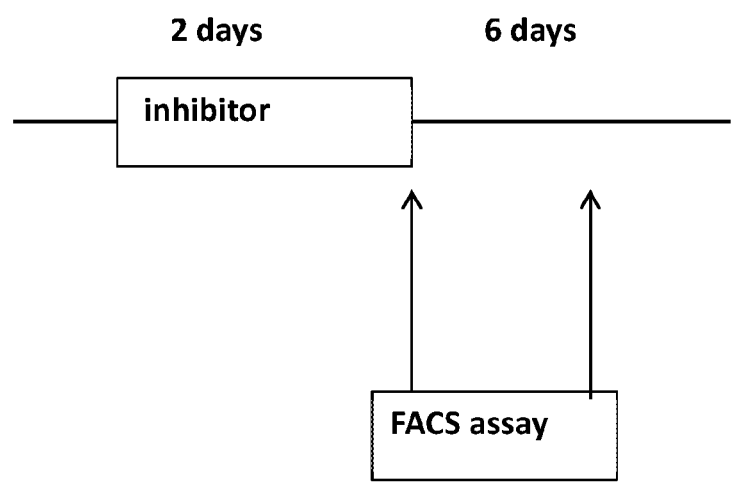
FIG. 3M shows a schematic of an experiment in which cultured mesenchymal, TIC-rich HMLE-TWIST cells were treated with chaetocin for 2 days, washed and then incubated in chaetocin-free media for two days. CD44/CD24 FACS analyses either were performed either immediately or 6 days after chaetocin removal. This experimental design will reveal whether a transient exposure to chaetocin is sufficient to cause an epigenetic change, which would persist even after chaetocin removal, reprogramming mesenchymal TICs into non-TICs.
Figure 3N:
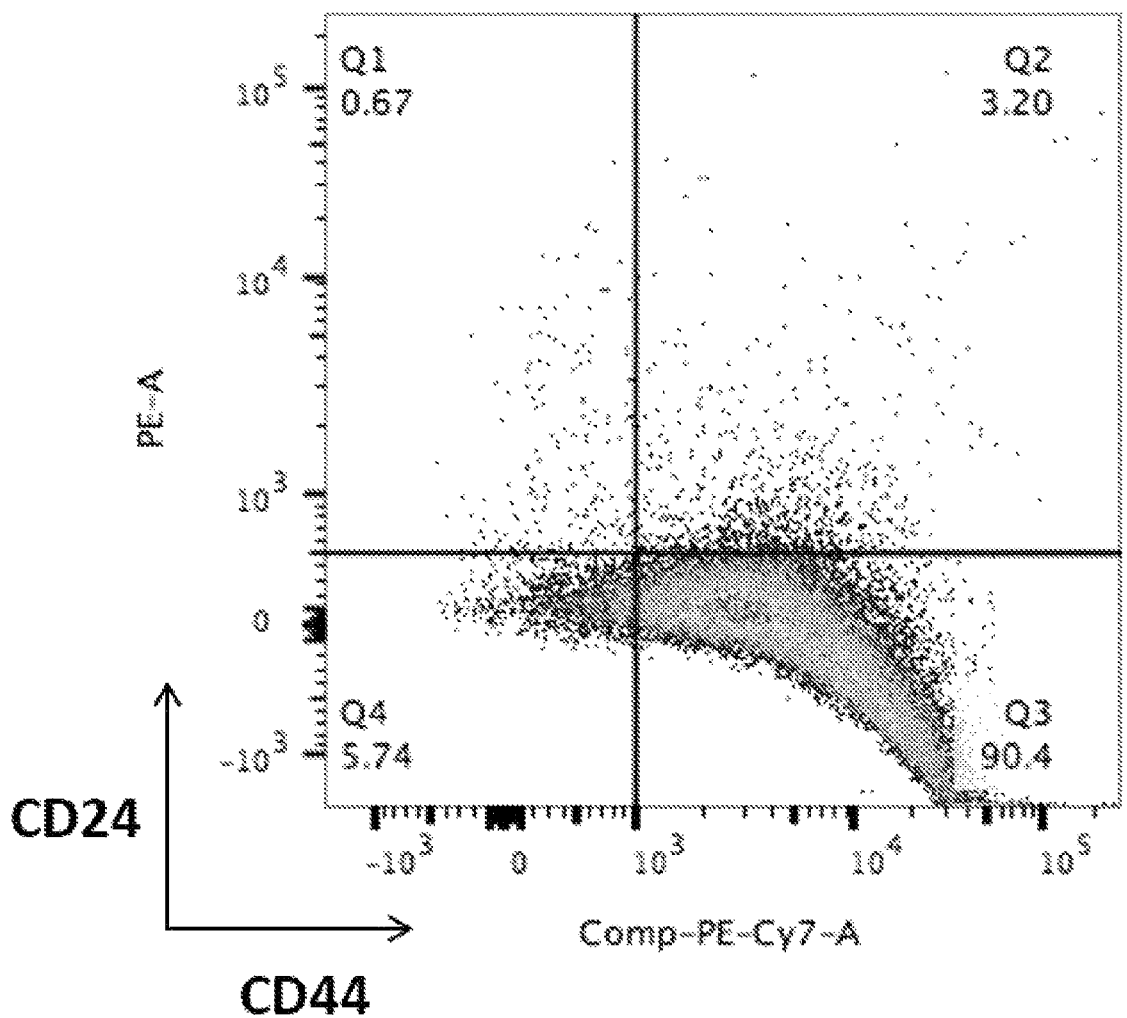
FIG. 3N shows FACS analysis of HMLE-TWIST cells under control condition (e.g., no chaetocin).
Figure 3O:
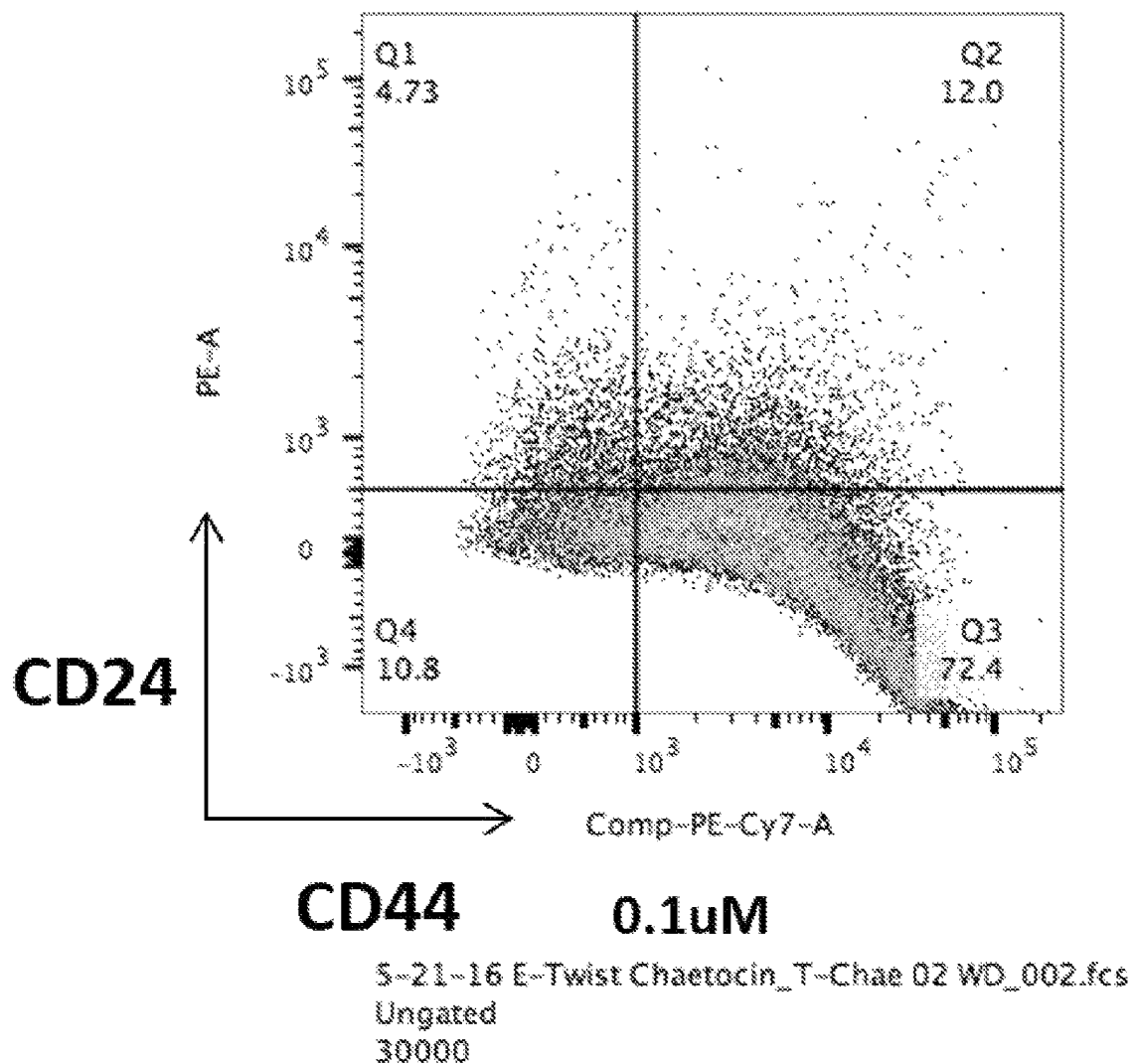
FIGS. 3O-3R show the results of FACS analysis immediately after treatment with four different concentrations of chaetocin (0.1 µM, FIG. 3O; 0.15 µM, FIG. 3P; 0.2 µM, FIG. 3Q; and 0.5 µM, FIG. 3R). Compared to FIG. 3N, these graphs show that chaetocin converts TICs into non-TICs in a dose dependent manner.
Figure 3P:
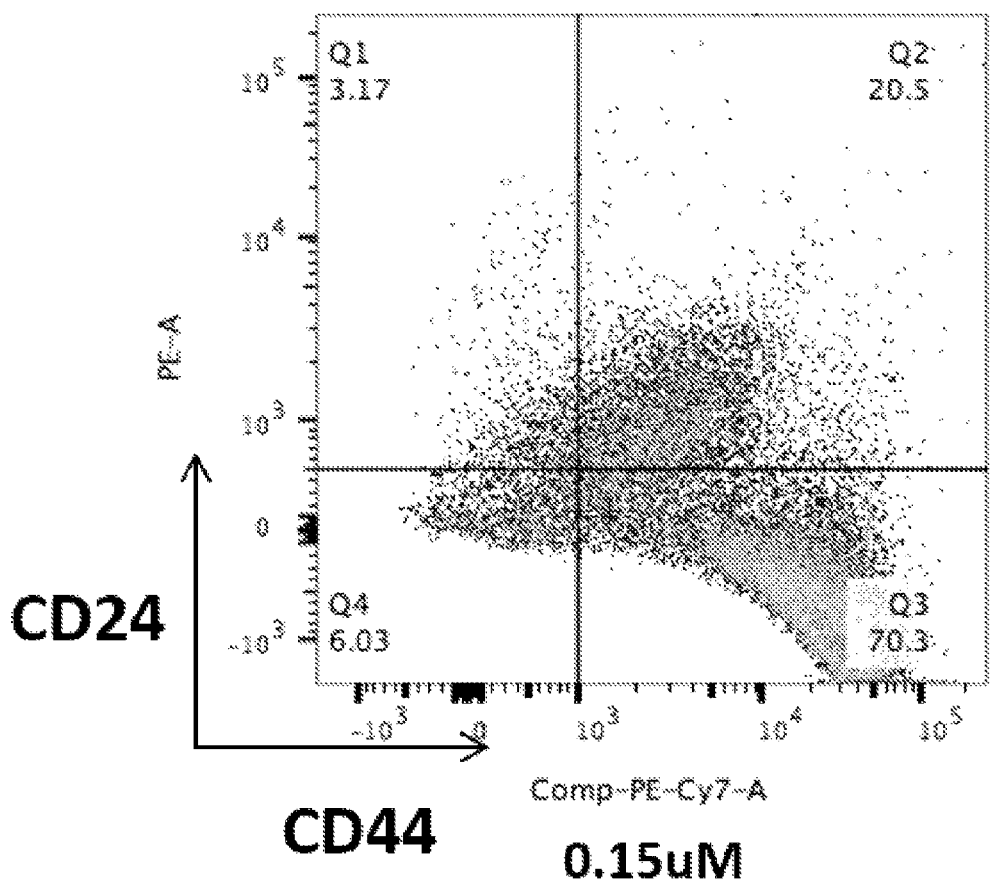
Figure 3Q:
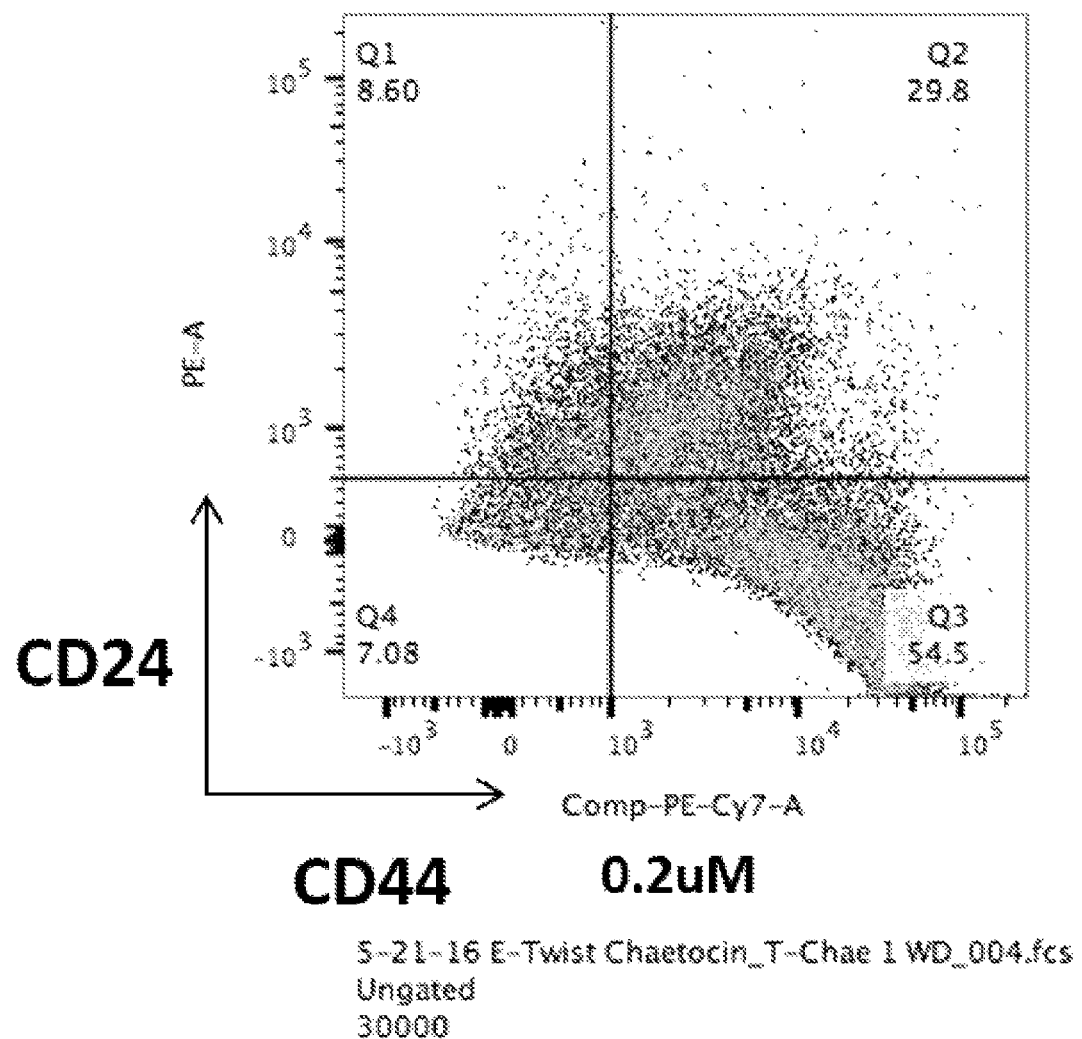
Figure 3R:
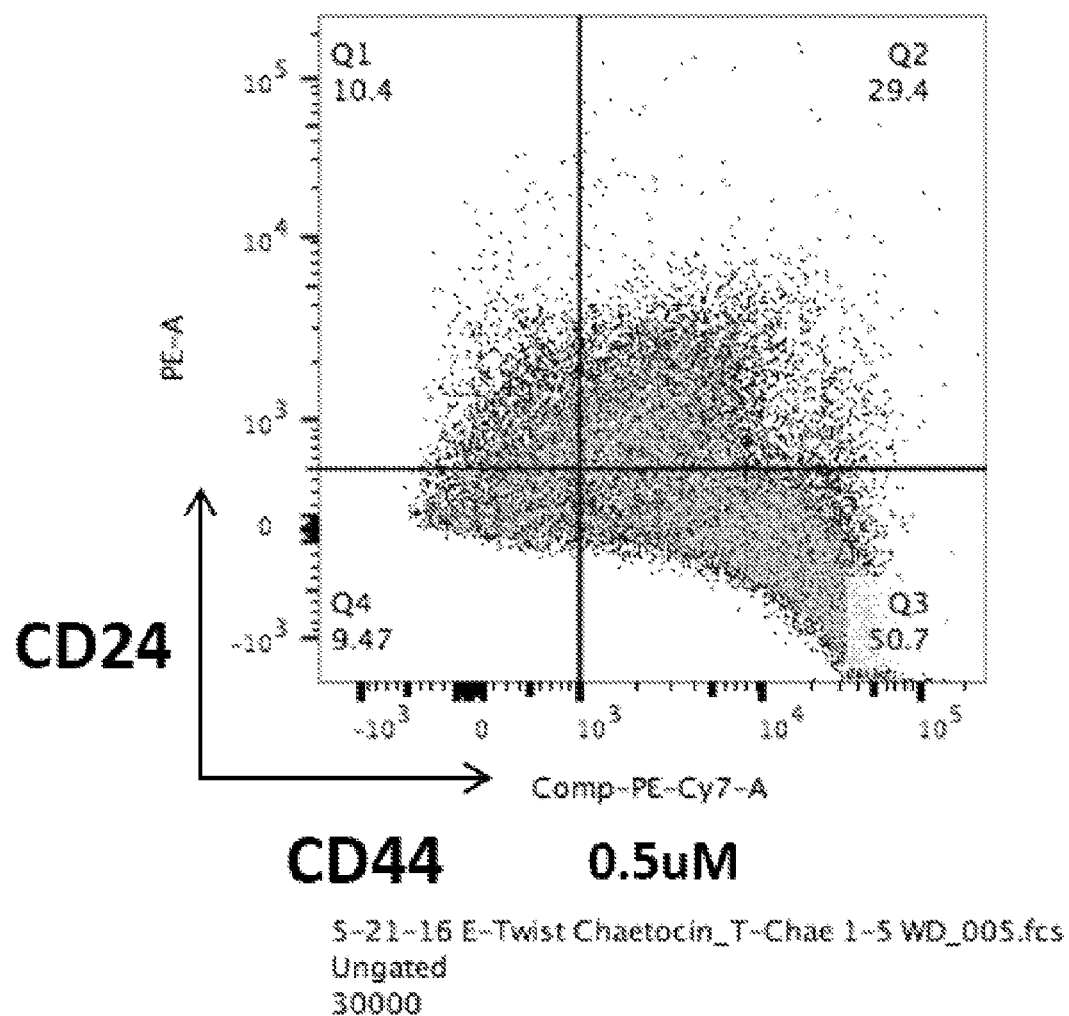
Figure 3S:
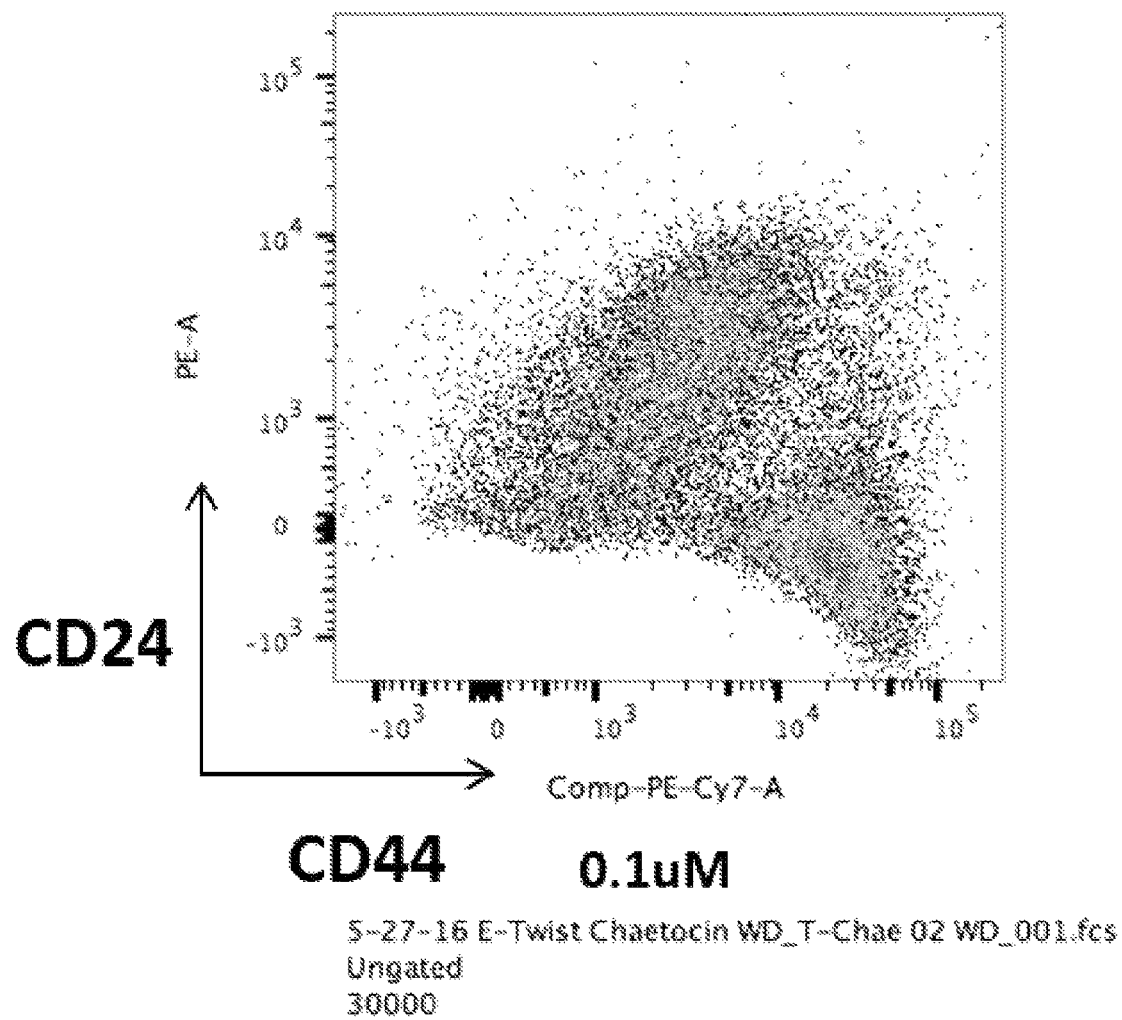
FIGS. 3S-3V show the results of FACS analysis of HMLE-TWIST cells 6 days after treatment with four different concentrations of chaetocin (0.1 µM, FIG. 3S; 0.15 µM, FIG. 3T; 0.2 µM, FIG. 3U; and 0.5 µM, FIG. 3V). Compared to FIG. 3N-V, these graphs show that the dose-dependent, chaetocin-mediated conversion of TICs into non-TICs persists for up to 6 days after the chaetocin removal. These data demonstrate that chaetocin treatment causes an epigenetic reprogramming of TICs into non-TICs.
Figure 3T:
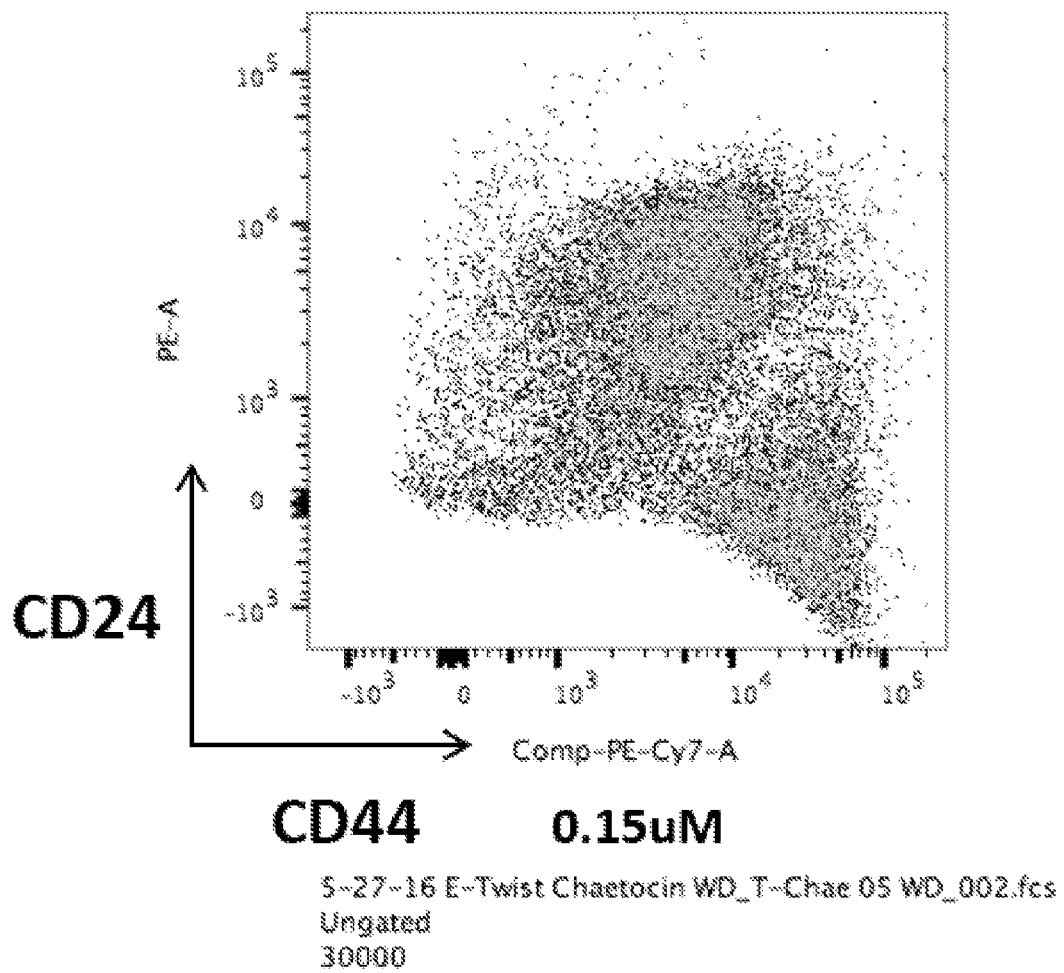
Figure 3U:
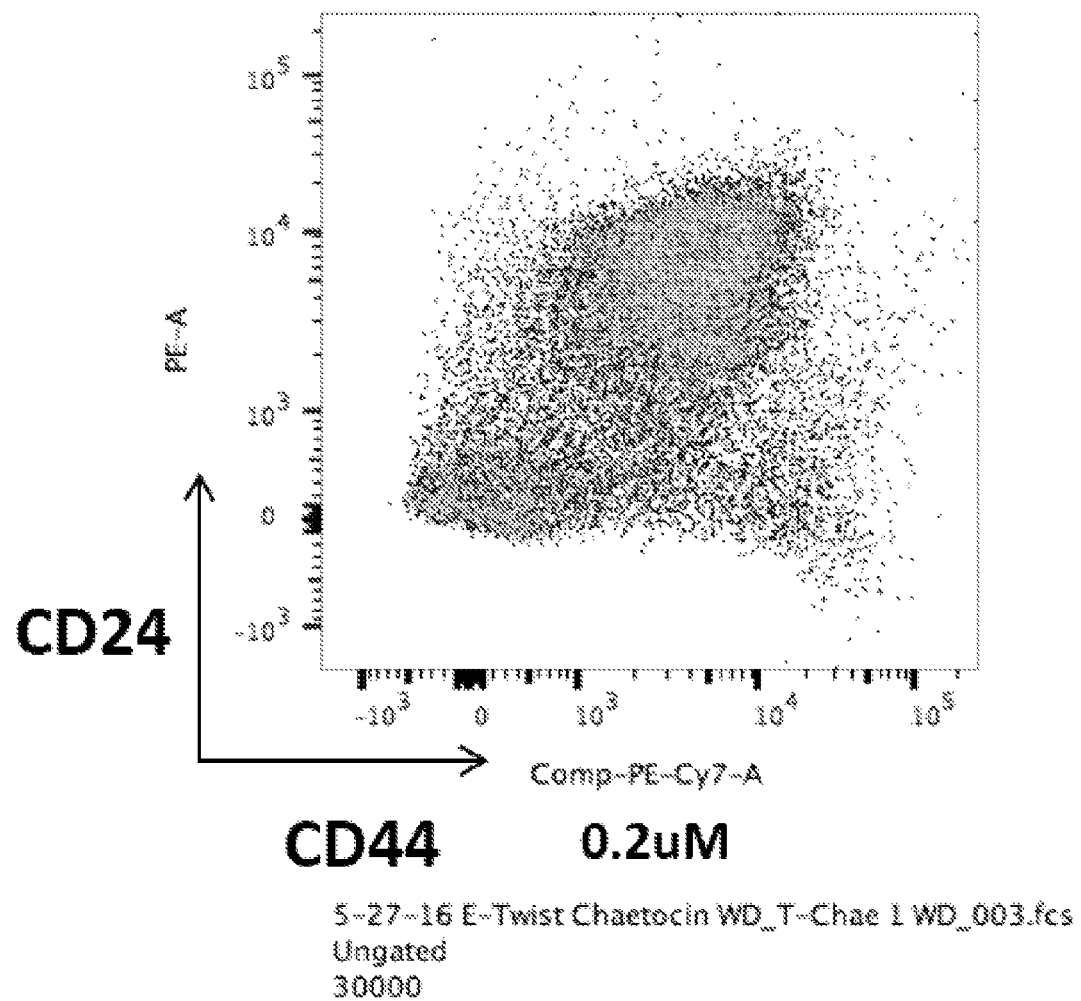
Figure 3V:
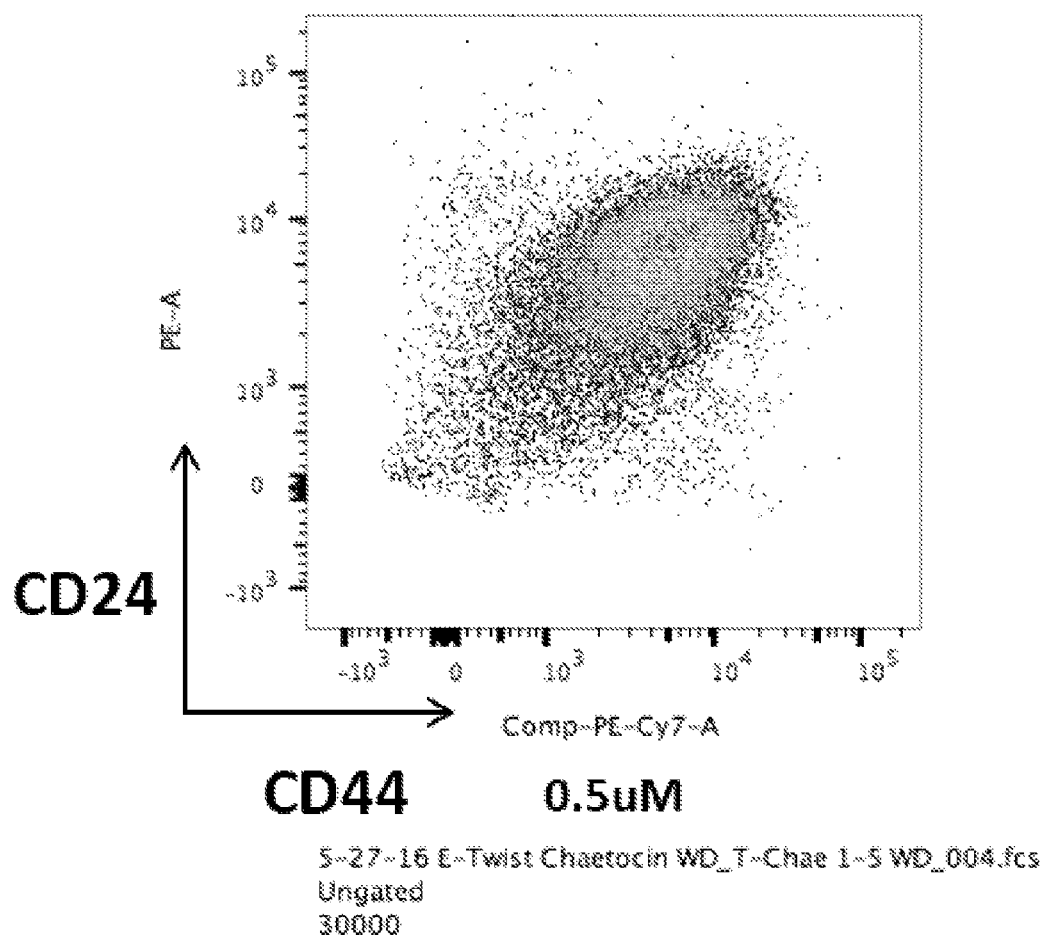
Figure 3W:
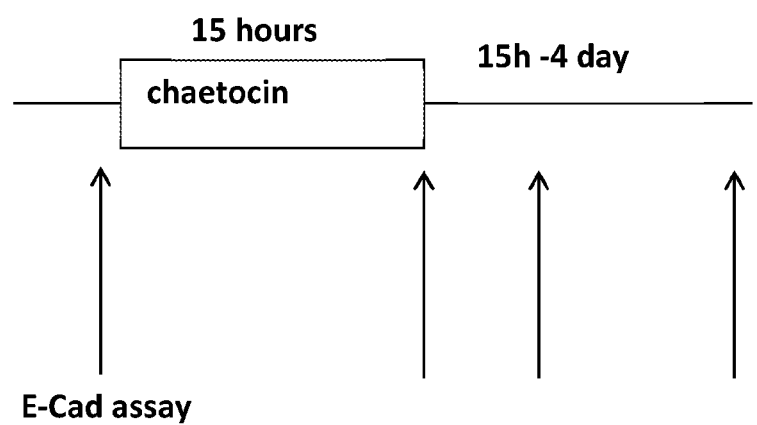
FIG. 3W shows a schematic of an experiment in which mesenchymal, TIC-rich HMLE-TWIST cells were treated with 80 nM or 200 nM dose of chaetocin for 15 hours (15H), washed and then incubated in chaetocin-free media for 1, 2, and 4 days (1D, 2D, and 4D). Levels of an epithelial marker, E-cadherin (E-cad) were assayed at 15H, 1 D, 2D, and 4D after chaetocin treatment and the fraction of E-cad positive cells was quantified.

Epigenetic changes are those in which the phenotypic change induced upon transient exposure to a signal persists stably even in the absence of the inducing signal. In the discussion below, the 'signal' is treatment with chaetocin, which is hypothesized to convert mesenchymal cells into epithelial fate via inhibiting constitutive heterochromatin proteins, namely Suv39H1/H2. If heterochromatin proteins are central epigenetic regulators of EMT, a transient inhibition of heterochromatin activity should be sufficient to reverse EMT and, potentially, sensitize cells to chemotherapy. To determine whether a short pulse of the Suv39H1/H2 inhibitor, chaetocin, is sufficient to bring about an epigenetic change, cultured HMLE-TWIST cells (also referred to as 'HMLE-TWIST TICs' or 'TICs') were exposed to different doses of chaetocin for two days, followed by washout, and replacement with regular media. Cells were tracked for their phenotypic fate (e.g., CD44/CD24 marker expression) for another two or 6 days in chaetocin-free media. In this cell line, high CD44 and low CD24 expression indicate TIC cell populations. Cells that express CD24 are considered non-TICs. This waiting period was done because epigenetic changes often take a several days to take hold, often involving massive changes to the chromatin and transcriptional program of cells. The rationale for this experiment follows the logic that if chaetocin has caused an epigenetic change in TIC cells, reprogramming them out of the TIC phenotype, then a pulse of chaetocin should be sufficient to force cells out of the TIC phenotype, even in chaetocin free media. Stated in another way, a pulse of chaetocin may initiate a cellular program that ultimately forces cells to exit the TIC state. FIG. 3C shows a schematic of the experimental design and FIG. 3D shows FACS analysis of HMLE-TWIST cells under control conditions (no treatment). FIG. 3E-3H show the results of FACS analysis of mesenchymal, TIC-rich HMLE-TWIST cells immediately after treatment with four different concentrations of chaetocin (0.1 µM, FIG. 3E; 0.15 µM, FIG. 3F; 0.2 µM, FIG. 3G; and 0.5 µM, FIG. 3H). Compared to FIG. 3D, the decrease in CD44 high/CD24 low (TICs) and an increase in CD24 high (non-TIC) populations indicate that chaetocin converts TICs into non-TICs in a dose dependent manner. FIGS. 3H-3L show the results of FACS analysis two days after treatment with the same set of concentrations of chaetocin (0.1 µM, FIG. 3H; 0.15 µM, FIG. 3J; 0.2 µM, FIG. 3K; and 0.5 µM, FIG. 3L). Supporting the prediction of the epigenetic change model, the persistent decrease in CD44 high/CD24 low (TICs) and an increase in CD24 high (non-TIC) populations two days after chaetocin removal indicate that the dose-dependent chaetocin-mediated conversion of TICs into non-TICs is epigenetic. Next, to determine whether the epigenetic change persists for periods longer than two days, a separate experiment was performed in which HMLE-TWIST cells were treated with chaetocin for two days, followed by FACS analysis of CD24/CD44 expression either immediately after or 6 days after, as schematized in the top panel of FIG. 3M. FIG. 3N shows FACS analysis of HMLE-TWIST cells under control condition (e.g., no chaetocin). FIGS. 3O-3R show the results of FACS analysis immediately after treatment with four different concentrations of chaetocin (0.1 µM, FIG. 3O; 0.15 µM, FIG. 3P; 0.2 µM, FIG. 3Q; and 0.5 µM, FIG. 3R). Compared to FIG. 3N, the decrease in CD44 high/CD24 low (TICs) and an increase in CD24 high (non-TIC) populations indicate that chaetocin converts TICs into non-TICs in a dose dependent manner. FIGS. 3S-3V show the results of FACS analysis 6 days after treatment with four different concentrations of chaetocin (0.1 µM, FIG. 3S; 0.15 µM, FIG. 3T; 0.2 µM, FIG. 3U; and 0.5 µM, FIG. 3V). Supporting the prediction of the epigenetic change model, the persistent decrease in CD44 high/CD24 low (TICs) and an increase in CD24 high (non-TIC) populations two days after chaetocin removal indicate that the dose-dependent chaetocin-mediated conversion of TICs into non-TICs is epigenetic. Together, these results indicate chaetocin treatment results in a stable epigenetic change, converting mesenchymal, TICs into epithelial non-TICs, which persist for up to six days after chaetocin removal.

Figure 3X:
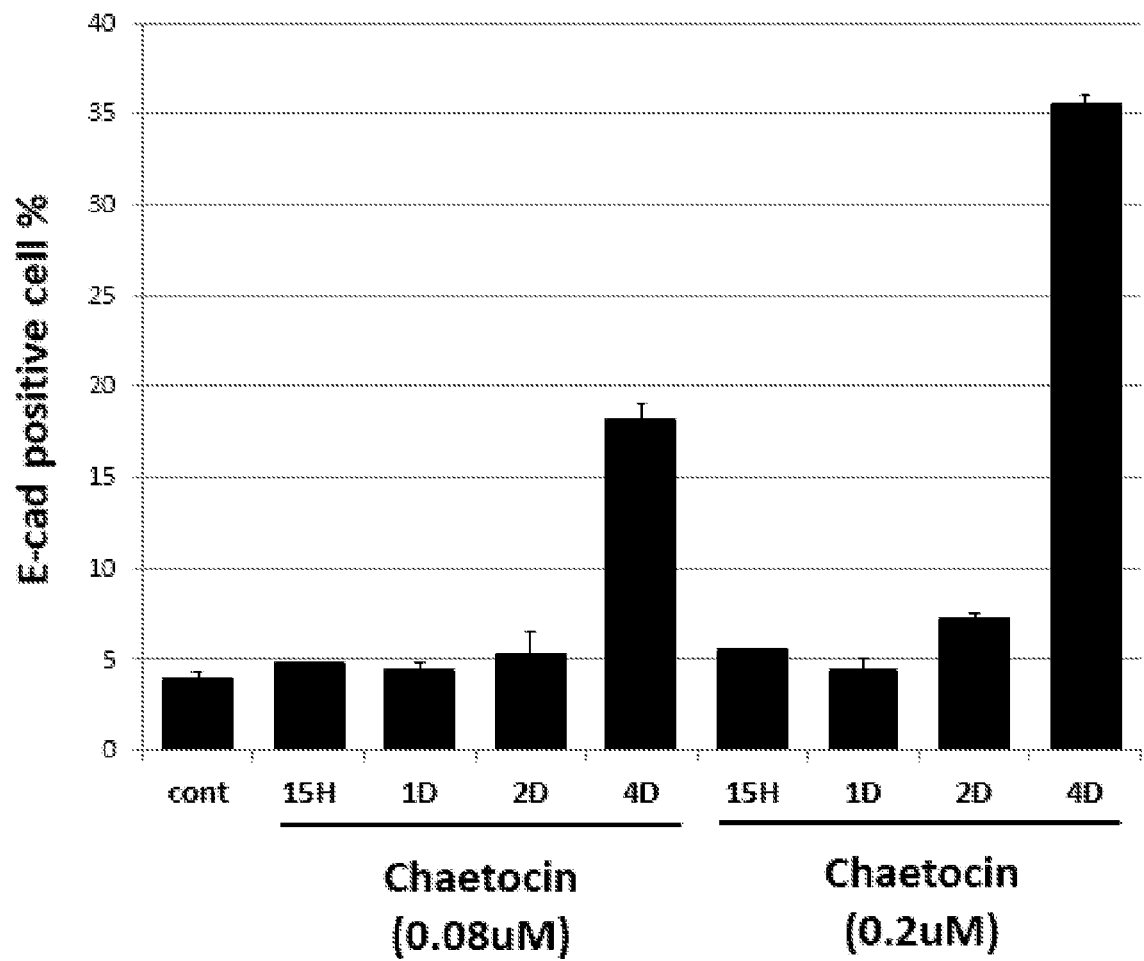

To molecularly test whether chaetocin treatment converts mesenchymal cells into epithelial cells, HMLE-TWIST cells were treated with a pulse of chaetocin for 15 hours (15H), washed and then incubated in chaetocin-free media for 1 day (1D), 2 days (2D), and 4 days (4D). Levels of the ubiquitous epithelial marker E-cadherin (E-cad) was assayed using Western blots throughout the experiment. FIG. 3X shows levels of E-cad in HMLE-TWIST cells at multiple time points after chaetocin treatment. Supporting the prediction of the epigenetic change model, a short pulse of chaetocin is sufficient to bring about a stable epigenetic change in cell phenotype converting mesenchymal cancer cells into epithelial ones.

Figure 4A:
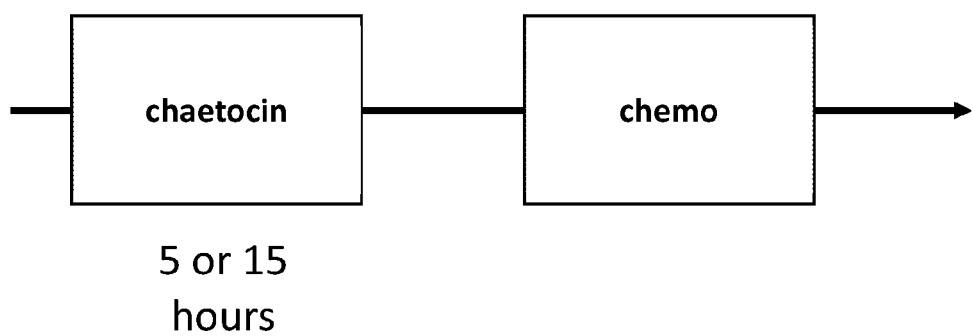
FIGS. 4A-4E show a series of bar plots demonstrating that a short treatment of mesenchymal, TIC-rich, chemotherapy-resistant breast, kidney or lung cancer cells with chaetocin causes an epigenetic change reversing their resistance to chemotherapy.
Figure 4B:
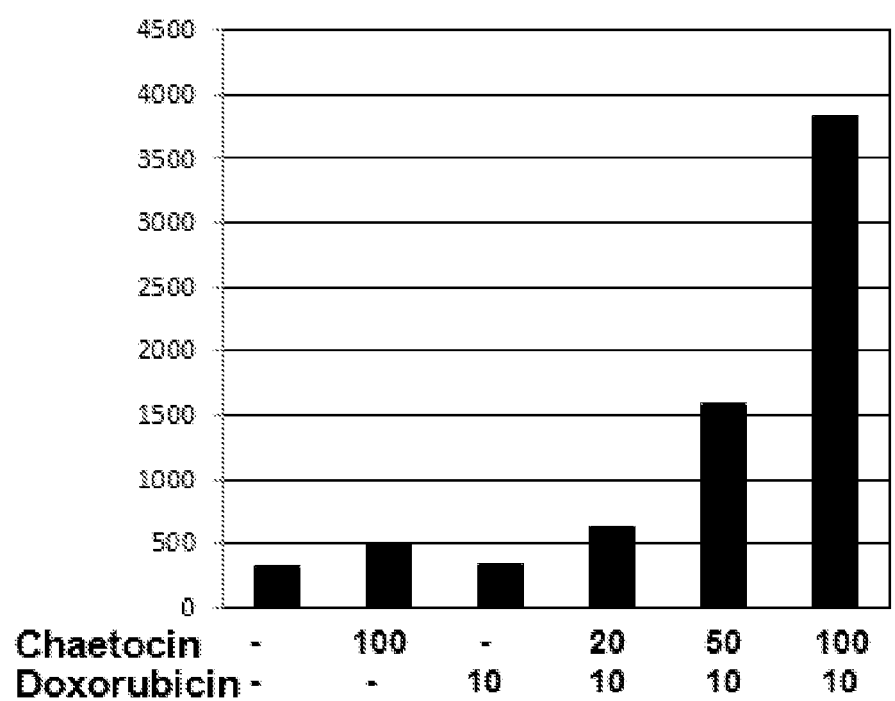
Figure 4C:
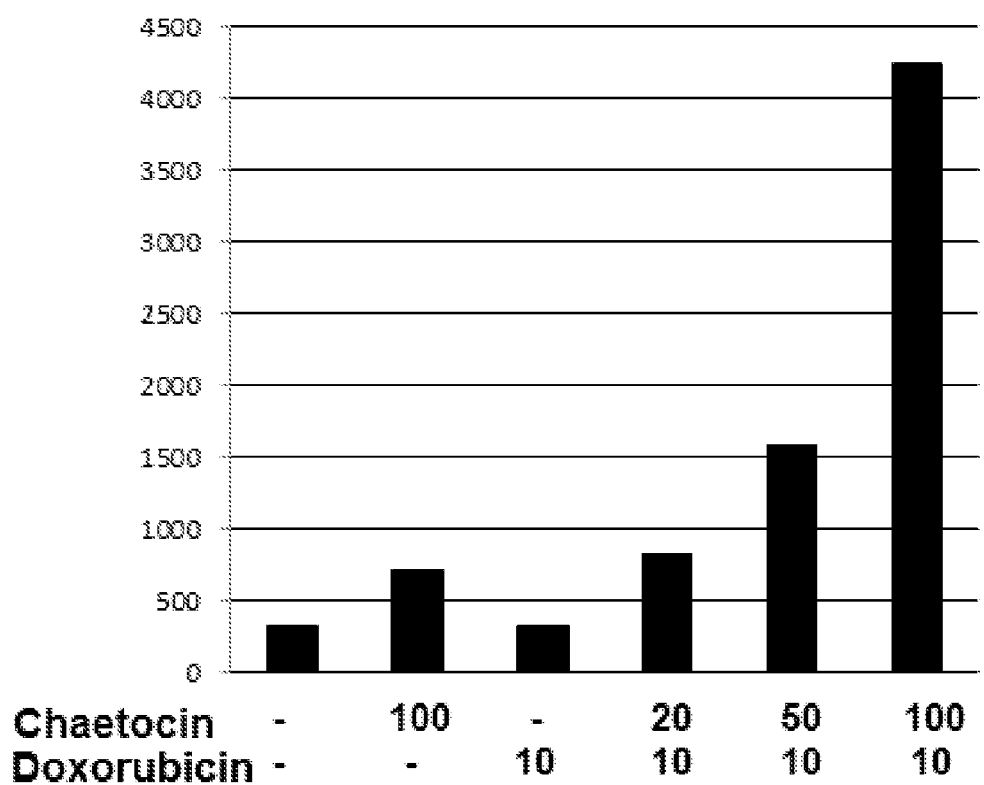

Example 4. Transient Treatment with Chaetocin Sensitizes TIC-Rich Cancer Cells to Chemotherapy To determine if EMT reversal with chaetocin can sensitize TIC-rich breast cancer cells, namely HMLE-TWIST cells, to conventional chemotherapeutic agents, cells were treated for 5 or 15 hours with different concentrations of chaetocin (20 nM, 50 nM, and 100 nM), as is schematized in FIG. 4A. Cells were then washed and incubated in chaetocin-free media for two days. Doxorubicin was then added, and cell death was assayed using FACS analysis of caspase-3 cleavage two days after doxorubicin addition. By comparing the cell death caused by chaetocin or doxorubicin alone versus chaetocin first and doxorubicin second treatments, the results indicate that a short treatment with chaetocin reverses chemotherapy resistance of mesenchymal, TIC-rich HMLE-TWIST cells to doxorubicin after both 5 hours (FIG. 4B) and 15 hours (FIG. 4C) of chaetocin treatment.

Figure 4D:
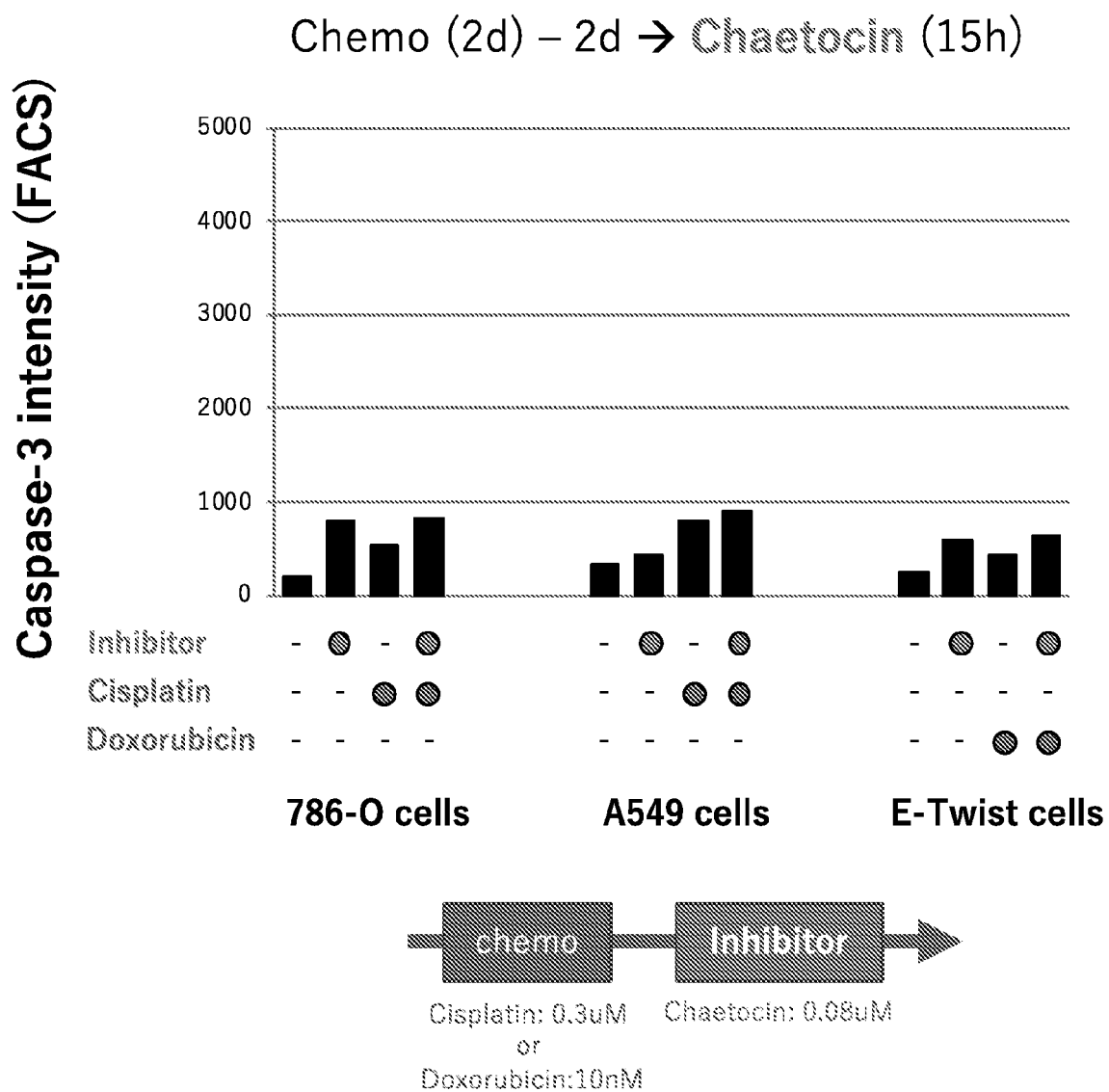
Figure 4E:
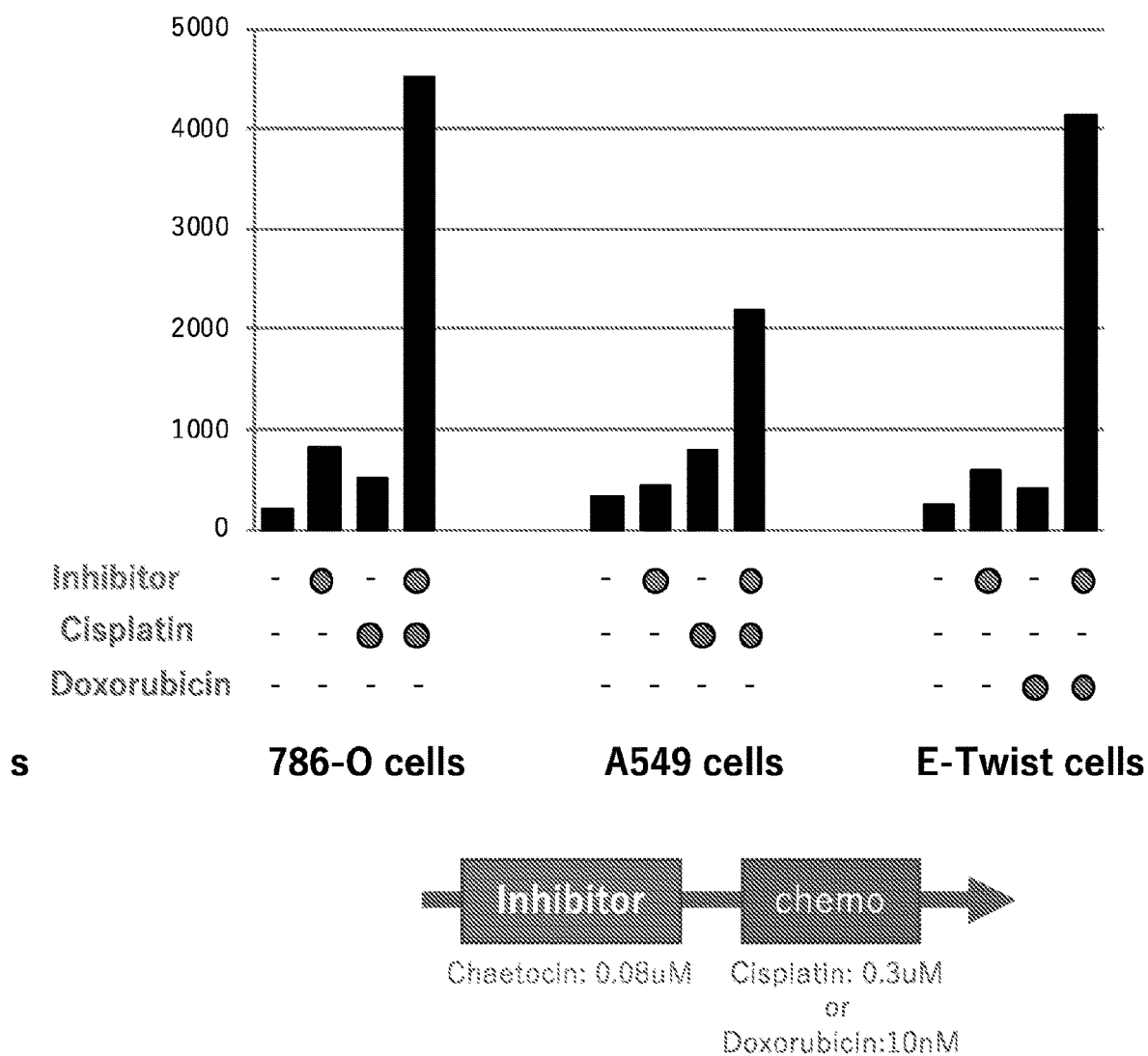

In a separate set of experiments, to test the generality of chaetocin in reversing the chemotherapy resistance of mesenchymal, TIC-rich cancers, well-characterized mesenchymal TIC-rich cell lines from ccRCC 786-0 and lung cancer cells (A549) were used along with HMLE-TWIST cells described above. As before, cells were treated with a pulse of chaetocin at low dose (80 nM) for 15 hours, after which the cells were washed and incubated for an additional 2 days in regular media. The cells were then treated with chemotherapeutic agents normally used to treat these cancers (cisplatin for renal and lung, and doxorubicin for breast cancer). Caspase-3 cleavage was used to measure apoptosis. As controls, cells were also treated with a single agent alone (inhibitor or chemotherapy), and experiments were performed in which the order of chaetocin and chemotherapy treatment were reversed. This was done to test a prediction of an epigenetic model: that the order of drug treatment is critical for reversing chemotherapy resistance. FIG. 4E shows bar plots demonstrating that treatment of resistant cancer cell lines with chaetocin first sensitizes them to chemotherapeutic killing. It also demonstrates that treatment with the chaetocin results in an epigenetic change, since reversing the order in which chaetocin and chemotherapy are added did not produce similar chemotherapeutic killing of cells (FIG. 4D). Because chaetocin has been shown to be a specific inhibitor of Suv39H1 and Suv39H2 heterochromatin proteins, these findings provide a model to probe whether heterochromatin proteins also contribute to chemotherapy resistance in cancers.

Figure 5A:
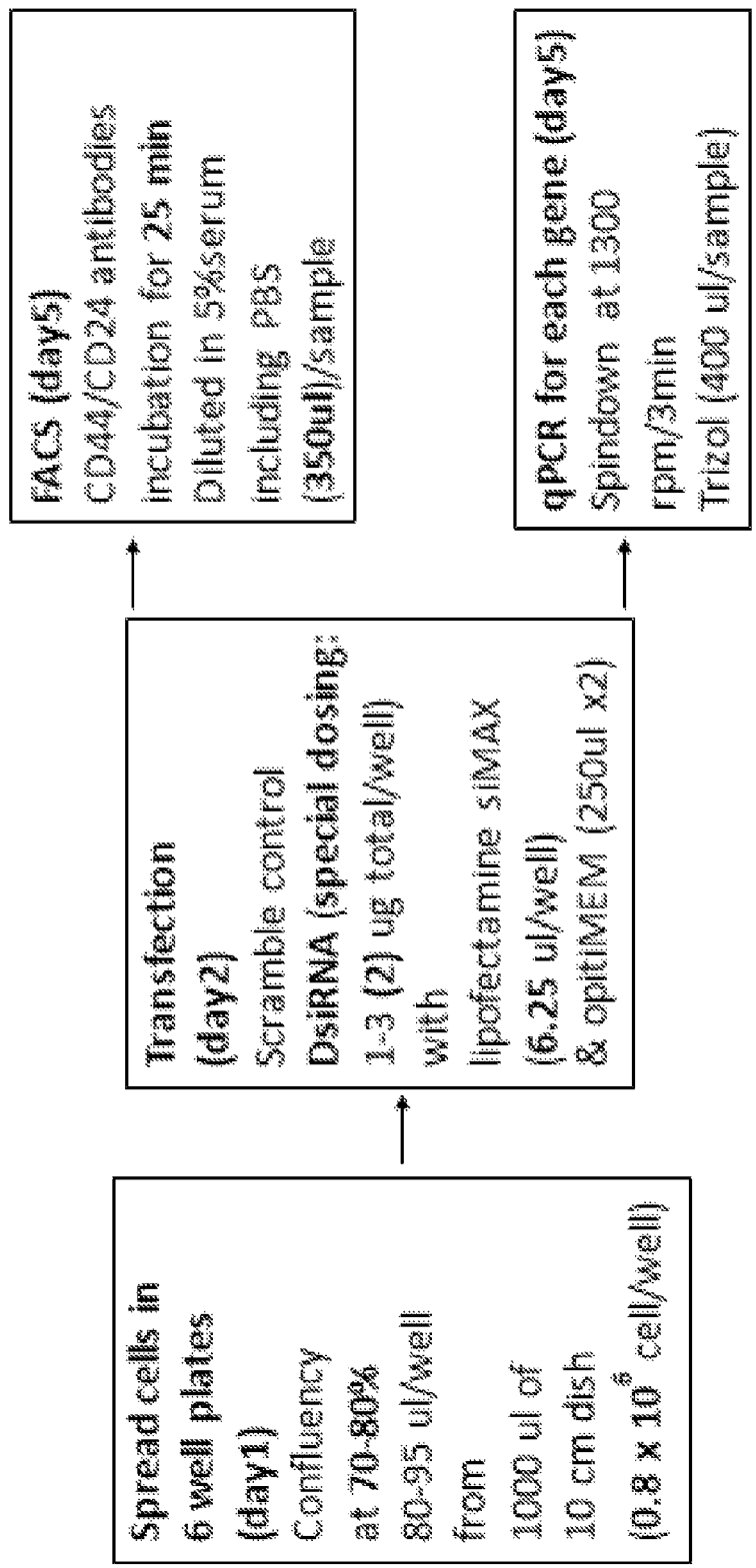
FIGS. 5A-5O show a series of experimental schematics and plots delineating RNA interference-mediated knockdown of different heterochromatin and other chromatin regulatory proteins designed to identify the molecular target of chaetocin in cancer cells.
Figure 5B:
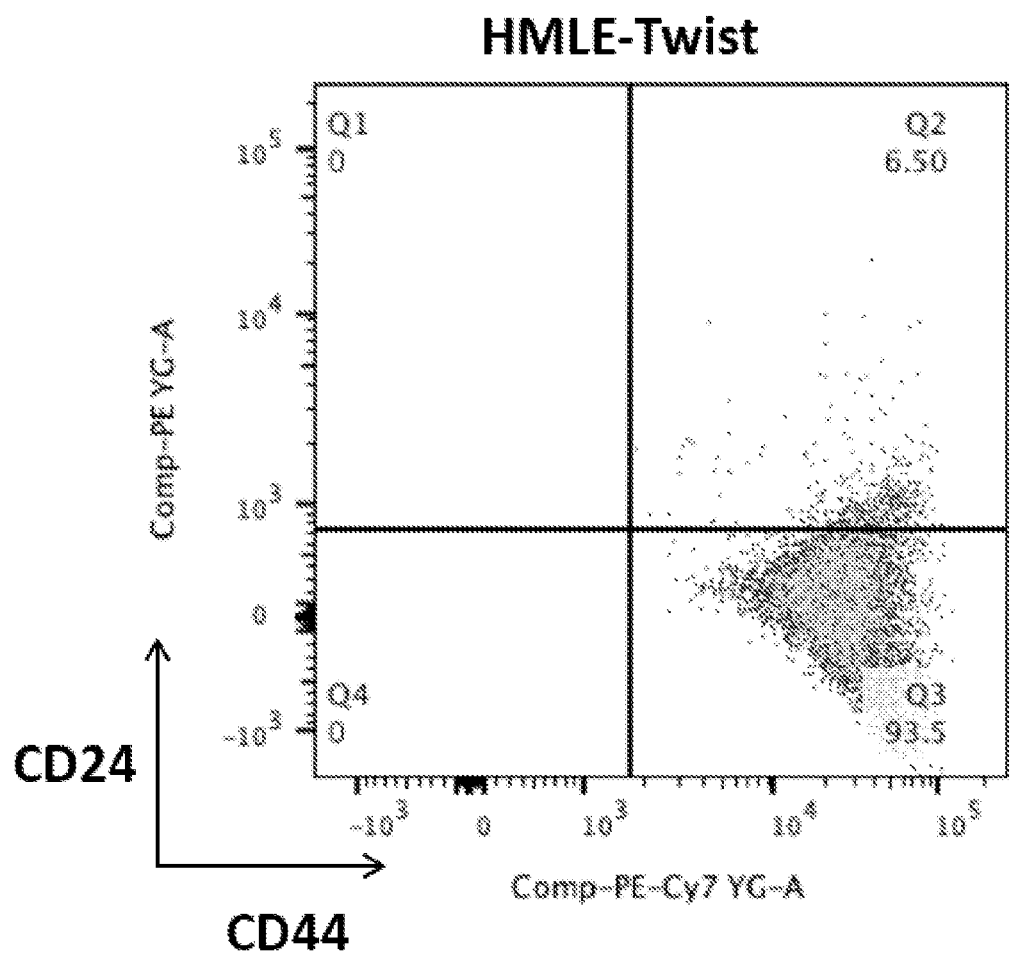
FIGS. 5B-5E show the FACS analysis of experiments described in FIG. 5A under control conditions (HMLE-TWIST.
Figure 5C:
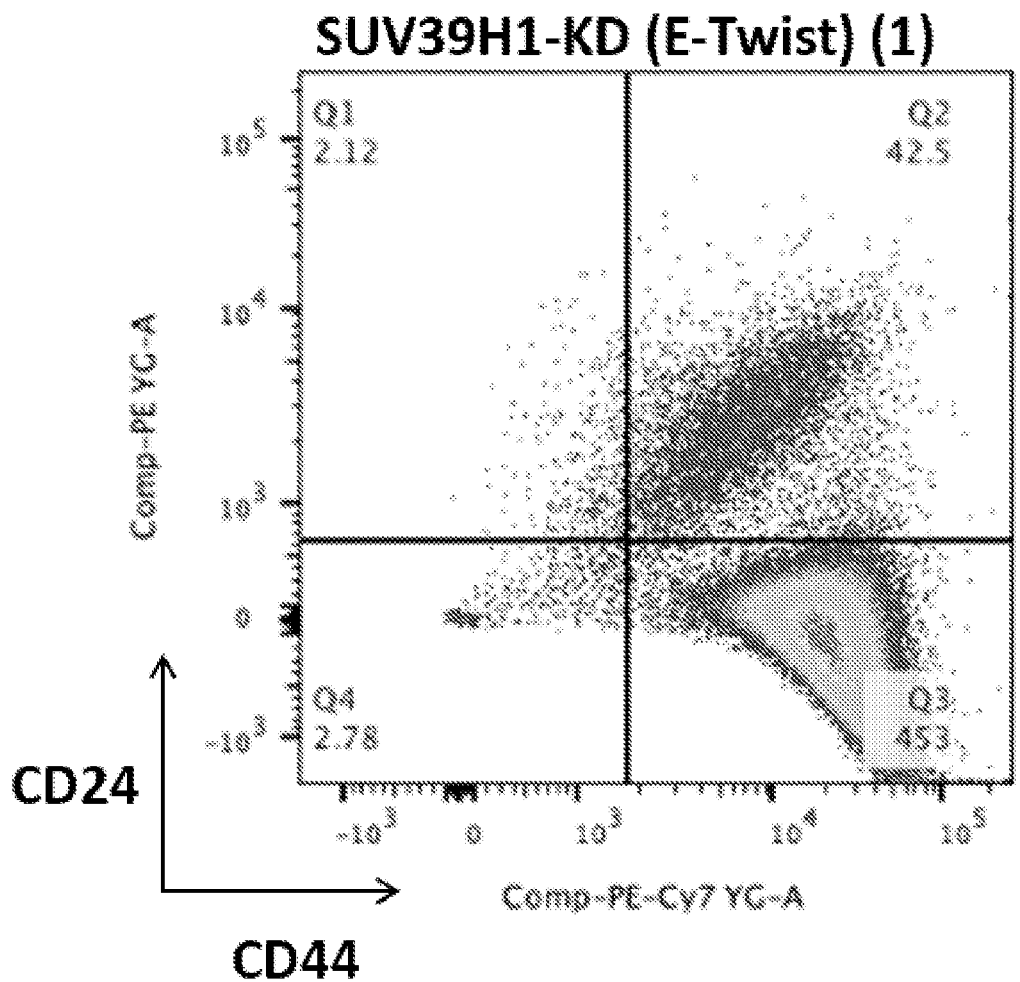
Figure 5D:
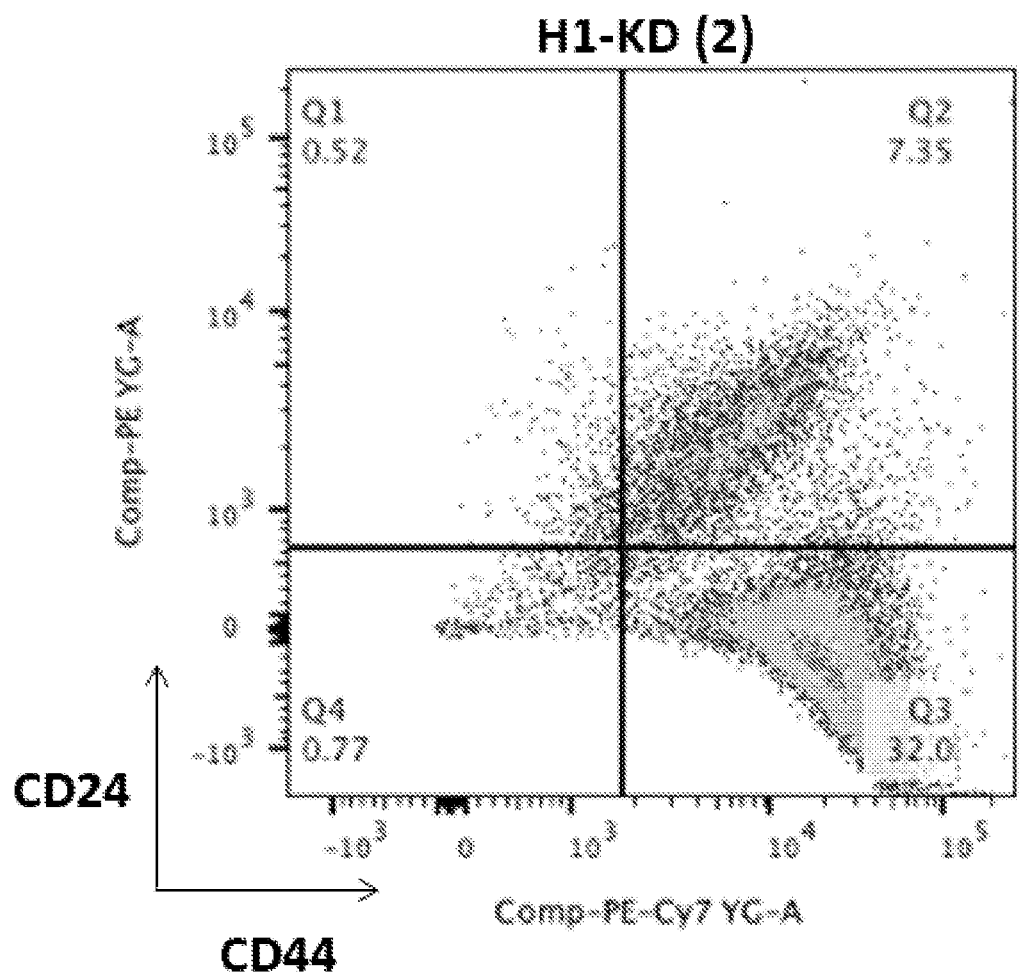
Figure 5E:
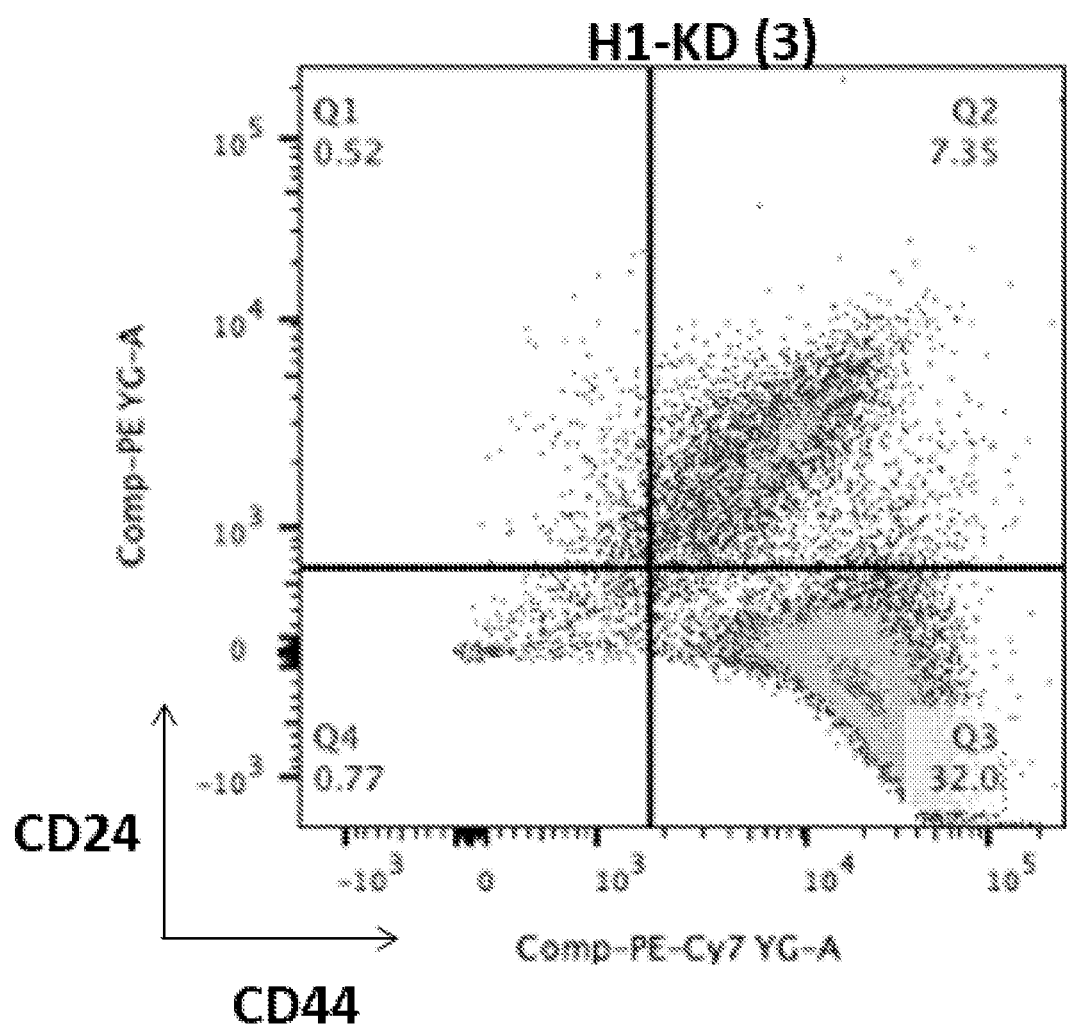
Figure 5F:
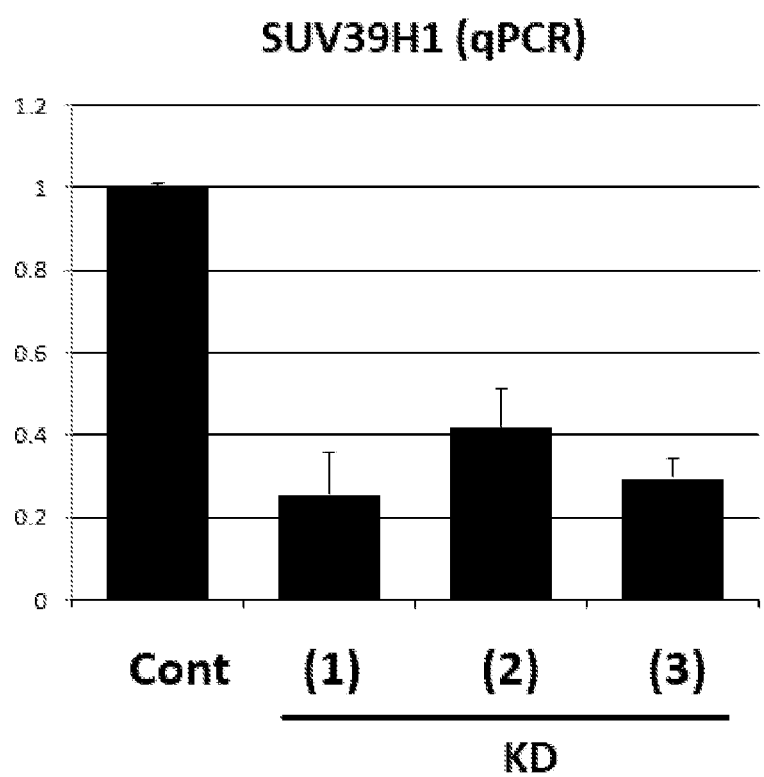
FIG. 5F is a bar plot showing the results of quantitative real-time, reverse-transcriptase PCR (qRT-PCR) analysis measuring Suv39H1 RNA levels in HMLE-TWIST cells for the three different dsiRNAs described above.
Figure 5G:
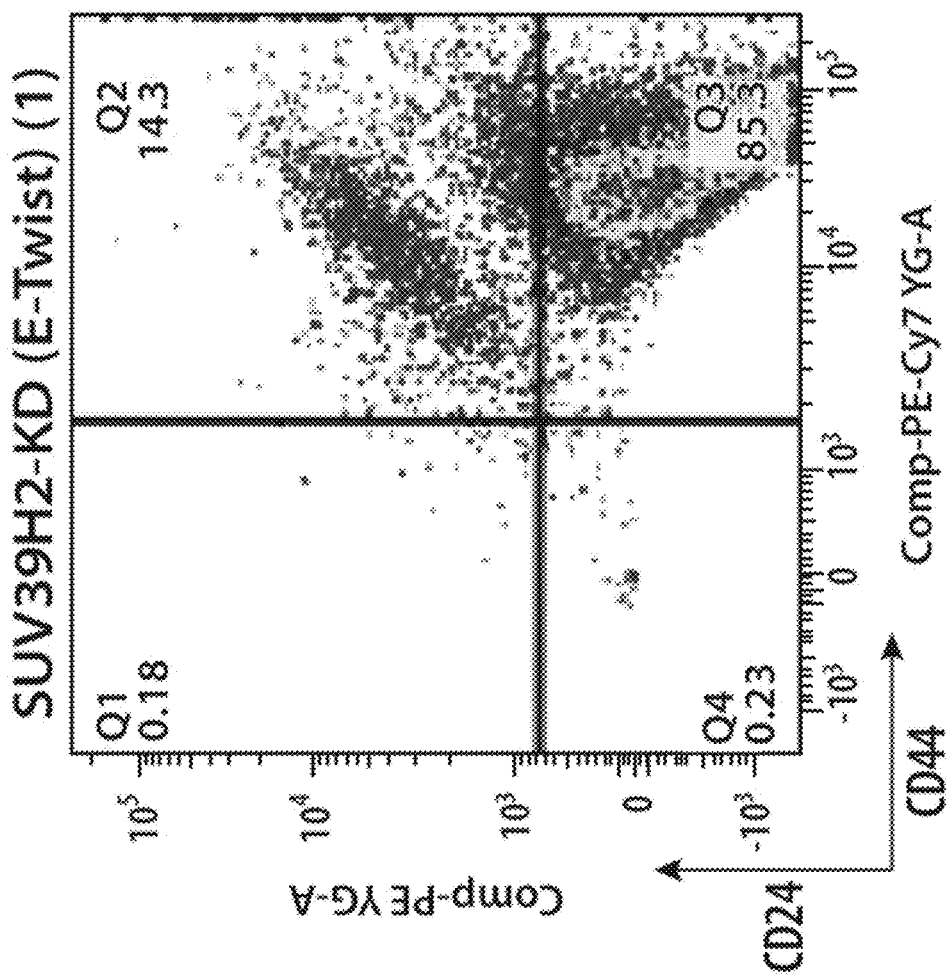
Figure 5H:
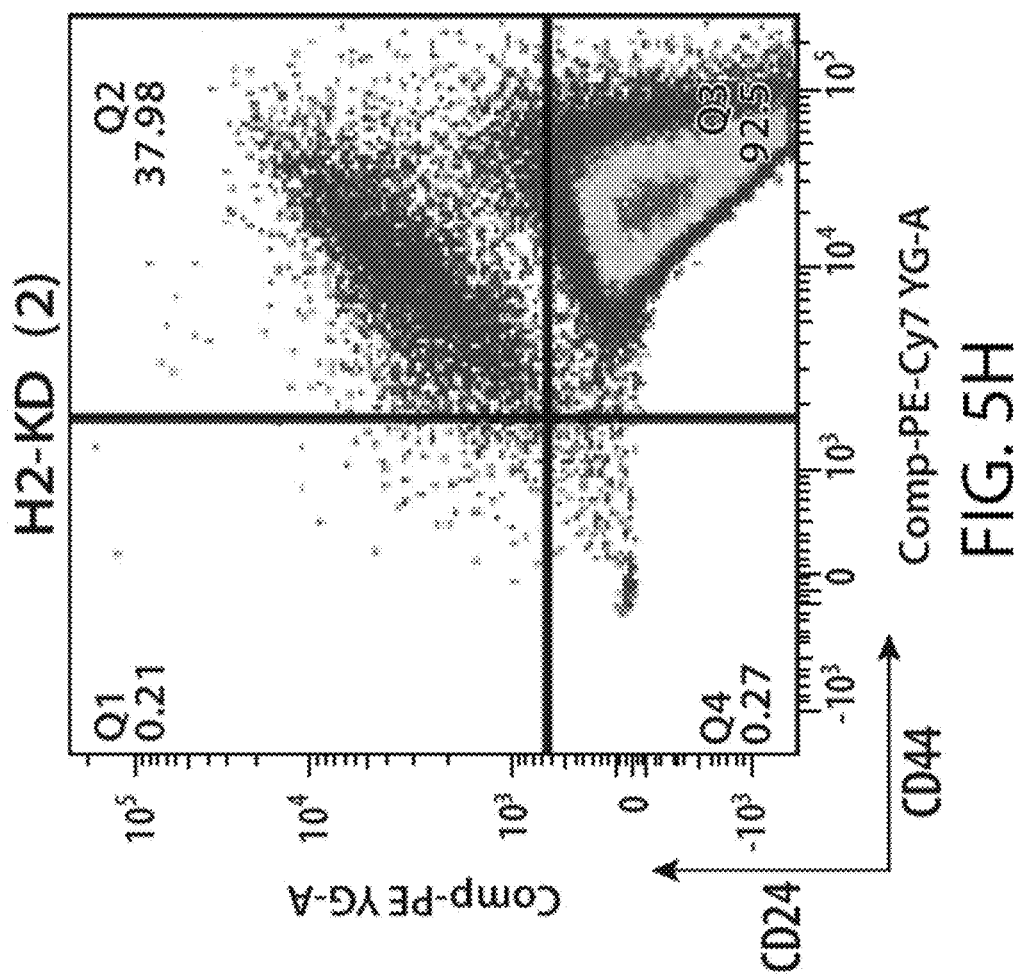
Figure 51:
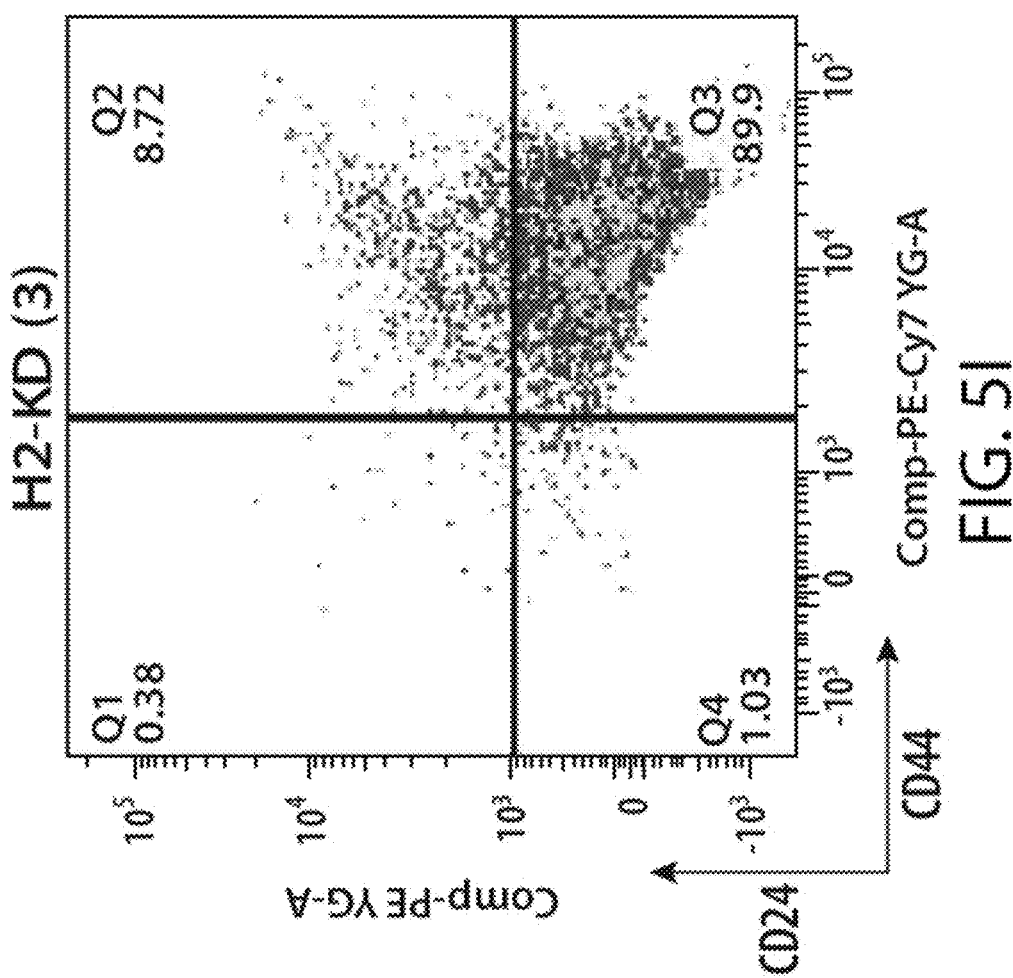
Figure 5J:
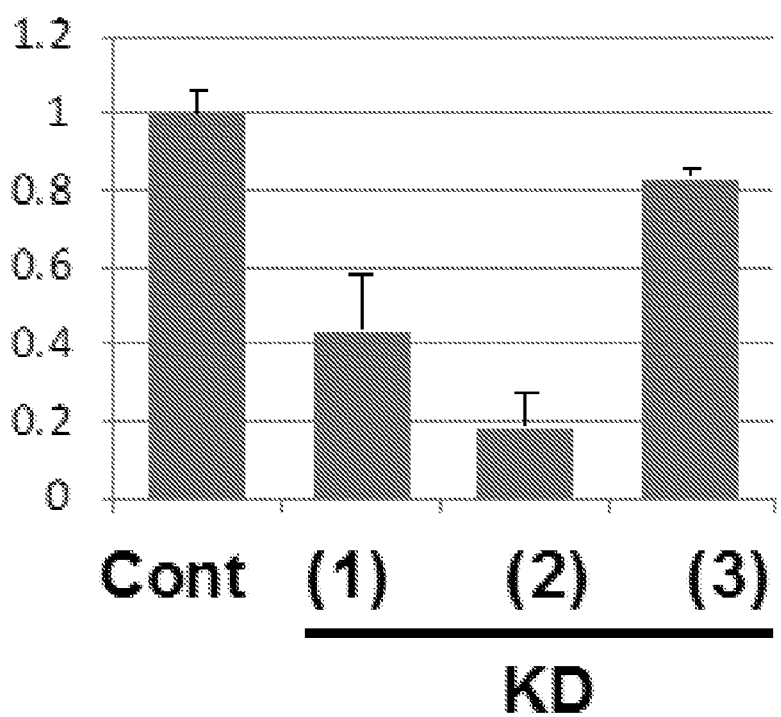
Figure 5K:
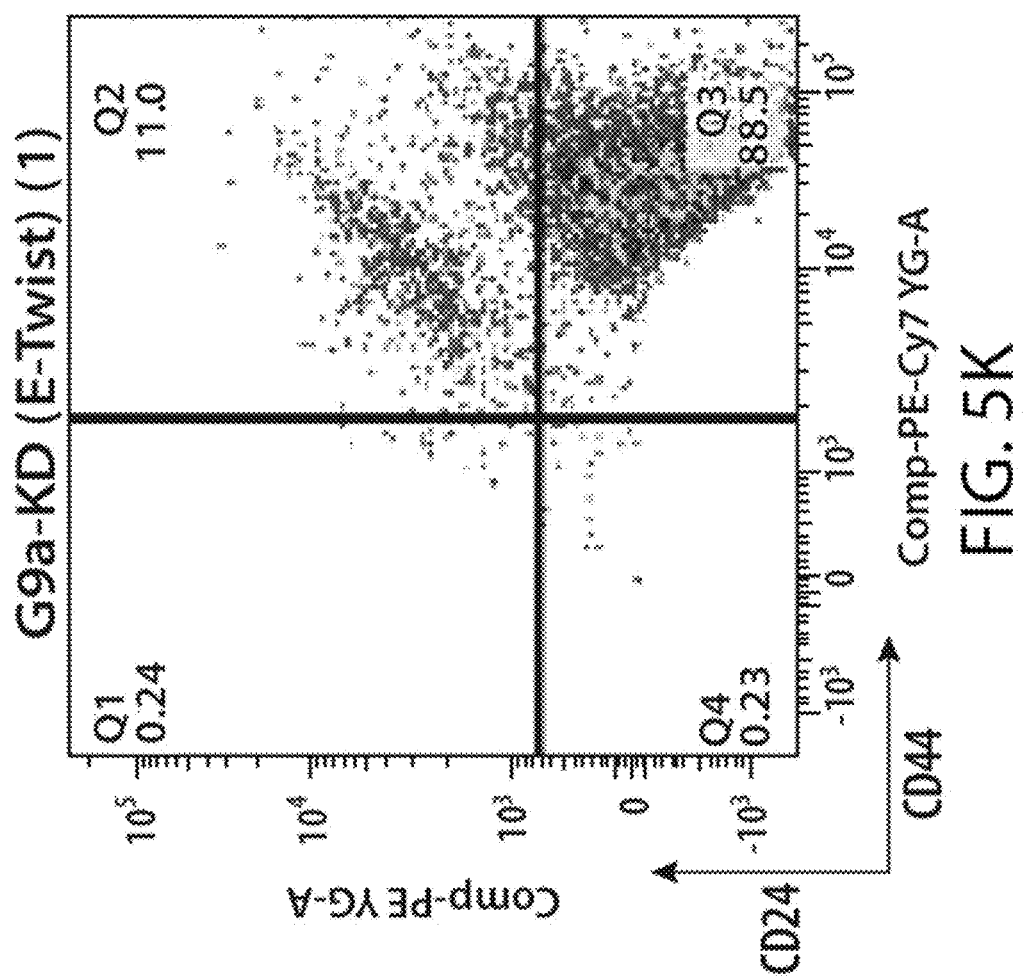
Figure 5L:
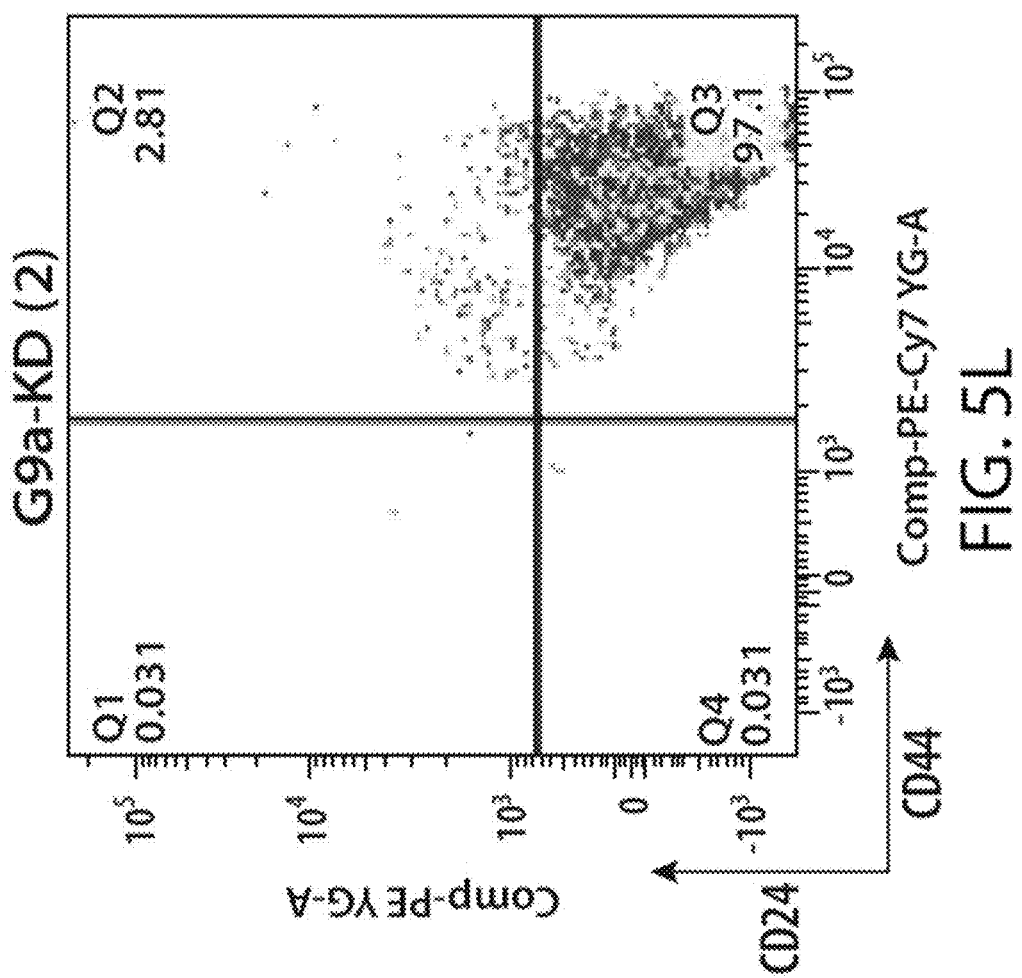
Figure 5N:
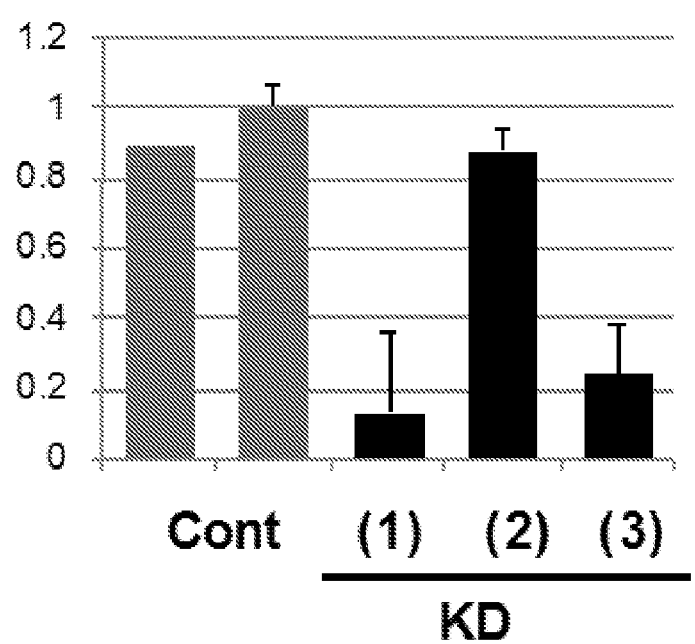

Example 5. Identification of Specific Constitutive Heterochromatin Factors Whose Knockdown Converts Mesenchymal Cells into Epithelial Cells If chaetocin epigenetic conversion of mesenchymal cells into epithelial cells is via inhibition of Suv39H1 and Suv39H2 proteins, then a knockdown of Suv39H1 and Suv39H2 should be sufficient to cause the same conversation. To test this hypothesis, Dicer-generated siRNA technology (dsiRNAs) was used to mediate the knockdown of central regulators of the heterochromatin pathway in HMLE-TWIST cells. Similar to before, the analysis was performed by tracking CD44/CD24 cell surface markers using FACS in HMLE-TWIST cells treated with different dsiRNA constructs. FIG. 5A provides a flowchart delineating the experimental design for these experiments. FIGS. 5B-5E show the FACS analysis of experiments described in FIG. 5A under control conditions (HMLE-TWIST; FIG. 5B), after knock-down of Suv39H1 (SUV39H1-KD (E-Twist)) using three different dsiRNA constructs ((1; FIG. 5C), (2; FIG. 5D), (3; FIG. 5E)). qRT-PCR analysis of Suv39H1 RNA was performed post disRNA treatment to measure knockdown efficiency (FIG. 5F). These results indicate the Suv39H1 was knocked down using three different dsiRNA constructs and that this knockdown converts mesenchymal, TIC cells to a non-TIC phenotype, similar to the effect of chaetocin. This effect is more pronounced the greater the efficiency of the Suv39H1 knockdown.

Figure 5O:
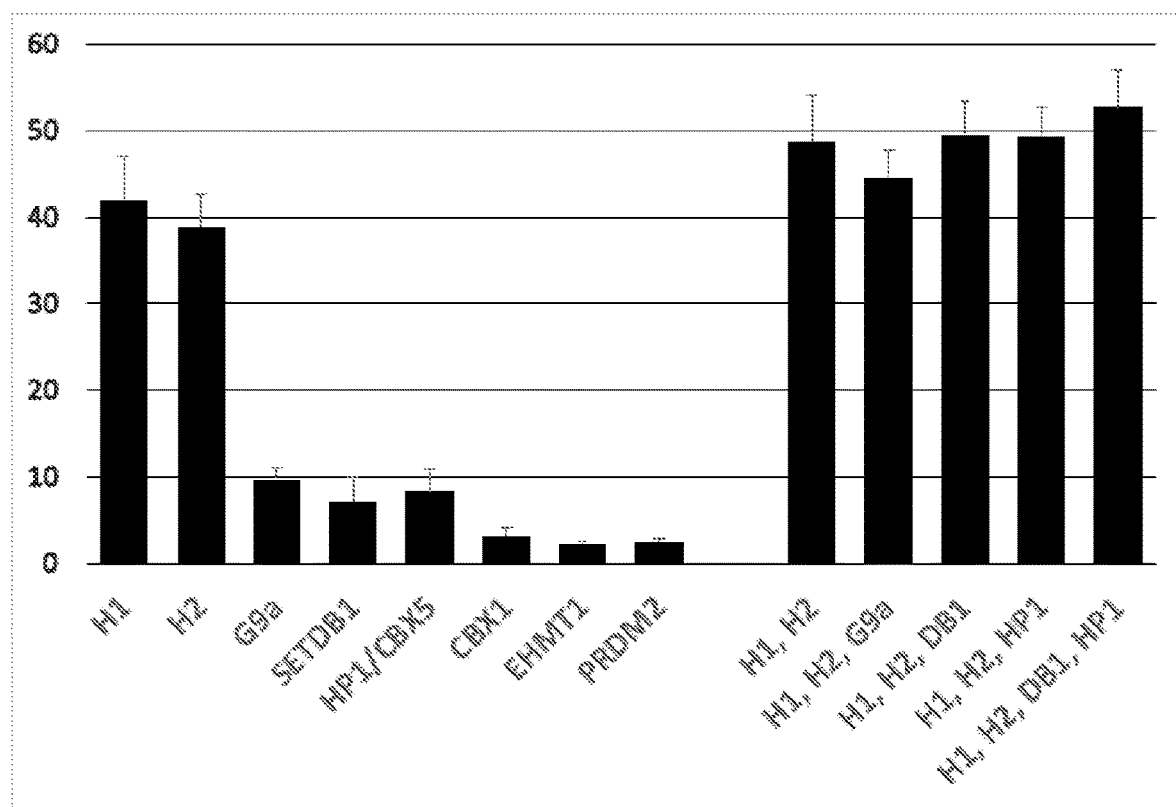

The same experiments were subsequently performed using dsiRNAs targeting Suv39H2 (FIGS. 5G-5J), and another histone methyltransferase, G9a (FIGS. 5K-5N). Again, three different dsiRNA constructs were used to knockdown the aforementioned genes. The extent of knockdown was assessed by qRT-PCR. These data reveal that single knockdown of Suv39H1, but not G9a, converts mesenchymal, TIC cells to a non-TIC phenotype, similar to the effect of chaetocin. FIG. 5O shows a bar plot summarizing the results of single, double, triple, and quadruple knockdown of different heterochromatin proteins in HMLE-TWIST cells. These data reveal that Suv39H1 (H1) and Suv39H2 (H2) have the largest effect in converting mesenchymal, TIC cells to a non-TIC phenotype, similar to the effect of chaetocin. Consistent with the reported specificity of the inhibitor to Suv39H1 and Suv39H2 (i.e., chaetocin), the heterochromatin knockdown experiments reveal a dose-dependent reversal of EMT in HMLE-TWIST cell lines. These data together strongly suggest that H3K9 methylation by these two enzymes is critical for survival and maintenance of mesenchymal, TICs, thus presenting a novel target for reversing resistance in several cancer models.

Example 6. Cancer Cell Killing Efficacy of Chaetocin and its Derivatives

To determine the cancer cell killing efficacy of chaetocin and related molecules, cultured cancer cells were treated with either chaetocin, its monomeric analogue (Movassaghi Lab), or its dimeric analogue (Movassaghi Lab).

The monomeric analogue has the following structure:

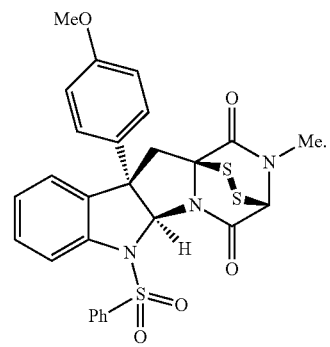

The dimeric analogue has the following structure:

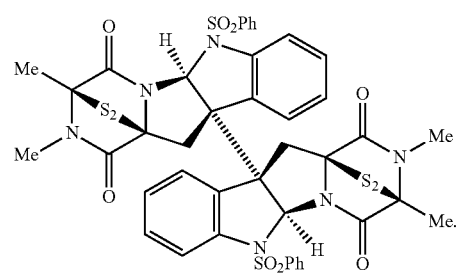

Figure 6A:
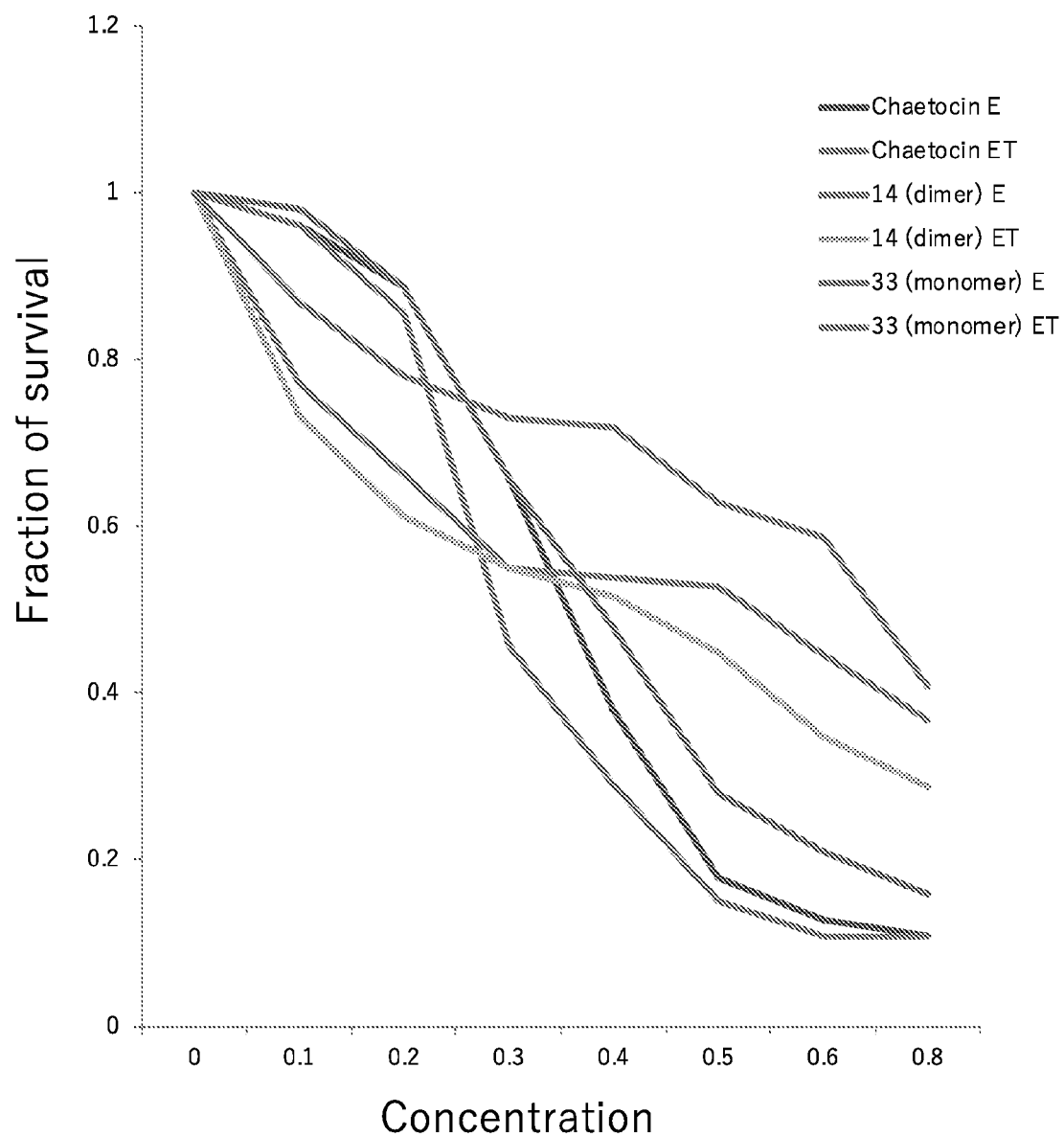
FIGS. 6A-6H show a series of plots demonstrating the fraction of cancer cells surviving following treatment with chaetocin versus its dimeric and monomeric derivatives. In all of FIGS. 6A-6H, the y-axis represents the fraction of cells surviving after drug treatment, the x-axis represents the concentration of the drug, 'E' cells correspond to chemotherapy-sensitive breast cancer cells (HMLE), and 'ET' cells correspond to chemotherapy-resistant breast cancer cells (HMLE-TWIST).
Figure 6B:
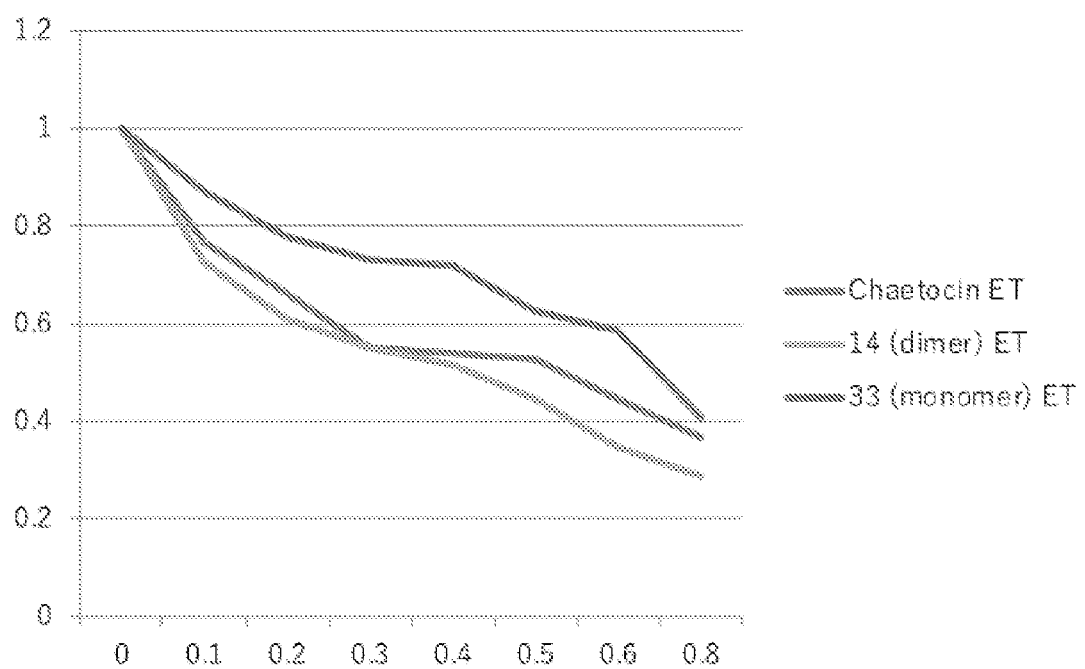
Figure 6C:
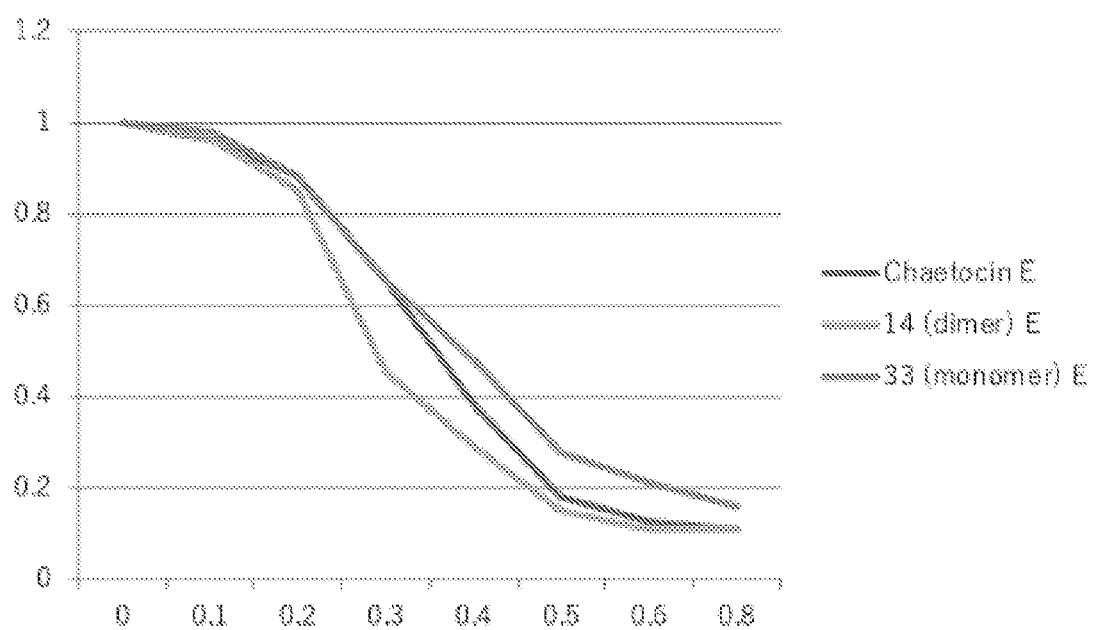
Figure 6D:
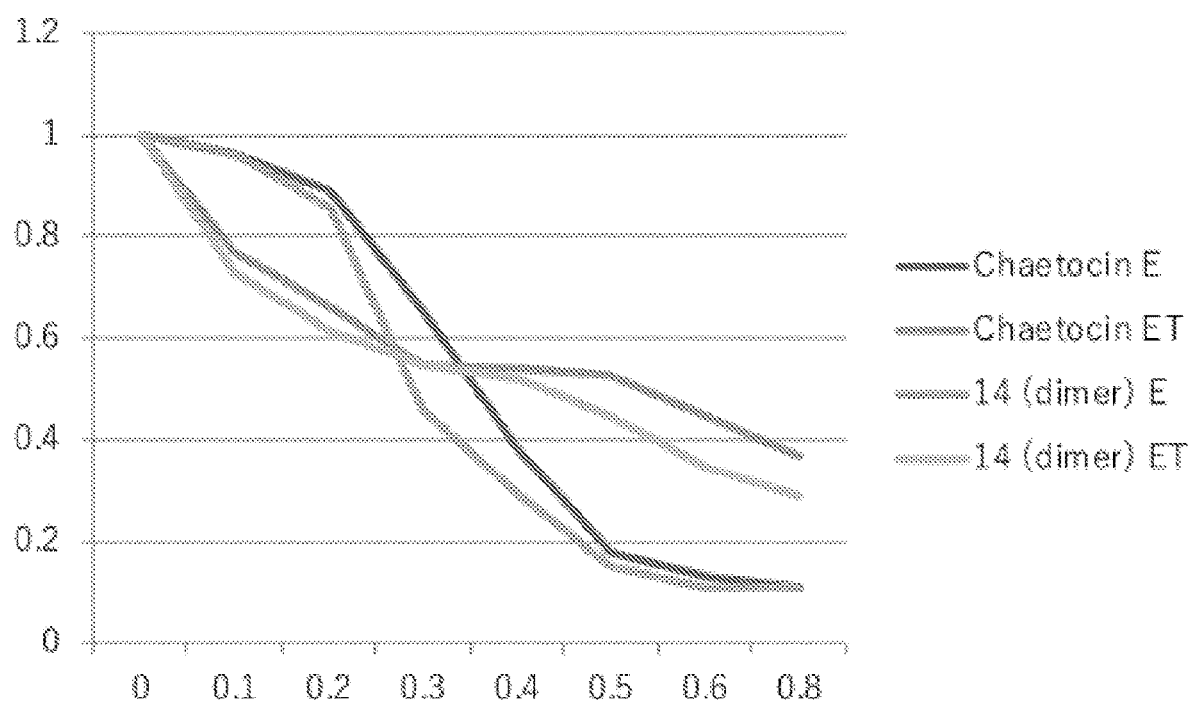
Figure 6E:
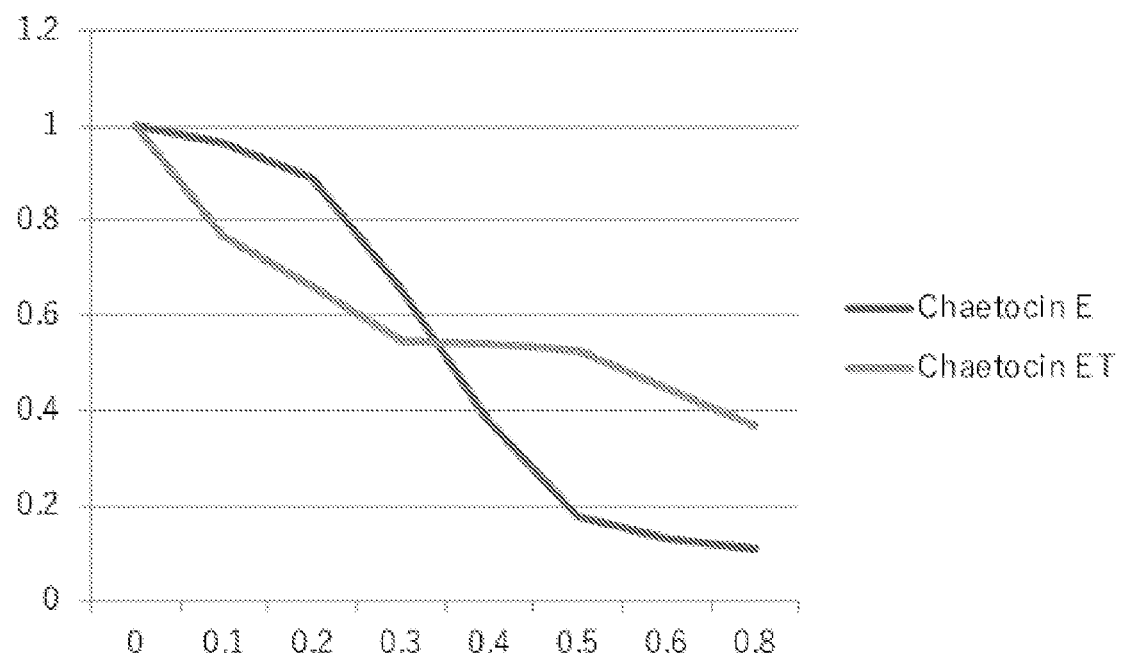
Figure 6F:
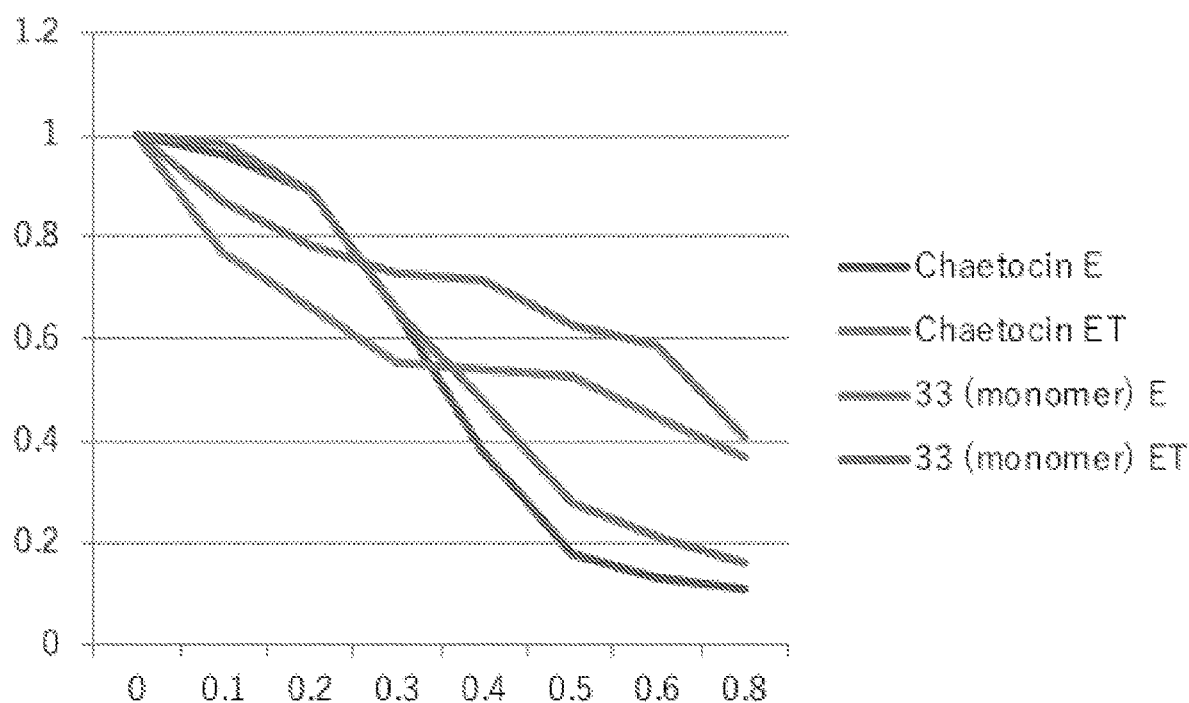
Figure 6G:
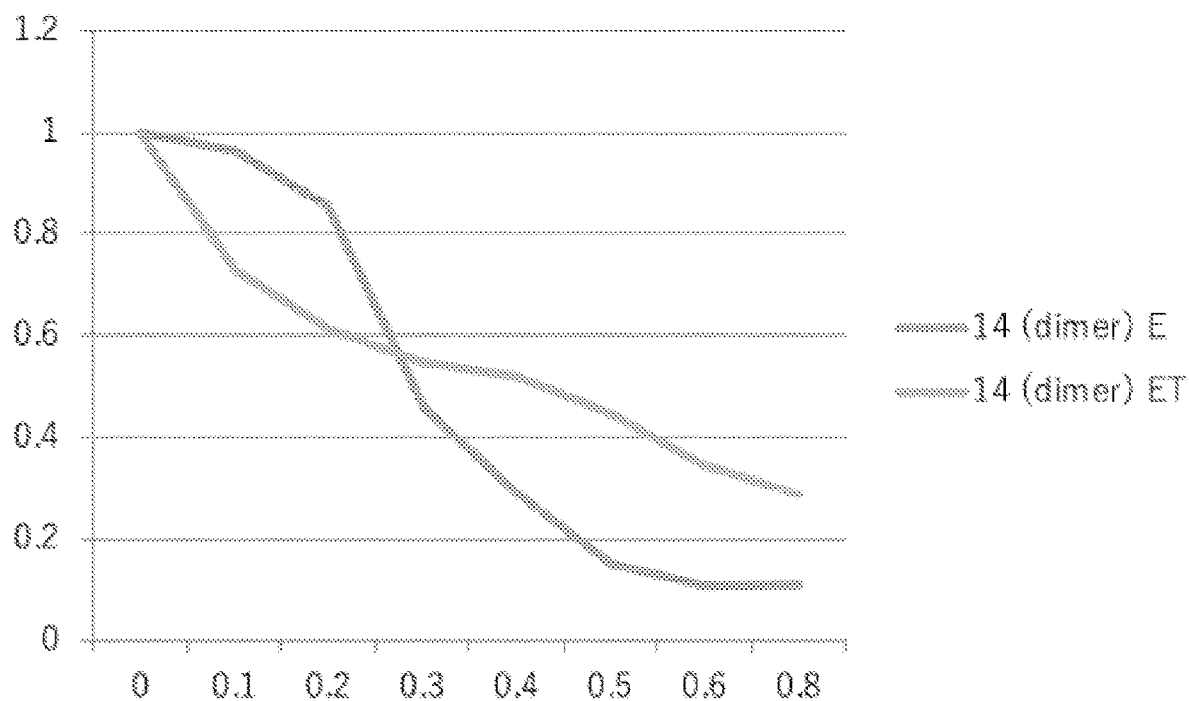
Figure 6H:
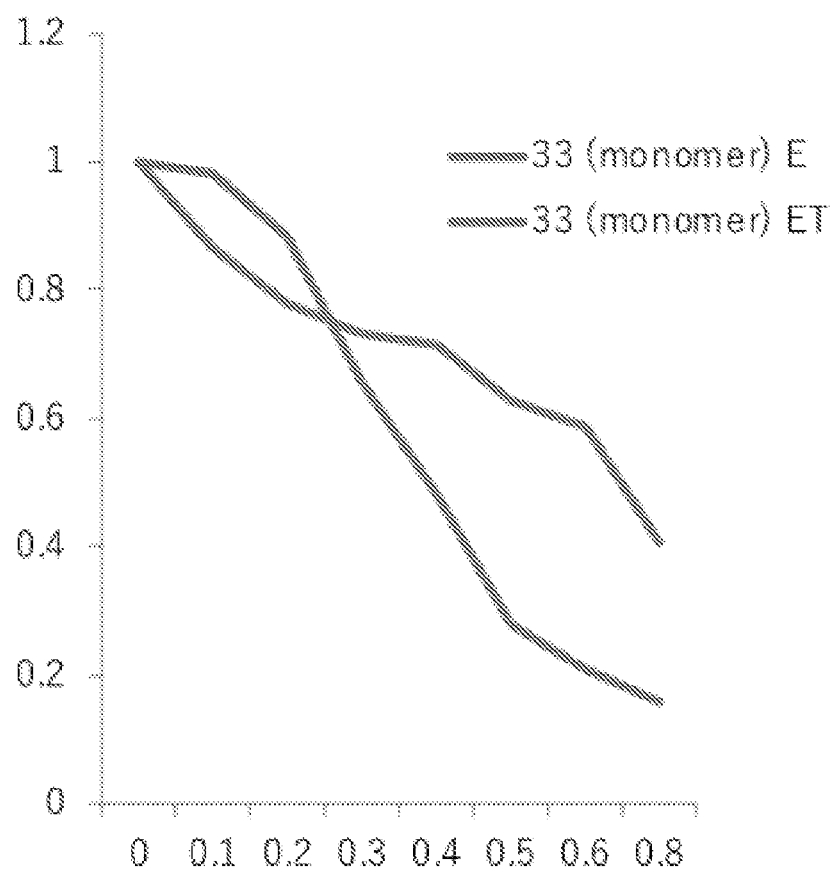

Two different cancer cell lines were tested, including chemotherapy-sensitive, human epithelial breast cancer cell lines (HMLE) ('E') and chemotherapy-resistant, TIC-rich, breast cancer cell line HMLE-TWIST ('ET'). Of note, E and ET cells are genetically identical, wherein the only difference between them is overexpression of TWIST, one of the inducers of EMT, converting these cells into mesenchymal, TIC-rich chemotherapy resistant cells. Sensitivity and resistance to chemotherapy was defined on the basis of responsiveness of these cells to conventional chemotherapeutics. In FIGS. 6A-6H, the y-axis represents the fraction of cancer cells surviving after drug treatment, the x-axis represents the concentration of the drug. FIG. 6A shows the fraction of E or ET cancer cells surviving following treatment with chaetocin or its dimeric or monomeric derivatives. FIGS. 6B-6C show the fraction of ET (FIG. 6B) and E (FIG. 6C) breast cancer cells surviving following treatment with chaetocin or its dimeric or monomeric derivatives. FIGS. 6D-6E show the fraction of E and ET cells surviving following treatment with chaetocin and its dimeric derivative (FIG. 6D) or with chaetocin alone (FIG. 6E). FIGS. 6F-6H show the fraction of E or ET cells surviving following treatment with chaetocin or its monomeric derivative (FIG. 6F), treatment with the dimeric chaetocin derivative (FIG. 6G), and treatment with the monomeric chaetocin derivative (FIG. 6H). These findings indicate that the dimeric derivative of chaetocin is more effective at killing mesenchymal cancer cells compared to chaetocin or its monomeric derivative.

Figure 7A:
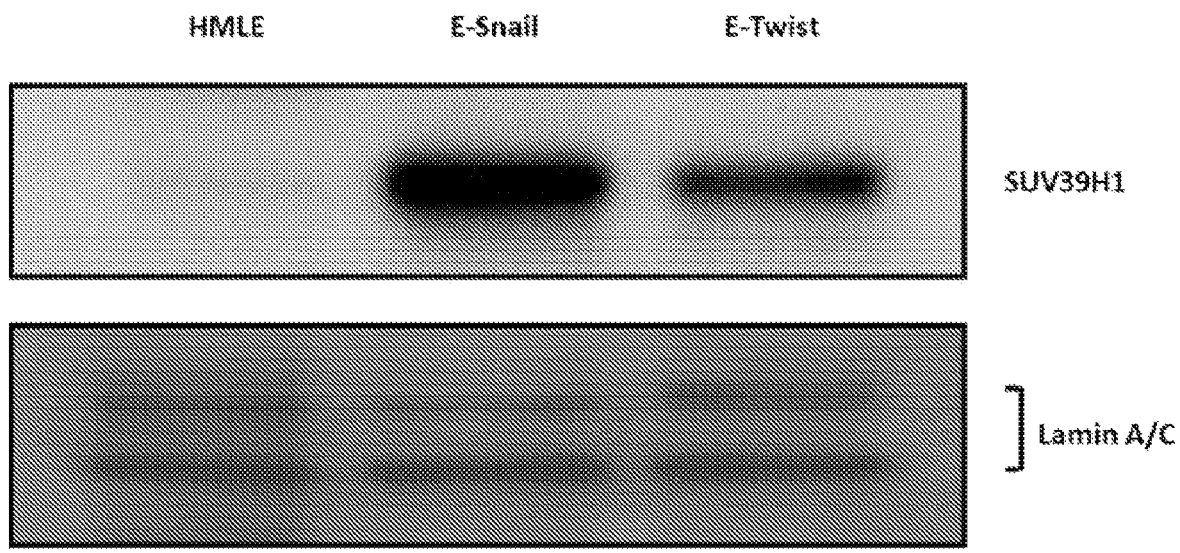
FIG. 7A is a Western blot of epithelial HMLE, and its isogenic mesenchymal derivatives, HMLE-SNAIL (E-Snail) and HMLE-TWIST (E-Twist) cells in which the expression of Suv39H1 was assayed using an anti-Suv39H1 antibody (#8792, Cell Signaling Technology). Lamin A/C antibody (H-110, santa Cruz biotechnology-20681) was used to detect these proteins which serve as the loading control for this experiment.
Figure 7B:
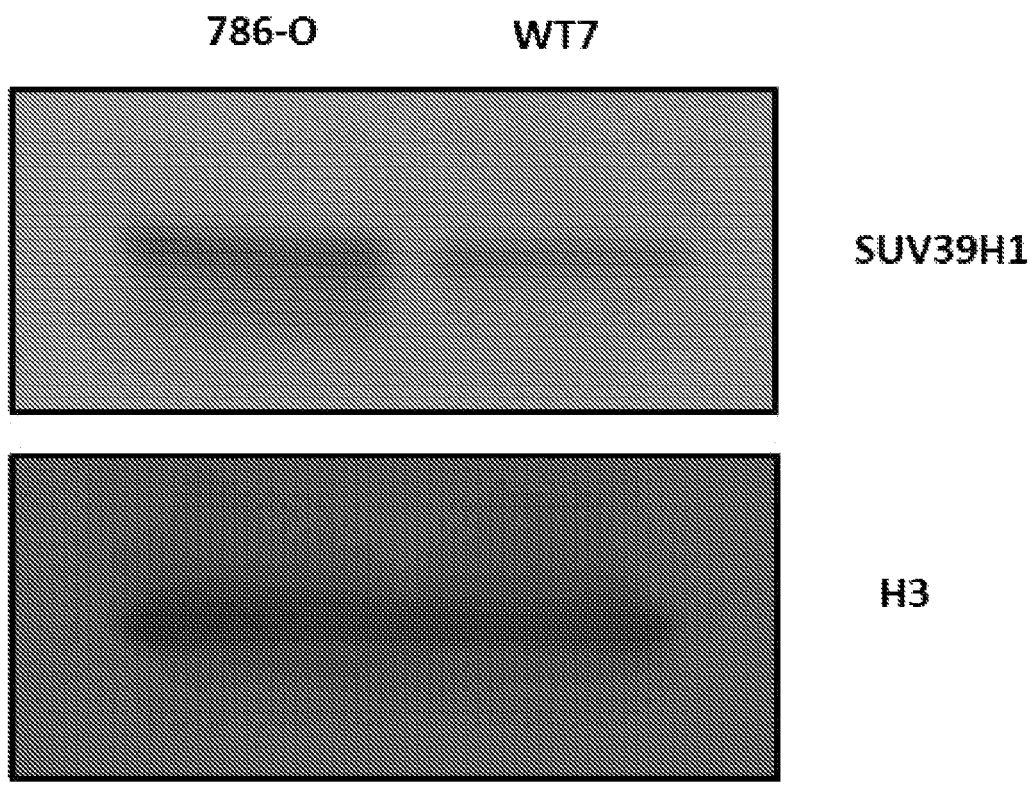
FIG. 7B is a Western blot of epithelial WT-7 and its isogenic mesenchymal derivative 786-0 cells in which the expression of Suv39H1 was assays using an anti-Suv39H1 antibody (Cell Signaling Technology). Histone H3 (abcam 12079) was used as the loading control in this experiment.

Example 7. Suv39H1 Expression is Higher in Mesenchymal, Tumor Initiating Cells Compared to Epithelial, Chemosensitive Cells In this example, the levels of Suv39H1 protein in mesenchymal cells were investigated. Western blot analyses were performed on HMLE and HMLE-TWIST cells, and WT-7 and 786-O cells. Human mammary epithelial cells (HMLE) cells, overexpressing the human telomerase reverse transcriptase (hTERT) and simian virus 40 (SV40) T antigen is an epithelial cell lines that is especially sensitive to chemotherapeutic agents. On the other hand, HMLE-TWIST (E-TWIST) and HMLE-SNAIL (E-SNAIL) cell line are HMLE cell line in which TWIST (Snai2) or SNAIL (Snail) is overexpressed. SNAIL and TWIST are transcription factors whose overexpression converts epithelial, TIC-deplete, chemotherapy sensitive cancer cells into mesenchymal, TIC-rich, chemotherapy resistant cell lines through a process called epithelial-to-mesenchymal transition. Also, 786-O is a clear cell renal cell carcinoma (ccRCC) cell line, which is defective in the Von Hippel-Lindau tumor suppressor (VHL), enriched in TIC, and difficult to eliminate by conventional chemotherapy in patients carrying this mutation. WT7 cell line is a modified 786-O cell line in which VHL is re-introduced artificially, rendering them epithelial, TIC-depleted and susceptible to chemotherapy. These cell lines were used because they are otherwise genetically identical except for the presence of a single gene whose expression impacts EMT. Using an antibody against Suv39H1 (8792, Cell Signaling Technology), we found that Suv39H1 protein level is significantly higher in both mesenchymal cell lines (FIGS. 7A and 7B).

The data in this Example together with the data presented in the rest of this application suggest that (1) Suv39H1 expression can be used as a marker for chemotherapy resistance, and (2) Suv39H1 is a target for eliminating EMT-induced resistance.

Figure 8:
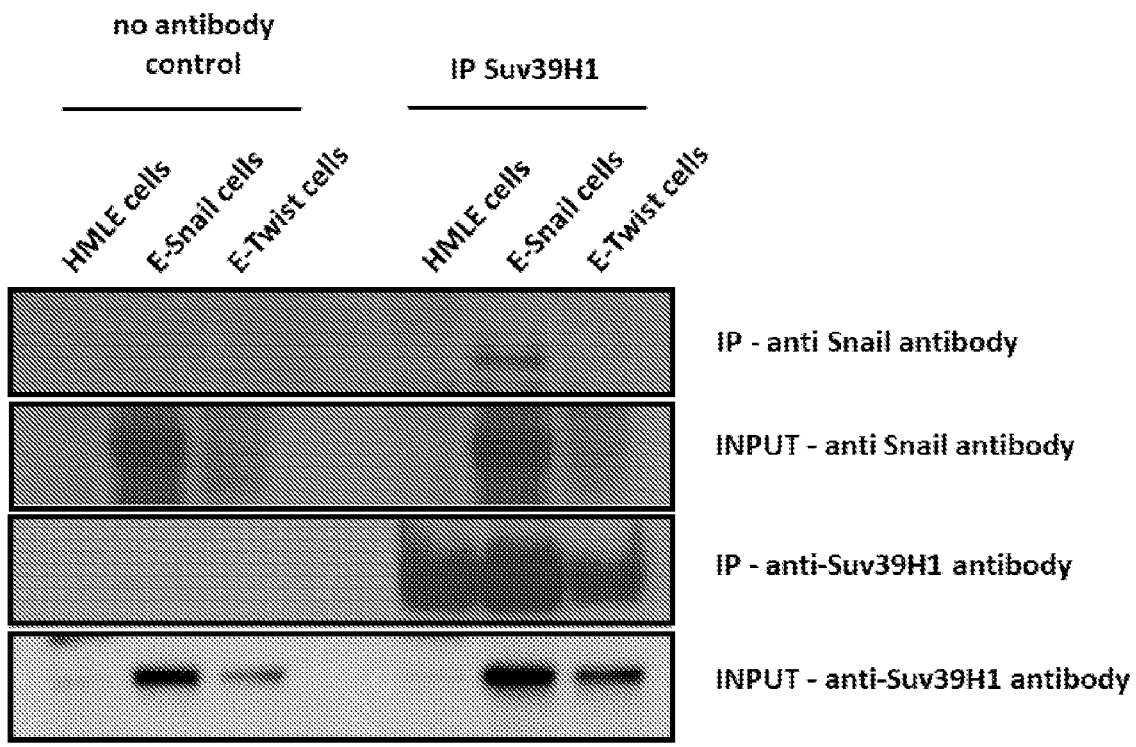
FIG. 8 depicts the result of a co-immunoprecipitation (co-IP) experiment performed on nuclear lysates of HMLE, HMLE-Snail and HMLE-TWIST cells using anti-Suv39H1 antibody. Nuclear lysates were prepared according to standard protocols and sonicated to solubilize chromatin bound proteins. The precleared extracts were then incubated with SUV39H1 antibody (1:150) at 4° C. overnight. A no-antibody control was also performed. Western blot of input and IP samples were performed using Snail antibody (4719—Cell Signaling) and SUV39H1 antibody (8729—Cell Signaling). We found that (1) level of Suv39H1 is higher in HMLE-SNAIL and HMLE-TWIST cells and (2) Snail is co-immunoprecipitated with Suv39H1 in HMLE-SNAIL cells specifically.
Figure 9:
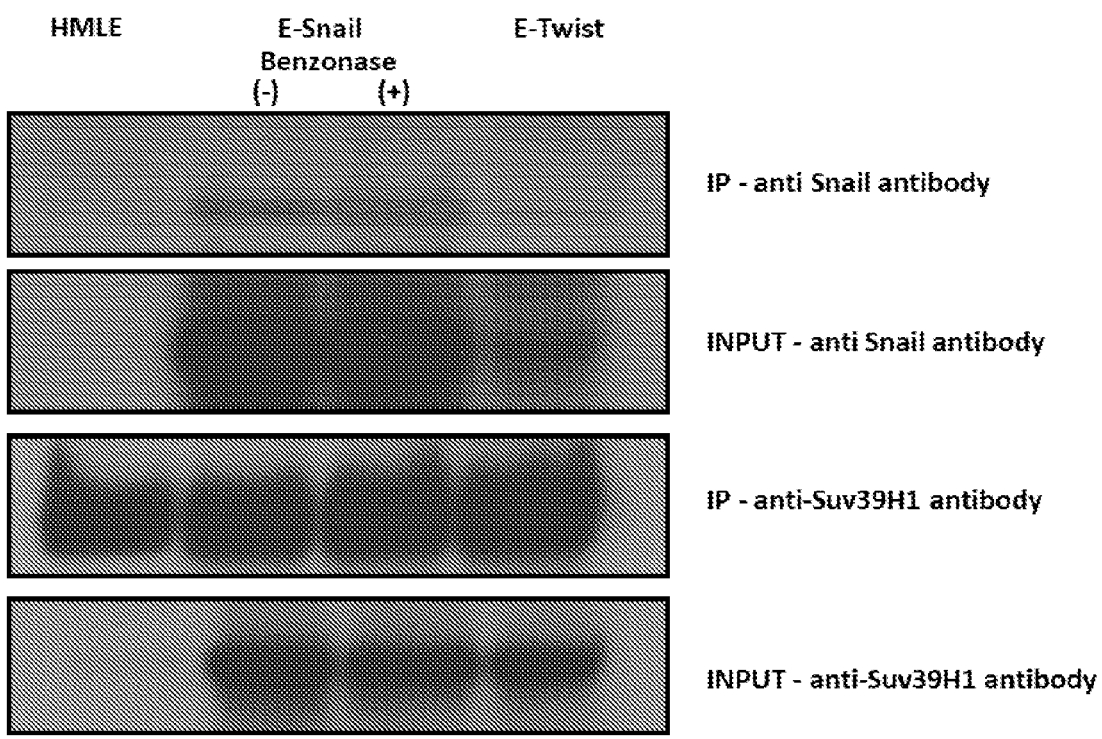
FIG. 9 depicts the results of co-immunoprecipitation (co-IP) experiment performed on nuclear lysates of HMLE, HMLE-SNAIL and HMLE-TWIST cells using anti-Suv39H1 antibody performed in presence or absence of benzonase, an enzyme which degrades chromatin and RNA effectively. Nuclear lysates were prepared as described in FIG. 8 and the precleared extracts were incubated with Suv39H1 antibody (1:150) at 4° C. overnight. Western blot of input and IP samples were performed using Snail antibody (4719—Cell Signaling) and SUV39H1 antibody (8729—Cell Signaling). Snail is co-immunoprecipitated with Suv39H1 in HMLE-SNAIL cells specifically and that this interaction increases in benzonase-treated cells, suggesting that this interaction occurs on chromatin.

Example 8. Suv39H1 Physically Interacts with SNAIL in Mesenchymal, Tumor Initiating Cells In this example, the mechanism of how Suv39H1 regulates and helps establish the mesenchymal state was investigated. To that end, the presence of any physical interactions between Suv39H1 and the EMT transcription factor, SNAIL, was assessed. Such an interaction would provide a molecular basis for how Suv39H1 is recruited to specific genes in mesenchymal cells, specifically those which are bound by SNAIL. Co-immunoprecipitation (Co-IP) experiments were performed using anti-Suv39H1 antibody. The results revealed that Suv39H1 physically interacts with Snail in HMLE-SNAIL and HMLE-TWIST cells (FIG. 8). This interaction occurs independently of RNA, DNA, and chromatin as revealed by performing these experiments in the presence or absence of benzonase, an enzyme which degrades chromatin and RNA (FIG. 9). The increase in interaction with Suv39H1 and Snail suggest that this interaction occurs between these proteins and associated complexes on chromatin.

Considering the observed Suv39H1-SNAIL interaction, inhibition of Suv39H1 can reverse EMT-induced chemotherapy resistance by transcriptional reprogramming of mesenchymal cells. Because Suv39H1 is involved in repression of gene expression, its inhibition can lead to activation of SNAIL-repressed genes.

Figure 10:
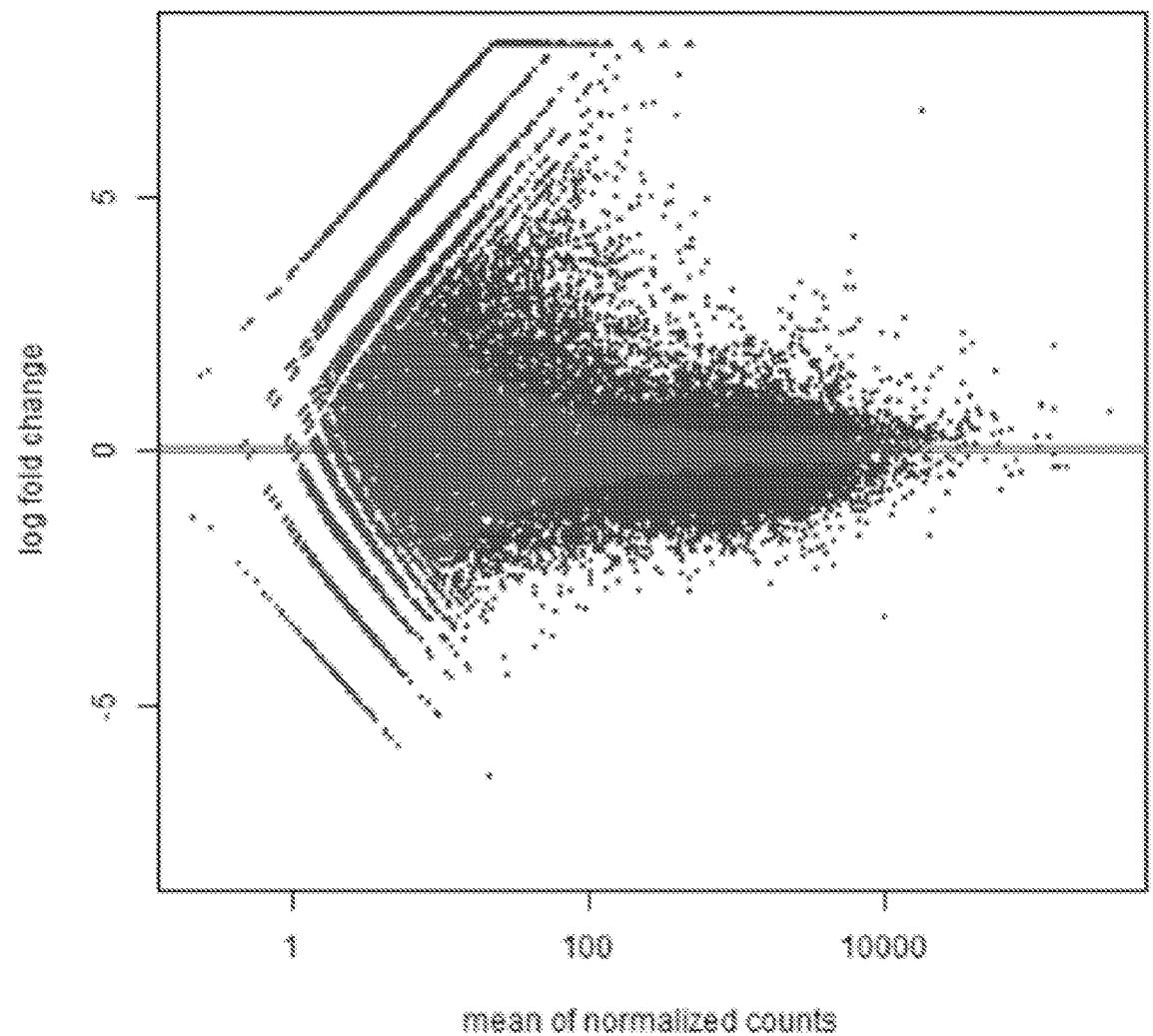
FIG. 10 depicts the change in transcriptome of HMLE-TWIST cells treated with 0.3 uM of chaetocin for 15 hours versus untreated cells. Two biological replicates were used to produce these results. Red dots denote transcripts whose expression is significantly altered upon chaetocin treatment.

Example 9. Chaetocin Treatment Causes an Increase in Expression of Epithelial and a Decrease in Expression of Mesenchymal Genes The data presented herein demonstrate that a short treatment with chaetocin alters the mesenchymal properties of cells as assayed by CD44 and CD24 marks on HMLE-TWIST cell lines. To determine whether the transcriptional changes associated with chaetocin treatment support this apparent change in cell state (reversal of mesenchymal fate), RNA-seq experiments were performed on cells treated for 15 hours with 0.3 µM of chaetocin after which total RNA was extracted and subjected to deep sequencing. FIG. 10 shows the change in transcriptome of chaetocin treated versus untreated cells. Table 4 and 5 show a select list of genes whose expression increase or decrease in response to chaetocin treatment, respectively. The results reveal that chaetocin treatment results in the increase in expression of several epithelial genes (Table 4) and the decrease in the expression of mesenchymal genes and cancer stem cell genes (Table 5). These data demonstrate that chaetocin treatment results in reversal of mesenchymal fate.

TABLE 4

Epithelial Genes Whose Expression Is Increased in Response to Chaetocin Treatment

|  | Gene name | Log2foldChange | Adjusted P value |
| --- | --- | --- | --- |
| E-cadherin | CDH1 | 4.25 | 0.00130 |
| Collagen 2(A2) | COL2A1 | 4.34 | 7.06E-05 |
| survivin-1 | BIRC5 | 0.491 | 0.000580 |
| Keratins | KRT8 | 1.30 | 2.05E-24 |
|  | KRT18 | 1.95 | 2.87E-42 |
|  | KRT34 | 5.49 | 1.66E-16 |
|  | KRT7 | 1.59 | 0.000232 |
|  | KRT80 | 1.24 | 9.08E-06 |
|  | KRT19 | 4.46 | 0.000532 |
|  | KRT81 | 1.47 | 0.00120 |
|  | KRT86 | 3.10 | 1.91E-06 |
| Claudins | CLDN6 | 7.30 | 4.56E-19 |
|  | CLDN4 | 3.68 | 6.97E-12 |
|  | CLDN2 | 6.00 | 0.000950 |
|  | CLDN9 | 4.59 | 0.000257 |
|  | CLDN23 | 1.18 | 0.0296 |
|  | CLDN16 | 2.77 | 0.0564 |
| increased expression in epithelial cells | | | |
|  | CRB1 | 9.40 | 6.37E-09 |
|  | CST6 | 2.12 | 0.0520 |

TABLE 5

Mesenchymal Genes and Cancer Stem Cell Markers

|  | Gene name | Log2foldChange | Adjusted P value |
|---|---|---|---|
| *Mesenchymal genes whose expression is repressed in response to chaetocin treatment* | | | |
| EMT TFs | TWIST1 | −0.549 | 7.04E−05 |
|  | SNAI2 | −0.623 | 0.000479 |
|  | ZEB1 | −0.666 | 9.06E−07 |
| Activated by TWIST | LAMB1 | −1.05 | 5.47E−15 |
| Activated by Slug | MMP14 | −1.14 | 7.43E−13 |
| Activated in mesenchymal cells | WISP1 | −1.06 | 1.81E−07 |
| *Cancer Stem cell markers whose expression decrease in response to chaetocin treatment* | | | |
|  | CD24 | −0.912 |  |
|  | GLI-2 | −0.941 |  |
|  | ALDH1A1 | −2.01 |  |
|  | Errb2 | −0.829 |  |
|  | GJA1 | −0.627 |  |
|  | PTEN | −0.780 |  |
|  | Nanog | −2.21 |  |
|  | O ct4 | −1.76 |  |
|  | NRF-2 | −0.862 |  |

Figure 11:
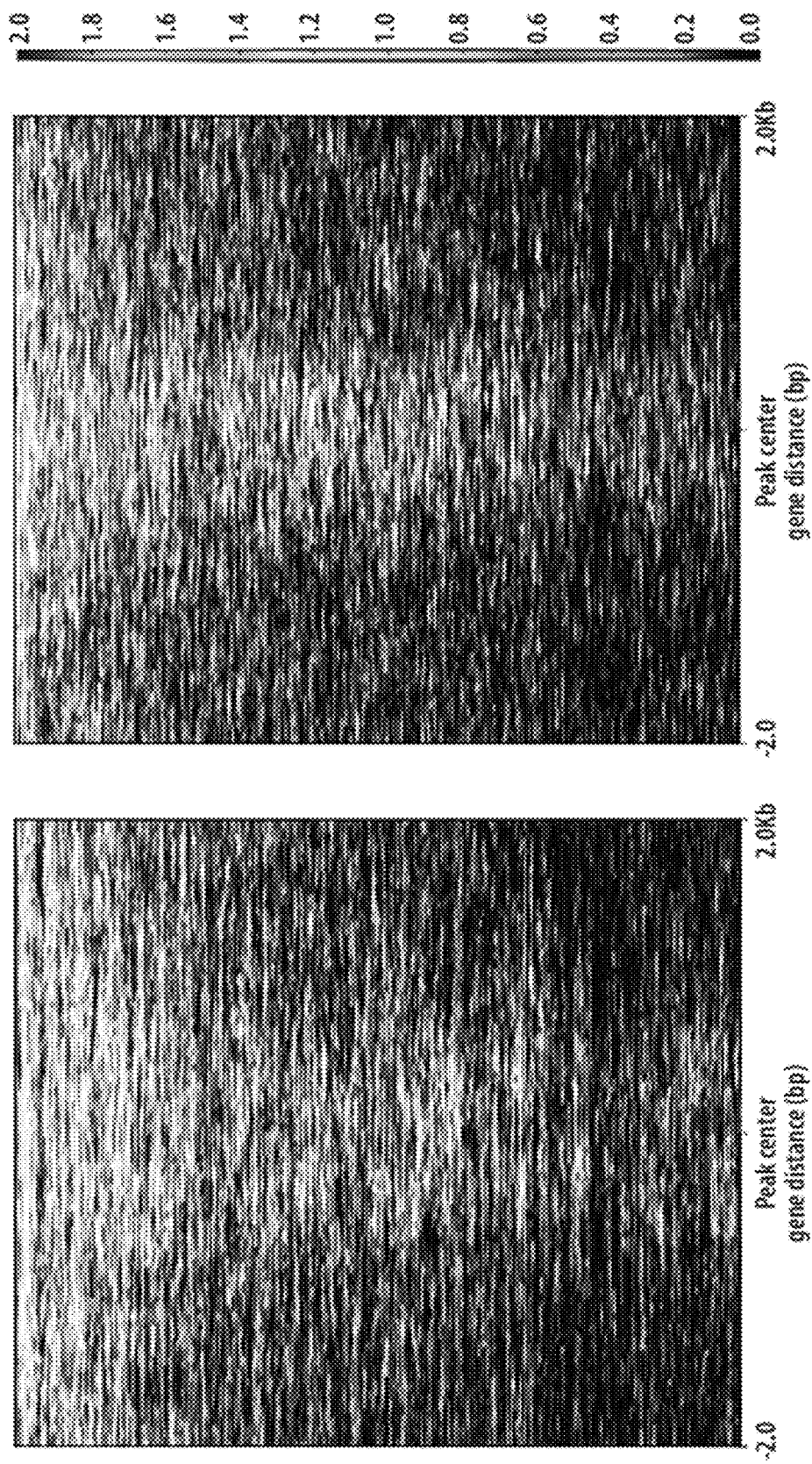
FIG. 11 is a meta-plot depicting the H3K9me3 peaks in HMLE-TWIST cells treated (right graph) with 0.3 µM of chaetocin for 15 hours versus untreated cells (left graph). Two biological replicates were used to produce these results. The decrease in red and yellow color and an increase in blue color is consistent with chaetocin-induced inhibition of Suv39H1 and Suv39H2 activities resulting in a decrease in H3K9me3 throughout the chaetocin-treated HMLE-TWIST cells.

Example 10. Chaetocin Treatment Causes a Decrease in H3K9Me3 in Mesenchymal Cells Chaetocin is an inhibitor of Suv39H1 and Suv39H2 enzymes, whose catalytic activities trimethylates lysine 9 of histone H3. To demonstrate that a short pulse of chaetocin can result in a decrease in H3K9me3, we performed chromatin immunoprecipitation experiments using a specific H3K9me3 antibody (abcam) followed by deep sequencing of the purified DNA fragment. FIG. 11 shows the change in H3K9me3 profile of HMLE-TWIST cells in response to a short pulse (0.3 μM for 15 hours) of chaetocin treatment versus untreated cells. Table 6 shows a select list of genes which display a decrease in H3K9me3 in response to chaetocin treatment. Consistent with our model, we find that genes involved in cell-cell adhesion (a strong marker for epithelial cells) display a specific loss of H3K9me3 in response to chaetocin treatment (Table 6). We also find that genes involved in neural differentiation also lose H3K9me3. These data demonstrate that chaetocin treatment results in specific loss of H3K9me3 over epithelial genes, supporting a role for Suv39H1 in establishing the transcriptional program of mesenchymal cells. Moreover, 60 genes display a simultaneous loss of H3K9me3 and an increase in their expression in chaetocin-treated cells (Table 7). These data together with the RNA-seq results demonstrate that chaetocin treatment results in reversal of mesenchymal state via inhibition of Suv391H1/1H2-dependent repression of select genes.

TABLE 6

Gene Ontology Biological Process (BPs) Enriched among Genes Which Lose H3K9me3 Upon Chaetocin Treatment (0.3 uM for 15 hours)

|  | # | # | expected | Fold Enrichment | +/− | raw P value | FDR |
|---|---|---|---|---|---|---|---|
| cell-cell adhesion | 494 | 27 | 10.82 | 2.49 | + | 0.0000358 | 0.0227 |
| neuron differentiation | 992 | 46 | 21.73 | 2.12 | + | 0.00000428 | 0.00452 |

TABLE 7

Genes Which Display a Loss of H3K9me and Transcriptional Repression in Response to Chaetocin Treatment (see FIGS. 10 and 11)

| PRKCZ | FAM20C | GABBR2 | DNAH10 | ZFP3 | ZNF556 |
|---|---|---|---|---|---|
| EPHA8 | CARD11 | CFL1 | TMEM132B | LRRC46 | DOHH |
| SAG | PPP1R9A | DLG2 | EEF1AKMT1 | USP36 | VAV1 |
| ITGA9 | PTPRN2 | NTM | C13orf46 | LDLRAD4 | ZNF557 |
| NEK11 | PNPLA4 | CTNNA3 | HSP90AA1 | NFATC1 | ZNF333 |
| TACC3 | PPP1R3F | LRMDA | ATP8B4 | CTDP1 | CPAMD8 |
| FRAS1 | CCNB3 | JAKMIP3 | RASGRF1 | ZNF341 | RYR1 |
| ZFP2 | MYOM2 | CD163L1 | HYDIN | COL20A1 | SPTBN4 |
| GRM4 | PXDNL | KRT86 | OSGIN1 | MADCAM1 | HSF2BP |
| DNAH8 | C8orf34 | KRT81 | TUBB3 | HCN2 | ITGB2 |

The genes presented in Table 7 are overrepresented in heterotypic cell-cell adhesion and receptor clustering gene ontology biological processes, among which the heterotypic cell-cell adhesion gene ontology is consistent with increase in epithelialization of mesenchymal HMLE-TWIST cells.

Suv39H1 inhibition can reverse EMT-induced chemotherapy resistance by transcriptional reprogramming of mesenchymal cells. Considering the role of Suv39H1 in repressing transcription, inhibition of Suv39H1 can lead to activation of SNAIL-repressed genes.

Figure 12:
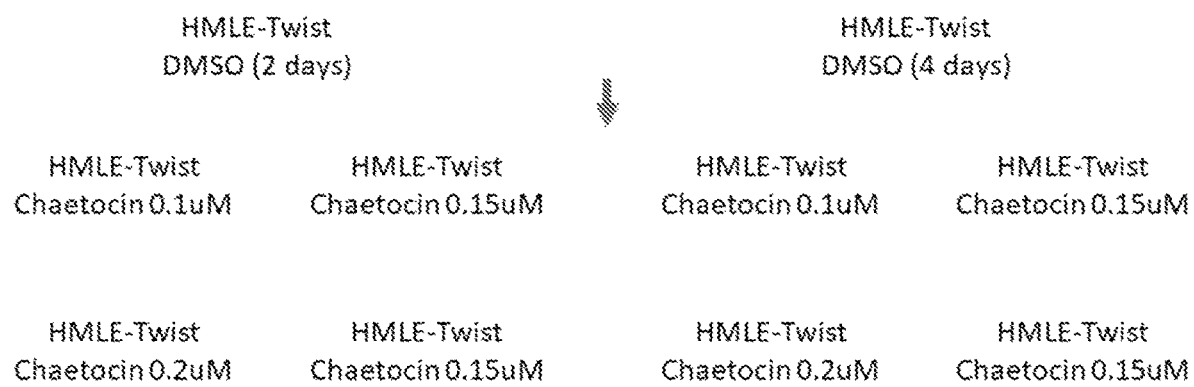
FIG. 12 depicts the experimental design used for RNA-seq experiments whose results are presented in Tables 5-6. Briefly, HMLE-TWIST cells were treated for two days with increasing doses of chaetocin (0.1, 0.15, 0.2, 0.5 uM). The cells were then washed and incubated for an additional 2 days in chaetocin-free media. Cells were collected before chaetocin treatment and at the 2-day and 4-day timepoints. Total RNA was extracted and subjected to deep sequencing. All chaetocin-treated transcriptomes were compared to cells treated with DMSO for 2 and 4 days which served as controls.

Example 11. Chaetocin Treatment Reprograms Mesenchymal Cells into an Epithelial Fate Using FACS (see FIGS. 3A-3X), it was shown that mesenchymal, TIC-rich HMLE-TWIST cells treated with increasing doses of chaetocin lose their mesenchymal properties. (Specifically, cells expressing high levels of CD44 and no expression of CD24 are considered TICs, whereas cells expressing CD24 are considered non-TICs. In these FIGS., chaetocin treatment reprogrammed TICs into a non-TIC phenotype as assayed by tracking CD44 and CD24 status of the cells using FACS. Moreover, the dose-dependent, chaetocin-mediated conversation of TICs into non-TICs persisted for up to 2 days after the chaetocin removal, demonstrating that chaetocin treatment causes an epigenetic reprogramming of TICs into non-TICs. To ask whether the transcriptional changes of chaetocin-treated cells support our FACS-based conclusions, we performed the same experiment and collected total RNA from cells before chaetocin treatment, after 2 days of chaetocin treatment, and 2 days after chaetocin removal (FIG. 12). All transcriptomes were compared to the corresponding DMSO-treated controls. Remarkably, using Enrichr gene enrichment analysis platform (https://amp.pharm.mssm.edu/Enrichr/), chaetocin treatment resulted in repression of several mesenchymal pathways and an increase in DNA repair and two important tumor suppressing pathways, p53 and Rb. Indeed, these transcriptional changes persist after chaetocin removal (Tables 8 and 9). Together these data establish that chaetocin treatment causes an epigenetic reprogramming of TICs into non-TICs.

TABLE 8

| Term | P-value | Adjusted P-value | Genes |
|---|---|---|---|
| Pathways down-regulated in HMLE-TWIST cells after two days of treatment with 150 µM of chaetocin | | | |
| miRNA targets in ECM and membrane receptors WP2911 | 1.95E−11 | 9.20E−09 | LAMB2; LAMA4; ITGA1; FN1; LAMC1; THBS1; COL3A1; COL1A2; COL5A1; COL4A1; COL5A3; COL5A2; ITGA11 |
| Focal Adhesion-PI3K-Akt-mTOR-signaling pathway WP3932 | 1.20E−09 | 2.82E−07 | LAMA5; CSF1; ATF6B; EPAS1; IRS1; ITGB4; LAMA4; ITGA2B; PTEN; PIK3CD; IRS2; LAMC1; THBS1; FOXO1; PIK3C2B; AKT2; PDGFC; ITGAV; IL6R; MAPK3; PDGFRB; SREBF1; PDGFRA; ANGPT1; LAMB2; FN1; PPP2R5A; LAMB1; EPOR; COL1A1; COL3A1; KITLG; COL1A2; COL5A1; COL4A1; COL4A4; ITGA10; COL5A3; COL5A2; ITGA11; ULK1; ITGA5; FGF13; FGFR3; ATF4; FGFR1 |
| Focal Adhesion WP306 | 9.06E−08 | 1.42E−05 | LAMA5; ITGB4; LAMA4; ITGA2B; PXN; PTEN; PIK3CD; LAMC1; THBS1; CCND3; AKT2; PDGFC; ERBB2; RAC3; ITGAV; MAPK3; PDGFRB; PDGFRA; CAV2; LAMB2; ITGA1; FN1; LAMB1; COL1A1; COL1A2; COL4A1; COL4A4; ITGA10; COL5A3; COL5A2; ITGA11; ITGA5 |
| Hypothesized Pathways in Pathogenesis of Cardiovascular Disease WP3668 | 5.52E−06 | 6.51E−04 | FBN2; TGFBR3; SERPINE1; LTBP1; RUNX2; CTGF; MAPK3; TGFBR2; FBN1 |
| PI3K-Akt Signaling Pathway WP4172 | 1.17E−05 | 0.00110303 | LAMA5; CSF1; ATF6B; IRS1; ITGB4; LAMA4; ITGA2B; PTEN; PIK3CD; LAMC1; THBS1; CCND3; AKT2; PDGFC; ITGAV; IL6R; MAPK3; PDGFRB; PDGFRA; ANGPT1; LAMB2; ITGA1; FN1; PPP2R5A; LAMB1; EPOR; COL1A1; KITLG; COL1A2; COL4A1; COL4A4; ITGA10; ITGA11; COL4A5; PKN1; ITGA5; FGF13; FGFR3; ATF4; FGFR1 |
| Inflammatory Response Pathway WP453 | 2.98E−05 | 0.00234525 | COL1A1; LAMA5; COL3A1; COL1A2; LAMB2; FN1; LAMB1; LAMC1; THBS1 |
| miR-509-3p alteration of YAP1/ECM axis WP3967 | 2.44E−04 | 0.01646427 | COL1A1; EDNRA; COL3A1; SPARC; COL5A1; FN1 |
| Alpha 6 Beta 4 signaling pathway WP244 | 4.23E−04 | 0.02492966 | LAMA5; IRS1; ITGB4; LAMB2; IRS2; LAMB1; LAMC1; MAPK3 |

TABLE 8-continued

| Term | P-value | Adjusted P-value | Genes |
|---|---|---|---|
| *Integrin-mediated Cell Adhesion WP185* | 5.91E−04 | 0.03100336 | CAV2; ITGB4; ITGA2B; PXN; ITGA1; ARAF; CAPN6; AKT2; ITGA10; ITGA11; RAC3; ITGAV; CAPN1; ITGA5; TNS1 |
| Primary Focal Segmental Glomerulosclerosis FSGS WP2572 | 7.19E−04 | 0.033914 | SCARB2; LAMA5; INF2; CD151; ITGB4; LAMB2; COL4A4; COL4A5; ITGAV; AGRN; DKK1; DNM1 |
| *Epithelial to mesenchymal transition in colorectal cancer WP4239* | 7.40E−04 | 0.03175257 | NOTCH2; FZD1; NOTCH3; SPARC; JUP; MMP2; WNT5A; FZD6; FN1; PIK3CD; TGFBR2; WNT6; LATS2; WNT11; COL4A1; AKT2; COL4A4; COL4A5; ITGA5; MAPK3 |
| Oncostatin M Signaling Pathway WP2374 | 0.00103803 | 0.04082935 | PIAS3; EGR1; IRS1; SERPINE1; PXN; PTK2B; RICTOR; IL6ST; LDLR; CYR61; MAPK3 |
| *Adipogenesis WP236* | 0.00116354 | 0.04224551 | FZD1; NCOA1; SREBF1; CEBPD; IRS1; EPAS1; STAT2; SERPINE1; IRS2; FOXO1; KLF6; BMP1; SPOCK1; IL6ST; PPARA; LPIN1; LPIN3 |
| *Hippo-Merlin Signaling Dysregulation WP4541* | 0.00130362 | 0.04395064 | PDGFRB; PDGFRA; ITGB4; ITGA2B; ITGA1; YY1AP1; CTGF; LATS2; PLCB4; ITGA10; ITGA11; ITGAV; CDH15; ITGA5; FGFR3; FGFR1 |
| *SREBF and miR33 in cholesterol and lipid homeostasis WP2011* | 0.00154147 | 0.04850487 | ABCA1; SREBF1; PPARA; MED15; LDLR |
| Pathways down-regulated in HMLE-TWIST cells after two days of treatment with 500 μM of chaetocin | | | |
| miRNA targets in ECM and membrane receptors WP2911 | 2.85E−09 | 1.35E−06 | LAMB2; LAMA4; SDC2; ITGA1; LAMC1; THBS1; COL3A1; COL1A2; COL5A1; COL4A2; COL4A1; COL5A2; ITGA11 |
| *Epithelial to mesenchymal transition in colorectal cancer WP4239* | 1.30E−06 | 3.07E−04 | NOTCH3; SPARC; LRP5; TWIST1; PIK3CD; HIF1A; PKD1; LRP6; WNT6; WNT11; AKT2; MEF2D; MAPK3; FZD1; TGFB2; JUP; MMP2; WNT5A; FZD6; MAPK14; MPP5; TGFBR2; LATS2; COL4A2; PIK3CA; COL4A1; MMP15; COL4A4; TRAF6; COL4A3; COL4A6; COL4A5; ITGA5 |
| *Focal Adhesion WP306* | 1.65E−06 | 2.59E−04 | ITGB1; LAMA5; ROCK1; LAMA4; ITGA2B; PXN; PTEN; PIK3CD; LAMC1; THBS1; PPP1CB; PPP1CC; CCND3; AKT2; PDGFC; ERBB2; RAC3; ITGAV; PAK4; MAPK3; PDGFRB; PDGFRA; ITGA4; CAV2; LAMB2; ITGA1; LAMB1; COL1A2; COL4A2; PIK3CA; COL4A1; COL4A4; ITGA10; COL5A2; ITGA11; RAPGEF1; COL4A6; ITGA5 |
| *Focal Adhesion-PI3K-Akt-mTOR-signaling pathway WP3932* | 9.69E−06 | 0.00114365 | ITGB1; ATF2; CDKN1A; CSF1; IRS1; ITGA2B; PTEN; PIK3CD; IRS2; LAMC1; PIK3C2B; AKT2; ITGAV; PDGFRB; PDGFRA; ITGA4; STRADA; F2R; TSC2; COL4A2; PIK3CA; COL4A1; COL4A4; COL4A6; ULK1; ITGA5; ATF4; LAMA5; ATF6B; LAMA4; LPAR1; HIF1A; THBS1; FOXO1; HSP90B1; PDGFC; MAPK3; ANGPT1; LAMB2; LAMB1; COL3A1; KITLG; COL1A2; COL5A1; ITGA10; COL5A2; ITGA11; RPS6KB2; FGFR1 |
| Oncostatin M Signaling Pathway WP2374 | 2.17E−05 | 0.00204591 | PIAS3; IRS1; SERPINE1; PXN; TYK2; MAPK14; HIF1A; CYR61; NFKBIA; CASP7; CDK2; PTK2B; CCL2; RICTOR; IL6ST; LDLR; MAPK3 |

TABLE 8-continued

| Term | P-value | Adjusted P-value | Genes |
|---|---|---|---|
| Primary Focal Segmental Glomerulosclerosis FSGS WP2572 | 2.44E-05 | 0.00192295 | SCARB2; ITGB1; LAMA5; CDKN1A; CD151; LAMB2; LRP5; DKK1; DNM1; CD2AP; LRP6; INF2; COL4A4; COL4A3; COL4A5; ITGAV; VIM; AGRN |
| Angiopoietin Like Protein 8 Regulatory Pathway WP3915 | 1.17E-04 | 0.00790986 | THRA; IRS1; PIK3CD; CBLB; IRS2; FOXO1; AKT2; RICTOR; SLC16A2; MAP2K7; MAP4K3; MAPK3; MAP4K2; PRKAB2; MAP3K1; MINK1; TSC2; MAPK14; SREBF2; PIK3CA; RPS6KB2; RAPGEF1; TRIP10; RHOQ; MAP3K12 |
| Hypothesized Pathways in Pathogenesis of Cardiovascular Disease WP3668 | 1.34E-04 | 0.00791924 | FBN2; POSTN; SERPINE1; MAPK14; LTBP1; CTGF; MAPK3; TGFBR2; FBN1 |
| *Adipogenesis WP236* | 2.38E-04 | 0.01250733 | FZD1; NCOA1; NCOA2; CDKN1A; CEBPD; IRS1; STAT2; SERPINE1; TWIST1; IRS2; HIF1A; FOXO1; NCOR2; RBL2; KLF6; NCOR1; ID3; SPOCK1; FAS; IL6ST; PPARA; MEF2D; LPIN3; PPARD |
| Signaling Pathways in Glioblastoma WP2261 | 4.69E-04 | 0.02214927 | PDGFRB; PDGFRA; CDKN1A; IRS1; PTEN; PIK3CD; TSC2; FOXO4; FOXO1; PIK3C2B; PIK3CA; AKT2; ERBB2; CDK2; MAP2K7; MAPK3; FGFR1 |
| IL-1 signaling pathway WP195 | 5.77E-04 | 0.02476774 | ATF2; MAP3K1; IL1R1; MAPK14; NFKBIA; TRAF6; MAPKAPK2; CCL2; TAB3; TAB2; UBE2V1; MAP2K7; MAPK3 |
| Structural Pathway of Interleukin 1 (IL-1) WP2637 | 6.61E-04 | 0.02601238 | NFKBIA; ATF2; MAP3K1; IL1R1; TRAF6; MAPKAPK2; IRF7; TAB3; TAB2; MAP2K7; MAPK14; MAPK3 |
| *PI3K-Akt Signaling Pathway WP4172* | 6.62E-04 | 0.02403748 | ITGB1; ATF2; LAMA5; CDKN1A; CSF1; ATF6B; IRS1; LAMA4; ITGA2B; LPAR1; PTEN; PIK3CD; LAMC1; THBS1; HSP90B1; CCND3; AKT2; PDGFC; ITGAV; MAPK3; PDGFRB; PDGFRA; ITGA4; ANGPT1; LAMB2; F2R; ITGA1; TSC2; LAMB1; RBL2; KITLG; COL1A2; COL4A2; PIK3CA; COL4A1; COL4A4; ITGA10; COL4A3; ITGA11; CDK2; RPS6KB2; COL4A6; COL4A5; PKN1; ITGA5; ATF4; FGFR1 |
| *Integrin-mediated Cell Adhesion WP185* | 8.04E-04 | 0.02710242 | ITGB1; ITGA4; ROCK1; CAV2; ITGA2B; PXN; ITGA1; CAPN6; CAPN7; AKT2; ITGA10; ITGA11; RAPGEF1; RAC3; ITGAV; CAPN1; ITGA5; TNS1; PAK4 |
| Insulin Signaling WP481 | 0.00103294 | 0.03250332 | STXBP3; IRS1; INPPL1; PTEN; PIK3CD; CBLB; IRS2; FOXO1; AKT2; MAP2K7; MAP4K3; MAPK3; MAP4K2; MAP3K1; MINK1; TSC2; MAPK14; ARHGAP33; EHD2; PFKL; PIK3CA; RPS6KB2; RAPGEF1; VAMP2; RHOQ; MAP3K12 |
| Wnt/beta-catenin Signaling Pathway in Leukemia WP3658 | 0.00105563 | 0.0311412 | JUP; ZBTB16; FZD6; LRP5; DKK1; PML; LRP6; PPARD |
| RIG-I-like Receptor Signaling WP3865 | 0.00137809 | 0.03826237 | DDX17; OTUD5; MAP3K1; MAPK14; ATG12; NFKBIA; CYLD; MAVS; TRAF6; IRF7; PIN1; TBKBP1; AZI2 |
| MicroRNAs in cardiomyocyte hypertrophy WP1544 | 0.00175991 | 0.04614883 | FZD1; HDAC5; CAMK2D; ROCK1; WNT5A; LRP5; PIK3CD; MAPK14; LRP6; HDAC7; NFATC4; PIK3CA; AKT2; IL6ST; MAP2K7; MAPK3 |
| *Sterol Regulatory Element-Binding Proteins (SREBP) signalling WP1982* | 0.00179121 | 0.04449747 | PRKAB2; SEC23A; SEC24A; INSIG1; MED15; SREBF2; PIK3CA; MVD; ACSS1; SEC24D; ATF6; LDLR; SEC24C; SEC31A |
| *NOTCH1 regulation of human endothelial cell calcification WP3413* | 0.00205955 | 0.04860529 | ITGA1; MGP; LPAR1; CALU; PLAT; SAT1 |

TABLE 8-continued

| Term | P-value | Adjusted P-value | Genes |
|---|---|---|---|
| *miR-509-3p alteration of YAP1/ECM axis WP3967* | 0.00205955 | 0.04629075 | EDNRA; COL3A1; SPARC; COL5A1; TWIST1; GPC6 |
| Pathways up-regulated in HMLE-TWIST cells after two days of treatment with 150 μM of chaetocin | | | |
| *DNA IR-damage and cellular response via ATR WP4016 | 6.01E−08 | 2.84E−05 | FEN1; PCNA; RMI1; XRCC5; H2AFX; FANCA; BRCA1; BRCC3; BRCA2; MLH1; BRIP1; RAD50; CDC45; TRIM28; EXO1; CHEK2; E2F1; USP1; RBBP8; CLSPN; TP53; ATRIP; ATR |
| Histone Modifications WP2369 | 1.06E−06 | 2.49E−04 | SETD4; HIST1H3J; SETD9; HIST1H4L; SETD1B; SETMAR; HIST1H4A; HIST1H3A; HIST1H3F; HIST1H3G; HIST1H4H; HIST1H3H; HIST1H4I; HIST2H3D; HIST1H3B; HIST1H4C; HIST1H3C; HIST1H3D; HIST1H4F |
| The effect of progerin on the involved genes in Hutchinson-Gilford Progeria Syndrome WP4320 | 3.85E−06 | 6.05E−04 | MBD3; HIST1H3J; HIST1H3A; E2F1; HIST1H3F; INPP5K; HIST1H3G; HIST1H3H; HIST1H3B; HIST2H3D; HIST1H3C; TP53; HIST1H3D |
| *Retinoblastoma Gene in Cancer WP2446 | 1.85E−05 | 0.00217712 | CDKN1B; RFC4; PCNA; RRM2; CDC7; HMGB1; CDC25A; SMC2; SAP30; DHFR; POLA1; CDC45; CCNE2; ORC1; KIF4A; HLTF; MCM3; E2F1; E2F2; TP53 |
| DNA IR-Double Strand Breaks (DSBs) and cellular response via ATM WP3959 | 2.38E−05 | 0.0022439 | BLM; DCLRE1C; PCNA; ACTL6A; H2AFX; BRCA1; BRCA2; RAD50; TRIM28; CDK5; EXO1; CHEK2; E2F1; TP53; ATR |
| DNA Damage Response WP707 | 2.42E−05 | 0.00190659 | CDKN1B; H2AFX; BRCA1; CDC25A; CCNB3; RAD50; CASP8; RRM2B; CCNE2; CDK5; CHEK2; E2F1; CYCS; SFN; TP53; ATRIP; ATR |
| miRNA Regulation of DNA Damage Response WP1530 | 4.41E−05 | 0.00297619 | CDKN1B; H2AFX; BRCA1; CDC25A; CCNB3; RAD50; CASP8; RRM2B; CCNE2; CDK5; CHEK2; E2F1; CYCS; SFN; TP53; ATRIP; ATR |
| NRF2-ARE regulation WP4357 | 4.55E−05 | 0.002686 | NQO1; AIMP2; GCLC; YES1; KEAP1; HMOX1; PGAM5; SLC7A11; GCLM |
| Phytochemical activity on NRF2 transcriptional activation WP3 | 8.65E−05 | 0.0045345 | NQO1; AIMP2; GCLC; KEAP1; HMOX1; SLC7A11; GCLM |
| DNA Replication WP466 | 9.38E−05 | 0.00442817 | ORC5; POLA1; PCNA; ORC6; CDC45; RFC4; ORC1; UBC; MCM3; MCM10; CDC7; CDC6 |
| Cell Cycle WP179 | 2.68E−04 | 0.01148935 | CDKN2D; CDKN1B; PCNA; YWHAB; CDC7; CDC6; PKMYT1; CDC25A; CCNB3; ORC5; ORC6; CDC45; CCNE2; ORC1; ESPL1; CHEK2; MCM3; E2F1; E2F2; SFN; TP53; ATR |
| G1 to S cell cycle control WP45 | 5.53E−04 | 0.02173412 | CDKN2D; CDKN1B; PCNA; CDC25A; ORC5; ORC6; CDC45; CCNE2; ORC1; CREB3L4; MCM3; E2F1; E2F2; TP53 |
| *ATM Signaling Network in Development and Disease WP3878 | 7.97E−04 | 0.02892879 | G6PD; RAD50; DCLRE1C; TRIM28; CDK5; CHEK2; RASGRF1; H2AFX; RBBP8; AURKB; ATR |
| Pyrimidine metabolism WP4022 | 0.00131202 | 0.04423398 | DTYMK; DUT; PNPT1; RRM2; CTPS1; NME1; DCTD; POLA1; RRM2B; POLR2A; POLR3B; POLR3G; NT5M; DCTPP1; POLR3K; POLR2L |
| Pathways up-regulated in HMLE-TWIST cells after two days of treatment with 500 μM of chaetocin | | | |
| *DNA IR-damage and cellular response via ATR WP4016 | 3.54E−06 | 0.00167164 | MDC1; PCNA; POLN; H2AFX; BRCA1; BRCC3; BRCA2; MLH1; PALB2; BRIP1; RAD50; CDC45; RAD51; MSH2; EXO1; FANCD2; |

TABLE 8-continued

| Term | P-value | Adjusted P-value | Genes |
|---|---|---|---|
| DNA IR-Double Strand Breaks (DSBs) and cellular response via ATM WP3959 | 5.41E−06 | 0.00127716 | USP1; RBBP8; CLSPN; TP53; ATRIP; MCM2; ATR MDC1; BLM; DCLRE1C; PCNA; ACTL6A; H2AFX; BRCA1; BRCA2; TERF2; RAD50; RAD51; CDK5; EXO1; FANCD2; CASP3; NABP2; TP53; ATR |
| miRNA Regulation of DNA Damage Response WP1530 | 2.10E−05 | 0.00330261 | MCM7; GADD45A; H2AFX; BRCA1; CDC25A; CDC20B; CCNB3; CCNB1; RAD50; RAD51; CCND1; CCNE2; CDK5; FANCD2; CASP3; CYCS; SFN; TP53; ATRIP; ATR |
| Cell Cycle WP179 | 2.66E−05 | 0.00314451 | PCNA; MCM7; YWHAB; PKMYT1; CDC20; CCNB3; ORC5; CCNB1; ORC6; CDC45; CCND1; E2F2; SFN; E2F3; E2F4; YWHAH; GADD45A; CDC7; CDC6; CDC25A; STAG1; DBF4; CCNE2; MCM3; TP53; MAD1L1; ATR; MCM2 |
| DNA Damage Response WP707 | 1.30E−04 | 0.01225552 | GADD45A; H2AFX; BRCA1; CDC25A; CCNB3; CCNB1; RAD50; RAD51; CCND1; CCNE2; CDK5; FANCD2; CASP3; CYCS; SFN; TP53; ATRIP; ATR |
| DNA Replication WP466 | 2.04E−04 | 0.0160872 | PCNA; RFC4; MCM7; MCM10; CDC7; CDC6; ORC5; ORC6; CDC45; DBF4; UBC; MCM3; MCM2 |
| *Retinoblastoma Gene in Cancer WP2446 | 4.43E−04 | 0.02986511 | DNMT1; RFC4; PCNA: RRM2; MCM7; CDC7; HMGB1; CDC25A; SAP30; DHFR; CCNB1; CDC45; CCND1; CCNE2; KIF4A; STMN1; MCM3; E2F2; E2F3; TP53 |
| G1 to S cell cycle control WP45 | 6.05E−04 | 0.0357193 | PCNA; MCM7; GADD45A; CDC25A; ORC5; CCNB1; ORC6; CDC45; CCND1; CCNE2; CREB3L4; MCM3; E2F2; E2F3; TP53; MCM2 |

TABLE 9

| Term | P-value | Adjusted P-value | Genes |
|---|---|---|---|
| Pathways down-regulated in HMLE-TWIST cells two days after chaetocin removal (@150 μM) | | | |
| miRNA targets in ECM and membrane receptors WP2911 | 2.16E−09 | 1.02E−06 | COL3A1; COL1A2; COL5A1; COL4A2; LAMB2; COL4A1; LAMA4; SDC2; ITGA1; COL5A2; FN1 |
| Focal Adhesion WP306 | 2.52E−06 | 5.94E−04 | FLT1; SHC1; LAMA4; ITGA2B; AKT2; PDGFC; ERBB2; RAC3; ITGAV; PAK4; MAPK3; PDGFRB; PDGFRA; ITGA4; CAV2; LAMB2; ITGA1; FN1; LAMB1; COL1A1; COL1A2; COL4A2; COL4A1; COL4A4; ITGA10; COL5A2; COL4A6 |
| Focal Adhesion-PI3K-Akt-mTOR-signaling pathway WP3932 | 1.14E−05 | 0.00178759 | FLT1; CSF1; ATF6B; IRS1; LAMA4; ITGA2B; LPAR1; IRS2; GYS1; AKT2; PDGFC; ITGAV; MAPK3; PDGFRB; SREBF1; PDGFRA; ITGA4; ANGPT1; LAMB2; FN1; LAMB1; EPOR; COL1A1; EFNA1; COL3A1; COL1A2; COL4A2; COL5A1; COL4A1; COL4A4; ITGA10; GNB2; COL5A2; COL4A6 |
| PI3K-Akt Signaling Pathway WP4172 | 5.28E−05 | 0.00622965 | FLT1; CSF1; ATF6B; PKN3; IRS1; LAMA4; ITGA2B; LPAR1; GYS1; AKT2; PDGFC; ITGAV; MAPK3; PDGFRB; PDGFRA; |

TABLE 9-continued

| Term | P-value | Adjusted P-value | Genes |
|---|---|---|---|
| | | | ITGA4; ANGPT1; LAMB2; ITGA1; FN1; LAMB1; EPOR; COL1A1; EFNA1; COL1A2; COL4A2; COL4A1; COL4A4; ITGA10; GNB2; CDK2; COL4A6; COL4A5; PKN1; SOS2 |
| *Inflammatory Response Pathway WP453* | 8.84E−05 | 0.00834457 | COL1A1; CD40; COL3A1; COL1A2; LAMB2; FN1; LAMB1; TNFRSF1A |
| *miR-509-3p alteration of YAP1/ECM axis WP3967* | 1.24E−04 | 0.00978137 | COL1A1; COL3A1; SPARC; COL5A1; FN1; GPC6 |
| Complement and Coagulation Cascades WP558 | 1.31E−04 | 0.00883403 | C3; SERPINA1; C6; PROC; C1S; C7; C1R; PROS1; SERPING1; TFPI; SERPINA5 |
| *Epithelial to mesenchymal transition in colorectal cancer WP4239* | 1.52E−04 | 0.00899473 | NOTCH3; TGFB2; SPARC; SHC1; MMP2; WNT5A; FZD6; FN1; LRP5; PKD1; LATS2; COL4A2; COL4A1; CTDSP1; AKT2; COL4A4; COL4A6; COL4A5; SOS2; MAPK3 |
| Hypothesized Pathways in Pathogenesis of Cardiovascular Disease WP3668 | 1.76E−04 | 0.00921742 | FBN2; TGFBR3; POSTN; SHC1; LTBP1; MAPK3; FBN1 |
| Human Complement System WP2806 | 3.54E−04 | 0.01671749 | CD40; C1S; C1R; PROS1; ITGA2B; LAMB1; DCN; GNAI2; C3; C6; C7; SERPING1; CALR; PRKACA |
| Pathways down-regulated in HMLE-TWIST cells two days after chaetocin removal (@500 µM) | | | |
| Cytoplasmic Ribosomal Proteins WP477 | 2.45E−18 | 1.16E−15 | RPL4; RPL30; RPL3; RPL32; RPL10; RPL31; RPL34; RPL12; RPLP0; RPL11; RPL10A; RPL9; RPS4X; RPS6KA3; RPL7A; RPS15A; RPS18; RPL37; RPS2; RPS27A; RPL39; RPS13; RPS12; RPS9; RPL41; RPL21; RPS8; RPL22; RPS6; RPL13A; RPL35A; RPS3A; RPSA; RPL23A; RPS27; RPS29; RPS6KB2; RPL24; RPL29 |
| *miRNA targets in ECM and membrane receptors WP2911* | 3.09E−10 | 7.30E−08 | LAMB2; LAMA4; SDC2; ITGA1; FN1; LAMC1; THBS1; COL3A1; COL1A2; COL5A1; COL4A2; COL4A1; COL5A2; COL6A3 |
| *Focal Adhesion WP306* | 3.50E−09 | 5.50E−07 | ITGB1; ROCK1; SHC1; LAMA4; PTEN; ILK; LAMC1; ARHGAP5; THBS1; PPP1CB; PPP1CC; CCND3; AKT3; PDGFC; ERBB2; RAC3; MAPK1; ITGAV; PAK4; MAPK3; PDGFRB; PDGFRA; PPP1R12A; ITGA4; CAV2; LAMB2; CAV1; ITGA1; FN1; PARVA; LAMB1; ACTN4; COL1A1; COL1A2; COL4A2; PIK3CA; COL4A1; COL4A4; ITGA10; COL5A2; COL4A6; CTNNB1; DOCK1; VCL; BIRC2 |
| Primary Focal Segmental Glomerulosclerosis FSGS WP2572 | 7.22E−07 | 8.52E−05 | SCARB2; ITGB1; CD151; MME; LAMB2; ILK; PARVA; ACTN4; DKK1; CD2AP; LRP6; INF2; COL4A4; COL4A5; CTNNB1; ITGAV; VIM; UTRN; TLR4; VCL; NCK1 |
| *Focal Adhesion-PI3K-Akt-mTOR-signaling pathway WP3932* | 1.50E−06 | 1.41E−04 | ITGB1; ATF2; CSF1; IRS1; PTEN; SLC2A3; LAMC1; PIK3C2B; FGF7; CREB3L2; AKT3; ITGAV; JAK1; PDGFRB; PDGFRA; ITGA4; RPS6; F2R; PPP2R5D; TBC1D1; COL4A2; PIK3CA; COL4A1; COL4A4; COL4A6; ATF6B; LAMA4; LPAR1; HIF1A; THBS1; HSP90B1; NRAS; GNG2; PDGFC; MAPK1; EIF4B; MAPK3; ANGPT1; LAMB2; FN1; LAMB1; COL1A1; EFNA1; COL3A1; KITLG; COL1A2; |

TABLE 9-continued

| Term | P-value | Adjusted P-value | Genes |
|---|---|---|---|
| | | | COL5A1; ITGA10; GNB2; COL5A2; RPS6KB2; GNB4; KRAS |
| EGF/EGFR Signaling Pathway WP437 | 1.95E−06 | 1.53E−04 | ROCK1; SHC1; INPPL1; PTEN; PEBP1; CBLB; AP2A1; IQGAP1; PLD1; PLD2; PIK3C2B; RPS6KA3; GJA1; ERBB2; REPS2; MAPK1; RICTOR; EPS15; AP2M1; NCK1; JAK1; STAT5B; PRKCI; MAP3K1; CAV2; CAV1; AP2B1; MAPK14; PLSCR1; SP1; RASA1; PXDN; KRAS; STAM2 |
| Nonalcoholic fatty liver disease WP4396 | 5.56E−06 | 3.75E−04 | COX7B; NDUFB7; UQCRB; IRS1; NDUFA12; NDUFB11; COX7A2; UQCR10; COX5B; COX7C; UQCRH; CASP7; AKT3; LEPR; CCL2; CYC1; NDUFV1; PRKAB2; NDUFA5; NDUFA4; NDUFA2; NDUFA1; SDHD; COX6B1; TNFRSF1A; PIK3CA; NDUFS5; UQCRC1; NDUFS3; NDUFS2; NDUFS1; UQCRC2 |
| Ebola Virus Pathway on Host WP4217 | 7.78E−06 | 4.59E−04 | ITGB1; CLTC; IQGAP1; MAPK1; ITGAV; EPS15; CTSB; MAPK3; GSN; ITGA4; CAV2; CAV1; ITGA1; HLA-B; HLA-C; EIF2AK2; ACTN4; HLA-A; HLA-F; RHOC; HLA-E; RHOB; PIK3CA; NPC2; TYRO3; RAB9A; MFGE8; TLR4 |
| Inhibition of exosome biogenesis and secretion by Manumycin A in CRPC cells WP4301 | 8.09E−06 | 4.24E−04 | RAB5B; NRAS; PDCD6IP; RRAS; ARAF; RAB27A; MAPK1; KRAS; MAPK3 |
| PI3K-Akt Signaling Pathway WP4172 | 1.08E−05 | 5.11E−04 | ITGB1; ATF2; CSF1; IRS1; PTEN; LAMC1; CCND3; FGF7; CREB3L2; AKT3; ITGAV; JAK1; PDGFRB; PDGFRA; ITGA4; RPS6; F2R; ITGA1; PPP2R5D; RBL2; COL4A2; PIK3CA; COL4A1; COL4A4; COL4A6; COL4A5; COL6A3; TLR4; ATF6B; LAMA4; LPAR1; THBS1; HSP90B1; NRAS; GNG2; PDGFC; MAPK1; EIF4B; MAPK3; ANGPT1; LAMB2; FN1; LAMB1; COL1A1; EFNA1; KITLG; COL1A2; G6PC3; ITGA10; GNB2; CDK2; RPS6KB2; GNB4; KRAS; PKN1 |
| Sterol Regulatory Element-Binding Proteins (SREBP) signalling WP1982 | 2.42E−05 | 0.00104014 | FDPS; SEC13; PRKAB2; SEC23A; SAR1A; INSIG1; CYP51A1; DBI; SREBF2; SQLE; PIK3CA; SP1; SEC24D; ATF6; LDLR; SEC24C; KPNB1; SEC31A |
| Electron Transport Chain (OXPHOS system in mitochondria) WP111 | 3.04E−05 | 0.00119557 | SURF1; COX7B; NDUFB7; UQCRB; NDUFA5; NDUFA12; NDUFA4; NDUFA2; NDUFA1; COX7A2; SDHD; UQCR10; COX5B; COX7C; UQCRH; COX6B1; NDUFS5; UQCRC1; NDUFS3; NDUFS2; NDUFS1; UQCRC2; NDUFV1 |
| Integrin-mediated Cell Adhesion WP185 | 6.69E−05 | 0.00242755 | ITGB1; ITGA4; ROCK1; SHC1; CAV2; CAV1; ITGA1; ARAF; ILK; CAPNS1; CAPN6; CAPN7; ITGA10; AKT3; RAC3; MAPK1; ITGAV; CAPN1; DOCK1; VCL; TNS1; PAK4 |
| Non-genomic actions of 1,25 dihydroxyvitamin D3 WP4341 | 1.29E−04 | 0.00436502 | IFI27L2; CAV1; STAT2; MAPK14; IFI44L; TNFRSF1A; RXRB; NRAS; SP1; CCL2; MAPK1; KRAS; PLCB1; TLR4; CAMK2G; JAK1; MAPK3 |

TABLE 9-continued

| Term | P-value | Adjusted P-value | Genes |
|---|---|---|---|
| *Regulation of Actin Cytoskeleton WP51* | 1.36E−04 | 0.00427095 | ROCK1; BRK1; IQGAP1; PIK3C2B; FGF7; NRAS; RRAS; CFL2; TMSB4X; RAC3; MAPK1; PIP4K2B; MYH10; WASF2; PAK4; MAPK3; PDGFRB; PDGFRA; PPP1R12A; GSN; F2R; ITGA1; FN1; PIK3CA; KRAS; DOCK1; VCL; ARHGEF6 |
| Oncostatin M Signaling Pathway WP2374 | 1.43E−04 | 0.00422021 | STAT5B; IRS1; SHC1; RPS6; MAPK14; HIF1A; CYR61; CASP7; CDK2; CCL2; MAPK1; RICTOR; KRAS; LDLR; JAK1; MAPK3 |
| *Inflammatory Response Pathway WP453* | 1.76E−04 | 0.00489378 | COL1A1; COL3A1; COL1A2; LAMB2; FN1; LAMB1; LAMC1; TNFRSF1B; THBS1; TNFRSF1A |
| Hypothesized Pathways in Pathogenesis of Cardiovascular Disease WP3668 | 1.91E−04 | 0.00500609 | FBN2; TGFBR3; POSTN; SHC1; MAPK1; MAPK14; LTBP1; MAPK3; FBN1 |
| DNA Damage Response (only ATM dependent) WP710 | 2.49E−04 | 0.00618968 | MAP3K1; IRS1; SHC1; WNT5A; PTEN; SOD2; PIK3C2B; RBL2; CCND3; NRAS; SCP2; BCL6; PIK3CA; AKT3; CAT; ERBB2; RAC3; MAPK1; CTNNB1; ATM; KRAS; LDLR |
| *RAC1/PAK1/p38/MMP2 Pathway WP3303* | 2.51E−04 | 0.00592705 | ITGB1; STAT5B; ANGPT1; MMP2; FN1; MAPK14; CASP7; NRAS; PIK3CA; RASA1; ERBB2; MAPK1; CTNNB1; KRAS; NCK1; MAPK3 |
| *miR-509-3p alteration of YAP1/ECM axis WP3967* | 3.87E−04 | 0.00869127 | COL1A1; COL3A1; SPARC; COL5A1; FN1; GPC6; TEAD1 |
| Homologous recombination WP186 | 4.94E−04 | 0.01059613 | POLD3; POLD4; POLD1; POLD2; RPA1; ATM |
| Nanoparticle-mediated activation of receptor signaling WP2643 | 5.05E−04 | 0.01035965 | ITGB1; COL1A1; NRAS; AKT3; ITGA1; FN1; MAPK1; KRAS; MAPK14 |
| Benzo(a)pyrene metabolism WP696 | 5.21E−04 | 0.01024099 | AKR1C1; AKR1C3; AKR1A1; AKR1C2; CYP1B1 |
| *VEGFA-VEGFR2 Signaling Pathway WP3888* | 5.24E−04 | 0.00988413 | YWHAE; ITGB1; ATF2; HDAC5; ROCK1; SHC1; CLTC; CTNND1; IQGAP1; GJA1; ADAMTS1; PBK; CTNNA1; CCL2; MAPK1; RICTOR; IGFBP7; ITGAV; EPS15; EIF2A; NCK1; MAPK3; PRKCI; CAV1; MMP2; TRPC1; RPS6; RHOC; MAPK14; SOD2; DKK1; MMP14; PIK3CA; TXNIP; CTNNB1; ATF6; VCL |
| Human Thyroid Stimulating Hormone (TSH) signaling pathway WP2032 | 5.76E−04 | 0.01046413 | RPS6; GNAI3; PLD1; MAPK14; GNAI1; GNAI2; RBL2; CCND3; GNG2; PIK3CA; CDK2; MAPK1; PLCB1; JAK1; MAPK3 |
| *TGF-beta Signaling Pathway WP366* | 5.89E−04 | 0.01029146 | ITGB1; ATF2; APP; KLF11; ROCK1; SHC1; CAV1; FN1; NEDD9; MAPK14; THBS1; PML; RBX1; PIAS1; TGFBR3; RBL2; KLF6; COPS5; COL1A2; SP1; CDK1; MAPK1; RNF111; SPTBN1 |
| *PDGFR-beta pathway WP3972* | 6.75E−04 | 0.01137075 | PDGFRB; STAT5B; MAP3K1; PIK3CA; SHC1; RASA1; EIF2AK2; MAPK3; JAK1 |
| *Angiogenesis WP1539* | 7.88E−04 | 0.01282701 | PDGFRA; ANGPT1; PIK3CA; TIMP2; ARNT; MAPK1; MAPK14; HIF1A |
| *Signal Transduction of S1P Receptor WP26* | 0.00106913 | 0.01682102 | AKT3; GNAI3; MAPK1; PLCB1; GNAI1; PIK3C2B; GNAI2; MAPK3 |
| Complement and Coagulation Cascades WP558 | 0.00150478 | 0.02291152 | C1S; C1R; PROS1; CLTC; F2R; TFPI; SERPINA5; C3; LMAN1; C6; PROC; SERPING1; CD46 |
| Prostaglandin Synthesis and Regulation WP98 | 0.0016228 | 0.02393628 | PTGFR; HPGD; ANXA2; PTGER2; AKR1C1; ANXA6; AKR1C3; S100A6; AKR1C2; PTGFRN; PTGS1 |

TABLE 9-continued

| Term | P-value | Adjusted P-value | Genes |
|---|---|---|---|
| AGE/RAGE pathway WP2324 | 0.00176955 | 0.02530991 | ATF2; STAT5B; MMP7; ROCK1; IRS1; SHC1; MMP2; MAPK14; HIF1A; LGALS3; MMP14; SP1; MAPK1; MAPK3 |
| Disorders of the Krebs cycle WP4236 | 0.00177113 | 0.02458746 | SUCLA2; DLST; SUCLG2; DHTKD1 |
| *Epithelial to mesenchymal transition in colorectal cancer WP4239* | 0.00181147 | 0.02442895 | NOTCH3; SPARC; SHC1; HIF1A; LRP6; AKT3; MAPK1; MAPK3; FZD1; TGFB2; MMP2; WNT5A; FZD6; FN1; MAPK14; MPP5; LATS2; COL4A2; PIK3CA; COL4A1; CTDSP1; COL4A4; COL4A6; COL4A5; CTNNB1; KRAS |
| Hippo-Merlin Signaling Dysregulation WP4541 | 0.00206112 | 0.0270236 | PDGFRB; ITGB1; PDGFRA; PPP1R12A; ITGA4; ITGA1; RBX1; PPP1CB; PPP1CC; NRAS; LATS2; PRKAR1A; ITGA10; CTNNA1; CDH24; CDH13; CTNNB1; ITGAV; KRAS; TEAD1; PAK4 |
| Signaling Pathways in Glioblastoma WP2261 | 0.00217158 | 0.02770228 | PDGFRB; PDGFRA; PRKCI; IRS1; ARAF; PTEN; PIK3C2B; NRAS; PIK3CA; AKT3; ERBB2; CDK2; MAPK1; ATM; KRAS; MAPK3 |
| Alzheimers Disease WP2059 | 0.00247196 | 0.03070432 | APP; MME; LRP1; ADAM10; TNFRSF1A; BACE1; APH1A; CASP7; NCSTN; MAPK1; CALM3; CAPN1; APOE; PLCB1; ATF6; MAPK3 |
| Leptin signaling pathway WP2034 | 0.00262103 | 0.03172115 | NCOA1; STAT5B; ROCK1; IRS1; SHC1; RPS6; PTEN; MAPK14; SP1; CFL2; ERBB2; LEPR; MAPK1; JAK1; MAPK3 |
| Proteasome Degradation WP183 | 0.00283608 | 0.03346579 | UBA7; RPN2; RPN1; HLA-B; HLA-C; HLA-A; HLA-F; HLA-E; PSMB6; PSMB4; PSMB5; UBB; PSMD5 |
| The human immune response to tuberculosis WP4197 | 0.00302587 | 0.03483445 | MED14; IFNGR1; STAT2; IFNGR2; IFIT1; PIAS1; JAK1 |
| *MAPK Cascade WP422* | 0.00307588 | 0.03456708 | NRAS; MAP3K1; RRAS; ARAF; MAPK1; KRAS; MAPK14; MAPK3 |
| Spinal Cord Injury WP2431 | 0.00380629 | 0.04178063 | IL1R1; RHOC; AQP1; RHOB; FKBP1A; LGALS3; GJA1; VCAN; COL4A1; PTPRA; CDK2; CCNG1; CDK1; CCL2; MAPK1; CD47; VIM; ROS1; TLR4; MAPK3 |
| Extracellular vesicle-mediated signaling in recipient cells WP2870 | 0.00387145 | 0.0415301 | TGFBR3; NRAS; TGFB2; ERBB2; WNT5A; CTNNB1; KRAS; MFGE8 |
| Pathways up-regulated in HMLE-TWIST cells two days after chaetocin removal (@150 μM) | | | |
| Photodynamic therapy-induced NF-kB survival signaling WP3617 | 3.87E−06 | 0.00182518 | IL1A; IL6; CSF2; CCND1; MMP1; IL1B; MMP3; PTGS2; VEGFA; BIRC3 |
| Photodynamic therapy-induced unfolded protein response WP3613 | 2.73E−05 | 0.00643359 | BCL2L11; WARS; EDEM1; DDIT3; DNAJB11; ASNS; TRIB3; ATF3 |
| mRNA Processing WP411 | 1.13E−04 | 0.01782893 | NCBP1; FUS; CSTF3; CPSF3; CSTF2; DDX20; U2AF1; DICER1; HNRNPAB; PPM1G; HNRNPM; NXF1; SFPQ; PRPF6; POLR2A; SNRPA1; SNRPF |
| Pathways up-regulated in HMLE-TWIST cells two days after chaetocin removal (@500 μM) | | | |
| No pathway was identified that met the 0.05 p value threshold. | | | |

After the RNA-seq samples were sequenced, the cells used in this experiment were found to have a mycoplasma infection. Table 8 lists all the biological pathways up- or down-regulated in response to two days of chaetocin treatment. The results for two representative chaetocin concentrations (150 μM and 500 μM) are shown. Other concentrations produced a highly similar list of pathways. Only pathways whose enrichment is associated with an adjusted p value of less than 0.05 are indicated. Pathways listed in italicized font are those which have a known role in promoting the formation of the mesenchymal state in published literature. The pathways marked with an asterisk in tables above are those having known roles as tumor suppressors.

Table 9 lists biological pathways up- or down-regulated two days after chaetocin removal. The results for two representative chaetocin concentrations (150 μM and 500 μM) are shown. Other concentrations produced a highly similar list of pathways. Only pathways whose enrichment is associated with an adjusted p value of less than 0.05 are indicated. Pathways listed in italicized font are those which have a known role in promoting the formation of the mesenchymal state in published literature. Pathways marked with an asterisk in the above tables are those having known roles as tumor suppressors.

These data reveal that (1) chaetocin treatment inactivates several pathways which are critical for maintaining the mesenchymal, TIC state, (2) several tumor suppressor pathways are activated in response to chaetocin treatment, and (3) the chaetocin effect persist even after its removal. Together these data demonstrate that chaetocin treatment results in an epigenetic change which reprograms mesenchymal, TICs into non-TICs.

Figure 13A:
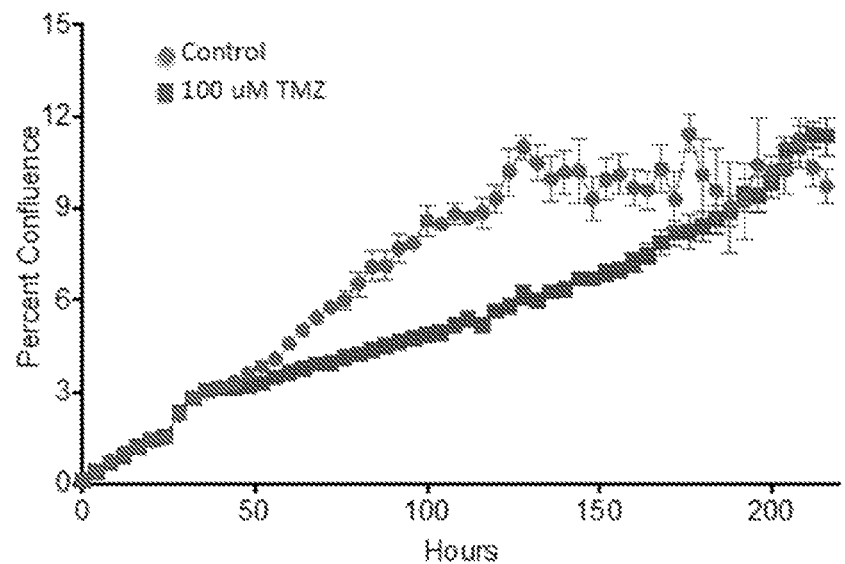
FIGS. 13A and 13B depict the response of a patient-derived TMZ-resistant glioblastoma (GBM) cell line to TMZ (Temozolomide). The cells were grown in suspension into spheroids after which they were treated with TMZ (100 uM), chaetocin (50 uM) or both (TMZ 100 uM, chaetocin 50 uM were administered at the same time). Cell confluence, an assay for spheroid size, was measured. The top graph depicts the response of the TMZ-resistant cell line to TMZ (100 uM) alone. Bottom graph depicts the response of the TMZ-resistant cell line to single agent and double agent treatments.
Figure 13B:
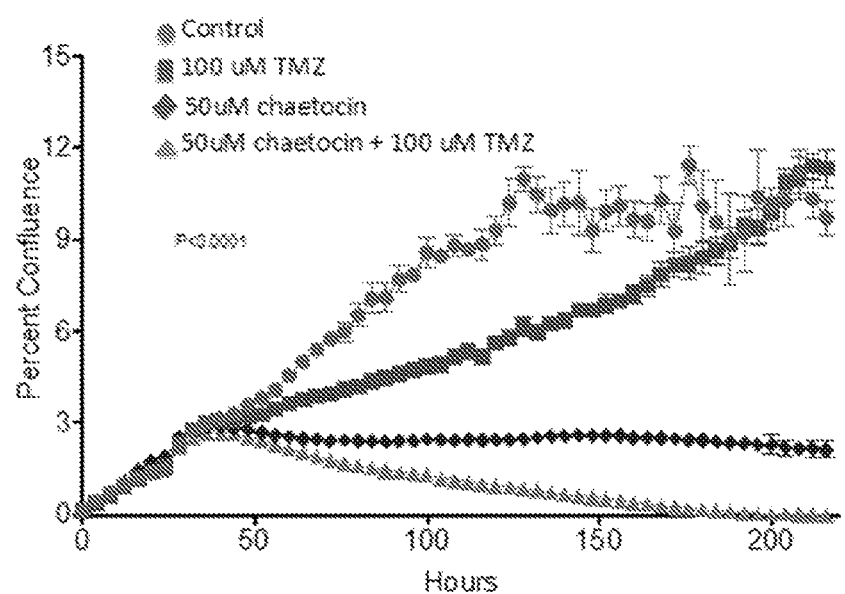

Example 12. Co-Treatment with Chaetocin and Temozolomide Sensitizes a Patient-Derived Temozolomide-Resistant Glioblastoma Cell Line to Temozolomide Treatment A short exposure to chaetocin is sufficient to cause an epigenetic change, reprogramming mesenchymal, TIC-rich cancer cells into an epithelial fate while sensitizing them to chemotherapy. Considering epigenetic changes are stable and can continue in the absence of the initial treatment, chaetocin treatment effects (mesenchymal reprogramming and sensitization to chemotherapy) should occur even if chaetocin is administered at the same time as the chemotherapy. To test this, a patient-derived Temozolomide (TMZ)-resistant glioblastoma (GBM) cell line was grown in suspension into spheroids and treated with chaetocin, TMZ, or both (administered at the same time). To clarify, when TMZ and chaetocin were administered together, they were added at the same time to the spheroids. Cell confluence, an assay for spheroid size, was measured to determine if cell growth was inhibited (flat curve) or spheroid sizes were reduced (indicator of cell death and spheroid shrinkage). FIG. 13 depicts the result of single treatment with TMZ at 100 uM, single treatment with chaetocin at 50 uM, and double treatment with TMZ at 100 uM and chaetocin at 50 uM. These data reveal that addition of chaetocin and TMZ at the same time results in sensitization of the TMZ-resistant cell line to TMZ treatment.

Figure 14:
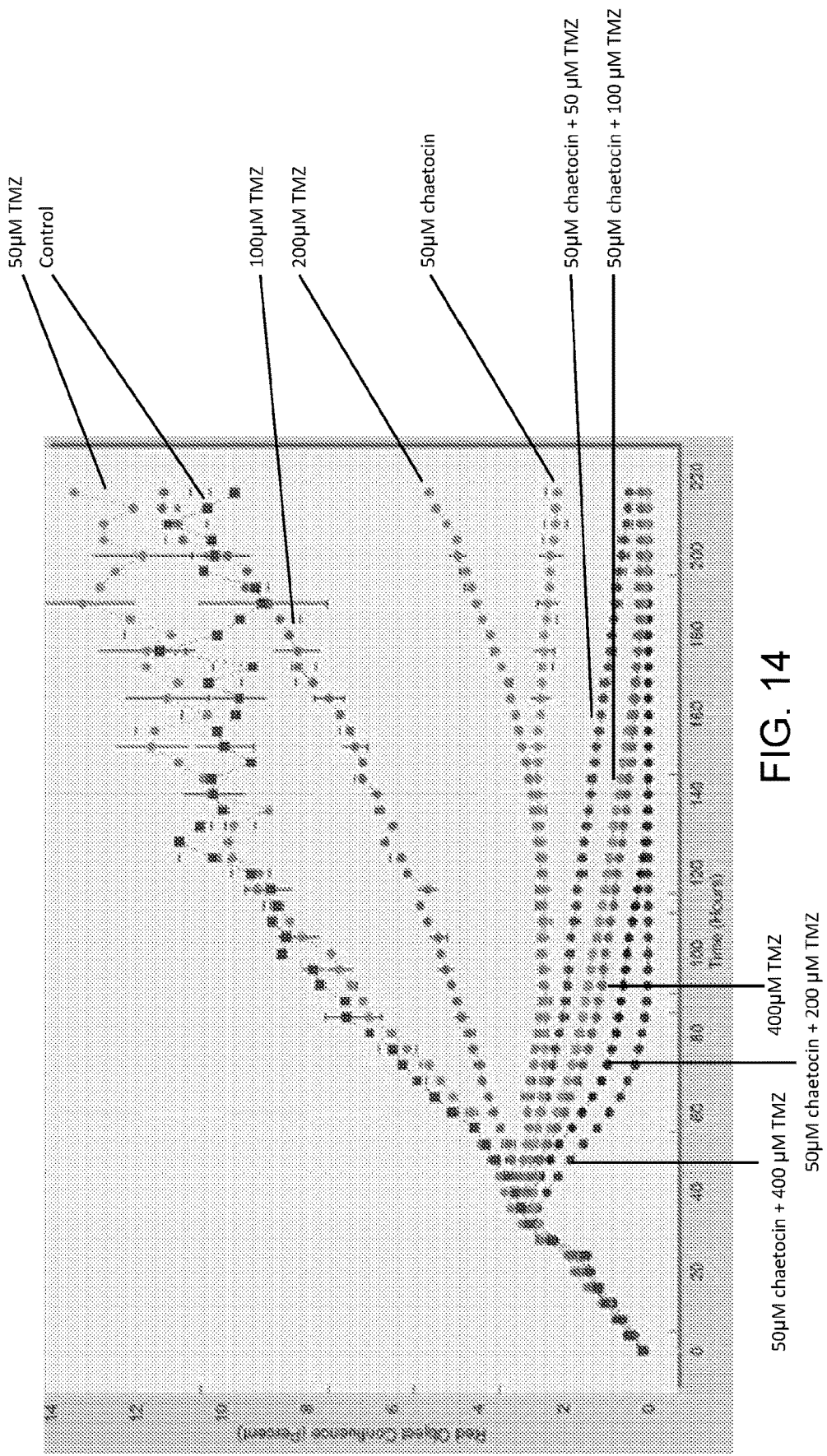
FIG. 14 depicts the response of a patient-derived TMZ-resistant glioblastoma (GBM) cell line to TMZ (Temozolomide). The cells were grown in suspension into spheroids after which they were treated with TMZ (50, 100, 200, 400 µM), chaetocin (50 uM) or both (TMZ at 50, 100, 200, or 400 µM together with chaetocin at 50 uM). When TMZ and chaetocin were administered together, they were added at the same time to the spheroids. Cell confluence, an assay for spheroid size, was measured. These data reveal that administration of TMZ and chaetocin together sensitizes these cells to TMZ.

This effect was tested against a range of TMZ concentrations. FIG. 14 depicts the result of this experiment against 50, 100, 200, and 400 uM of TMZ. Chaetocin concentration was kept at 50 uM. These data reveal that at all concentrations, the administration of chaetocin together with TMZ sensitizes the cells to TMZ treatment versus single treatment with TMZ or chaetocin.

Based on these data we claim that (1) chaetocin treatment works effectively to sensitize chemotherapy resistant GBM cells to chemotherapy; (2) administration of chaetocin together with TMZ is effective at sensitizing GBM cells to chemotherapy.

OTHER EMBODIMENTS

Various modifications and variations of the described disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure that are obvious to those skilled in the art are intended to be within the scope of the disclosure.

Other embodiments are in the claims.

What is claimed is:

1. A method of killing a chemoresistant cancer cell, the method comprising (i) contacting the chemoresistant cancer cell with an effective amount of chaetocin and pharmaceutically acceptable salts thereof, and (ii) contacting the cell with an anti-cancer agent or a pharmaceutically acceptable salt thereof;
    wherein the chemoresistant cancer cell is a chemoresistant breast mesenchymal cancer cell; and
    wherein step (ii) kills the chemoresistant cancer cell.

2. A method of treating a chemoresistant cancer in a subject, the method comprising (i) administering to the subject in need thereof a therapeutically effective amount of a chaetocin and pharmaceutically acceptable salts thereof, and, (ii) administering to the subject a therapeutically effective amount of an anti-cancer agent or a pharmaceutically acceptable salt thereof;
    wherein the chemoresistant cancer comprises a chemoresistant breast cancer cell; and
    wherein step (ii) treats the chemoresistant cancer in the subject.

3. A method of killing a chemoresistant breast cancer cell, the method comprising (i) contacting the chemoresistant breast cancer cell with an effective amount of chaetocin and pharmaceutically acceptable salts thereof, and, (ii) after a period of at least 5 hours, contacting the cell with an anti-cancer agent or a pharmaceutically acceptable salt thereof; wherein step (ii) kills the chemoresistant breast cancer cell.

4. The method of claim 3, wherein the period is 5 hours to 2 weeks.

5. The method of claim 4, wherein the period is 5 hours to 1 week.

6. The method of claim 5, wherein the period is 5 hours to 6 days.

7. The method of claim 6, wherein the period is 5 hours to 2 days.

8. The method of claim 7, wherein the period is 5 to 15 hours.

9. The method of claim 3, wherein the period is at least 15 hours.

10. A method of treating a chemoresistant breast cancer in a subject, the method comprising (i) administering to the subject in need thereof a therapeutically effective amount of a chaetocin and pharmaceutically acceptable salts thereof, and, (ii) after a period of at least 2 days, administering to the subject a therapeutically effective amount of an anti-cancer agent or a pharmaceutically acceptable salt thereof; wherein step (ii) treats the chemoresistant breast cancer in the subject.

11. The method of claim 10, wherein the period is 2 days to 2 weeks.

12. The method of claim 11, wherein the period is 2 days to 1 week.

13. The method of claim 12, wherein the period is 2 to 6 days.

14. A method of reversing chemoresistance of a chemoresistant breast cancer cell, the method comprising contacting the chemoresistant breast cancer cell with an effective amount of chaetocin and pharmaceutically acceptable salts thereof.

* * * * *